United States Patent
Soon-Shiong et al.

(10) Patent No.: US 12,290,558 B2
(45) Date of Patent: May 6, 2025

(54) SARS-COV-2 VACCINES COMPRISING HUMAN ADENOVIRUS VECTORS ENCODING SPIKE AND NUCLEOCAPSID-ETSD IMMUNOGENS

(71) Applicant: ImmunityBio, Inc., Culver City, CA (US)

(72) Inventors: Patrick Soon-Shiong, Culver City, CA (US); Peter Sieling, Culver City, CA (US); Kayvan Niazi, Culver City, CA (US); Shahrooz Rabizadeh, Agoura Hills, CA (US); Lise Geissert, Culver City, CA (US); Annie Shin, Culver City, CA (US); Adrian Rice, Culver City, CA (US); Elizabeth Gabitzsch, Culver City, CA (US); Jeffrey Safrit, Culver City, CA (US); Leonard Sender, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

(21) Appl. No.: 18/488,629

(22) Filed: Oct. 17, 2023

(65) Prior Publication Data
US 2024/0075129 A1 Mar. 7, 2024

Related U.S. Application Data

(63) Continuation of application No. 17/198,164, filed on Mar. 10, 2021, now Pat. No. 11,857,620, which is a (Continued)

(51) Int. Cl.
*A61K 39/215* (2006.01)
*C12N 15/861* (2006.01)
(Continued)

(52) U.S. Cl.
CPC .......... *A61K 39/215* (2013.01); *C12N 15/861* (2013.01); *A61K 39/39* (2013.01);
(Continued)

(58) Field of Classification Search
CPC ................ A61K 39/215; C12N 15/861; C12N 2710/10343; C12N 2770/20022; C12N 2770/20034
See application file for complete search history.

(56) References Cited

U.S. PATENT DOCUMENTS

| 6,133,036 A | 10/2000 | Putcha et al. |
| 6,716,392 B1 | 4/2004 | Putcha et al. |

(Continued)

FOREIGN PATENT DOCUMENTS

| CN | 1488646 A | 4/2004 |
| CN | 1572875 A | 2/2005 |

(Continued)

OTHER PUBLICATIONS

Lee, Y., et al., Oct. 2023, Immunogenicity of lipid nanoparticles and its impact on the efficacy of mRNA vaccines and therapeutics, Exp. Mol. Med. 55:2085-2096.*

(Continued)

*Primary Examiner* — Jeffrey S Parkin
(74) *Attorney, Agent, or Firm* — Martin Fessenmaier; Umberg Zipser LLP

(57) ABSTRACT

Disclosed herein are methods for inducing immunity against a virus such as a coronavirus in the mucosal tissue of a patient, include administering a vaccine composition to the patient by oral administration (e.g., nasal injection, nasal inhalation, oral inhalation, and/or oral ingestion). Also disclosed are compositions for assaying the presence of antiviral antibodies induced by the administered vaccine or the presence of viral proteins in a saliva sample include a (Continued)

Ad-S-Fusion

Ad-S-Fusion / N-ETSD stabilizing solution and may also include the use of aragonite particle beads. Compositions and methods are presented for prevention and/or treatment of a coronavirus disease wherein the composition comprises a recombinant entity. The recombinant entity is bivalent, comprising a nucleic acid encoding a coronavirus 2 nucleocapsid protein CoV2 nucleocapsid protein fused to an endosomal targeting sequence, and a nucleic acid encoding a CoV2 spike protein sequence optimized for cell surface expression.

11 Claims, 26 Drawing Sheets

Specification includes a Sequence Listing.

Related U.S. Application Data continuation-in-part of application No. 17/082,994, filed on Oct. 28, 2020, now abandoned, and a continuation-in-part of application No. 16/883,263, filed on May 26, 2020, now Pat. No. 11,684,668, and a continuation-in-part of application No. 16/880,804, filed on May 21, 2020, now abandoned.

(60) Provisional application No. 63/135,380, filed on Jan. 8, 2021, provisional application No. 63/121,102, filed on Dec. 3, 2020, provisional application No. 63/118,697, filed on Nov. 26, 2020, provisional application No. 63/117,922, filed on Nov. 24, 2020, provisional application No. 63/117,460, filed on Nov. 24, 2020, provisional application No. 63/117,847, filed on Nov. 24, 2020, provisional application No. 63/115,127, filed on Nov. 18, 2020, provisional application No. 63/082,145, filed on Sep. 23, 2020, provisional application No. 63/080,887, filed on Sep. 21, 2020, provisional application No. 63/069,598, filed on Aug. 24, 2020, provisional application No. 63/067,033, filed on Aug. 18, 2020, provisional application No. 63/064,157, filed on Aug. 11, 2020, provisional application No. 63/059,975, filed on Aug. 1, 2020, provisional application No. 63/053,691, filed on Jul. 19, 2020, provisional application No. 63/036,445, filed on Jun. 9, 2020, provisional application No. 63/022,146, filed on May 8, 2020, provisional application No. 63/016,048, filed on Apr. 27, 2020, provisional application No. 63/016,241, filed on Apr. 27, 2020, provisional application No. 63/009,960, filed on Apr. 14, 2020, provisional application No. 63/010,010, filed on Apr. 14, 2020, provisional application No. 62/991,504, filed on Mar. 18, 2020, provisional application No. 62/988,328, filed on Mar. 11, 2020.

(51) Int. Cl.
*A61K 39/00* (2006.01)
*A61K 39/39* (2006.01)
*A61P 31/14* (2006.01)
*C12N 15/86* (2006.01)

(52) U.S. Cl.
CPC .............. *A61K 2039/545* (2013.01); *A61K 2039/55505* (2013.01); *A61P 31/14* (2018.01); *C07K 2319/06* (2013.01); *C12N 15/86* (2013.01); *C12N 2710/10343* (2013.01); *C12N 2770/20022* (2013.01); *C12N 2770/20034* (2013.01)

(56) References Cited

U.S. PATENT DOCUMENTS

| | | |
|---|---|---|
| 7,618,817 B2 | 11/2009 | Campbell |
| 7,750,123 B2 | 7/2010 | Marasco et al. |
| 8,034,332 B2 | 10/2011 | Klingemann |
| 8,313,943 B2 | 11/2012 | Campbell |
| 9,150,636 B2 | 10/2015 | Campbell |
| 9,181,322 B2 | 11/2015 | Campbell |
| 10,695,417 B2 | 6/2020 | Jones et al. |
| 10,953,089 B1 | 3/2021 | Smith et al. |
| 11,104,916 B2 | 8/2021 | Jones et al. |
| 2004/0161388 A1 | 8/2004 | Liu et al. |
| 2005/0003548 A1 | 1/2005 | Korokhov et al. |
| 2006/0171962 A1 | 8/2006 | Enjuanes Sanchez et al. |
| 2007/0105193 A1 | 5/2007 | Vilalta et al. |
| 2010/0150923 A1 | 6/2010 | Jiang et al. |
| 2010/0196411 A1 | 8/2010 | Duke et al. |
| 2012/0076820 A1 | 3/2012 | Amara et al. |
| 2012/0107347 A1 | 5/2012 | Hodge et al. |
| 2012/0288502 A1 | 11/2012 | Diskin et al. |
| 2013/0123136 A1 | 5/2013 | Abassi et al. |
| 2016/0076053 A1 | 3/2016 | Jones et al. |
| 2016/0168591 A1 | 6/2016 | Brennan et al. |
| 2016/0223564 A1 | 8/2016 | Lee et al. |
| 2017/0224794 A1 | 8/2017 | Franzusoff et al. |
| 2017/0246276 A1 | 8/2017 | Palena et al. |
| 2018/0244756 A1 | 8/2018 | Graham et al. |
| 2018/0296663 A1 | 10/2018 | Hipp et al. |
| 2018/0306814 A1 | 10/2018 | Kulshrestha et al. |
| 2019/0307819 A1 | 10/2019 | Drew et al. |
| 2020/0054730 A1 | 2/2020 | Niazi |
| 2020/0164058 A1 | 5/2020 | Hashem |
| 2021/0283245 A1 | 9/2021 | Niazi et al. |
| 2021/0284713 A1 | 9/2021 | Niazi et al. |
| 2021/0284716 A1 | 9/2021 | Niazi et al. |
| 2021/0371822 A1 | 12/2021 | Chaudhary |
| 2022/0016234 A1 | 1/2022 | Rice et al. |

FOREIGN PATENT DOCUMENTS

| | | |
|---|---|---|
| CN | 102844329 A | 12/2012 |
| CN | 111249454 A | 6/2020 |
| CN | 111254155 A | 6/2020 |
| CN | 111330003 A | 6/2020 |
| CN | 111375055 A | 7/2020 |
| EP | 1508615 A1 | 2/2005 |
| JP | 2008505114 A | 2/2008 |
| JP | 2019521148 A | 7/2019 |
| JP | 2021167805 A | 10/2021 |
| KR | 101453923 B1 | 10/2014 |
| KR | 20220006125 A | 1/2022 |
| WO | 2003066820 A2 | 8/2003 |
| WO | 2005120565 A2 | 12/2005 |
| WO | 2006068663 A2 | 6/2006 |
| WO | 2006113214 A2 | 10/2006 |
| WO | 2009006479 A2 | 1/2009 |
| WO | 2011129468 A1 | 10/2011 |
| WO | 2012109404 A1 | 8/2012 |
| WO | 2014031178 A1 | 2/2014 |
| WO | 2016112188 A1 | 7/2016 |
| WO | 2016116398 A1 | 7/2016 |
| WO | 2018014008 A1 | 1/2018 |
| WO | 2018140456 A1 | 8/2018 |
| WO | 2018200389 A1 | 11/2018 |
| WO | 2019143606 A1 | 7/2019 |
| WO | 2020086745 A1 | 4/2020 |
| WO | 2020219974 A1 | 10/2020 |
| WO | 2021165448 A1 | 8/2021 |
| WO | 2021183665 A1 | 9/2021 |
| WO | 2021183717 A1 | 9/2021 |
| WO | 2021188599 A1 | 9/2021 |
| WO | 2021212021 A2 | 10/2021 |
| WO | 2021248853 A1 | 12/2021 |
| WO | 2021250467 A2 | 12/2021 |

(56) References Cited

FOREIGN PATENT DOCUMENTS

| WO | 2021254287 A1 | 12/2021 |
|---|---|---|
| WO | 2022132625 A1 | 6/2022 |

OTHER PUBLICATIONS

Hou, X., et al., Dec. 2021, Lipid nanoparticles for mRNA delivery, Nat. Rev. Mat. 6:1078-1094.*
Sharon D., and A. Kamen, 2018, Advancements in the design and scalable production of viral gene transfer vectors, Biotechnology and Bioengineering, 115:25-40.*
Abdelzaher, H. M., et al., 2021, RNA Vaccines against Infectious Diseases: Vital Progress with Room for Improvement, Vaccines 9: 1-23.*
Lei et al., "Yeast Surface-Displayed H5N1 Avian Influenza Vaccines", Hindawi publishing Corporation, 2016, pp. 1-12.
Kim et al., "Oral Immunization With Whole Yeast Producing Viral Capsid Antigen Provokes a Stronger Humoral Immune Response Than Purified Viral Capsid Antigen", Letters in Applied Microbiology, 2013, vol. 58, pp. 285-291.
Safdari et al., "Use of Single-Chain Antibody Derivatives for Targeted Drug Delivery", Molecular Medicine, 2016, vol. 22, pp. 258-270.
"Sorrento Develops STI-4398 (COVIDTRAPTm PROTEIN) for Potential Prevention and Treatment of SARS-COV-2 Coronavirus Disease (COVID-19)", Sorrento Therapeutics, 2020, 4 pages.
Levin et al. Fc fusion as a platform technology: potential for modulating immunogenicity. Trends Biotechnol. Jan. 2015;33(1):27-34.
Renegar et al. Role of IgA versus IgG in the Control of Influenza Viral Infection in the Murine Respiratory Tract. J Immunol. 2004; 173:1978-1986.
Raftery et al., "Chitosan for Gene Delivery and Orthopedic TissueEngineering Applications", Molecules, 2013, vol. 18, pp. 5611-5647.
Cunningham et al., "Effective Long-term Preservation of Biological Evidence", Bode Technology, 2014, 153 pages.
Roth et al., "Functionalized Calcium Carbonate Microparticles for the Delivery of Proteins", European Journal of Pharmaceutic,s and Biopharmaceutics, 2017, 38 pages.
Rogers et al., "Isolation of potent SARS-COV-2 neutralizing antibodies and protection from disease in a small animal model", Science, 2020, 12 pages.
Wec et al., "Broad sarbecovirus neutralizing antibodies define a key site of vulnerability on the SARSCOV-2 spike protein", Version 2. bioRxiv., 2020, 18 pages.
Yuan et al., "A highly conserved cryptic epitope in the receptor binding domains of SARS-COV-2 and SARS-COV", Science, 2020, vol. 368, pp. 1-4.
Glasgow et al., "Engineered ACE2 receptor traps potently neutralize SARS-COV-2", Pnas, 2020, 25 pages.
Rice et al., "A Next Generation Bivalent Human Ad5 COVID-19 Vaccine Delivering Both Spike and Nucleocapsid Antigens Elicits Th1 Dominant CD4+, CD8+ T-cell and Neutralizing Antibody Responses", BioRxiv, 2020, 36 pages.
UniProtKB - Q9BYF1 (ACE2 H U Man), Aug. 2, 2005.
See et al., "Comparative evaluation of two severe acute respiratory syndrome (SARS) vaccine candidates in mice challenged with SARS coronavirus", Journal of General Virology, 2006, vol. 87, pp. 641-650.
Sieling et al., "Th1 Dominant Nucleocapsid and Spike Antigen-Specific CD4+ and CD8+ Memory T CellRecall Induced by hAd5 S-Fusion + N-ETSD Infection of Autologous Dendritic Cells fromPatients Previously Infected with SARS- CoV-2", Medrxiv the preprint server for health sciences, 2020, 44 pages.
Gabitzsch et al., "Complete Protection of Nasal and Lung Airways Against SARS-COV-2 Challengeby Antibody Plus Th1 Dominant N- and S-Specific T-Cell Responses to SubcutaneousPrime and Thermally-Stable Oral Boost Bivalent hAd5 Vaccination in an NHP Study", Biorxiv the preprint server for biology, 2020, 31 pages.
Seif et al., "Yeast (Saccharomyces cerevisiae) Polarizes Both M-CSF- and GM-CSF-Differentiated Macrophages Toward an M1-Like Phenotype", Inflammation, 2016, 14 pages.
Biondo et al., "Recognition of yeast nucleic acids triggers a host-protective type I interferon response", Eur. J. Immunol., 2011, vol. 41, pp. 1969-1979.
International Search Report and Written Opinion received for PCT Application Serial No. PCT/1B2021/054887 dated Sep. 6, 2021, 13 pages.
Khodaei et al., "Covalent Immobilization of Protein A on Chitosan and Aldehyde Double-Branched Chitosan as Biocompatible Carriers for Immunoglobulin G (lgg) Purification", Journal of Chromatographic Science, 2018, pp. 1-8.
Bymes et al., "A SARS-COV-2 serological assay to determine the presence of blocking antibodies that compete for human ACE2 binding", medRxiv, 2020, 23 pages.
Wang et al., "A human monoclonal antibody blocking SARS-COV-2 infection", Nature Communications, 2020, vol. 11, No. 2251, pp. 1-6.
International Search Report and Written Opinion received for PCT Application Serial No. PCT/US2021/021737 dated Jun. 25, 2021, 11 pages.
Zhao et al., "Identification and characterization of dominant helper T-cell epitopes in the nucleocapsid protein of severe acute respiratory syndrome coronavirus", Journal of Virology, 2007, vol. 81, No. 11, pp. 6079-6088.
Gabitzsch et al., "Anti-tumor immunotherapy despite immunity to adenovirus using a novel adenoviral vector Ad5 [El-, E2b-]-CEA", Cancer Immunology Immunotherapy, 2010, vol. 59, pp. 1131-1135.
Fan et al., "The nucleocapsid protein of coronavirus infectious bronchitis virus: crystal structure of its N-terminal domain and multimerization properties", Structure, 2005, vol. 13, pp. 1859-1868.
International Search Report and Written Opinion received for PCT Application Serial No. PCT/US2021/021819 dated Jun. 21, 2021, 20 pages.
Oi-Wing et al.,"Substitution at Aspartic Acid 1128 in the SARSCoronavirus Spike Glycoprotein Mediates Escape from aS2 Domain-Targeting Neutralizing Monoclonal Antibody", Plos one, 2014, vol. 9, No. 7, pp. 1-11.
Pak et al., "Structural Insights into Immune Recognition of theSevere Acute Respiratory Syndrome Coronavirus SProtein Receptor Binding Domain", Journal of Molecular Biology, 2009, vol. 388, pp. 815-823.
Park et al., "Spike protein binding prediction with neutralizing antibodies of SARS-COV-2", bioRxiv , 2020, 22 pages.
Tripp et al., "Monoclonal antibodies to SARS-associated coronavirus (SARS-COV): Identification of neutralizing and antibodies reactive to S, N, M and E viral proteins", Journal of Virological Methods, 2005, vol. 128, pp. 21-28.
Zheng et al., "Monoclonal antibodies for the S2 subunit of spike of SARS-COV-1 cross-react with the newly-emerged SARS-COV-2", Eurosurveillance, 2020, vol. 25, No. 28, pp. 19-28.
Pietravalle et al., "Cleavage of membrane-bound CD40 ligand is not required for inducing B cell proliferation and differentiation", Eur. J. Immunol, vol. 26, 1996, pp. 725-728.
Tan, Y. W., et al., Amino acid residues critical for RNA-binding in the N-terminal domain of the nucleocapsid protein are essential determinants for the infectivity of coronavirus in cultured cells, Nucleic Acids Res. 34(17): 4816-4825.
Lin, H .- X., et al., 2008, Identification of residues in the receptor-binding domain (RBD) of the spike protein of human coronavirus NL63 that are critical for the RBD-ACE2 receptor interaction, J. Gen. Virol. 89:1015-1024.
Lu, Y., et al., 2008, Importance of SARS-COV spike protein Trp-rich region in viral infectivity, Biochem. Biophys. Res. Comm. 371: 356-360.
Guo, Y., et al., 2009, Identification of a new region of Sars-Cov S protein critical for viral entry, J. Mol. Biol. 394:600-605.
Bhatti, J. S., et al., Nov. 2020, Therapeutic Strategies in the Development of Anti-viral Drugs and Vaccines Against SARS-COV-2 Infection, Mol. Neurobiol., DOI: 10. 1007/s12035-020-02074-2, published online Aug. 18, 2020, pp. 1-22.
Rice et al., "Intranasal plus subcutaneous prime vaccination with a dual antigen COVID 19 vaccine elicits T cell and antibody responses in mice" Scientific Reports, (2021) 11:14917 p. 1-15.

(56) References Cited

OTHER PUBLICATIONS

Zhou, W., et al., 2023, Vaccines' New Era-RNA Vaccine, Viruses 15, 1760, pp. 1-19.
International Preliminary Report on Patentability received for PCT Application Serial No. PCT/IB2021/054887 dated Feb. 2, 2023, 06 pages.
International Preliminary Report on Patentability received for PCT Application Serial No. PCT/US2021/021737 dated Sep. 6, 2022, 06 pages.
Office Action received in Canada Patent Application Serial No. 3170513 dated Aug. 21, 2023, 05 pages.
Office Action received in Canada Patent Application Serial No. 3170513 dated Oct. 22, 2024, 03 pages.
Extended European Search Report received in European Patent Application Serial No. 21768699.7 dated Mar. 18, 2024, 15 pages.
Enjuanes, L. et al. (2008) Vaccines to prevent severe acute respiratory syndrome coronavirus-induced disease. Virus Research, vol. 133, No. 1, 45 - 62, ISSN: 0168-1702, Doi: 10.1016/J.VIRUSRES. 2007.01.021.
Shi, J. et al. (2015) Epitope-based vaccine target screening against highly pathogenic Mers- Cov: an in silico approach applied to emerging infectious diseases. Plos One, vol. 10, No. 12, e0144475, US Issn: 1932-6203, DOI: 10.1371/journal.pone.0144475.
Partial Supplementary European Search Report received in European Patent Application Serial No. 21846127.5 dated Aug. 2, 2024, 14 pages.
Bosnjak Berislav et al.: "Low serum neutralizing anti-SARS-COV-2 S antibody levels in mildly affected COVID-19 convalescent patients revealed by two different detection methods", Cellular & Molecular Immunology, vol. 18, No. 4, Nov. 2, 2020 (Nov. 2, 2020), pp. 936-944, XP037390037, Issn: 1672-7681, DOI:10.1038/S41423-020-00573-9.
Abe Kento T et al.: "A simple protein-based surrogate neutralization assay for SARS-COV-2", JCI Insight, vol. 5, No. 19, Oct. 2, 2020 (Oct. 2, 2020), XP055780531, ISSN: 2379-3708, DOI: 10.1172/jci.insight. 142362 Retrieved from the Internet: URL:https://www.ncbi.nlm.nih.gov/pmc/articles/PMC7566699/pdf/jciinsight-5-142362.pdf.
Edward P. Gniffke et al.: "Plasma from recovered COVID19 subjects inhibits spike protein binding to ACE2 in a microsphere-based inhibition assay.", MEDRXIV, Jun. 11, 2020 (Jun. 11, 2020), XP055769440, DOI: 10.1101/2020.06.09.20127050 Retrieved from the Internet: URL:https://www.medrxiv.org/content/10.1101/2020.06.09.20127050v1.full.pdf>.
Tan Chee Wah et al.: "A SARS-COV-2 surrogate virus neutralization test based on antibody-mediated blockage of ACE2-spike protein-protein interaction", Nature Biotechnology, Nature Publishing Group US, New York, vol. 38, No. 9, Jul. 23, 2020 (Jul. 23, 2020), pp. 1073-1078, XP037237853, ISSN: 1087-0156, DOI: 10.1038/ S41587-020-0631-Z [retrieved on Jul. 23, 2020].
Extended European Search Report received in European Patent Application Serial No. 21846127.5 dated Nov. 5, 2024, 16 pages.
Rosales-Mendoza Sergio et al.: "What Does Plant-Based Vaccine Technology Offer to the Fight against COVID-19?", Vaccines, vol. 8, No. 2, Apr. 14, 2020 (Apr. 14, 2020), p. 183, XP093151469, CH ISSN: 2076-393X, Doi: 10.3390/vaccines8020183.
Wang Ning et al.: "Aluminum Nanoparticles Acting as a Pulmonary Vaccine Adjuvant-Delivery System (VADS) Able to Safely Elicit Robust Systemic and Mucosal Immunity", Journal of Inorganic and Organometallic Polymers and Materials, Springer US, New York, vol. 30, No. 10, May 9, 2020 (May 9, 2020), pp. 4203-4217, XP037246387, ISSN: 1574-1443, Doi: 10.1007/S10904-020-01572-Z [retrieved on May 9, 2020].
First Examination Report received in Australia Patent Application Serial No. 2021236141 dated Apr. 9, 2024, 05 pages.
Notice of Acceptance for Patent Application received in Australia Patent Application Serial No. 2021236141 dated May 17, 2024, 03 pages.
First Examination Report received in Australia Patent Application Serial No. 2021312381 dated May 22, 2024, 04 pages.
Second Examination Report received in Australia Patent Application Serial No. 2021312381 dated Jun. 24, 2024, 05 pages.
Third Examination Report received in Australia Patent Application Serial No. 2021312381 dated Sep. 4, 2024, 03 pages.
Fourth Examination Report received in Australia Patent Application Serial No. 2021312381 dated Oct. 8, 2024, 08 pages.
Ali, Amanat, et al., Dynamics of the ACE2-SARS-COV-2/SARS-COV spike protein interface reveal unique mechanisms', 2020, Scientific reports, vol. 10(1), pages (2020), Article 14214.
Fukushi, Shuetsu., 'Competitive ELISA for the detection of serum antibodies specific for middle east respiratory syndrome coronavirus (MERS-COV)', 2020, Coronaviruses: Methods and Protocols, pp. 55-65.
Neumann MM , Volodkin D . Porous antibody-containing protein microparticles as novel carriers for ELISA. Analyst. Feb. 1, 20207;145(4): 1202-1206. doi: 10.1039/c9an01888c. PMID: 31859691.
Zhuang, Wei, et al. "Sensitive and portable electrochemical immunoassay for lipoprotein-associated phospholipase A 2 using BSA-doped $CaCO_3$ nanospheres to regulate pH readout." Analytical Methods 11.12 (2019): 1631-1638.
Peng J, Feng LN, Zhang K, Li XH, Jiang LP, Zhu JJ. Calcium carbonate-gold nanocluster hybrid spheres: synthesis and versatile application in immunoassays. Chemistry. Apr. 2, 20123;18(17):5261-8. doi: 10.1002/chem.201102876. Epub Mar. 1, 20125. PMID: 22422592.
Mou, Huihui et al. "Mutations from bat ACE2 orthologs markedly enhance ACE2-Fc neutralization of SARS-COV-2." bioRxiv : the preprint server for biology 2020.06.29.178459. Jun. 30, 2020, doi: 10.1101/2020.06.29.178459. Preprint.
Request for the Submission of an Opinion received in Korea Patent Application Serial No. 10-2023-7006003 dated Oct. 25, 2024, 11 pages. (including English Translation).
Seth J. zost et al., nature, (Jul. 15, 2020), vol. 584, and the pp. 443-449.
First Office Action received in China Patent Application Serial No. 202180020795.0 dated Jun. 19, 2024, 18 pages. (including English Translation).
Notice of Reasons for Refusal received in Japan Patent Application Serial No. 2022-554944 dated Dec. 26, 2023, 11 pages. (including English Translation).
Decision of Refusal received in Japan Patent Application Serial No. 2022-554944 dated Aug. 2, 2024, 06 pages. (including English Translation).
Notice of Reasons for Refusal received in Japan Patent Application Serial No. 2023-503132 dated Aug. 13, 2024, 13 pages. (including English Translation).
Decision to Grant a Patent received in Japan Patent Application Serial No. 2023-503132 dated Nov. 5, 2024, 05 pages. (including english translation).
Liniger et al., "Induction of neutralising antibodies and cellular immune responses against SARS coronavirus by recombinant measles virus", Vaccine, 2008, vol. 26, pp. 2164-2174.
Wu et al., "A new coronavirus associated with human respiratory disease in China", Nature, 2020, vol. 579, pp. 265-271.
Gen Bank MN908947.3, Severe acute respiratory syndrome coronavirus 2 isolate Wuhan-Hu-1, complete genome, Mar. 2020, 12 pages.
Nilvebrant, J., and J. Rockberg, 2018, An introduction to epitope mapping, Meth. Mol. Biol. 1785:1-10.
Sanchez-Trincado, J. L., et al., 2017, Fundamentals and methods for T- and B-cell epitope prediction, J. Immunol. Res. Article ID 2680160, pp. 1-14.
Lavarone, C., et al., 2017, Mechanism of action of mRNA-based vectors, Exp. Rev. Vaccines 16(9):871-881.
Robert-Guroff, M., 2007, Replicating and non-replicating viral vectors for vaccine development, Curr. Opin. Biotechnol. 18:546-556.
Office Action received for CN application No. 202180020795.0 dated Jan. 22, 2025, 09 pages (including english translation).
Chen et al., "Fusion protein linkers: property, design and functionality", Adv Drug Deliv Rev, vol. 65, No. 10, 32 pages.
Battle et al., "Soluble angiotensin-converting enzyme 2: a potential approach for coronavirus infection therapy?", Clinical Science, 2020, vol. 134, pp. 543-545.

(56) References Cited

OTHER PUBLICATIONS

Kruse Robert L., "Therapeutic strategies in an outbreak scenario to treat the novel coronavirus originating in Wuhan, China [version 2; peerreview: 2 approved]", F1000 Research, 2020, vol. 9, No. 7, 14 pages.
Lu et al., "Arg15-Lys17-Arg18 Turkey Ovomucoid Third Domain Inhibits Human Furin", The Journal of Biological Chemistry, 1993, vol. 268, No. 20, p. 14583-14585.
Coutard et al., "The spike glycoprotein of the new coronavirus 2019-nCOV contains a furin-like cleavage site absent in CoV of the same Glade", Antiviral Research, 2020, No. 176, 6 pages.
Yao et al., "Polyethyleneimine-coating enhances adenoviral transduction of mesenchymal stem cells", Biochemical and Biophysical Research Communications, 2014, vol. 447, No. 3, pp. 383-387.
Yin et al., "[Measurement of subsets of blood T lymphocyte in 93 patients with severe acute respiratory syndrome and its clinical significance]", Chinese Journal of Tuberculosis and Respiratory Diseases, 2003, vol. 26, No. 6, 1 page.
Lei et al., "Potent neutralization of 2019 novel coronavirus by recombinant ACE2-Ig", bioRxiv, 2020, 11 pages.
Amalfitano et al., "Production and Characterization of Improved Adenovirus Vectors with the El, E2b, and E3 Genes Deleted", Journal of Virology, 1998, vol. 72, No. 2, pp. 926-933.
Yan et al., "Structural basis for the recognition of the SARS-COV-2 by full-length human ACE2", Science, 2020, pp. 1-9.
Zhang et al."Angiotensin-converting enzyme 2(ACE2) as a SARS-COV-2 receptor: molecular mechanisms and potential therapeutic target", Intensive Care Med, 2020, 5 pages.
Zhonghua Yi Xue Za Zhi, "Dynamic Changes of T-lymphocytes and Immunoglobulins in Patients With Severe Acute Respiratory Syndrome", Natl Med J China, Jun. 25, 2003, vol. 83, No. 12, pp. 1014-1017.
"The Involvement of Natural Killer Cells in thePathogenesis of Severe Acute Respiratory Syndrome", National Research Project for SARS, Beijing Group, American Journal of Clinical Pathology, 2004, vol. 121, pp. 507-511.
Bergamaschi et al., "Intracellular Interaction of Interleukin-15 with Its Receptor alpha during Production Leads to Mutual Stabilization andIncreased Bioactivity", The Journal of Biological Chemistry, 2008, vol. 283, No. 7, pp. 4189-4199.
Bessard et al., "High Antitumor Activity of RLI, an interleukin-15 (IL-15)-IL-15 Receptor Alpha Fusion Protein, in Metastatic Melanoma and Colorectal Cancer", Mal Cancer Ther, 2009, vol. 8, No. 9, pp. 2736-2745.
Chan et al., "A familial cluster of pneumonia associated with the 2019 novel coronavirus indicating person-to-person transmission: a study of a family cluster", lancet, vol. 395, pp. 514-523.
Clay et al., "Severe Acute Respiratory Syndrome-Coronavirus Infection in Aged Nonhuman Primates Is Associated With Modulated Pulmonary and Systemic Immune Responses", Immunity & Ageing, 2014, vol. 11, No. 4, pp. 1-16.
Dubois et al., "Preassociation of IL-15 With IL-15R alpha-IgG1-Fc Enhances Its Activity on Proliferation of NK and CD8 +/CD44high T cells and its antitumor action", The Journal of Immunology, 2008, vol. 180, pp. 2099-2106.
Duitman et al., "How a Cytokine Is Chaperoned Through the Secretory Pathway by Complexing With Its Own Receptor: Lessons From interleukin-15 (IL-15)/IL-15 Receptor Alpha", molecular and Cellular Biology, Aug. 2008, vol. 28, No. 15, pp. 4851-4861.
Ellis-Connell et al., "ALT-803 Transiently Reduces Simian Immunodeficiency Virus Replication in the Absence of Akritiretroviral Treatment", Journal of Virology, 2018, vol. 92, No. 3, pp. 1-21.
Epardaud et al., "Interleukin-15/interleukin-15R Alpha Complexes Promote Destruction of Established Tumors by Reviving Tumor-Resident CD8+ T Cells", Cancer Research, 2008, vol. 68, No. 8, pp. 2972-2983.
Fehniger et al., "Interleukin-2 and interleukin-15: Immunotherapy for Cancer", Cytokine Growth Factor Rev, 2002, vol. 13, No. 2, pp. 169-183.

Furuya et al., "Effectiveness of two different dose administration regimens of an IL-15 superagonist complex (ALT-803) in an orthotopic bladder cancer mouse model", Journal of translational Medicine, 2019, vol. 17, No. 29, pp. 1-12.
Gomes-Giacoia et al., "Intravesical ALT-803 and BCG Treatment Reduces Tumor Burden in a Carcinogen Induced Bladder Cancer Rat Model; A Role for Cytokine Production and NK Cell Expansion", Plos One, 2014, vol. 9, No. 6, pp. 1-11.
Guan et al., "Clinical Characteristics of Coronavirus Disease 2019 in China", The New England Journal of Medicine, 2020, 13, pages.
Guilliams et al., "The function of Fc gamma receptors in dendritic cells and macrophages", Nature Reviews Immunology, 2014, vol. 14, pp. 94-108.
Huang et al., "Clinical features of patients infected with 2019 novel coronavirus in Wuhan, China", Lancet, 2020, vol. 395, No. 10223, pp. 1-10.
Huntington et al., "IL-15 transpresentation promotes both human T-cell reconstitution and T-cell-dependent antibody responses in vivo", Proceedings of the National Academy of Sciences, 2011, vol. 108, No. 15, pp. 6217-6222.
Jones et al., "A Subset of Latency-Reversing Agents Expose HIV-Infected Resting CD4+ T-Cells to Recognition by Cytotoxic T-Lymphocytes", Plos Pathogens, 2016, pp. 1-25.
Kim et al., "IL-15 superagonist/IL-15RaSushi-Fc Fusion Complex (IL-15SA/IL-15RaSu-Fc; ALT-803) Markedly Enhances Specific Subpopulations of NK and Memory CD8+ T Cells, and Mediates Potent Anti-Tumor Activity Against Murine Breast and Colon Carcinomas", Oncotarget, 2016, vol. 7, No. 13, 16130-16145.
Law et al., "Chemokine Up-Regulation in SARS-coronavirus-infected, Monocyte-Derived Human Dendritic Cells", Blood, 2005, vol. 106, No. 7, pp. 2366-2374.
Mah et al., "Glycolytic Requirement for NK Cell Cytotoxicity and Cytomegalovirus Control", JCI Insight, 2017, vol. 2, No. 23, 18 pages.
Margolin et al., "Phase I Trial of ALT-803, A Novel Recombinant IL15 Complex, in Patients With Advanced Solid Tumors", Clinical Cancer Research, 2018, vol. 24, No. 22, pp. 555-5561.
Mathias et al., "Therapeutic Administration of IL-15 Superagonist Complex ALT-803 Leads to Long-Term Survival and Durable Antitumor Immune Response in a Murine Glioblastoma Model", International Journal of Cancer, 2016, vol. 138, pp. 187-194.
McBrien et al., "Robust and persistent reactivation of SIV and HIV by N-803 and depletion of CD8+ cells", Nature, Feb. 6, 2020, vol. 578, pp. 154-159.
Mortier et al., "Soluble Interleukin-15 Receptor a (IL-15Ra)-sushi as a Selective and Potent Agonist of IL-15 Action through IL-15R(3/y Hyperagonist IL-15-IL-15Ra Fusion Proteins", Journal of Biological Chemistry, 2006, vol. 281, No. 3, pp. 1612-1619.
Rhode et al., "Comparison of the Superagonist Complex, ALT-803, to IL15 as Cancer Immunotherapeutics in Animal Models", Cancer Immunol Res, 2016, vol. 4, pp. 1-12.
Romee et al., "First-in-human Phase 1 Clinical Study of the IL-15 Superagonist Complex ALT-803 to Treat Relapse After Transplantation", Blood, 2018, vol. 131, No. 23, pp. 2515-2527.
Rosario et al., "The IL-15-Based ALT-803 Complex Enhances FcyRIIIa-Triggered NK Cell Responses and In Vivo Clearance of B Cell Lymphomas", Clinical Cancer Research, 2016, vol. 22, No. 3, pp. 596-608.
Seay et al., "In Vivo Activation of Human NK Cells by Treatment With an Interleukin-15 Superagonist Potently Inhibits Acute In Vivo HIV-1 Infection in Humanized Mice", Journal of Virology, 2015, 46 pages.
Spiegel et al., "Inhibition of Beta Interferon Induction by Severe Acute Respiratory Syndrome Coronavirus Suggests a Two-Step Model for Activation of Interferon Regulatory Factor 3", Journal of Virology, 2005, vol. 79, No. 4, pp. 2079-2086.
Waldmann Thomas A., "The biology of interleukin-2 and interleukin-15: implications for cancer therapy and vaccine design", Nature Reviews Immunology vol. 2006, vol. 6, pp. 595-601.
Wang et al., "IgG Fc engineering to modulate antibody effector functions", 2017, 11 pages.

(56) References Cited

OTHER PUBLICATIONS

Webb et al., "The human IL-15 superagonist ALT-803 directs SIV-specific CD8+ T cells into B-cell follicles", Blood Advances, 2018, vol. 2, No. 2, pp. 76-84.

Weiss et al., "Coronavirus Pathogenesis and the Emerging Pathogen Severe Acute Respiratory Syndrome Coronavirus", Microbiology and molecular Biology Reviews, 2005, vol. 69, No. 4, 31 pages.

Wrangle et al., "ALT-803, an IL-15 Superagonist, in Combination With Nivolumab in Patients With Metastatic Non- Small Cell Lung Cancer: A Non-Randomised, Open-Label, Phase 1 b Trial", Lancet Oncol, 2018, vol. 19, No. 5, pp. 1-11.

Xu et al., "Efficacy and Mechanism-Of-Action of a Novel Superagonist interleukin-15: Interleukin-15 Receptor aSu/Fc Fusion Complex in Syngeneic Murine Models of Multiple Myeloma", Cancer Research, 2013, vol. 73, No. 10, pp. 3075-3086.

Zhu et al. "Novel Human Interleukin-15 Agonists", The Journal of Immunology, 2009, vol. 183, pp. 3598-3607.

Zhu et al., "MHC Class I-Related Neonatal Fc Receptor for IgG Is Functionally Expressed in Monocytes, Intestinal Macrophages, and Dendritic Cells", The Journal of immunology, 2001, vol. 166, pp. 3266-3276.

Saiki et al., "Induction of Humoral Responses Specific for Paraneoplastic Cerebellar Degeneration-Associated Antigen by Whole Recombinant Yeast Immunization", Journal of Autoimmunity, 2005, vol. 24, pp. 203-208.

* cited by examiner

Fig. 6

Anti-Spike Antibodies

Anti-Nucleocapsid Antibodies

ELISpot a. IFN-γ b. IL-4

SEQUENCE LISTING

```
Sequence total quantity: 13
SEQ ID NO: 1           moltype = AA  length = 473
FEATURE                Location/Qualifiers
REGION                 1..473
                       note = SARS-COV2 Nucleocapsid protein
source                 1..473
                       mol_type = protein
                       organism = synthetic construct
SEQUENCE: 1
MSDNGPQNQR NAPRITFGGP SDSTGSNQNG ERSGARSKQR RPQGLPNNTA SWFTALTQHG   60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTGAIKLD DKDPNFKDQV ILLNKHIDAY  360
```

```
KTFPPTEPKK DKKKKADETQ ALPQRQKKQQ TVTLLPAADL DDFSKQLQQS MSSADSTQAG    420
PGPGNLVPMV ATVGPGPGML IPIAVGGALA GLVLIVLIAY LIGKKHCSYQ DIL           473

SEQ ID NO: 2                moltype = AA  length = 516
FEATURE                     Location/Qualifiers
REGION                      1..516
                            note = SARS-CoV2 Nucleocapsid protein tagged with ETSD
                            signal
source                      1..516
                            mol_type = protein
                            organism = synthetic construct
SEQUENCE: 2
MLLLPFQLLA VLFPGGNSED YKDDDDKGGG SGGGSGGGSG GGSMSDNGPQ NQRNAPRITF    60
GGPSDSTGSN QNGERSGARS KQRRPQGLPN NTASWFTALT QHGKEDLKFP RGQGVPINTN   120
SSPDDQIGYY RRATRRIRGG DGKMKDLSPR WYFYYLGTGP EAGLPYGANK DGIIWVATEG   180
ALNTPKDHIG TRNPANNAAI VLQLPQGTTL PKGFYAEGSR GGSQASSRSS SRSRNSSRNS   240
TPGSSRGTSP ARMAGNGGDA ALALLLLDRL NQLESKMSGK GQQQQGQTVT KKSAAEASKK   300
PRQKRTATKA YNVTQAFGRR GPEQTQGNFG DQELIRQGTD YKHWPQIAQF APSASAFFGM   360
SRIGMEVTPS GTWLTYTGAI KLDDKDPNFK DQVILLNKHI DAYKTFPPTE PKKDKKKKAD   420
ETQALPQRQK KQQTVLLPA ADLDDFSKQL QQSMSSADST QAGPGPGNLV PMVATVGPGP   480
GMLIPIAVGG ALAGLVLIVL IAYLIGKKHC SYQDIL                             516

SEQ ID NO: 3                moltype = DNA  length = 1551
FEATURE                     Location/Qualifiers
misc_feature                1..1551
                            note = N-ETSD cargo in AdV. Seq I.(2)
source                      1..1551
                            mol_type = other DNA
                            organism = synthetic construct
SEQUENCE: 3
atgctgctgc tgcccttcca gttgctggct gtcctctttc ccggcggcaa ctccgaggat    60
tacaaggacg acgacgacaa gggtggaggc tctggaggtg gctctggtgg aggttccggt   120
ggcggatcta tgagcgacaa cggtccccag aatcaaagaa atgcgcccag aattacattc   180
ggcggccctt ctgatagcac tggtccaaat caaaacgggg agagaagcgg agccaggtcc   240
aaacagcgga gaccccaagg cctgcctaat aacaccgctt cctggttcac agctctgacg   300
caaacacggca aggaggatct gaagtttcca cggggtcagg gcgtcccgat aaacacgaac   360
tctagcccag atgaccaaat agggtactac agaagagcga caaggcggat cagaggaggc   420
gatggaaaaa tgaaggatct gtcccctagg tggtatttct attacctggg cacaggccct   480
gaagctgggt tgccttacgg cgcaaacaaa gatggaatta tatggtgtgc caccgaggtgg   540
gcgttgaaca cccccaaagga tcacatcgga acgaggaatc ccgccaacaa tgctgctata   600
gtgctccaac tgccacaggg aacaaccctg cctaagggct tctacgccga ggggagccgc   660
ggtggcagcc aggccagctc cagaagttcc tcccgcagcc ggaacagctc tagaaacagc   720
actcccggca gctccagagg gacaagccca gccagaatgg cgggcaacgg   780
gccctcgcac ttctgttgct tgatcggctc aatcaactcg aaagcaaaat gtccggcaag   840
ggacaacaac agcaaggaca gaccgttaca aaaaaaagcg ccgccgaggc tagcaagaag   900
cccagacaga agcgaaccgc aacaaggcc tataatgtaa cacaagcctt tggaaggcgg   960
ggacccgaac agacccaggg aaattttggc gaccaggaac tgatccggca agggacagac  1020
tataaacatt ggccacagat agcgcaattt gctccctccg cctccgcctt ctttggcatg  1080
tcaagaatag gcatggaagt aactccttct ggaacctggc tgacgtacac tggggcaatc  1140
aagttggatg ataaggaccc taatttcaag gaccaagtta ttttgctcaa caagcatata  1200
gacgcctaca agactttccc gcctaccgaa cctaaaaagg ataagaagaa gaaagcagac  1260
gagacccagg ccctgcctca acggcaaaag aagcagcaaa ctgtgacact cctgcccgcc  1320
gctgacttgg atgattttc aaaaacagct caacagagta tgagcagcgc cgatagcacc  1380
caagctggac cgggtccggg caacctggtg ccgatggtgg cgaccgtggg tccaggaccg  1440
ggtatgctga tccccatcgc cgtgggcggg gccctggccg gcctcgtgct gatcgtcctt  1500
atcgcctacc tcatcggcaa gaagcactgc tcatatcagg acatcctgtg a            1551

SEQ ID NO: 4                moltype = AA  length = 1282
FEATURE                     Location/Qualifiers
REGION                      1..1282
                            note = spike protein
source                      1..1282
                            mol_type = protein
                            organism = synthetic construct
SEQUENCE: 4
MFVFLVLLPL VSSYPYDVPD YAQCVNLTTR TQLPPAYTNS FTRGVYYPDK VFRSSVLHST    60
QDLFLPFFSN VTWFHAIHVS GTNGTKRFDN PVLPFNDGVY FASTEKSNII RGWIFGTTLD   120
SKTQSLLIVN NATNVVIKVC EFQFCNDPFL GVYYHKNNKS WMESEFRVYS SANNCTFEYV   180
SQPFLMDLEG KQGNFKNLRE FVFKNIDGYF KIYSKHTPIN LVRDLPQGFS ALEPLVDLPI   240
GINITRFQTL LALHRSYLTP GDSSSGWTAG AAAYYVGYLQ PRTFLLKYNE NGTITDAVDC   300
ALDPLSETKC TLKSFTVEKG IYQTSNFRVQ PTESIVRFPN ITNLCPFGEV FNATRFASVY   360
AWNRKRISNC VADYSVLYNS ASFSTFKCYG VSPTKLNDLC FTNVYADSFV IRGDEVRQIA   420
PGQTGKIADY NYKLPDDFTG CVIAWNSNNL DSKVGGNYNY LYRLFRKSNL KPFERDISTE   480
IYQAGSTPCN GVEGFNCYFP LQSYGFQPTN GVGYQPYRVV VLSFELLHAP ATVCGPKKST   540
NLVKNKCVNF NFNGLTGTGV LTESNKKFLP FQQFGRDIAD TTDAVRDPQT LEILDITPCS   600
FGGVSVITPG TNTSNQVAVL YQDVNCTEVP VAIHADQLTP TWRVYSTGSN VFQTRAGCLI   660
GAEHVNNSYE CDIPIGAGIC ASYQTQTNSP RRARSVASQS IIAYTMSLGA ENSVAYSNNS   720
IAIPTNFTIS VTTEILPVSM TKTSVDCTMY ICGDSTECSN LLLQYGSFCT QLNRALTGIA   780
VEQDKNTQEV FAQVKQIYKT PPIKDFGGFN FSQILPDPSK PSKRSFIEDL LFNKVTLADA   840
```

```
GFIKQYGDCL GDIAARDLIC AQKFNGLTVL PPLLTDEMIA QYTSALLAGT ITSGWTFGAG    900
AALQIPFAMQ MAYRFNGIGV TQNVLYENQK LIANQFNSAI GKIQDSLSST ASALGKLQDV    960
VNQNAQALNT LVKQLSSNFG AISSVLNDIL SRLDKVEAEV QIDRLITGRL QSLQTYVTQQ   1020
LIRAAEIRAS ANLAATKMSE CVLGQSKRVD FCGKGYHLMS FPQSAPHGVV FLHVTYVPAQ   1080
EKNFTTAPAI CHDGKAHFPR EGVFVSNGTH WFVTQRNFYE PQIITTDNTF VSGNCDVVIG   1140
IVNNTVYDPL QPELDSFKEE LDKYFKNHTS PDVDLGDISG INASVVNIQK EIDRLNEVAK   1200
NLNESLIDLQ ELGKYEQYIK WPWYIWLGFI AGLIAIVMVT IMLCCMTSCC SCLKGCCSCG   1260
SCCKFDEDDS EPVLKGVKLH YT                                            1282

SEQ ID NO: 5           moltype = DNA  length = 3849
FEATURE                Location/Qualifiers
misc_feature           1..3849
                       note = S-HA cargo in AdV. Seq I.(2)
source                 1..3849
                       mol_type = other DNA
                       organism = synthetic construct
SEQUENCE: 5
atgttcgttt ttctcgttct cctcccgctt gtgagcagct atccgtatga tgtgccggat     60
tatgcgcaat gtgtcaacct caccacaagg acacagctcc ctcccgcata tcgaatagc    120
tttaccagag gcgtatacta tcctgataag gtctttagga gctcagtact gcatagcact    180
caggatctct tcctgccgtt cttcagtaat gttacttggt ttcacgccat tcatgttccc    240
gggaccaatg gcaccaaacg gttcgataat ccagtgcttc cctcaacga tggggtgtac    300
tttgccagca ctgaaaaatc taatataatt cggggatgga ttttcggaac cacactcgat    360
tccaagactc agtccctctt gatcgttaac aacgctacta atgttgtcat taaggtgtgt    420
gagtttcagt tctgcaacga cccttttcctg ggtgtctact accataaaaa taacaagagc    480
tggatggagt ccgaatttcg cgtctactca agcgccataa attgcacttt tgagtatgtg    540
tcccagccct ttttgatgga tctggaggga aagcagggca atttcaaaaa tctgagagaa    600
ttcgttttta agaatataga tggatacttc aaaatctaca gcaaacacac acccataaat    660
cttgtgcgcg atcttcccca gggcttcagc gcgttggaac cccttgttga cttgccccata    720
ggcatcaaca ttaccaggtt ccaaaacgctg tccgccctcc accgcagcta cttgacaccc    780
ggggattcca gctccggatg gaccgccggc gccgcagcgt attatgtggg gtacctgcaa    840
cccaggacat ttttgctcaa gtacaatgag aatgggacca tcacagatgc ggtagactgt    900
gcactggatc cactcagcga aactaaatgt accctgaaaa gctttaccgt ggagaaagga    960
atctaccaaa ccagcaactt cagggtccaga ccccactgaat ccatcgttag atttccaaat   1020
ataactaatt tgtgtccatt tggagaggtg ttcaatgcta caaggttcgc gtctgtatac   1080
gcttggaacc ggaagcgcat ctcaaattgc gtggctgatt atagcgttct ttacaacagc   1140
gcttcctttt ccacgttcaa gtgctatggt gtatccccga caaagctgaa tgacttgtgc   1200
ttcaccaatg tgtatgcgga ttcttttcgtt attcgaggcg atgaagtcag acaaattgcg   1260
cctggccaga ccggaaagat tgccgactac aactataaac tgccggacga cttttactgt   1320
tgcgtgatcg cttggaacag caataatctt gatagtaaag ttggaggaaa ctacaattac   1380
ctctatagac tgttcagaaa gagcaacttg aagccattcg aacgggatat ctctacggag   1440
atctatcaag ctggcagcac ccctgcaatg gtgtgtaagt gctttaattg ttatttttcct   1500
ttgcagagct atggcttcca acctaccaac ggagtgggct accagcccta cagagtggtg   1560
gtgctcagct ttgaactgct gcatgccccg gccacagttt gcgggcccaa aaaaagcacg   1620
aatctggtta agaacaaatg cgtcaacttc aatttaatg ggttgacagg tacaggcgta   1680
ctgaccgaat ccaacaaaaa gttcctgcct tttcagcagt tcgggagaga tatcgccgac   1740
actacagacg ccgtcaggga tccccaaaca ctcgaaattc tggacatcac accttgttcc   1800
ttcggcgggg tatctgtgat tactccgggc acaaatacca gtaaccaggt agcggtgctt   1860
taccaggatg tcaactgtac ggaagtacct gtcgctattc atgcggatca actcactcct   1920
acctggagag tttattccac tgggtccaac gtgtttcaga cccgagccgg ctgcttgatt   1980
ggcgcgaac atgttaacaa ctcctacgaa tgtgacatcc ctatcggagc tggcatctgt   2040
gcttcctatc aaacgcaaac gaacagccca cggcgggcca gatccgtagc ctctcaaagc   2100
atcatcgctt atactatgtc cttggggggct gaaaacagcg ttgcctattc caacaatagc   2160
atcgctatcc ctaccaactt taccatttcc gtgaccacag aaatactgcc ggtgagcatg   2220
acaaagactt ctgtggactg taccatgtat atatgcggag atagcacaga gtgttctaat   2280
ttgctgctgc agtacggcag cttttgtacc caactcaaca gagcacttac agggattgcc   2340
gtcgagcagg ataaaaacac ccaggaggtt tcgcccagg ttaagcagat ctacaagacc   2400
ccaccaatca aggatttcgg cggcttcaat ttttcccaga tactgcccga tccttccaag   2460
ccatccaaaa ggagctttat agaggatctg tgttcaaca aggtgactct ggccgacgct   2520
ggctttcatc agcaatatgg cgattgcctg ggggatattg ccgctaggga ccttatctgc   2580
gctcaaaaat tcaacggtct taccgttctc ccgcccctgc tcaccgacga tgatagcc   2640
cagtacacga gcgcactttt ggccggcacg ataaccagcg ctggacatt cggtgccggg   2700
gccgctcttc aaatcccctt tgccatgcag atggcctaca gatttaatgg ataggcgtg   2760
acacaaaatg tcttgtatga aaatcagaaa ctgattgcaa accagtttaa tagcgctatt   2820
ggcaagatcc aagatagcct ttcctccacc gcatccgctc tgggaaagtt gcaagacgtc   2880
gtgaatcaaa acgcccaagc tctgaatacc ctcgtgaagc agcttagctc aactttggc   2940
gcgatatcct ccgtgctgaa cgatatcctg tccagattgg acaaggtcga ggcagaagtc   3000
cagatcgata gattgataac cggcagactc cagtctctgc agacatatgt gactcagcag   3060
ttgataagag cggccgaaat acgagcgtct gcaaatctcg cagcaacgaa aatgtcagaa   3120
tgtgtattgg ggcaaagtaa aagagtagat ttcgtggaa agggttacca tctgatgtca   3180
ttccccagt ctgcaccaca tggagtagtt ttttgcatg tgacttatgt gcctgcccag   3240
gagaaaaatt tcaccactgc acctgcgatc tgtcatgacg gcaaggcaca tttccctaga   3300
gaaggcgtct tcgtatcaaa tggaacacac tggtttgtaa cccaaaggaa cttttacgag   3360
ccccaaatta taactaccga caacaccttc gtaagcggaa actgcgacgt cgttataggg   3420
atagtcaata atacggtcta tgaccctctt cagccggaac tggactcctt taaagaagaa   3480
ctggataagt acttcaagaa ccatacgtct ccggatgtgg atctcggaga tataagtgga   3540
atcaacgcaa gcgtagtaaa cattcagaag gagatagacc gactcaatga ggttgctaaa   3600
aacctgaacg aaagcttgat agacttgcag gagctgggta agtacgaaca gtacattaag   3660
tggccatggt atatctggtt gggcttcata gcaggactca tagctatcgt catggtgaca   3720
```

```
ataatgcttt gttgtatgac cagctgttgt tcttgtctga aaggctgctg cagctgtggc   3780
agctgttgta aatttgacga agatgattcc gagcctgtgc ttaagggcgt aaaactccac   3840
tatacatga                                                           3849

SEQ ID NO: 6           moltype = AA  length = 1298
FEATURE                Location/Qualifiers
REGION                 1..1298
                       note = Spike fusion construct prt
source                 1..1298
                       mol_type = protein
                       organism = synthetic construct
SEQUENCE: 6
MFVFLVLLPL VSSYPYDVPD YAGGGSGGGS GGGSGGGSQC VNLTTRTQLP PAYTNSFTRG     60
VYYPDKVFRS SVLHSTQDLF LPFFSNVTWF HAIHVSGTNG TKRFDNPVLP FNDGVYFAST    120
EKSNIIRGWI FGTTLDSKTQ SLLIVNNATN VVIKVCEFQF CNDPFLGVYY HKNNKSWMES    180
EFRVYSSANN CTFEYVSQPF LMDLEGKQGN FKNLREFVFK NIDGYFKIYS KHTPINLVRD    240
LPQGFSALEP LVDLPIGINI TRFQTLLALH RSYLTPGDSS SGWTAGAAAY YVGYLQPRTF    300
LLKYNENGTI TDAVDCALDP LSETKCTLKS FTVEKGIYQT SNFRVQPTES IVRFPNITNL    360
CPFGEVFNAT RFASVYAWNR KRISNCVADY SVLYNSASFS TFKCYGVSPT KLNDLCFTNV    420
YADSFVIRGD EVRQIAPGQT GKIADYNYKL PDDFTGCVIA WNSNNLDSKV GGNYNYLYRL    480
FRKSNLKPFE RDISTEIYQA GSTPCNGVEG FNCYFPLQSY GFQPTNGVGY QPYRVVVLSF    540
ELLHAPATVC GPKKSTNLVK NKCVNFNFNG LTGTGVLTES NKKFLPFQQF GRDIADTTDA    600
VRDPQTLEIL DITPCSFGGV SVITPGTNTS NQVAVLYQDV NCTEVPVAIH ADQLTPTWRV    660
YSTGSNVFQT RAGCLIGAEH VNNSYECDIP IGAGICASYQ TQTNSPRRAR SVASQSIIAY    720
TMSLGAENSV AYSNNSIAIP TNFTISVTTE ILPVSMTKTS VDCTMYICGD STECSNLLLQ    780
YGSFCTQLNR ALTGIAVEQD KNTQEVFAQV KQIYKTPPIK DFGGFNFSQI LPDPSKPSKR    840
SFIEDLLFNK VTLADAGFIK QYGDCLGDIA ARDLICAQKF NGLTVLPPLL TDEMIAQYTS    900
ALLAGTITSG WTFGAGAALQ IPFAMQMAYR FNGIGVTQNV LYENQKLIAN QFNSAIGKIQ    960
DSLSSTASAL GKLQDVVNQN AQALNTLVKQ LSSNFGAISS VLNDILSRLD KVEAEVQIDR   1020
LITGRLQSLQ TYVTQQLIRA AEIRASANLA ATKMSECVLG QSKRVDFCGK GYHLMSFPQS   1080
APHGVVFLHV TYVPAQEKNF TTAPAICHDG KAHFPREGVF VSNGTHWFVT QRNFYEPQII   1140
TTDNTFVSGN CDVVIGIVNN TVYDPLQPEL DSFKEELDKY FKNHTSPDVD LGDISGINAS   1200
VVNIQKEIDR LNEVAKNLNE SLIDLQELGK YEQYIKWPWY IWLGFIAGLI AIVMVTIMLC   1260
CMTSCCSCLK GCCSCGSCCK FDEDDSEPVL KGVKLHYT                           1298

SEQ ID NO: 7           moltype = DNA  length = 3897
FEATURE                Location/Qualifiers
misc_feature           1..3897
                       note = spike fusion construct dna
source                 1..3897
                       mol_type = other DNA
                       organism = synthetic construct
SEQUENCE: 7
atgttcgttt ttctcgttct cctcccgctt gtgagcagct atccgtatga tgtgccggat     60
tatgcgggtg gaggctctgg aggtggctct ggtggaggtt ccggtggcgg atctcaatgt    120
gtcaacctca ccacaaggac acagctccct ccgcatata cgaatagctt taccagaggc     180
gtatactatc ctgataaggt cttaggagc tcagtactgc atagcactca ggatctcttc     240
ctgccgttct tcagtaatgt tacttggttt cacgccattc atgtttccgg gaccaatggc    300
accaaaacgg tcgataatcc agtgcttccc ttcaacgatg gggtgtactt tgccagcact    360
gaaaatctca atataattcg gggatggatt ttcggaacca cactcgattc caagactcag    420
tccctcttga tcgttaacaa cgctactaat gttgtcatta aggtgtgtga gtttcagttc    480
tgcaacgacc cttttcctgg gtgtctactac cataaaaata acaagagctg gatggagtcc    540
gaatttcgcg tctactcaag cgccaataat gcacttttg agtatgtgtc ccagcccttt     600
ttgatggatc tggagggaaa gcagggcaat tcaaaaatc tgagagaatt cgttttttaag    660
aatatagatg gatacttcaa aatctacagc aaacacacca ccataaatct tgtcgcgat    720
cttccccagg gcttcagcgc gttggaaccc cttgttgact tgcccatagg catcaacatt    780
accaggttcc aaacgctgct cgccctccac cgcagctact tgacacccgg ggattccagc    840
tccgatgga ccgccggcgc cgcagcgtat tatgtgggggt acctgcaacc caggacatt     900
ttgctcaagt acaatgagaa tgggaccatc acagatgcgg tagactgtgc actgagtcca    960
ctcagcgaaa ctaaatgtac cctgaaaagc tttaccgtgg agaaagggaat ctaccaaacc   1020
agcaacttca gggtccagcc cactgaatcc atcgttagat tccaaatat aactaatttg    1080
tgtccatttg gagaggtgtt caatgctaca aggttcgcgt ctgtatacgc ttggaaccgg    1140
aagcgcatct caaattgcgt ggctgattat agcgttcttt acaacagcgc ttcctttttcc   1200
acgttcaagt gctatggtgt atccccgaca aagctgaatg acttgtgctt caccaatgtg   1260
tatgcggatt ctttcgttat tcgaggcgat gaagtcagac aaattgcgcc tggccagacc   1320
ggaaagattg ccgactacaa ctataaactg ccggacgact ttactggttg cgtgatcgct   1380
tggaacagca ataatcttga tagtaaagtt ggaggaaact acaattacct ctatagactg   1440
ttcagaaaga gcaacttgaa gccattcgaa cgggatatct ctaccgagat ctatcaagct   1500
ggcagcaccc cctgcaatgg tgtggaaggc tttaattgtt attttccttt gcagagctat   1560
ggcttccaac ctaccaacgg agtgggctac cagccctaca gagtggtggt gctcagcttt   1620
gaactgctgc atgccccggc cacagtttgc gggcccaaaa aaagcacgaa tctggttaag   1680
aacaaatgcg tcaacttcaa tttaatggg ttgacaggta caggcgtact gaccgaatcc   1740
aacaaaaagt tcctgccttt tcagcagttc gggagagata tcgccgacac tacagacgcc   1800
gtcagggata cccaaaacact cgaaattctg gacatcacac cttgttcctt cggcggggta   1860
tctgtgatta ctccgggcac aaataccagt aaccaggtag cggtgcttta ccaggatgtc   1920
aactgtacgg aagtacctgt cgctattcat gcggatcaac tcactcctac ctggagagtt   1980
tattccactg gtccaacgt gtttcagacc cgagccggct gcttgattgg cgcggaacat   2040
gttaacaact cctacgaatg tgacatccct atcggagctg gcatcgtgc ttcctatcaa   2100
acgcaaacga acagcccacg gcgggccaga tccgtagcct ctcaaagcat catcgcttat   2160
```

-continued

```
actatgtcct tggggctgaa aacagcgtt gcctattcca acaatagcat cgctatccct    2220
accaacttta ccatttccgt gaccacagaa atactgccgg tgagcatgac aaagacttct    2280
gtggactgta ccatgtatat atgcggcgat agcacagagt gttctaattt gctgctgcag    2340
tacggcagct tttgtaccca actcaacaga gcacttacag ggattgccgt cgagcaggat    2400
aaaaacaccc aggaggtttt cgcccaggtt aagcagatct acaagacccc accaatcaag    2460
gatttcggcg gcttcaattt ttcccagata ctgcccgatc cttccaagcc atccaaaagg    2520
agctttatag aggatctgct gttcaacaag gtgactctgg ccgacgctgg ctttatcaag    2580
caatatggcg attgcctggg ggatattgcc gctagggacc ttatctgcgc tcaaaaattc    2640
aacggtctta ccgttctccc gccccctgctc accgacgaga tgatagccca gtacacgagc    2700
gcacttttgg ccggcacgat aaccagcggc tggacattcg gtgccggggc cgctcttcaa    2760
atccccttg ccatgcagat ggcctacaga tttaatggga taggcgtgac acaaaatgtc    2820
ttgtatgaaa atcagaaact gattgcaaac cagtttaata gcgctattgg caagatccaa    2880
gatagccttt cctccaccgc atccgctctg gaaaagttgc aagacgtcgt gaatcaaaac    2940
gcccaagctc tgaatacccct cgtgaagcag cttagctcca actttggcgc gatatcctcc    3000
gtgctgaacg atatcctgtc cagattggac aaggtcgagg cagaagtcca gatcgataga    3060
ttgataaccg gcagactcca gtctctgcag acatatgtga ctcagcagtt gataagagcg    3120
gccgaaatac gagcgtctgc aaatctcgca gcaacgaaaa tgtcagagtg tgtattgggg    3180
caaagtaaaa tgtactaaaa tctgtggaaag ggttaccatc tgatgtcatt cccccagtct    3240
gcaccacatg gagtagtttt tttgcatgtg acttatgtgc ctgcccagga gaaaaatttc    3300
accactgcac ctgcgatctg tcatgacggc aaggcacatt tccctagaga aggcgtcttc    3360
gtatcaaatg gaacacactg gtttgtaacc caaaggaact tttacgagcc ccaaattata    3420
actaccgaca acaccttcgt aagcggaaac tgcgacgtcg ttataggat agtcaataat    3480
acggtctatg accctcttca gccggaactg gactccttta aagaagaact ggataagtac    3540
ttcaagaacc atacgtctcc ggatgtggat ctcggagata taagtggaat caacgcaagc    3600
gtagtaaaca ttcagaagga gatagaccga ctcaatgagg ttgctaaaaa cctgaacgaa    3660
agcttgatag acttgcagga gctgggtaag tacgaacagt aattaagtg gccatggtat    3720
atctggttgg gcttcatagc aggactcata gctatcgtca tggtgacaat aatgctttgt    3780
tgtatgacca gctgttgttc ttgtctgaaa ggctgctgca gctgtggcag ctgttgtaaa    3840
tttgacgaag atgattccga gcctgtgctt aagggcgtaa aactccacta tacatga      3897

SEQ ID NO: 8              moltype = AA   length = 805
FEATURE                   Location/Qualifiers
REGION                    1..805
                          note = Human ACE2 protein
source                    1..805
                          mol_type = protein
                          organism = synthetic construct
SEQUENCE: 8
MSSSSWLLLS LVAVTAAQST IEEQAKTFLD KFNHEAEDLF YQSSLASWNY NTNITEENVQ     60
NMNNAGDKWS AFLKEQSTLA QMYPLQEIQN LTVKLQLQAL QQNGSSVLSE DKSKRLNTIL   120
NTMSTIYSTG KVCNPDNPQE CLLLEPGLNE IMANSLDYNE RLWAWESWRS EVGKQLRPLY   180
EEYVVLKNEM ARANHYEDYG DYWRGDYEVN GVDGYDYSRG QLIEDVEHTF EEIKPLYEHL   240
HAYVRAKLMN AYPSYISPIG CLPAHLLGDM WGRFWTNLYS LTVPFGQKPN IDVTDAMVDQ   300
AWDAQRIFKE AEKFFVSVGL PNMTQGFWEN SMLTDPGNVQ KAVCHPTAWD LGKGDFRILM   360
CTKVTMDDFL TAHHEMGHIQ YDMAYAAQPF LLRNGANEGF HEAVGEIMSL SAATPKHLKS   420
IGLLSPDFQE DNETEINFLL KQALTIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
NSFVGWSTDW SPYADQSIKV RISLKSALGD KAYEWNDNEM YLFRSSVAYA MRQYFLKVKN   660
QMILFGEEDV RVANLKPRIS FNFFVTAPKN VSDIIPRTEV EKAIRMSRSR INDAFRLNDN   720
SLEFLGIQPT LGPPNQPPVS IWLIVFGVVM GVIVVGIVL IFTGIRDRKK KNKARSGENP   780
YASIDISKGE NNPGFQNTDD VQTSF                                        805

SEQ ID NO: 9              moltype = AA   length = 594
FEATURE                   Location/Qualifiers
REGION                    1..594
                          note = Soluble ACE2 mutant constructs
SITE                      4
                          note = MISC_FEATURE - Can be Gln or Leu
SITE                      7
                          note = MISC_FEATURE - Can be Thr, Phe, Trp, or Tyr
SITE                      10
                          note = MISC_FEATURE - Can be Asp, Glu, Leu
SITE                      14
                          note = MISC_FEATURE - Can be His, Glu, Phe, Lys, Met, Trp,
                           Tyr, or Ala
SITE                      18
                          note = MISC_FEATURE - Can be Asp, Glu, Met, or Phe
SITE                      335
                          note = MISC_FEATURE - Can be Asp or Leu
source                    1..594
                          mol_type = protein
                          organism = synthetic construct
SEQUENCE: 9
IEEXAKXFLX KFNXEAEXLF YQSSLASWNY NTNITEENVQ NMNNAGDKWS AFLKEQSTLA     60
QMYPLQEIQN LTVKLQLQAL QQNGSSVLSE DKSKRLNTIL NTMSTIYSTG KVCNPDNPQE   120
CLLLEPGLNE IMANSLDYNE RLWAWESWRS EVGKQLRPLY EEYVVLKNEM ARANHYEDYG   180
DYWRGDYEVN GVDGYDYSRG QLIEDVEHTF EEIKPLYEHL HAYVRAKLMN AYPSYISPIG   240
CLPAHLLGDM WGRFWTNLYS LTVPFGQKPN IDVTDAMVDQ AWDAQRIFKE AEKFFVSVGL   300
```

-continued

```
PNMTQGFWEN SMLTDPGNVQ KAVCHPTAWD LGKGXFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 10          moltype = AA  length = 1298
FEATURE                Location/Qualifiers
REGION                 1..1298
                       note = SARS-CoV2 spike mutant (p35)
source                 1..1298
                       mol_type = protein
                       organism = synthetic construct
SEQUENCE: 10
MFVFLVLLPL VSSYPYDVPD YAGGGSGGGS GGGSGGGSQC VNLTTRTQLP PAYTNSFTRG  60
VYYPDKVFRS SVLHSTQDLF LPFFSNVTWF HAIHVSGTNG TKRFDNPVLP FNDGVYFAST  120
EKSNIIRGWI FGTTLDSKTQ SLLIVNNATN VVIKVCEFQF CNDPFLGVYY HKNNKSWMES  180
EFRVYSSANN CTFEYVSQPF LMDLEGKQGN FKNLREFVFK NIDGYFKIYS KHTPINLVRD  240
LPQGFSALEP LVDLPIGINI TRFQTLLALH RSYLTPGDSS SGWTAGAAAY YVGYLQPRTF  300
LLKYNENGTI TDAVDCALDP LSETKCTLKS FTVEKGIYQT SNFRVQPTES IVRFPNITNL  360
CPFGEVFNAT RFASVYAWNR KRISNCVADY SVLYNSASFS TFKCYGVSPT KLNDLCFTNV  420
YADSFVIRGD EVRQIAPGQT GKIADYNYKL PDDFTGCVIA WNSNNLDSKV GGNYNYLYRL  480
FRKSNLKPFE RDISTEIYQA GSTPCNGVEG FNCYFPLQSY GFQPTNGVGY QPYRVVVLSF  540
ELLHAPATVC GPKKSTNLVK NKCVNFNFNG LTGTGVLTES NKKFLPFQQF GRDIADTTDA  600
VRDPQTLEIL DITPCSFGGV SVITPGTNTS NQVAVLYQDV NCTEVPVAIH ADQLTPTWRV  660
YSTGSNVFQT RAGCLIGAEH VNNSYECDIP IGAGICASYQ TQTNSPSAAG SVASQSIIAY  720
TMSLGAENSV AYSNNSIAIP TNFTISVTTE ILPVSMTKTS VDCTMYICGD STECSNLLLQ  780
YGSFCTQLNR ALTGIAVEQD KNTQEVFAQV KQIYKTPPIK DFGGFNFSQI LPDPSKPSKR  840
SFIEDLLFNK VTLADAGFIK QYGDCLGDIA ARDLICAQKF NGLTVLPPLL TDEMIAQYTS  900
ALLAGTITSG WTFGAGAALQ IPFAMQMAYR FNGIGVTQNV LYENQKLIAN QFNSAIGKIQ  960
DSLSSTASAL GKLQDVVNQN AQALNTLVKQ LSSNFGAISS VLNDILSRLD KVEAEVQIDR  1020
LITGRLQSLQ TYVTQQLIRA AEIRASANLA ATKMSECVLG QSKRVDFCGK GYHLMSFPQS  1080
APHGVVFLHV TYVPAQEKNF TTAPAICHDG KAHFPREGVF VSNGTHWFVT QRNFYEPQII  1140
TTDNTFVSGN CDVVIGIVNN TVYDPLQPEL DSFKEELDKY FKNHTSPDVD LGDISGINAS  1200
VVNIQKEIDR LNEVAKNLNE SLIDLQELGK YEQYIKWPWY IWLGFIAGLI AIVMVTIMLC  1260
CMTSCCSCLK GCCSCGSCCK FDEDDSEPVL KGVKLHYT                         1298

SEQ ID NO: 11          moltype = DNA  length = 40866
FEATURE                Location/Qualifiers
misc_feature           1..40866
                       note = p35 vector sequence
source                 1..40866
                       mol_type = other DNA
                       organism = synthetic construct
SEQUENCE: 11
tattattgat gatgttaatt aacatgcatg gatcctacgt ctcgaccgat gcccttgaga  60
gccttcaacc cagtcagctc cttccggtgg gcgcggggca tgactatcgt cgccgcactt  120
atgactgtct tctttatcat gcaactcgta ggacaggtgc cggcagcgct ctgggtcatt  180
ttcggcgagg accgctttcg ctggagcgcg acgatgatcg gcctgtcgct tgcggtattc  240
ggaatcttgc acgccctcgc tcaagccttc gtcactggtc ccgccaccaa acgtttcggc  300
gagaagcagg ccattatcgc cggcatggcg gccgacgcgc tgggctacgt cttgctggcg  360
ttcgcgacgc gaggctggat ggccttcccc attatgattc ttctcgcttc cggcggcatc  420
gggatgcccg cgttgcaggc catgctgtcc aggcaggtag atgacgacca tcagggacag  480
cttcaaggat cgctcgcggc tcttaccagc ctaacttcga tcattggacc gctgatcgtc  540
acggcgattt atgccgcctc ggcgagcaca tggaacgggt tggcatggat tgtaggcgcc  600
gccctatacc ttgtctgcct ccccgcgttg cgtcgcggtg catggagccg ggccacctcg  660
acctgaatgg aagccggcgg cacctcgcta acggattcac cactccaaga attggagcca  720
atcaattctt gcggagaact gtgaatgcgc aaaccaaccc ttggcagaac atatccatcg  780
cgtccgccat ctccagcagc cgcacgcggc gcatctcggg cagcgttggg tcctggccac  840
gggtgcgcat gatcgtgctc ctgtcgttga ggacccggct aggctggcgg ggttgcctta  900
ctggttagca gaatgaatca ccgatacgcg agcgaacgtg aagcgactgc tgctgcaaaa  960
cgtctgcgac ctgagcaaca acatgaatgg tcttcggttt ccgtgtttcg taaagtctgg  1020
aaacgcggaa gtcagcgccc tgcaccatta tgttccggat ctgcatcgca ggatgctgct  1080
ggctaccctg tggaacacct acatctgtat taacgaagcg ctggcattga ccctgagtga  1140
tttttctctg gtcccgccgc atccataccg ccagttgttt accctcacaa cgttccagta  1200
accgggcatg ttcatcatca gtaacccgta tcgtgagcat cctctctcgt ttcatcggta  1260
tcattacccc catgaacaga aatccccctt acacggaggc atcagtgacc aaacaggaaa  1320
aaaccgccct taacatggcc cgctttatca gaagccagac attaacgctt ctggagaaac  1380
tcaacgagct ggacgcggat gaacaggcag acatctgtga atcgcttcac gaccacgctg  1440
atgagcttta ccgcagctgc ctcgcgcgtt tcggtgatga cggtgaaaac ctctgacaca  1500
tgcagctccc ggagacggtc acagcttgtc tgtaagcgga tgccgggagc agacaagccc  1560
gtcagggcgc gtcagcgggt gttggcgggt gtcggggcgc agccatgacc cagtcacgta  1620
gcgatagcgg agtgtatact ggcttaacta tgcggcatca gagcagattg tactgagagt  1680
gcaccatatg cggtgtgaaa taccgcacag atgcgtaagg agaaaatacc gcatcaggcg  1740
ctcttccgct tcctcgctca ctgactcgct gcgctcggtc gttcggctgc ggcgagcggt  1800
atcagctcac tcaaaggcgg taatacggtt atccacagaa tcaggggata acgcaggaaa  1860
gaacatgtga gcaaaaggcc agcaaaaggc caggaaccgt aaaaaggccg cgttgctggc  1920
gtttttccat aggctccgcc cccctgacga gcatcacaaa aatcgacgct caagtcagag  1980
gtggcgaaac ccgacaggac tataaagata ccaggcgttt ccccctggaa gctccctcgt  2040
```

```
gcgctctcct gttccgaccc tgccgcttac cggatacctg tccgcctttc tcccttcggg   2100
aagcgtggcg ctttctcata gctcacgctg taggtatctc agttcggtgt aggtcgttcg   2160
ctccaagctg ggctgtgtgc acgaaccccc cgttcagccc gaccgctgcg ccttatccgg   2220
taactatcgt cttgagtcca acccggtaag acacgactta tcgccactgg cagcagccac   2280
tggtaacagg attagcagag cgaggtatgt aggcggtgct acagagttct tgaagtggtg   2340
gcctaactac ggctacacta gaaggacagt atttggtatc tgcgctctgc tgaagccagt   2400
taccttcgga aaaagagttg gtagctcttg atccggcaaa caaaccaccg ctggtagcgg   2460
tggttttttt gtttgcaagc agcagattac gcgcagaaaa aaggatctc aagaagatcc   2520
tttgatcttt tctacggggt ctgacgctca gtggaacgaa aactcacgtt aagggatttt   2580
ggtcatgaga ttatcaaaaa ggatcttcac ctagatcctt ttaaattaaa aatgaagttt   2640
taaatcaatc taaagtatat atgagtaaac ttggtctgac agttaccaat gcttaatcag   2700
tgaggcacct atctcagcga tctgtctatt tcgttcatcc atagttgcct gactccccgt   2760
cgtgtagata actacgatac gggagggctt accatctggc cccagtgctg caatgatacc   2820
gcgagaccca cgctcaccgg ctccagattt atcagcaata aaccagccag ccggaagggc   2880
cgagcgcaga agtggtcctg caactttatc cgcctccatc cagtctatta attgttgccg   2940
ggaagctaga gtaagtagtt cgccagttaa tagtttgcgc aacgttgttg ccattgctgc   3000
agccatgaga ttatcaaaaa ggatcttcac ctagatcctt ttcacgtaga aagccagtcc   3060
gcagaaacgg tgctgacccc ggatgaatgt cagctactgg gctatctgga caagggaaaa   3120
cgcaagcgca aagagaaagc aggtagcttg cagtgggctt acatggcgat agctagactg   3180
ggcggtttta tggacagcaa gcgaaccgga attgccagct ggggcgccct ctggtaaggt   3240
tgggaagccc tgcaaagtaa actggatggc tttcttgccg ccaaggatct gatggcgcag   3300
gggatcaagc tctgatcaag agacaggatg aggatcgttt cgcatgattg aacaagatgg   3360
attgcacgca ggttctccgg ccgcttgggt ggagaggcta ttcggctatg actgggcaca   3420
acagacaatc ggctgctctg atgccgccgt gttccggctg tcagcgcagg ggcgcccggt   3480
tctttttgtc aagaccgacc tgtccggtgc cctgaatgaa ctgcaagacg aggcagcgcg   3540
gctatcgtgg ctggccacga cgggcgttcc ttgcgcagcg tgtctcgacg ttgtcactga   3600
agcgggaagg gactggctgc tattgggcga agtgccgggg caggatctcc tgtcatctca   3660
ccttgctcct gccgagaaag tatccatcat ggctgatgca atgcggcggc tgcatacgct   3720
tgatccggct acctgcccat tcgaccacca agcgaaacat cgcatcgagc gagcacgtac   3780
tcggatggaa gccggtcttg tcgatcagga tgatctggac gaagagcatc aggggctcgc   3840
gccagccgaa ctgttcgcca ggctcaaggc gagcatgccc gacggcgagg atctcgtcgt   3900
gacccatggc gatgcctgct tgccgaatat catggtggaa aatggccgct tttctggatt   3960
catcgactgt ggccggctgg gtgtggcgga ccgctatcag gacatagcgt tggctacccg   4020
tgatattgct gaagagcttg gcggcgaatg ggctgaccgc ttcctcgtgc tttacggtat   4080
cgccgctccc gattcgcagc gcatcgcctt ctatcgcctt cttgacgagt tcttctgaat   4140
tttgttaaaa ttttttgttaa atcagctcat tttttaacca ataggccgaa atcggcaaaa   4200
tcccttataa atcaaaagaa tagaccgaga tagggttgag tgttgttcca gtttggaaca   4260
agagtccact attaaagaac gtggactcca acgtcaaagg gcgaaaaacc gtctatcagg   4320
gcgatggccc actacgtgaa ccatcaccct aatcaagttt tttggggtcg aggtgccgta   4380
aagcactaaa tcggaaccct aaagggagcc cccgatttag agcttgacgg ggaaagccgg   4440
cgaacgtggc gagaaaggaa gggaagaaag cgaaaggagc gggcgctagg gcgctggcaa   4500
gtgtagcggt cacgctgcgc gtaaccacca cacccgccgc gcttaatgcg ccgctacagg   4560
gcgcgtccat tcgccattca ggatcgaatt aattcttaat taacatcatc aataatatac   4620
cttattttgg attgaagcca atatgataat gaggggggtgg agtttgtgac gtggcgcggg   4680
gcgtgggaac gggcgggtg acgtagtagt gtggcggaag tgtgatgttg caagtgtggc   4740
ggaacacatg taagcgacgg atgtggcaaa agtgacgttt ttggtgtgcg ccggtgtaca   4800
caggaagtga caatttttcgc gcggttttag gcggatgttg tagtaaattt gggcgtaacc   4860
gagtaagatt tggccatttt cgcgggaaaa ctgaataaga ggaagtgaaa tctgaataat   4920
tttgtgttac tcatagcgcg taatactgta atagtaatca attacggggt cattagttca   4980
tagcccatat atggagttcc gcgttacata acttacggta aatggcccgc ctggctgacc   5040
gcccaacgac ccccgcccat tgacgtcaat aatgacgtat gttcccatag taacgccaat   5100
agggactttc cattgacgtc aatgggtgga gtatttacgg taaactgccc acttggcagt   5160
acatcaagtg tatcatatgc caagtacgcc ccctattgac gtcaatgacg gtaaatggcc   5220
cgcctggcat tatgcccagt acatgacctt atgggacttt cctacttggc agtacatcta   5280
cgtattagtc atcgctatta ccatggtgat gcggttttgg cagtacatca atgggcgtgg   5340
atagcggttt gactcacggg gatttccaag tctccacccc attgacgtca atggagtttt   5400
gttttggcac caaaatcaac gggactttcc aaaatgtcgt aacaactccg ccccattgac   5460
gcaaatgggc ggtaggcgtg tacggtggga ggtctatata agcagagctg tttagtgaa   5520
ccgtcagatc cgctagagat ctggtaccgt cgacgcggcc gctcgagcct aagcttatgt   5580
tcgttttttct cgttctcctc ccgcttgtga gcagctatcc gtatgatgtg ccggattatg   5640
cgggtggagg ctctgaggt ggctctggtg gaggttccgg tggcggatct caatgtgtca   5700
acctcaccac aaggacacag ctccctcccg catatacgaa tagctttacc agaggcgtat   5760
actatcctga taaggtcttt aggagctcag tactgcatag cactcaggat ctcttcctgc   5820
cgttcttcag taatgttact tggtttcacg ccattcagtc ttcccggaac aatggcacca   5880
aacggttcga taatccagtg cttcccttca acgatggggt gtactttgcc agcactgaaa   5940
aatctaatat aattcgggga tggattttcg gaaccacact cgattccaag actcagtccc   6000
tcttgatcgt taacaacgct actaatgttg tcattaaggt gtgtgagttt cagttctgca   6060
acgaccctt cctgggtgtc tactaccata aaaataacaa gagctggatg gagtccgaat   6120
ttcgcgtcta ctcaagcgcc aataattgca cttttgata tgtcccag cccttttga   6180
tggatctgga gggaaagcag ggcaatttca aaaatctgag agaattcgtt tttaagaata   6240
tagatggata cttcaaaatc tacagcaaac acacacccat aaatcttgtg cgcgatcttc   6300
cccagggctt cagcgcgttg gaaccccttg ttgacttgcc cataggcatc aacattacca   6360
ggttccaaac gctgctcgcc ctccaccgca gctacttgac acccggggat tccagctccg   6420
gatgaccgc cggcgccgca gcgtattatg tggggtgcag gcaacccagg acatttttgc   6480
tcaagtacaa tgagaatggg accatcacag atgcggtaga ctgtgcactg gatccactca   6540
gcgaaactaa atgtaccctg aaaagcttta ccgtggagaa aggaatctac caaaccagca   6600
acttcagggt ccagcccact gaatccatcg ttagatttcc aaaatataact aatttgtgtc   6660
catttggaga ggtgttcaat gctacaaggt tcgcgtctgt atacgcttgg aaccggaagc   6720
gcatctcaaa ttgcgtggct gattatagcg ttctttacaa cagcgcttcc ttttccacgt   6780
```

```
tcaagtgcta tggtgtatcc ccgacaaagc tgaatgactt gtgcttcacc aatgtgtatg   6840
cggattcttt cgttattcga ggcgatgaag tcagacaaat tgcgcctggc cagaccggaa   6900
agattgccga ctacaactat aaactgccgg acgactttac tggttgcgtg atcgcttgga   6960
acagcaataa tcttgatagt aaagttggag gaaactacaa ttacctctat agactgttca   7020
gaaagagcaa cttgaagcca ttcgaacggg atatctctac ggagatctat caagctggca   7080
gcaccccctg caatggtgtg gaaggcttta attgttattt tcctttgcag agctatggct   7140
tccaacctac caacggagtg ggctaccagc cctacagagt ggtggtgctc agctttgaac   7200
tgctgcatgc cccggccaca gtttgcgggc ccaaaaaaag cacgaatctg gttaagaaca   7260
aatgcgtcaa cttcaatttt aatggggtga caggtacagg cgtactgacc gaatccaaca   7320
aaaagttcct gccttttcag cagttcggga gagatatcgt cgacactaca gacgccgtca   7380
gggatcccca aacactcgaa attctggaca tcacaccttg ttccttcggc ggggtatctg   7440
tgattactcc gggcacaaat accagtaacc aggtagcggt gctttaccag gatgtcaact   7500
gtacggaagt acctgtcgct attcatgcgg atcaactcac tcctacctgg agagtttatt   7560
ccactgggtc caacgtgttt cagacccgag ccggctgctt gattggcgcg gaacatgtta   7620
acaactccta cgaatgtgac atccctatcg gagctggcat ctgtgcttcc tatcaaacgc   7680
aaaacgaacag cccatctgct gctggttccg tagcctctca aagcatcatc gcttatacta   7740
tgtccttggg ggctgaaaac agcgttgcct attccaacaa tagcatcgct atccctacca   7800
actttaccat ttccgtgacc acagaaatac tgccggtgag catgacaaag acttctgtgg   7860
actgtaccat gtatatatgc ggcgatagca cagagtgttc taatttgctg ctgcagtacg   7920
gcagcttttg tacccaactc aacagagcac ttacagggat tgccgtcgag caggataaaa   7980
acacccagga ggttttcgcc caggttaagc agatctacaa gaccccacca atcaaggatt   8040
tcggcggctt caatttttcc cagatactgc ccgatcctc caagccatcc aaaaggagct   8100
ttatagagga tctgctgttc aacaaggtga ctctggccga cgctggcttt atcaagcaat   8160
atggcgattg cctgggggat attgccgcta gggaccttat ctgcgctcaa aaattcaacg   8220
gtcttaccgt tctcccgccc ctgctcaccg acgagatgat agcccagtac acgagcgcac   8280
ttttgccggg cacgataacc aagtgctgga cattcggtgc cggggccgct cttcaaatcc   8340
cctttgccat gcagatggcc tacagattta atggatgag cgtgacacaa aatgtcttgt   8400
atgaaaatca gaaactgatt gcaaaccagt taatagcgc tattggcaag atccaagata   8460
gcctttcctc caccgcatcc gctctgggaa agttgcaaga cgtcgtgaat caaaacgccc   8520
aagctctgaa tacctcgtg aagcagctta gctccaactt tggcgcgata tcctccgtga   8580
tgaacgatat cctgtccaga ttggacaagg tcgaggcaga agtccagatc gatagattga   8640
taaccggcag actccagtct ctgcagacat atgtgactca gcagttgata agagcggccg   8700
aaatacgagc gtctgcaaat ctcgcagcaa cgaaaatgtc agagtgtgta ttgggggcaaa  8760
gtaaaagagt agatttctgt ggaaagggtt accatctgat gtcattcccc cagtctgcac   8820
cacatggagt agttttttg catgtgactt atgtgcctgc ccaggagaaa aatttcacca   8880
ctgcacctgc gatctgtcat gacggcaagg cacatttccc tagagaaggc gtcttcgtat   8940
caaatgaac acactggttt gtaacccaaa ggaactttta cgagcccaa attataacta   9000
ccgacaacac cttcgtaagc ggaaactgcg acgtcgttat agggatgtc aataatacgg   9060
tctatgaccc tcttcagccg gaactggact cctttaaaga agaactggat aagtacttca   9120
agaaccatac gtctccggat gtggatctcg gagatataag tggaatcaac gcaagctag   9180
taaacattca gaaggagata gaccgactca atgaggttgc taaaaacctg aacgaaagct   9240
tgatagactt gcaggagctg ggtaagtacg aacagtacat taagtggcca tggtatatct   9300
ggcttgcctt catagcagga ctcataagcta tcgtcatggt gacaataatg cttttgttgta   9360
tgaccagctg ttgttcttgt ctgaaaggct gctgcagctg tggcagctgt tgtaaatttg   9420
acgaagatga ttccgagcct gtgcttaagg gcgtaaaact ccactataca tgagatatcc   9480
gatccaccgg atctagataa ctgatcataa tcagccatac cacatttgta gaggttttac   9540
ttgcttttaaa aaacctccca caccctcccc tgaacctgaa acataaaatg aatgcaattg   9600
ttgttgttaa cttgtttatt gcagcttata atggttacaa ataaagcaat agcatcacaa   9660
atttcacaaa taaagcattt ttttcactgc atttcagttg tggtttgtcc aaactcatca   9720
atgtatctta ggtttagtga accgtcagat ccgctagcgt tacataactt acggtaaatg   9780
gcccgcctgg ctgaccgccc aacgacccc gcccattgac gtcaataatg acgtatgttc   9840
ccatagtaac gccaatgggg actttccatt gacgtcaatg ggtggagtat ttacggtaaa   9900
ctgcccactt ggcagtacat caagtgtatc atatgccaag tacgccccct attgacgtca   9960
atgacggtaa atggcccgcc tggcattatg cccagtacat gaccttatgg gactttccta  10020
cttggcagta catctacgta ttagtcatcg ctattaccat ggtgatgcgg ttttggcagt  10080
acatcaatgg gcgtggatag cggtttgact cacggggatt tccaagtctc caccccattg  10140
acgtcaatgg gagtttgttt tggcaccaaa atcaacggga ctttccaaaa tgtcgtaaca  10200
actccgcccc attgacgcaa atgggcggta ggcgtgtacg gtgggaggtc tatataagca  10260
gagctggttt agtgaaccgt cagatccgct agagatctgg taccgtcgac gcggccgctc  10320
gagcctaagc ttatgctgct gctgcccttc cagttcgctg ctgtcctctt tcccgcgcgc  10380
aactccgagg attacaagga cgacgacgac aagggtggag gctctggagg tggctctggt  10440
ggaggttccg gtgcggatc tatgagcgac aacggtcccc agaatcaaag aaatgcgccc  10500
agaattacat tcggcggccc ttctgatagc actggctcaa atcaaaacgg ggagagaagc  10560
ggagccaggt ccaaacagcg gagacccaa ggcctgccta ataacaccgc ttcctggttc  10620
acagctctga cgcaacacgg caaggaggat ctgaagtttc acggggtca gggcgtcccg  10680
attaacacga actctagccc agatgaccaa ataggggtact acagaagagc gacaaggcgg  10740
atcagaggag gcgatggaaa aatgaaggat ctgtccccta ggtggtattt ctattacctg  10800
ggcacaggg ctgaagctgg gttgccttac ggcgcaaaca aagatggaat tatatgggtg  10860
gccaccgagg gggcgttgaa caccccaaag gatcacatcg aacgaggaa tcccgccaac  10920
aatgctgcta tagtgctcca actgccacag ggaacaaccc tgcctaaggg cttctacgcc  10980
gaggggagcc gcgtggcag ccaggccagc tccagaagtt cctcccgcag ccggaacagc  11040
tctagaaaca gcactcccgg cagctccaga gggacaagcc cagccagaat ggccggcaat  11100
ggcggcgacg ctgccctcgc acttctgttg cttgatcggc tcaatcaact cgaaagcaaa  11160
atgagcaaca agcaagga cagccgtta caaaaaaaag cgccgccgag  11220
gctagcaaga agcccagaca gaagcgaacc gcaacaaagg cctataatgt aacacaagcc  11280
tttgaaaggc ggggacccga acagacccag ggaaatttg cgaccaggaa actgatccgg  11340
caagggacag actataaaca ttggccacag atagcgcaat tgctccctc cgcctccgcc  11400
ttctttggca tgtcaagaat aggcatgaa gtaactcctg ctggaacctg gctgacgtac  11460
actggggcaa tcaagttgga tgataaggac cctaatttca aggaccaagt tattttgctc  11520
```

```
aacaagcata tagacgccta caagactttc ccgcctaccg aacctaaaaa ggataagaag   11580
aagaaagcag acgagaccca ggccctgcct caacggcaaa agaagcagca aactgtgaca   11640
ctcctgcccg ccgctgactt ggatgatttt tcaaaacagc tccaacagag tatgagcagc   11700
gccgatagca cccaagctgg accgggtccg ggcaacctgg tgccgatggt ggcgaccgtg   11760
ggtccaggac cgggtatgct gatccccatc gccgtgggcg gggccctggc cggcctcgtg   11820
ctgatcgtcc ttatcgccta cctcatcggc aagaagcact gctcatatca ggacatcctg   11880
tgagatatcc gatccaccgg atctagataa ctgatcataa tcagccatac cacatttgta   11940
gaggttttac ttgctttaaa aaacctccca cacctccccc tgaacctgaa acataaaatg   12000
aatgcaattg ttgttgttaa cttgtttatt gcagcttata atggttacaa ataaagcaat   12060
agcatcacaa atttcacaaa taaagcattt ttttcactgc attctagttg tggtttgtcc   12120
aaactcatca atgtatctta acgcggatct gggcgtggtt aagggtggga aagaatatat   12180
aaggtggggg tcttatgtag ttttgtatct gttttgcagc agccgccgcc gccatgagca   12240
ccaactcgtt tgatggaagc attgtgagct catatttgac aacgcgcatg cccccatggg   12300
ccggggtgcg tcagaatgtg atgggctcca gcattgatgg tcgccccgtc ctgcccgcaa   12360
actctactac cttgacctac gagaccgtgt ctggaacgcc gttggagact gcagcctccg   12420
ccgccgcttc agccgctgca gccaccgccc gcgggattgt gactgacttt gctttcctga   12480
gcccgcttgc aagcagtgca gcttcccgtt catccgcccg cgatgacaag ttgacggctc   12540
ttttggcaca attggattct ttgacccggg aacttaatgt cgtttctcag cagctgttgg   12600
atctgcgcca gcaggtttct gccctgaagg cttcctcccc tcccaatgcg gtttaaaaca   12660
taaataaaaa accagactct gtttggattt ggatcaagca agtgtcttgc tgtctttatt   12720
tagggggtttt gcgcgcgcgg taggcccggg accagcggtc tcggtcgttg agggtcctgt   12780
gtatttttc caggacgtgg taaaggtgac tctggatgtt cagatacatg ggcataagcc   12840
cgtctctggg gtgaggtag caccactgca gagcttcatg ctgcggggtg gtgttgtaga   12900
tgatccagtc gtagcaggag cgctgggcgt ggtgcctaaa aatgtctttc agtagcaagc   12960
tgattgccag gggcaggccc ttggtgtaag tgtttacaaa gcggttaagc tgggatgggt   13020
gcatacgtgg ggatatgaga tgcatcttgg actgtatttt taggttggct atgttcccag   13080
ccatatccct ccggggattc atgttgtgca gaaccaccag cacagtgtat ccggtgcact   13140
tgggaaattt gtcatgtagc ttagaaggaa atgcgtggaa gaacttggag acgcccttgt   13200
gacctccaag atttttccatg cattcgtcca taatgatggc aatgggccca cgggcggcgg   13260
cctggcgaa gatatttctg ggatcactaa cgtcatagtt gtgttccagg atgagatcgt   13320
cataggccat ttttacaaag cgcgggcgga gggtgccaga ctgcggtata atggttccat   13380
ccggcccagg ggcgtagtta ccctcacaga tttgcatttc ccacgctttg agttcagatg   13440
gggggatcat gtctacctgc ggggcgatga agaaaacggt ttccggggta ggggagatca   13500
gctgggaaga aagcaggttc ctgagcagct gcgacttacc gcagccggtg ggcccgtaaa   13560
tcacacctat taccggctgc aactggtagt taagagagct gcagctgccg tcatccctga   13620
gcaggggggc cacttcgtta agcatgtccc tgactcgcat gttttccctg accaaatccg   13680
ccagaaggcg ctcgccgccc agcgatagca gttcttgcaa ggaagcaaag tttttcaacg   13740
gtttgagacc gtccgccgta ggcatgcttt tgagcgtttg accaagcagt tccaggcggt   13800
cccacagctc ggtcacctgc tctacgcat ctcgatccag catatctcct cgtttcgcgg   13860
gttgggcggg ctttcgctgt acggcagtag tcggtgctcg tccagacggg ccagggtcat   13920
gtctttccac gggcgcaggg tcctcgtcag cgtagtctgg gtcacggtga aggggtgcgc   13980
tccgggctgc gcgctggcca gggtgcgctt gaggctggtc ctgctggtgc tgaagcgctg   14040
ccggtcttcg ccctgcgcgt cggccaggta gcatttgacc atggtgtcat agtccagccc   14100
ctccgcggcg tggcccttgg cgcgcagctt gcccttggag gaggcgccgc acgaggggca   14160
gtgcagactt tgagggcgt agagcttggg cgcgagaaat accgattccg gggagtaggc   14220
atccgcgccg caggccccgc agacggtctc gcattccacg agcaggtga gctctggccg   14280
ttcgggtca aaaaccaggt ttcccccatg ctttttgatg cgtttcttac ctctggtttc   14340
catgagccgg tgtccacgct cggtgacgaa aaggctgtcc gtgtcccgt atacagactt   14400
gagaggcctg tcctcgagcg tgttccgcg gtcctcctcg tatagaaact cggaccactc   14460
tgagacaaag gctcgcgtcc aggccagcac gaaggaggct aagtgggagg ggtagcggtc   14520
gttgtccact aggggggtcca ctcgctccag ggtgtgaaga cacatgtgc cctcttcgtg   14580
atcaaggaag gtgattggtt tgtaggtgta ggcacgtga ccgggtgttc ctgaaggggg   14640
gctataaaag ggggtggggg cgcgttcgtc tcactctct tccgcatcgc tgtctgcgag   14700
ggccagctgt tgggtgagt actccctctg aaaagcgggc atgacttctg cgctaagatt   14760
gtcagtttcc aaaaacgagg aggatttgat attcacctgg cccgcggtga tgcctttgag   14820
ggtggccgca tccatctggt cagaaaagac aatctttttg ttgtcaagct tggtggcaaa   14880
cgacccgtag agggcgttgg acagcaactt ggcgatggag cgcagggttt ggttttttgtc   14940
gcgatcggcc cgctccttgg ccgcgatgtt tagctgcacg tattcgcgcg caacgcaccg   15000
ccattcggga aagacggtgg tgcgctcgtc gggcaccagg tgcacgcgcc aaccgcggtt   15060
gtgcagggtg acaaggtcaa cgctcggtggc tacctctccg cgtaggccgt cgttggtcca   15120
gcagaggcgg ccgcccttgc gcgagcagaa tggcggtagg gggtctagct gcgtctcgtc   15180
cgggggtct gcgtccacgg taaagacccc gggcagcagg cgcgcgtcga agtagtctat   15240
cttgcatcct tgcaagtcta gcgcctgctg ccatgcgcgg gcggcaagcg cgcgctcgta   15300
tgggttgagt gggggacccc atgcatggg gtgggtgagc gcaggaagcg acatgccgca   15360
aatgtcgtaa acgtagaggg gctctctgag tattccaaga tatgtagggt agcatcttcc   15420
accgcgatg ctggcgcgca cgtaatcgta tagttcgtgc gagggagcga ggaggtcggg   15480
accgaggttg ctacgggcgg gctgctctgc tcggaagact atctgcctga agatggcatg   15540
tgagttggat gatatggttg gacgctggaa gacgttgaag ctggcgtctg tgagacctac   15600
cgcgtcacgc acgaaggagg cgtaggagtc gcgcagcttg tgaccagct cggcgggtgac   15660
ctgcacgtct agggcgcagt agtccaggt ttccttgatg atgtcatact tatcctgtcc   15720
ctttttttc cacagctcgc ggttgaggac aaactcttcg cggtctttcc agtactcttg   15780
gatcggaaac ccgtcggcct ccgaacggta agagcctagc atgtagaact ggttgacggc   15840
ctggtaggcg cagcatccct ttctacggg tagcgcgtat gcctgcgcgg ccttccggca   15900
tgaccatcat gaaaggcacg agctgcttcc caaaggcccc catccaagta taggtctcta   15960
catcgtaggt gacaaagaga cgctcggtgc gaggatgcga gccgatcggg aagaactgga   16020
tctcccgcca ccaattggag gagtggctat tgatgtggtg aaagtagaag tccctgcgac   16080
gggccgaaca ctcgtgctgg cttttgtaaa acgtgcgca gtactggcag cggtgcacgg   16140
gctgtacatc ctgcacgagg ttgacctgac gaccgcgcac aaggaagcag agtgggaatt   16200
tgagcccctc gcctggcggg tttggctggt ggtcttctac ttcggctgct tgtccttgac   16260
```

```
cgtctggctg ctcgagggga gttacggtgg atcggaccac cacgccgcgc gagcccaaag  16320
tccagatgtc cgcgcgcggc ggtcggagct tgatgacaac atcgcgcaga tgggagctgt  16380
ccatggtctg gagctcccgc ggcgtcaggt caggcgggag ctcctgcagg tttacctcgc  16440
atagacgggt cagggcgcgg gctagatcca ggtgatacct aatttccagg ggctggttgg  16500
tggcggcgtc gatggcttgc aagaggccgc atccccgcgc cgcgactacg gtaccgcgcg  16560
gcgggcggtg ggccgcgggg gtgtccttgg atgatgcatc taaaagcggt gacgcgggcg  16620
agccccggga ggtagggggg gctccggacc cgccgggaga gggggcaggg gcacgtcggc  16680
gccgcgcgcg ggcaggagct ggtgctgcgc gcgtaggttg ctggcgaacg cgacgacgcg  16740
gcggtttgatc tcctgaatct ggcgcctctg cgtgaagacg acgggcccgg tgagcttgaa  16800
cctgaaagag agttcgacag aatcaatttc ggtgtcgttg acggcggcct ggcgcaaaat  16860
ctcctgcacg tctcctgagt tgtcttgata ggcgatctcg gccatgaact gctcgatctc  16920
ttcctcctgg agatctccgc gtccggctcg ctccacggtg gcggcgaggt cgttggaaat  16980
gcgggccatg agctgcgaga aggcgttgag gcctccctcg ttccagacgc ggctgtagac  17040
cacgcccccct tcggcatcgc gggcgcgcat gaccacctgc gcgagattga gctccacgtg  17100
ccgggcgaag acggcgtagt ttcgcaggcg ctgaaagagg tagttgaggg tggtggcggt  17160
gtgttctgcc acgaagaagt acataaccca gcgtcgcaac gtggattcgt tgataattgt  17220
tgtgtaggta ctccgccgcc gagggacctg agcgagtccg catcgaccgg atcggaaaac  17280
ctctcgagaa aggcgtctaa ccagtcacag tcgcaaggta ggctgcac cgtggcgggc  17340
ggcagcgggc ggcggtcggg gttgtttctg gcggaggtgc tgctgatgat gtaattaaag  17400
taggcggtct tgagacggcg gatggtcgac agaagcacca tgtccttggg tccggcctgc  17460
tgaatgcgca ggcggtcggc catgcccag gcttcgtttt gacatcggcg caggtctttg  17520
tagtagtctt gcatgagcct ttctaccggc acttcttctt ctccttcctc ttgtcctgca  17580
tctcttgcat ctatcgctgc ggcggcggcg gagtttggcc gtaggtggcg ccctcttcct  17640
cccatgcgtg tgaccccgaa gcccctcatc ggctgaagca gggctaggtc ggcgacaacg  17700
cgctcggcta atatggcctg ctgcacctgc gtgagggtag actggaagtc atccatgtcc  17760
acaaagcggt ggtatgcgcc cgtgttgatg gtgtaagtgc agttggccat aacggaccag  17820
ttaacggtct ggtgacccgg ctgcgagagc tcggtgtacc tgagacgcga gtaagccctc  17880
gagtcaaata cgtagtcgtt gcaagtccgc accaggtact ggtatcccac caaaaagtgc  17940
ggcggcggct ggcggtagag gggccagcgt agggtggccg gggctccggg ggcgagatct  18000
tccaacataa ggcgatgata tccgtagatg tacctggaca tccaggtgat gccggcgggg  18060
gtggtggagg cgcgcggaaa gtcgcggacg cggttccaga tgttgcgcag cggcaaaaag  18120
tgctccatgg tcgggacgct ctggccggtc aggcgcgcgc aatcgttgac gctctagcgt  18180
gcaaaaggag agcctgtaag cgggcactct tccgtggtct ggtggataaa ttcgcaaggg  18240
tatcatgcgg gacgaccggg gttcgagccg cgtatccggc cgtccgccgt gatccatgcg  18300
gttaccgccc gcgtgtcgaa cccaggtgtg cgacgtcaga caacgggga gtgctccttt  18360
tggcttcctt ccaggcgcgg cggctgctgc gctagctttt ttggccactg gccgcgcgca  18420
gcgtaagcgg ttaggctgga aagcgaaagc attaagtggc tcgctccctg tagccggagg  18480
gttatttcc aaggggttgag tcgcgggacc cccggttcga gtctcggacc ggccggactg  18540
cggcgaacgg gggtttgcct ccccgtcatg caagacccgc cttgcaaatt cctccggaaa  18600
cagggacgag cccctttttt gcttttccca gatgcatccg gtgctgcggc agatgcgccc  18660
ccctcctcag cagcggcaag agcaagagca gcggcagaca tgcagggcac cctcccctcc  18720
tcctaccgcg tcaggagggg cgacatccgc ggttgacgcg gcagcagatg gtgattacga  18780
accccgcgg cgccggggccc ggcactacct ggacttggag gagggcgagg gcctggccgg  18840
gctaggagcg ccctctcctg agcggcaccc aaggggtgcag ctgaagcgtg atacgcgtga  18900
ggcgtacgtg ccgcggcaga acctgtttcg cgaccgcgag ggagaggagc ccgaggagat  18960
gcgggatcga aagttccacg cagggcgcga gctgcggcat ggcctgaatc gcgagcggtt  19020
gctgcgcgag gaggactttg agcccgacgc gcgaaccggg attagtcccg gcgcgcaca  19080
cgtggcggcc gccgacctgg taaccgcata cgagcagacg gtgaaccagg agattaactt  19140
tcaaaaaagc tttaacaacc acgtgcgtac gcttgtggcg cgcgaggagg tggctatagg  19200
actgatgcat ctgtgggact ttgtaagcgc gctggagcaa aacccaaata gcaagccgct  19260
catggcgcag ctgttcctta tagtcagca cagcagggac aacgaggcat tcagggatgc  19320
gctgctaaac atagtagagc ccgagggccg ctgctgctc gatttgataa acatcctgca  19380
gagcatagtg tgcaggagc gcagcttgag cctggctgac aagtggccgc ccatcaacta  19440
ttccatgctt agcctgggca gttttacgc ccgcaagata taccatacc cttacgttcc  19500
catagacaag gaggtaaaga tcgaggggtt ctacatgcgc atggcgctga aggtgcttac  19560
cttgagcgac gacctgggcg tttatcgcaa cgagccgatc cacaaggccg tgagcgtgag  19620
ccggcggcgc gagctcagcg accgcgagct gatgcacagc ctgcaaaggg ccctggctgg  19680
cacgggcagc ggcgatagag aggccgagtc ctactttgac gcgggcgctg acctgcgctg  19740
ggccccaagc cgacgcgccc tggaggcagc tgggccggaa cctggctgg cggtggcagc  19800
cgcgcgcgct ggcaacgtcg gcggcgttgga ggaatatgac gaggacgatg agtacgagcc  19860
agaggacggc gagtactaag cggtgatgtt tctgatcaga tgatgcaaga cgcaacggac  19920
ccggcggtgc gggcggcgct gcagagccag ccgtccggcc ttaactccac ggacgactgg  19980
cgccaggtca tggaccgcat catgtcgctg actcgcgca atcctgacgc gttccggcag  20040
cagccgcagg ccaaccggct ctccgcaatt ctggaacggg tggtcccggc gcgcgaaac  20100
cccacgcacg agaaggtgct ggcgatcgta aacgcgctgg ccgaaaacag ggccatccgg  20160
cccgacgagg ccggcctggt ctacgacgcg ctgcttcagc gcgtggctcg ttacaacagc  20220
ggcaacgtgc agaccaacct ggaccggctg gtggggatg tgcgcgaggc cgtggcgcag  20280
cgtgagcgcg cgcagcagcg gggcaacctg ggctccatgg ttgcactaaa cgccttcctg  20340
agtacacagc ccgccaacgt gccgcggga caggaggact acaccaactt tgtgagcgca  20400
ctgcggctaa tggtgactga gacaccgcaa agtgaggtgt accagtctgg gccagactat  20460
ttttccaga ccagtagaca aggcctgcag accgtaaacc tgagcaggc tttcaaaaac  20520
ttgcaggggc tgtgggggt gcgggctccc acaggcgacc gcgcgaccgt gtctagcttg  20580
ctgacgccca actcgcgcct gttgctgctg ctaatagcgc ccttcacgga cagtggcagc  20640
gtgtcccggg acacataccc aggtcacttg ctgacactgt acaggtcag  20700
gcgcatgtgg acgagcatac ttttcaggag attacaagtg tcagccgcgc gctggggcag  20760
gaggacacgg gcagcctgga ggcaacccta aactaccgtc tgaccaaccg gcggcagaag  20820
atcccctcgt tgcacagttt aaacagcgag gaggagcgca ttttgcgcta cgtgcagcag  20880
agcgtgagcc ttaacctgat gcgcgacggg gtaacgccca gcgtggcgct ggacatgacc  20940
gcgcgcaaca tggaacgggg catgtatgcc tcaaaccggc cgtttatcaa ccgcctaatg  21000
```

```
gactacttgc atcgcgcggc cgccgtgaac cccgagtatt tcaccaatgc catcttgaac  21060
ccgcactggc taccgcccc  tggtttctac accgggggat tcgaggtgcc cgagggtaac  21120
gatggattcc tctgggacga catagacgac agcgtgtttt ccccgcaacc gcagaccctg  21180
ctagagttgc aacagcgcga gcaggcagag gcggcgctgc gaaaggaaag cttccgcagg  21240
ccaagcagct tgtccgatct aggcgctgcg gccccgcgct cagatgctag tagcccattt  21300
ccaagcttga tagggtctct taccagcact cgcaccaccc gcccgcgcct gctgggcgag  21360
gaggagtacc taaacaactc gctgctgcag ccgcagcgcg aaaaaaacct gcctccggca  21420
tttcccaaca acgggataga gagcctagtg gacaagatga gtagatggaa gacgtacgcg  21480
caggagcaca gggacgtgcc aggcccgcgc ccgcccaccc gtcgtcaaag gcacgaccgt  21540
cagcggggtc tggtgtggga ggacgatgac tcggcagacg acagcagcgt cctggatttg  21600
ggagggagtg gcaacccgtt tgcgcacctt cgcccaggc  tggggagaat gttttaaaaa  21660
aaaaaaagca tgatgcaaaa taaaaaactc accaaggcca tggcaccgag cgttggtttt  21720
cttgtattcc ccttagtatg cggcgcgcgg cgatgtatga ggaaggtcct cctccctcct  21780
acgagagtgt ggtgagcgcg gcgccagtgg cggcggcgct gggttctccc ttcgatgctc  21840
ccctggaccc gccgtttgtg cctccgcggt acctgcggcc taccgggggg agaaacagca  21900
tccgttactc tgagttggca ccctattcg  acaccacccg tgtgtacctg gtggacaaca  21960
agtcaacgga tgtggcatcc ctgaactacc agaacgacca cagcaacttt ctgaccacgg  22020
tcattcaaaa caatgactac agcccggggg aggcaagcac acagaccatc aatcttgacg  22080
accggtcgca ctgggcggc  gacctgaaaa ccatcctgca taccaacatg ccaaatgtga  22140
acgagttcat gtttaccaat aagtttaagg cgcgggtgat ggtgtcgcgc ttgcctacta  22200
aggacaatca ggtggagctg aaatacgagt gggtggagtt cacgctgccc gagggcaact  22260
actccgagac catgaccata gacttatga  acaacgcgat cgtgggagcc tacttgaaag  22320
tgggcagaca gaacgggagtt ctggaaagcg acatcggggt aaagtttgac acccgcaact  22380
tcagactggg gtttgacccc gtcactggtc ttgtcatgcc tggggtatat acaaacgaag  22440
ccttccatcg agacatcatt ttgctgccag gatgcgggt  ggacttcacc cacagccgcc  22500
tgagcaactt gttgggcatc cgcaagcggc aaccctttca ggagggcttt aggatcacct  22560
acgatgatct ggagggtggt aacattcccg cactgttgga tgtggacgcc taccaggcga  22620
gcttgaaaga tgacaccgaa cagggcgggg gtggcgcagg cggcagcaac agcagtggca  22680
gcggcgcgga agagaactcc aacgcggcag ccgcggcaat gcagccggtg gaggacatga  22740
acgatcatgc cattcgcggc gacacctttg ccacacgggc tgaggagaag cgcgctgagg  22800
ccgaagcagc ggccgaagct gccgcccccg ctgcgcaacc cgaggtcgag aagcctcaga  22860
agaaccggt  gatcaaaccc ctgacagagg acagcaagaa acgcagttac aacctaataa  22920
gcaatgacag caccttcacc cagtaccgca gctggtacct tgcatacaac tacggcgacc  22980
ctcagaccgg aatccgctca tggacctgc  tttgcactcc tgacgtaacc tgcggctcgg  23040
agcaggtcta ctggtcgttg ccagacatga tgcaagaccc cgtgaccttc cgctccacgc  23100
gccagatcag caactttccg gtggtgggcg ccgagctgtt gccgtgcac  tccaagagct  23160
tctacaacga ccaggccgtc tactcccaac tcatccgcca gtttacctct ctgacccacg  23220
tgttcaatcg ctttcccgag aaccagattt tggcgcgccc gccagccccc accatcacca  23280
ccgtcagtga aaacgttcct gctctcacag atcacggagc gctaccgctg cgcaacagca  23340
tcggaggagt ccagcgagtg accattactg acgccagacg ccgcacctgc ccctacgttt  23400
acaaggccct gggcatagtc tcgccgcgcg tcctatcgag ccgcactttt tgagcaagca  23460
tgtccatcct tatatcgccc agcaataaca caggctgggg cctgcgcttc caagcaaga  23520
tgtttggcgg ggcaagaag cgctccgacc aacacccagt ggcggcactac  23580
gcgcgcc tg gggcgcgcac aaacgcggcc gcactgggcg caccaccgtc gatgacgcca  23640
tcgacgcggt ggtggaggag gcgcgcaact acacgcccac gccgcaccca gtgtccacag  23700
tggacgcggc cattcagacc gtggtgcgcg gagccggcc  ctatgctaaa atgaagagac  23760
ggcggaggca cgtagcacgt cgccaccgcc gccgacccgg cactgccgcc caacgcgcgg  23820
cggcggcct  cgcttaaccgc gcacgtcgca ccggccgacg ggcggccatg cgggccgctc  23880
gaaggctggc cgcgggtatt gtcactgtgc ccccaggtc  caggcgacga gcggccgccg  23940
cagcagccgc ggccattagt gctatgactc agggtcgcag gggcaacgtg tattgggtgc  24000
gcgactcggt tagcggcctg cgcgtgcccg tgcgcacccg cccccgcgc aactagattg  24060
caagaaaaaa ctacttagac tcgtactgtt gtatgtatcc agcggcggcg gcgcgcaacg  24120
aagctatgtc caagcgcaaa atcaaagaag agatgctcca ggtcatcgcg ccggagatct  24180
atggcccccc gaagaaggaa gagcaggatt acaagcccg  aaagctaaag cgggtcaaaa  24240
agaaaagaa agatgatgat gatgaacttg acgacgaggt ggaactgctg cacgctaccg  24300
cgcccaggcg acgggtacag tggaaaggtc gacgcgtaaa acgtgttttg cgaccccgga  24360
ccaccgtagt ctttacgccc ggtgagcgct ccacccgcac ctacaagcgc gtgtatgatg  24420
aggtgtacgg cgacgaggac ctgcttgagc aggccaacga gcgcctcggg gagtttgcct  24480
acggaaagcg gcataaggac atgctggcgt tgcccgtgga cgagggcaac ccaacacctga  24540
gcctaaagcc cgtaacactg cagcaggtgc tgcccgcgct tgcaccgtcc gaagaaaagc  24600
gcggcctaaa gcgcgagtct ggtgacttgg cacccaccgt gcagctgatg gtacccaagc  24660
gccagcgact ggaagatgtc ttggaaaaaa tgaccgtgga acctgggctg agcccgagg  24720
tccgcgtgcg gccaatcaag caggtggcgc cgggactggg cgtgcagacc gtggacgttc  24780
agatacccac taccagtagc accagtattg ccaccgccac agagggcatg gagacacaaa  24840
cgtcccgggt tgcctcagcg gtgcgcgatg ccgcggtcga ggcggtcgct gcggccgcgt  24900
ccaagacctc tacggaggtg caaacgacc  cgtggatgtt tcgcgtttca gccccccggc  24960
gcccgcgcc  ttcgaggaag tacggcgccg ccagcgcgct actgcccgaa tatgccctac  25020
atccttccat tgcgcctacc cccggctatc gtggctacac ctaccgcccc agaagacgag  25080
caactacccg acgccgaacc accactggaa cccgcccgt  ccgtcgccgt cgccagccga  25140
tgctggcccc gatttccgtg cgcagggtgg ctcgcgaagg aggcaggacc ctggtgctgc  25200
caacagcgcg ctaccacccc agcatcgtttt aaaagccggt ctttgtggtt cttgcagata  25260
tggccctcac ctgccgcctc cgtttccgg  tgccgggatt ccgaggaaga atgcaccgta  25320
ggaggggcat ggccggccac ggcctgacgg gcggcatgcg tcgtgcgcac caccggcggc  25380
ggcgcgcgtc gcaccgtcgc atgcgcggcg gtatcctgcc cctccttatt ccactgatcg  25440
ccgcggcgat tggcgccgtg cccggaattg catccgtggc cttgcaggcg cagagacact  25500
gattaaaaac aagttgcatg tggaaaaatc aaaataaaaa gtctggactc tcacgctcgc  25560
ttggtcctgt aactattttg tagaatgaa  gacatcaact ttgcgtctct ggccccgcga  25620
cacggctcgc gcccgttcat gggaaactgg caagatatcg gcaccagcaa tatgagcggt  25680
ggcgccttca gctgggctc  gctgtggagc ggcattaaaa atttcggttc caccgttaag  25740
```

```
aactatggca gcaaggcctg gaacagcagc acaggccaga tgctgaggga taagttgaaa  25800
gagcaaaatt tccaacaaaa ggtggtagat ggcctggcct ctggcattag cggggtggtg  25860
gacctggcca accaggcagt gcaaaataag attaacagta agcttgatcc ccgccctccc  25920
gtagaggagc ctccaccggc cgtggagaca gtgtctccag aggggcgtgg cgaaaagcgt  25980
ccgcgccccg acagggaaga aactctggtg acgcaaatag acgagcctcc ctcgtacgag  26040
gaggcactaa agcaaggcct gcccaccacc cgtcccatcg cgcccatggc taccggagtg  26100
ctgggccagc acacacccgt aacgctggac ctgcctcccc ccgccgacac ccagcagaaa  26160
cctgtgctgc caggcccgac cgccgttgtt gtaacccgtc ctagccgcgc gtccctgcgc  26220
cgcgccgcca gcggtccgcg atcgttgcgg cccgtagcca gtggcaactg gcaaagcaca  26280
ctgaacagca tcgtgggtct ggggggtgca a tcccgaagc gccgacgatg cttctgatag  26340
ctaacgtgtc gtatgtgtgt catgtatgcg tccatgtcgc cgccagagga gctgctgagc  26400
cgccgcgcgc ccgctttcca agatggctac cccttcgatg atgccgcagt ggtcttacat  26460
gcacatctcg ggccaggacg cctcggagta cctgagcccc gggctggtgc agtttgcccg  26520
cgccaccgag acgtacttca gcctgaataa caagtttaga aacccacgg tggcgcctac  26580
gcacgacgtg accacagacc ggtcccagcg tttgacgctg cggttcatcc ctgtggaccg  26640
tgaggatact gcgtactcgt acaaggcgcg gttcacccta gctgtgggtg ataaccgtgt  26700
gctggacatg gcttccacgt actttgacat ccgcggcgtg ctggacaggg gccctacttt  26760
taagccctac tctggcactg cctacaacgc cctggctccc aagggtgccc caaatcctgc  26820
cgaatgggat gaagctgcta ctgctcttga aataaaccta gaagaagagg acgatgacaa  26880
cgaagacgaa gtagacgagc aagctgagca gcaaaaaact cacgtatttg ggcaggcgcc  26940
ttattctggt ataaatatta caaggagggg tattcaaata ggtgtcgaag gtcaaacacc  27000
taaatatgcc gataaaacat ttcaacctga acctcaaata ggagaatctc agtggtacga  27060
aacagaaatt aatcatgcag ctgggagagt cctaaaaaag actacccaa tgaaaccatg  27120
ttacggttca tatgcaaaac ccacaaatga aaatggaggg caaggcattc ttgtaaagca  27180
acaaaatgga aagctagaaa gtcaagtgga aatgcaattt ttctcaacta ctgaggcagc  27240
cgcaggcaat ggtgataact tgactcctaa agtggtattg tacagtgaag atgtagatat  27300
agaaacccca gacactcata tttcttacat gcccactatt aaggaaggta actcacgaga  27360
actaatgggc caacaatcta tgcccaacag gcctaattac attgcttta gggacaattt  27420
tattggtcta atgtattaca acagcacggg taatatgggt gttctggcgg gccaagcatc  27480
gcagttgaat gctgttgtag attttgcaaga cagaaacaca gagctttcat accagctttt  27540
gcttgattcc attggtgata gaaccaggta ctttttctatg tggaatcagg ctgttgacag  27600
ctatgatcca gatgttagaa ttattgaaaa tcatgaact gaagatgaac ttccaaatta  27660
ctgcttttcca ctgggaggtg tgattaatac agagactctt accaaggtaa aacctaaaac  27720
aggtcaggaa aatggatggg aaaaagatgc tacagaattt tcagataaaa atgaaataag  27780
agttggaaat aattttgcca tggaaatcaa tctaaatgcc aacctgtgga gaaatttcct  27840
gtactccaac atagcgctgt atttgcccga caagctaaag tacagtcctt ccaacgtaaa  27900
aatttctgat aacccaaaca cctacgacta catgaacaag cgagtggtgg ctcccgggct  27960
agtggactgc tacattaacc ttggagcacg ctggtccctt gactatatgg acaacgtcaa  28020
cccattaac caccaccgca atgctgcct gcgctacctc tcaatgttgc tgggcaatgg  28080
tcgctatgtg cccttccaca tccaggtgcc tcagaagttc tttgccatta aaaacctcct  28140
tctcctgccg ggctcataca cctacgagtg gaacttcagg aaggatgtta acatggttct  28200
gcagagctcc ctaggaaatg acctaagggt tgacggagcc agcattaagt ttgatagcat  28260
ttgccttac gccaccttct tccccatggc ccacaacacc gcctccacgc ttgaggccat  28320
gcttagaaac gacaccaacg accagtcctt taacgactat ctctccgccg ccaacatgct  28380
ctacccttata cccgccaacg ctaccaacgt gcccatatcc atcccctccc gcaactgggc  28440
ggctttccgc ggctgggcct tcacgcgcct taagactaag gaaacccat cactgggctc  28500
gggctacgac ccttattaca cctactctgg ctctatacca tacctagatg gaacctttta  28560
cctcaaccac acctttaaga aggtggccat taccctttgac tcttctgtca gctggcctgg  28620
caatgaccgc ctgcttaccc ccaacgagtt tgaaattaag cgctcagttg acggggaggg  28680
ttacaacgtt gcccagtgta acatgaccaa agactggttc ctggtacaaa tgctagctaa  28740
ctataacatt ggctaccagg gcttctatat cccagagagc tacaaggacc gcatgtactc  28800
cttctttaga aacttccagc ccatgagccg tcaggtggtg gatgatacta aatacaagga  28860
ctaccaacag gtgggcatcc tacaccaaca caacaactct ggatttgttg gctaccttgc  28920
ccccaccatg cgcgaaggac aggcctaccc tgctaacttc ccctatcgc ttataggcaa  28980
gaccgcagtt gacagcatta cccagaaaaa gtttcttttgc gatcgcaccc tttggcgcat  29040
cccattctcc agtaacttta tgtccatggg cgcactcaca gacctgggcc aaaaccttct  29100
ctacgccaac tccgcccacg cgctagacat gacttttgag gtggatccca tggacgagcc  29160
caccccttctt tatgtttttgt ttgaagtctt tgacgtggtc cgtgtgcacc agccgcaccg  29220
cggcgtcatc gaaaccgtgt acctgcgcac gccctttctcg gccggcaacg ccacaacata  29280
aagaagcaag caacatcaac aacagctgcc gccatgggct ccagtgagca ggaactgaaa  29340
gccattgtca aagatcttgg ttgtgggcca tatttttttgg gcacctatga caagcgcttt  29400
ccaggctttg tttctccaca caagctcgcc tgcgccatag tcaatacggc cggtcgcgag  29460
actggggcg tacactggat ggccttttgcc tggaacccgc actcaaaaac atgtacctc  29520
tttgagccct ttggcttttc tgaccagcga ctcaagcagg tttaccagtt tgagtacgag  29580
tcactcctgc gccgtagcgc cattgcttct tccccccgacc gctgctataac gctgaaaag  29640
tccacccaaa gcgtacaggg gcccaactcg gccgcctgtg gactattctg ctgcatgttt  29700
ctccacgcct tgccaactg gccccaaact cccatggatc acaaccccac catgaacctt  29760
attaccgggg tacccaactc catgctcaac agtccccagg tacagcccac cctgcgtcgc  29820
aaccaggaac agctctacag cttcctggag cgccactcc cctacttccg cagccacgat  29880
gcgcagatta ggagcgccac ttctttttgt cacttgaaaa acatgtaaaa ataatgtact  29940
agagacactt tcaataaagg caaatgcttt tatttgtaca ctctcgggtg attatttacc  30000
cccaccctt ccgtctgcgc cgtttaaaaa tcaaggggt tctgccgcgc atcgctatgc  30060
gccactggca gggacacgtt gcgatactgg tgtttagtgc tccacttaaa ctcaggcaca  30120
accatcgcag gaagttttca tccacaggc tgcgaccat caccaacgcg  30180
tttagcaggt cgggcgccga tatcttgaag tcgcagttgg ggcctccgcc ctgcgcgcgc  30240
gagttgcgat acacagggtt gcagcactgg aacactatca gcgccgggtg gtgcacgctg  30300
gccagcacgc tcttgtcgga gatcagatcc gcgtccaggt cctccgcgtt gctcaggcgc  30360
aacggagtca actttggtag ctgccttccc aaaaagggcg cgtgcccagg ctttgagttg  30420
cactcgcacc gtagtggcat caaaggtgac ccgtgcccgg tctgggcgtt aggatacagc  30480
```

```
gcctgcataa aagccttgat ctgcttaaaa gccacctgag cctttgcgcc ttcagagaag   30540
aacatgccgc aagacttgcc ggaaaactga ttggccggac aggccgcgtc gtgcacgcag   30600
caccttgcgt cggtgttgga gatctgcacc acatttcggc cccaccggtt cttcacgatc   30660
ttggccttgc tagactgctc cttcagcgcg cgctgcccgt tttcgctcgt cacatccatt   30720
tcaatcacgt gctccttatt tatcataatg cttccgtgta gacacttaag ctcgccttcg   30780
atctcagcgc agcggtgcag ccacaacgcg cagcccgtgg gctcgtgatg cttgtaggtc   30840
acctctgcaa acgactgcag gtacgcctgc aggaatcgcc ccatcatcgt cacaaaggtc   30900
ttgttgctgg tgaaggtcag ctgcaacccg cggtgctcct cgttcagcca ggtcttgcat   30960
acggccgcca gagcttccac ttggtcaggc agtagtttga agttcgcctt tagatcgtta   31020
tccacgtggt acttgtccat cagcgcgcgc gcagcctcca tgcccttctc ccacgcagac   31080
acgatcggca cactcagcgg gttcatcacc gtaatttcac tttccgcttc gctgggctct   31140
tcctcttcct cttgcgtccg cataccacgc gccactgggt cgtcttcatt cagccgccgc   31200
actgtgcgct tacctccttt gccatgcttg attagcaccg gtgggttgct gaaacccacc   31260
atttgtagcg ccacatcttc tcttcttcc tcgctgtcca cgattaccctc tggtgatggc   31320
gggcgctcgg gcttgggaga agggcgcttc ttttcttct tgggcgcaat ggccaaatcc   31380
gccgccgagg tcgatggccg cgggctgggt gtgcgcggca ccagcgcgtc ttgtgatgag   31440
tcttcctcgt cctcggactc gatacgccgc ctcatccgct tttttggggg cgcccgggga   31500
ggcggcggcg acggggacgg ggacgacacg tcctccatgg ttgggggacg tcgcgccgca   31560
ccgcgtccgc gctcggggt ggtttcgcgc tgctcctctt cccgactggc catttccttc   31620
tcctataggc agaaaaagat catggagtca gtcgagaaga aggacagcct aaccgccccc   31680
tctgagttcg ccaccaccgc ctccaccgat gccgccaacg cgcctaccac cttccccgtc   31740
gaggcacccc cgcttgagga ggaggaagtg attatcgaag aggacccagg ttttgtaagc   31800
gaagacgacg aggaccgctc agtaccaaca gaggataaaa agcaagacca ggacaacgca   31860
gaggcaaacg aggaacaagt cgggcggggg gacgaaaggc atggcgacta cctagatgtg   31920
ggagacgacg tgctgttgaa gcatctgcag cgccagtgcg ccattatctg cgacgcgttg   31980
caagagcgca gcgatgtgcc cctcgccata gcggatgtca gccttgccta cgaacgccac   32040
ctattctcac cgcgcgtacc ccccaaacgc caagaaaacg gcacatgcga gcccaacccg   32100
cgcctcaact tctaccccgt atttgccgtg ccagaggtgc ttgccaccta tcacatcttt   32160
ttccaaaact gcaagatacc cctatcctgc cgtgccaacc gcagccgagc ggacaagcag   32220
ctggccttgc ggcagggcgc tgtcatacct gatatcgcct cgctcaacga agtgccaaaa   32280
atctttgagg gtcttggacg cgacgagaag cgcgcggcaa acgctctgca acaggaaaac   32340
agcgaaaatg aaagtcactc tggagtgttg gtggaactcg agggtgacaa cgcgcgccta   32400
gccgtactaa aacgcagcat cgaggtcacc cactttgcct acccggcact taacctaccc   32460
cccaaggtca tgagcacagt catgagtgag ctgatcgtgc gccgtgcgca gccccctggag   32520
agggatgcaa atttgcaaga acaaacagag gagggcctac ccgcagttgg cgacgagcag   32580
ctagcgcgct ggcttcaaac gcgcgagcct gccgacttgg aggagcgacg caaactaatg   32640
atggccgcag tgctcgttac cgtggagctt gagtgcatgc agcggttctt tgctgacccg   32700
gagatgcagc gcaagctaga ggaaacattg cactacacct ttcgacaggg ctacgtacgc   32760
caggcctgca gatctccaa cgtggagctc tgcaacctgg tctcctacct tggaattttg   32820
cacgaaaacc gccttgggca aaacgtgctt cattccacgc tcaagggcga ggcgcgccgc   32880
gactacgtcc gcgactgcgt ttacttattt ctatgctaca cctggcagac ggccatgggc   32940
gtttggcagc agtgcttgga ggagtgcaac ctcaaggagc tgcagaaact gctaaagcaa   33000
aacttgaagg acctatggac ggccttcaac gagcgctccg tgccgcgca cctggcggac   33060
atcattttcc ccgaacgcct gcttaaaacc ctgcaacagg gtctgccaga cttcaccagt   33120
caaagcatgt tgcagaactt taggaacttt atcctagagc gctcaggaat cttgcccgcc   33180
acctgctgtg cacttcctag cgactttgtg cccattaagt accgcgaatg ccctccgccg   33240
ctttgggcc actgctacct tctgcagcta gccaactaca ttgcctacca ctctgacata   33300
atggaagacg tgagcggtga cggtctactg gagtgtcact gtcgctgcaa cctatgcacc   33360
ccgcaccgct ccctggtttg caattcgcag ctgcttaacg aaagtcaaat tatcggtacc   33420
tttgagctgc agggtcctc gcctgacgaa aagtccgcgg ctccggggtt gaaactcact   33480
ccgggctgt ggacgtcggc ttaccttcgc aaatttgtac ctgaggacta ccacgccac   33540
gagattaggt tctacgaaga ccaatcccgc ccgcctaatg cggagcttac cgcctgcgtc   33600
attcccagg gccacattct tggccaattg caagccatca acaaagcccg ccaagagttt   33660
ctgctacgaa agggacgggg ggtttacttg daccccagt ccggcgagga gctcaaccca   33720
atccccccgc cgccgcagcc ctatcagcag cagccgcggg cccttgcttc ccaggatggc   33780
acccaaaaag aagctgcagc tgccgccgcc acccacggac gaggaggaat actgggacag   33840
tcaggcagag gaggttttgg acgaggagga ggaggacatg atggaagact gggagagcct   33900
agacgaggaa gcttccgagg tcgaagaggt gtcagacgaa acaccgtcac cctcggtcgc   33960
attccctcg ccggcgcccc agaaatcggc aaccggttcc agcatggcta caacctccgc   34020
tcctcaggcc ccgccgcggcac tgccgcttcg ccgacccaac cgtagatggg acaccactgg   34080
aaccagggcc ggtaagtcca agcagccgcc gccgttagcc caagagcaac aacagcgcca   34140
aggctaccgc tcatgcgcg ggcacaagaa cgccatagtt gcttgcttgc aagactgtgg   34200
gggcaacatc tccttcgccc gccgctttct tctctaccat cacggcgtgg ccttccccg   34260
taacatcctg cattactacc gtcatctcta cagccatc tgcaccggcg gcagcggcag   34320
caacagcagc ggccacacag aagcaaaggc gaccggatag caagactctg acaaagccca   34380
agaaatccac agcggcggca gcagcaggag gaggagcgct cgtctgcgcg cccaacgaac   34440
ccgtatcgac ccgcgagctt agaaacagga tttttcccac tctgtatgct atatttcaac   34500
agagcagggg ccaagaacaa gagctgaaaa taaaaaacag gtctctgcga tccctcaccc   34560
gcagctgcct gtatcacaaa agcgaagatc agcttcggc cacgctggaa gacgcggagg   34620
ctctcttcag taaatactgc gcgctgactc ttaaggacta gtttcgcgcc ctttctcaaa   34680
tttaagcgcg aaaactacgt catctccagc ggccacaccc ggcgcagca cctgttgtca   34740
gcgccattat gagcaaggaa attcccacgc cctacatgtg gagttaccag ccacaaatgg   34800
gacttgcggc tggagctgcc caagactact caacccgaat aaactacatg agcgcgggac   34860
ccacatgat atcccgggtc aacggaatac gcgccaccg cttcctgaac   34920
aggcggctat taccaccaca cctcgtaata accttaatcc ccgtagttgg cccgctgccc   34980
tggtgtacca ggaaagtccc gctcccacca ctgtggtact tcccagagac gcccaggccg   35040
aagttcagat gactaactca ggggcgcagc ttgcgggcgg ctttcgtcac agggtgcggt   35100
cgcccgggca gggtataact cacctgacaa tcagagggcg aggtattcag ctcaacgacg   35160
agtcggtgag ctcctcgctt ggtctccgtc cggacgggac atttcagatc ggcggcgccg   35220
```

```
gccgctcttc attcacgcct cgtcaggcaa tcctaactct gcagacctcg tcctctgagc   35280
cgcgctctgg aggcattgga actctgcaat ttattgagga gtttgtgcca tcggtctact   35340
ttaacccctt ctcgggacct cccggccact atccggatca atttattcct aactttgacg   35400
cggtaaagga ctcggcggac ggctacgact gaatgttaag tggagaggca gagcaactgc   35460
gcctgaaaca cctggtccac tgtcgccgcc acaagtgctt tgcccgcgac tccggtgagt   35520
tttgctactt tgaattgccc gaggatcata tcgagggccc ggcgcacggc gtccggctta   35580
ccgcccaggg agagcttgcc cgtagcctga ttcgggagtt tacccagcgc ccctgctag    35640
ttgagcggga caggggaccc tgtgttctca ctgtgatttg caactgtcct aaccctggat   35700
tacatcaaga tcctctagtt aatgtcaggt cgcctaagtc gattaactag agtacccggg   35760
gatcttattc cctttaacta ataaaaaaaa ataataaagc atcacttact taaaatcagt   35820
tagcaaattt ctgtccagtt tattcagcag cacctccttg ccctcctccc agctctggta   35880
ttgcagcttc ctcctggctg caaactttct ccacaatcta aatggaatgt cagtttcctc   35940
ctgttcctgt ccatccgcac ccactatctt catgttgttg cagatgaagc gcgcaagacc   36000
gtctgaagat accttcaacc ccgtgtatcc atatgcacg agaaccggtc ctccaactgt    36060
gccttttctt actcctccct ttgtatcccc caatgggttt caagagagtc ccctcggggt   36120
actctctttg cgcctatccg aacctctagt tacctccaat ggcatgcttg cgctcaaaat   36180
gggcaacggc ctctctctgg acgaggccgg caaccttacc tcccaaaatg taaccactgt   36240
gagcccacct ctcaaaaaaa ccaagtcaaa cataaacctg aaaatatctg caccccctcac  36300
agttacctca gaagccctaa ctgtggctgc cgccgcacct ctaatggtcg cgggcaacac   36360
actcaccatg caatcacagg cccgctaac cgtgcacgac tccaaactta gcattgccac    36420
ccaaggaccc ctcacagtgt cagaaggaaa gctagccctg caaacatcag gccccctcac   36480
caccaccgat agcagtaccc ttactatcac tgcctcaccc cctctaacta ctgccactgg   36540
tagcttgggc attgacttga aagagcccat ttatacacaa aatggaaaac taggactaaa    36600
gtacgggct  cctttgcatg taacagacga cctaaacact ttgaccgtag caactggtcc    36660
aggtgtgact attaataata cttccttgca aactaaagtt actggagcct tgggttttga   36720
ttcacaaggc aatatgcaac ttaatgtagc aggaggacta aggattgatt ctcaaaacag   36780
acgccttata cttgatgtta gttatccgtt tgatgctcaa aaccaactaa atctaagact   36840
aggacaggc cctcttttta taaactcagc ccacaacttg gatattaact acaacaaagg     36900
cctttacttg tttacagctt caaacaattc caaaaagctt gaggttaacc taagcactgc   36960
caagggggttg atgtttgacg ctacagccat agccattaat gcaggagtg ggcttgaatt    37020
tggttcacct aatgcaccaa acacaaatcc cctcaaaaca aaaattggcc atggcctaga   37080
atttgattca aacaaggcta tggttcctaa actaggaact ggcctagtt ttgcagcac     37140
aggtgccatt acagtaggaa acaaaaataa tgataagcta actttgtgga ccacaccagc   37200
tccatctcct aactgtagac taaatgcaga gaaagatgct aaactcactt tggtcttaac   37260
aaaatgtggc agtcaaatac ttgctacagt ttcagttttg gctgttaaag gcagtttgcc   37320
tccaatatct ggaacagttc aaagtgctca tcttattata agatttgacg aaaatggagt   37380
gctactaaac aattccttcc tggacccaga atattggaac tttagaaatg gagatcttac   37440
tgaaggcaca gcctatacaa acgctgttgg atttatgcct aacctatcag cttatccaaa   37500
atctcacggt aaaactgcca aaagtaacat tgtcagtcaa gtttacttaa acggagcaa    37560
aactaaacct gtaacactaa ccattacact aaacggtaca caggaaacag gagcacaac    37620
tccaagtgca tactctatgt cattttcatg ggactggtct ggccacaact acattaatga   37680
aatatttgcc acatcctctt cacttttttc atacattgcc caagaataaa gaatcgtttg   37740
tgttatgttt caacgtgttt attttttcaat tgcagaaaat ttcaagtcat ttttcattca   37800
gtagtatagc cccaccacca catagcttat acagatcacc gtaccttaat caaactcaca   37860
gaacccctagt attcaacctg ccacctcct cccaacacac agagtacaca gtcctttctc    37920
cccggctggc cttaaaaagc atcatatcat gggtaacaga catattctta ggtgttatat   37980
tccacacgtt ttcctgtcga gccaaacgct catcagtgat attaataaac tccccgggca   38040
gctcacttaa gttcatgtcg ctgtccagct gctgagccaa aggctgctgt ccaacttgcg   38100
gttgcttaac gggcggcgaa ggagaagtcc acgcctacat ggggtagag tcataatcgt     38160
gcatcaggat agggcggtgg tgctgcagca gcgcgcgaat aaactgctgc cgccgccgct   38220
ccgtcctgca ggaatacaac atggcagtgg tctcctcagc gatgattcgc accgcccgca   38280
gcataaggcg ccttgtcctc cgggcacagc agcgcaccct gatctcactt aaatcagcac   38340
agtaactgca gcacagcacc acaatattgt tcaaaatccc acagtgcaag gcgctgtatc    38400
caaagctcat ggcggggacc acagaaccca cgtggccatc ataccacaag cgcaggtaga   38460
ttaagtggcg acccctcata aacacgctgg acataaacat tacctctttt ggcatgttgt   38520
aattcaccac ctcccggtac catataaacc tctgattaaa catggcgcca tccaccacca   38580
tcctaaacca gctggccaaa acctgcccgc cggctataca ctgcaggaa ccgggactgg     38640
aacaatgaca gtggagagcc caggactcgt aaccatggat catcatgctc gtcatgtatt   38700
caatgttggc acaacacagg cacacgtgca tacacttcct caggattaca agctcctccc   38760
gcgttagaac catatcccag ggaacaaccc attcctgaat cagcgtaaat cccacactgg   38820
agggaagacc tcgcacgtaa ctcacgttgt gcattgtcaa agtgttacat tcgggcagca   38880
gcggatgatc ctccagtatg gtagcgcggg tttctgtctc aaaaggaggt agacgatccc   38940
tactgtacgg agtcgccga gacaaccgag atcgtgttgc tcgtagtgtc atgccaaatg     39000
gaacgccgga cgtagtcata tttcctgaag caaaaccagg tgcgggcgtg acaaacagat    39060
ctgcgtctcc ggtctcgccg cttagatcgc tctgtgtagt agttgtagta tatccactct   39120
ctcaaagcat ccaggcgccc cctgcttcg ggttctatgt aaactccttc atgcgccgct     39180
gccctgataa catccaccac cgcagaataa gccacaccca gccaacctac acattcgttc   39240
tgcgagtcac acacgggagg agcgggaaga gctggaagaa ccatgttttt tttttattc    39300
caaaagatta tccaaaacct caaaatgaag atcattaag tgaacgcgct ccctccggt      39360
ggcgtggtca aactctacag ccaaagaaca gataatggca tttgtaagat gttgcacaat   39420
ggcttccaaa aggcaaacgg ccctcacgtc caagtggacg taaaggctaa acccttcagg   39480
gtgaatctcc tctataaaca ttccagcacc ttcaaccatg cccaaataat tctcatctcg   39540
ccaccttctc aatatatctc taagcaaatc ccgaatatta agtccggcca ttgtaaaaat   39600
ctgctccaga gcgccctcca cctcagcct caagcagcga atcatgattg caaaaattca   39660
ggttcctcac agacctgtat aagattcaaa agcggaacat taacaaaaat accgcgatcc   39720
cgtaggtccc ttcgcagggc cagctgaaca taatcgtgca ggtctgcacg gaccagcgcg   39780
gccacttccc cgccaggaac catgacaaaa gaacccacac tgattatgac acgcatactc   39840
ggagctatgc taaccagcgt agcccgatg taagcttgtt gcatgggcgg cgatataaaa    39900
tgcaaggtgc tgctcaaaaa atcaggcaaa gcctcgcgca aaaagaaag cacatcgtag     39960
```

-continued

```
tcatgctcat gcagataaag gcaggtaagc tccggaacca ccacagaaaa agacaccatt    40020
tttctctcaa acatgtctgc gggttttctg ataaacacaa aataaaataa caaaaaaaca    40080
tttaaacatt agaagcctgt cttcaacag gaaaaacaac cctataagc ataagacgga     40140
ctacggccat gccggcgtga ccgtaaaaaa actggtcacc gtgattaaaa agcaccaccg    40200
acagctcctc ggtcatgtcc ggagtcataa tgtaagactc ggtaaacaca tcaggttgat    40260
tcacatcggt cagtgctaaa aagcgaccga aatagcccgg gggaatacat acccgcaggc    40320
gtagagacaa cattacagcc cccataggag gtataacaaa attaatagga gagaaaaaca    40380
cataaacacc tgaaaaaccc tcctgcctag gcaaaatagc accctcccgc tccagaacaa    40440
catacagcgc ttccacagcg gcagccataa cagtcagcct taccagtaaa aaagaaaacc    40500
tattaaaaaa acaccactcg acacggcacc agctcaatca gtcacagtgt aaaaaagggc    40560
caagtgcaga gcgagtatat ataggactaa aaaatgacgt aacggttaaa gtccacaaaa    40620
aacacccaga aaaccgcacg cgaacctacg cccagaaacg aaagccaaaa acccacaac    40680
ttcctcaaat cgtcacttcc gttttcccac gttacgtcac ttcccatttt aagaaaaacta   40740
caattcccaa cacatacaag ttactccgcc ctaaaaccta cgtcacccgc cccgttccca   40800
cgccccgcgc cacgtcacaa actccacccc ctcattatca tattggcttc aatccaaaat    40860
aaggta                                                              40866
```

```
SEQ ID NO: 12           moltype = AA   length = 1285
FEATURE                 Location/Qualifiers
REGION                  1..1285
                        note = SARS-CoV2 spike mutant (p68)
source                  1..1285
                        mol_type = protein
                        organism = synthetic construct
SEQUENCE: 12
MLLLPFQLLA VLFPGGNSEY PYDVPDYAGG GSGGGSGGGS GGGSQCVNLT TRTQLPPAYT    60
NSFTRGVYYP DKVFRSSVLH STQDLFLPFF SNVTWFHAIH VSGTNGTKRF DNPVLPFNDG   120
VYFASTEKSN IIRGWIFGTT LDSKTQSLLI VNNATNVVIK VCEFQFCNDP FLGVYYHKNN   180
KSWMESEFRV YSSANNCTFE YVSQPFLMDL EGKQGNFKNL REFVFKNIDG YFKIYSKHTP   240
INLVRDLPQG FSALEPLVDL PIGINITRFQ TLLALHRSYL TPGDSSSGWT AGAAAYYVGY   300
LQPRTFLLKY NENGTITDAV DCALDPLSET KCTLKSFTVE KGIYQTSNFR VQPTESIVRF   360
PNITNLCPFG EVFNATRFAS VYAWNRKRIS NCVADYSVLY NSASFSTFKC YGVSPTKLND   420
LCFTNVYADS FVIRGDEVRQ IAPGQTGKIA DYNYKLPDDF TGCVIAWNSN NLDSKVGGNY   480
NYLYRLFRKS NLKPFERDIS TEIYQAGSTP CNGVEGFNCY FPLQSYGFQP TNGVGYQPYR   540
VVVLSFELLH APATVCGPKK STNLVKNKCV NFNFNGLTGT GVLTESNKKF LPFQQFGRDI   600
ADTTDAVRDP QTLEILDITP CSFGGVSVIT PGTNTSNQVA VLYQDVNCTE VPVAIHADQL   660
TPTWRVYSTG SNVFQTRAGC LIGAEHVNNS YECDIPIGAG ICASYQTQTN SPSAAGSVAS   720
QSIIAYTMSL GAENSVAYSN NSIAIPTNFT ISVTTEILPV SMTKTSVDCT MYICGDSTEC   780
SNLLLQYGSF CTQLNRALTG IAVEQDKNTQ EVFAQVKQIY KTPPIKDFGG FNFSQILPDP   840
SKPSKRSFIE DLLFNKVTLA DAGFIKQYGD CLGDIAARDL ICAQKFNGLT VLPPLLTDEM   900
IAQYTSALLA GTITSGWTFG AGAALQIPFA MQMAYRFNGI GVTQNVLYEN QKLIANQFNS   960
AIGKIQDSLS STASALGKLQ DVVNQNAQAL NTLVKQLSSN FGAISSVLND ILSRLDKVEA  1020
EVQIDRLITG RLQSLQTYVT QQLIRAAEIR ASANLAATKM SECVLGQSKR VDFCGKGYHL  1080
MSFPQSAPHG VVFLHVTYVP AQEKNFTTAP AICHDGKAHF PREGVFVSNG THWFVTQRNF  1140
YEPQIITTDN TFVSGNCDVV IGIVNNTVYD PLQPELDSFK EELDKYFKNH TSPDVDLGDI  1200
SGINASVVNI QKEIDRLNEV AKNLNESLID LQELGKYEQY IKWPWYIWLG FIAGLIAIVM  1260
VTIMLCCMTS CCSCLKKHCS YQDIL                                        1285
```

```
SEQ ID NO: 13           moltype = DNA   length = 40827
FEATURE                 Location/Qualifiers
misc_feature            1..40827
                        note = p68 vector sequence
source                  1..40827
                        mol_type = other DNA
                        organism = synthetic construct
SEQUENCE: 13
tattattgat gatgttaatt aacatgcatg gatcctacgt ctcgaccgat gcccttgaga     60
gccttcaacc cagtcagctc cttccggtgg gcgcggggca tgactatcgt cgccgcactt    120
atgactgtct tctttatcat gcaactcgta ggacaggtgc cggcagcgct ctgggtcatt    180
ttcggcgagg accgctttcg ctggagcgcg acgatgatcg gcctgtcgct gcgggtattc    240
ggaatcttgc acgccctcgc tcaagccttc gtcactggtc ccgccaccaa acgtttcggc    300
gagaagcagg ccattatcgc cggcatggcg gccgacgcgc tgggctacgt cttgctggcg    360
ttcgcgacgc gaggctggat ggccttcccc attatgattc ttctcgcttc cggcggcatc    420
gggatgcccg cgttgcaggc catgctgtcc aggcaggtag atgacgacca tcagggacag    480
cttcaaggat cgctcgcggc tcttaccagc ctaacttcga tcattggacc gctgatcgtc    540
acggcgattt atgccgcctc ggcgagcaca tggaacgggt tggcatggat tgtaggcgcc    600
gccctatacc ttgtctgcct ccccgcgttg cgtcgcggtg catggagccg gccacctcg     660
acctgaatgg aagccggcgg cacctcgcta acggattcac cactccaaga attggagcca    720
atcaattctt gcggagaact gtgaatgcgc aaaccaaccc ttggcagaac atatccatcg    780
cgtccgccat ctccagcagc cgcacgcggc gcatctcggg cagcgttggg tcctggccac    840
gggtgcgcat gatcgtgctc ctgtcgttga ggacccggct aggctggcgg ggttgcctta    900
ctggttagca gaatgaatca ccgatacgcg agcgaacgtg aagcgactgc tgctgcaaaa    960
cgtctgcgac ctgagcaaca acatgaatgg tcttcggttt ccgtgtttcg taaagtctgg   1020
aaagcggaa gtcagcgccc tgcaccatta gcacattacg gatgtctgct ggctaccctg   1080
ggctaccctg tggaacacct acatctgtat taacgaagcg ctggcattga ccctgagtgt   1140
ttttttctctg gtcccgccgc atccatacg ccagttgttt accctcacaa cgttccagta   1200
accgggcatg ttcatcatca gtaacccgta tcgtgagcat cctctctcgt ttcatcggta   1260
tcattacccc catgaacaga aatccccctt acacggaggc atcagtgacc aaacaggaaa   1320
aaaccgccct taacatggcc cgctttatca gaagccagac attaacgctt ctggagaaac   1380
```

```
tcaacgagct ggacgcggat gaacaggcag acatctgtga atcgcttcac gaccacgctg   1440
atgagcttta ccgcagctgc ctcgcgcgtt tcggtgatga cggtgaaaac ctctgacaca   1500
tgcagctccc ggagacggtc acagcttgtc tgtaagcgga tgccgggagc agacaagccc   1560
gtcagggcgc gtcagcgggt gttggcgggt gtcgggcgc agccatgacc cagtcacgta    1620
gcgatagcgg agtgtatact ggcttaacta tgccgcatca gagcagattg tactgagagt   1680
gcaccatatg cggtgtgaaa taccgcacag atgcgtaagg agaaaatacc gcatcaggcg   1740
ctcttccgct tcctcgctca ctgactcgct gcgctcggtc gttcggctgc ggcgagcggt   1800
atcagctcac tcaaaggcgg taatacggtt atccacagaa tcaggggata acgcaggaaa   1860
gaacatgtga gcaaaaggcc agcaaaaggc caggaaccgt aaaaaggccg cgttgctggc   1920
gttttttccat aggctccgcc cccctgacga gcatcacaaa aatcgacgct caagtcagag   1980
gtggcgaaac ccgacaggac tataaagata ccaggcgttt ccccctggaa gctccctcgt   2040
gcgctctcct gttccgaccc tgccgcttac cggatacctg tccgcctttc tcccttcggg   2100
aagcgtggcg ctttctcata gctcacgctg taggtatctc agttcggtgt aggtcgttcg   2160
ctccaagctg ggctgtgtgc acgaaccccc cgttcagccc gaccgctgcg ccttatccgg   2220
taactatcgt cttgagtcca acccggtaag acacgactta tcgccactgg cagcagccac   2280
tggtaacagg attagcagag cgaggtatgt aggcggtgct acagagttct tgaagtggtg   2340
gcctaactac ggctacacta gaaggacagt atttggtatc tgcgctctgc tgaagccagt   2400
taccttcgga aaaagagttg gtagctcttg atccggcaaa caaaccaccg ctggtagcgg   2460
tggtttttt gtttgcaagc agcagattac gcgcagaaaa aaaggatctc aagaagatcc   2520
tttgatcttt tctacggggt ctgacgctca gtggaacgaa aactcacgtt aagggatttt   2580
ggtcatgaga ttatcaaaaa ggatcttcac ctagatcctt ttaaattaaa aatgaagttt   2640
taaatcaatc taaagtatat atgagtaaac ttggtctgac agttaccaat gcttaatcag   2700
tgaggcacct atctcagcga tctgtctatt tcgttcatcc atagttgcct gactccccgt   2760
cgtgtagata actacgatac gggagggctt accatctggc cccagtgctg caatgatacc   2820
gcgagaccca cgctcaccgg ctccagattt atcagcaata accagccag ccggaagggc   2880
cgagcgcaga agtggtcctg caactttatc cgcctccatc cagtctatta attgttgccg   2940
ggaagctaga gtaagtagtt cgccagttaa tagtttgcgc aacgttgttg ccattgctgc   3000
agccatgaga ttatcaaaaa ggatcttcac ctagatcctt ttcacgtaga aagccagtcc   3060
gcagaaacgt tgctgacccc ggatgaatgt cagctactgg gctatctgga caagggaaaa   3120
cgcaagcgca aagagaaagc aggtagcttg cagtgggctt acatggcgat agctagactg   3180
ggcggtttta tggacagcaa gcgaaccgga attgccagct ggggcgccct ctggtaaggt   3240
tgggaagccc tgcaaagtaa actggatggc tttcttgccg ccaaggatct gatgcgcag    3300
gggatcaagc tctgatcaag agacaggatg aggatcgttt cgcatgattg aacaagatgg   3360
attgcacgca ggttctccgg ccgcttgggt ggagaggcta ttcggctatg actgggcaca   3420
acagacaatc ggctgctctg atgccgccgt gttccggctg tcagcgcagg ggcgcccggt   3480
tcttttttgtc aagaccgacc tgtccggtgc cctgaatgaa ctgcaagacg aggcagcgcg   3540
gctatcgtgg ctggccacga cgggcgttcc ttgcgcagct gtgctcgacg ttgtcactga   3600
agcgggaagg gactggctgc tattgggcga agtgccgggg caggatctcc tgtcatctca   3660
ccttgctcct gccgagaaag tatccatcat ggctgatgca atgcggcggc tgcatacgct   3720
tgatccggct acctgcccat tcgaccacca agcgaaacat cgcatcgagc gagcacgtac   3780
tcggatggaa gccggtcttg tcgatcagga tgatctggac gaagagcatc aggggctcgc   3840
gccagccgaa ctgttcgcca ggctcaaggc gagcatgccc gacggcgagg atctcgtcgt   3900
gacccatggc gatgcctgct tgccgaatat catggtggaa aatggccgct tttctggatt   3960
catcgactgt ggccggctgg gtgtggcgga ccgctatcag acatagcgt tggctacccg    4020
tgatattgct gaagagcttg gcggcgaatg ggctgaccgc ttcctcgtgc tttacggtat   4080
cgccgctccc gattcgcagc gcatcgcctt ctatcgcctt cttgacgagt tcttctgaat   4140
tttgttaaaa tttttgttaa atcagctcat tttttaacca ataggccgaa atcggcaaaa   4200
tcccttataa atcaaaagaa tagaccgaga tagggttgag tgttgttcca gtttggaaca   4260
agagtccact attaaagaac gtggactcca acgtcaaagg gcgaaaaacc gtctatcagg   4320
gcgatggccc actacgtgaa ccatcaccct aatcaagttt ttttggggtcg aggtgccgta   4380
aagcactaaa tcggaaccct aaagggagcc ccgatttag agcttgacgg ggaaagccgg   4440
cgaacgtggc gagaaaggaa gggaagaaag cgaaaggagc gggcgctagg gcgctggcaa   4500
gtgtagcggt cacgctgcgc gtaaccacca cacccgccgc gcttaatgcg ccgctacagg   4560
gcgcgtccta tcgccattca ggatcgaatt aattcttaat taacatcatc aataatatac   4620
cttatttttgg attgaagcca atatgataat gaggggtgg agtttgtgac gtggcgcggg    4680
gcgtgggaac ggggcgggtg acgtagtagt gtggcggaag tgtgatgttg caagtggtgg   4740
ggaacacatg taagcgacgg atgtggcaaa agtgacgttt ttggtgtgcg ccggtgtaca   4800
caggaagtga caattttcgc gcggttttag gcggatgttg tagtaaattt gggcgtaacc   4860
gagtaagatt tggccatttt cgcggtaaaa ctgaataaga ggaagtgaaa tctgaataat   4920
tttgtgttac tcatagcgcg taatactgta atagtaatca attacggggt cattagttca   4980
tagcccatat atggagttcc gcgttacata acttacggta aatggcccgc ctggctgacc   5040
gcccaacgac ccccgcccat tgacgtcaat aatgacgtat gttcccatag taacgccaat   5100
agggactttc cattgacgtc aatgggtgga gtatttacgg taaactgccc acttggcagt   5160
acatcaagtg tatcatatgc caagtacgcc ccctattgac gtcaatgacg gtaaatggcc   5220
cgcctggcat tatgcccagt acatgacctt atgggacttt cctacttggc agtacatcta   5280
cgtattagtc atcgctatta ccatggtgat gcggttttgg cagtacatca atgggcgtgg   5340
atagcggttt gactcacggg gatttccaag tctccacccc attgacgtca atgggagttt   5400
gttttggcac caaaatcaac gggactttcc aaaatgtcgt aacaactccg ccccattgac   5460
gcaaatgggc ggtaggcgtg tacggtggga ggtctatata agcagagctg gtttagtgaa   5520
ccgtcagatc cgctagagat ctggtaccgt cgacgcggcc gctcgagcct aagcttatgc   5580
ttctgcttcc tttccaattg ctggctgttc tctttcctgg aggtaactct gaatatccgt   5640
atgatgtgcc ggattatgcg ggtggaggct ctggaggtgg ctctggtgga ggttccggtg   5700
gcggatctca atgtgtcaac ctcaccacaa ggacacagct ccctcccgca tatacgaata   5760
gctttaccag aggcgtatac tatcctgata aggtcttttag gagctcagta ctgcatagca   5820
ctcaggatct cttcctgccg ttcttcagta atgttacttg gtttcacgcc attcatgttt   5880
ccgggaccaa tggcaccaaa cggttcgata atccagtgct tcccttcaac gatgggtgt    5940
actttgccag cactgaaaaa tctaatataa ttcggggatg gattttcgga accacactcg   6000
attccaagac tcagtccctc ttgatcgtta acaacgctac taatgttgtc attaaggtgt   6060
gtgagtttca gttctgcaac gacccttttcc tgggtgtcta ctaccataaa aataacaaga   6120
```

```
gctggatgga gtccgaattt cgcgtctact caagcgccaa taattgcact tttgagtatg  6180
tgtcccagcc cttttttgatg gatctggagg gaaagcaggg caatttcaaa aatctgagag  6240
aattcgtttt taagaatata gatggatact tcaaaatcta cagcaaacac acacccataa  6300
atcttgtgcg cgatcttccc cagggcttca gcgcgttgga accccttgtt gacttgccca  6360
taggcatcaa cattaccagg ttccaaacgc tgctcgccct ccaccgcacg tacttgacac  6420
ccggggattc cagctccgga tggaccgccg cgcgccgcagc gtattatgtg gggtacctgc  6480
aacccaggac atttttgctc aagtacaatg agaatgggac catcacagat gcggtagact  6540
gtgcactgga tccactcagc gaaactaaat gtaccctgaa aagctttacc gtggagaaag  6600
gaatctacca aaccagcaac ttcagggtcc agcccactga atccatcgtt agatttccaa  6660
atataactaa tttgtgtcca tttggagagg tgttcaatgc tacaaggttc cgtctgtat  6720
acgcttggaa ccggaagcgc atctcaaatt gcgtggctga ttatagcgtt ctttacaaca  6780
gcgcttcctt ttccacgttc aagtgctatg gtgtatcccc gacaaagctg aatgacttgt  6840
gcttcaccaa tgtgtatgcg gattctttcg ttattcgagg cgatgaagtc agacaaattg  6900
cgcctggcca gaccggaaag attgccgact acaactataa actgccggac gactttactg  6960
gttgcgtgat cgcttggaac agcaataatc ttgatagtaa agttggagga aactacaatt  7020
acctctatag actgttcaga aagagcaact tgaagccatt cgaacgggat atctctacgg  7080
agatctatca agctggcagc acccccctgca atggtgtgga aggctttaat tgttattttc  7140
ctttgcagag ctatgccttc caacctacca acggagtggg ctaccagccc tacagagtgg  7200
tggtgctcag ctttgaactg ctgcatgccc cggccacagt ttgcgggccc aaaaaaagca  7260
cgaatccggt taagaacaaa tgcgtcaact tcaattttaa tggggttgaca ggtacaggcg  7320
tactgaccga atccaacaaa aagttcctgc ctttttcagca gttcgggaga gatatcgccg  7380
acactacaga cgccgtcagg gatccccaaa cactcgaaat tctggacatc acaccttgtt  7440
ccttcggcgg ggtatctgtg attactccgg gcacaaatac cagtaaccag gtagcggtgc  7500
tttaccagga tgtcaactgt acggaagtac ctgtcgctat tcatgcggat caactcactc  7560
ctacctgag agtttattcc actgggtcca acgtgtttca gacccgagcc ggctgcttga  7620
ttggcgcgga acatgttaac aactcctacg aatgtgacat ccctatcgga gctggcatct  7680
gtgcttccta tcaaacgcaa acgaacagcc catctgctgc tggttccgta gcctctcaaa  7740
gcatcatcgc ttatactatg tccttggggg ctgaaaacag cgttgcctat tccaacaata  7800
gcatcgctat ccctaccaac tttaccattt ccgtgaccac agaaatactg ccggtgagca  7860
tgacaaagac ttctgtgac tgtaccatgt atatatgcgg cgatagcaca gagtgttcta  7920
atttgctgct gcagtacggc agcttttgta cccaactcaa cagagcactt acagggattg  7980
ccgtcgagca ggataaaaac acccaggagg ttttcgccca ggttaagcag atctacaaga  8040
ccccaccaat caaggatttc ggcggcttca attttttccca gatactgccc gatccttcca  8100
agccatccaa aaggagcttt atagaggtact tgctgttcaa caaggtgact ctggccgagg  8160
ctggctttat caagcaatat ggcgattgcc tggggggatat tgcctgctagg gaccttatct  8220
gcgctcaaaa attcaacggt cttaccgttc tccccggccct gctcaccgac gagatgatag  8280
cccagtacac gagcgcactt ttggccggca cgataaccag cggctggaca ttcggtgccg  8340
gggccgctct tcaaatcccc tttgccatgc agatggccta cagatttaat gggataggcg  8400
tgacaaaaaa tgtcttgtat gaaaatcaga aactgattgc aaaccagttt aatagcgcta  8460
ttggcaagat ccaagatagc ctttcctcca ccgcatccgc tctgggaaag ttgcaagacg  8520
tcgtgaatca aaacgcccaa gctctgaata ccctcgtgaa gcagcttagc tccaactttg  8580
gcgcgatatc ctccgtgctg aacgatatcc tgtccagatt ggacaaggtc gaggcagaag  8640
tccagatcga tagattgata accggcagac tccagtctct gcagacatat tgactcagc  8700
agttgataag agcggccgaa atacgagcgt ctgcaaatct cgcagcaacg aaaatgtcag  8760
agtgtgtatt gggcaaagt aaaagagtag atttctgtgg aaagggttac catctgatgt  8820
cattccccca gtctgcacca catggagtag ttttttttgca tgtgacttat gtgcctgccc  8880
aggagaaaaa tttcaccact gcacctgcga tctgtcatga cggcaaggca catttcccta  8940
gagaaggcgt cttcgtatca aatgaacac actggtttgt aacccaaagg aacttttacg  9000
agccccaaat tataactacc gacaacacct tcgtaagcgg aaactgcgac gtcgttatag  9060
ggatagtcaa taatacggtc tatgacccte ttcagccgga actggactcc ttttaaagaag  9120
aactggataa gtacttcaag aaccatacgt ctccggatgt ggatctcgga gatataagtg  9180
gaatcaacgc aagcgtagta aacattcaga aggagataga ccgactcaat gaggttgcta  9240
aaaacctgaa cgaaagcttg atagacttgc aggagctggg taagtacgaa cagtacatta  9300
agtggccatg gtatatctgg ttgggcttca tagcaggact catagctatc gtcatggtga  9360
caataatgct ttgttgtatg accagctgtt gttcttgtct gaagaagcac tgctcatatc  9420
aggacatcct gtgagatatc cgatccaccg gatctagata actgatcata atcagccata  9480
ccacatttgt agaggtttta cttgctttaa aaaacctccc acacctcccc ctgaacctga  9540
aacataaaat gaatgcaatt gttgttgtta acttgtttat tgcagcttat aatggttaca  9600
aataaagcaa tagcatcaca aatttcacaa ataaagcatt ttttttcactg cattctagtt  9660
gtggtttgtc caaactcatc aatgtatctt aggtttagtg aaccgtcaga tccgctagcg  9720
ttacataact tacggtaaat ggcccgcctg gctgaccgcc caacgacccc cgcccattga  9780
cgtcaataat gacgtatgtt cccatagtaa cgccaatagg gactttccat tgacgtcaat  9840
gggtggagta tttacggtaa actgcccact tggcagtaca tcaagtgtat catatgccaa  9900
gtacgcccc tattgacgtc aatgacggta aatggcccgc ctggcattatg cccagtaca  9960
tgaccttatg ggactttcct acttggcagt acatctacgt attagtcatc gctattacca  10020
tggtgatgcg gttttggcag tacatcaatg ggcgtggata gcggtttgac tcacggggat  10080
ttccaagtct ccaccccatt gacgtcaatg ggagtttgtt ttggcaccaa aatcaacggg  10140
actttccaaa atgtcgtaac aactccgccc cattgacgca aatgggcggt aggcgtgtac  10200
ggtgggaggt ctatataagc agagctggtt tagtgaaccg tcagatccgc tagagatctg  10260
gtaccgtcga cgcggccgct cgagcctaag cttatgctgc tgctgccctt ccagttgctg  10320
gctgtcctct ttcccggcgg caactccgag gattacaagg acgacgacga caagggtgga  10380
ggctctggag gtggctctgg tggaggttcc ggtggcggat ctatgagcga caacggtccc  10440
cagaatcaaa gaaatgcgcc cagaattaca ttcgcggcc cttctgatag cactggctca  10500
aacgaaaacg gggagaaag cggagccagg tccaaacagg agaagcca aggcctgcct  10560
aataacaccg cttcctggtt cacagctctg acgcaacacg gcaaggagga tctgaagttt  10620
ccacggggtc agggcgtccc gattaacacg aactctagcc cagatgacca aataggtac  10680
tacagaagag cgacaaggcg gatcagagga ggcgatggaa aaatgaagga tctgtcccct  10740
aggtggtatt tctattacct gggcacaggc cctgaagctg gttgccctta cggcgcaaac  10800
aaagatggaa ttatatgggt ggccaccgag ggggcgttga acaccccaaa ggatcacatc  10860
```

```
ggaacgagga atcccgccaa caatgctgct atagtgctcc aactgccaca gggaacaacc   10920
ctgcctaagg gcttctacgc cgaggggagc cgcggtggca gccaggccag ctccagaagt   10980
tcctcccgca gccggaacag ctctagaaac agcactcccg gcagctccag agggacaagc   11040
ccagccagaa tggccggcaa tggcggcgac gctgccctcg cacttctgtt gcttgatcgg   11100
ctcaatcaac tcgaaagcaa aatgtccggc aagggacaac aacagcaagg acagaccgtt   11160
acaaaaaaaa gcgccgccga ggctagcaag aagcccagac agaagcgaac cgcaacaaag   11220
gcctataatg taacacaagc cttttggaagg cggggacccg aacagaccca gggaaatttt   11280
ggcgaccagg aactgatccg gcaagggaca gactataaac attggccaca gatagcgcaa   11340
tttgctccct ccgcctccgc cttctttggc atgtcaagaa taggcatgga agtaactcct   11400
tctggaacct ggctgacgta cactggggca atcaagttgg atgataagga ccctaatttc   11460
aaggaccaag ttattttgct caacaagcat atagacgcct acaagacttt cccgcctacc   11520
gaacctaaaa aggataagaa gaagaaagca gacgagaccc aggccctgcc tcaacggcaa   11580
aagaagcagc aaactgtgac actcctgccc gccgctgact tggatgattt ttcaaaacag   11640
ctccaacaga gtatgagcag cgccgatagc acccaagctg aacgggtcc gggcaacctg   11700
gtgccgatgg tggcgaccgt gggtccagga ccgggtatgc tgatccccat cgccgtgggc   11760
ggggccctgg ccggcctcgt gctgatcgtc cttatcgcct acctcatcgg caagaagcac   11820
tgctcatatc aggacatcct gtgagatatc cgatccaccg gatctagata actgatcata   11880
atcagccata ccacatttgt agaggtttta cttgctttaa aaaacctccc acacctcccc   11940
ctgaacctga aacataaaat gaatgcaatt gttgttgtta acttgtttat tgcagcttat   12000
aatggttaca aataaagcaa tagcatcaca aatttcacaa ataaagcatt tttttcactg   12060
cattctagtt gtggtttgtc caaactcatc aatgtatctt aacgcggatc tgggcgtggt   12120
taagggtggg aaagaatata taaggtgggg tcttatgta gttttgtatc tgttttgcag   12180
cagccgccgc cgccatgagc accaactcgt ttgatggaag cattgtgagc tcatatttga   12240
caacgcgcat gccccatgg gccggggtgc gtcagaatgt gatgggctcc agcattgatg   12300
gtcgcccgt cctgccgca aactctacta ccttgaccta cgagaccgtg tctggaacgc   12360
cgttggagac tgcagcctcc gccgccgctt cagccgctgc agccaccgcc gcgggattg   12420
tgactgactt tgcttcctg agcccgcttg caagcagtgc agcttccgt tcatccgccc   12480
gcgatgacaa gttgacggct ctttggcac aattggattc tttgacccgg gaacttaatg   12540
tcgtttctca gcagctgttg gatctgcgcc agcaggtttc tgccctgaag gcttcctccc   12600
ctcccaatgc ggtttaaaac ataaataaaa aaccagactc tgtttggatt tggatcaagc   12660
aagtgtcttg ctgtctcttat ttaggggttt tgcgcgcgcg gtaggccgg gaccagcggt   12720
ctcggtcgtt gagggtcctg tgtattttt ccaggacgtg gtaaaggtga ctctggatgt   12780
tcagatacat gggcataagc ccgtctctgg ggtggaggta gcaccactgc agagcttcat   12840
gctgcgggt ggtgttgtag atgatccagt cgtagcagga gcgctgggcg tggtgcctaa   12900
aaatgtcttt cagtagcaag tcgattgcca ggggcaggcc cttggtgtaa gtgtttacaa   12960
agcggttaag ctgggatggg tgcatacgtg gggatatgag atgcatcttg gactgtattt   13020
ttaggttggc tatgttccca gccatatccc tccggggatt catgttgtgc agaaccacca   13080
gcacagtgta tccggtgcac ttgggaaatt tgtcatgtag cttagaagga aatgcgtgga   13140
agaacttgga gacgcccttg tgacctccaa gattttccat gcattcgtcc ataatgatgg   13200
caatgggccc acgggcggcg gcctgggcga agatatttct gggatcacta acgtcatagt   13260
tgtgttccag gatgagatcg tcataggcca ttttttacaaa gcgcgggcgg agggtgccag   13320
actgcggtat aatggttcca tccggcccag gggcgtagtc accctcacag atttgcattt   13380
cccacgcttt gagttcagat gggggggatca tgtctacctg cggggcgatg aagaaaacgg   13440
tttccggggt aggggagatc agctgggaag aaagcaggtt cctgagcagc tgcgacttac   13500
cgcagccggt gggcccgtaa atcacaccta ttaccggctg caactggtag ttaagagagc   13560
tgcagctgcc gtcatccctg agcagggggg ccacttcgtt aagcatgtcc ctgactcgca   13620
tgttttccct gaccaaatcc gccagaaggc gctcgccgcc cagcgatagc agttcttgca   13680
aggaagcaaa gttttcaac ggtttgagac cgtccgccgt aggcatgctt ttgagcgttt   13740
gaccaagcag ttccaggcgg tcccacagct cggtcacctg ctctacggca tctcgatcca   13800
gcatatctcc tcgtttcgcg ggttgggcg gctttcgctg tacggcagta gtcggtgctc   13860
gtccagacgg gccagggtca tgtctttcca cgggcgcagg gtcctcgtca gcgtagtctg   13920
ggtcacggtg aagggtgcg ctccgggctg cgcgctggcc agggtgcgct tgaggctggt   13980
cctgctggtg ctgaagcgct gccggtcttc gcccgtcgcg tcggccaggt agcatttgac   14040
catggtgtca tagtccagcc cctccgcggc gtggcccttg gcgcgcagct tgcccttgga   14100
ggaggcgcg cacgaggggc agtgcagact tttgagggcg tagagcttgg gcgcgagaaa   14160
taccgattcc ggggagtagg catccgcgcc gcaggcccg cagacggtct cgcattccac   14220
gagccaggtg agctctggcc gttcgggtc aaaaaccagg tttcccccat gcttttttgat   14280
gcgtttctta cctctggttt ccatgagccg gtgtccacgc tcggtgacga aaaggctgtc   14340
cgtgtccccg tatacagact tgagaggcct gtcctcgagc ggtgttccgc ggtcctcctc   14400
gtatagaaac tcggaccact ctgagacaaa ggctcgcgtc caggccagca cgaaggaggc   14460
taagtgggag gggtagcggt cgttgtccac tagggggtcc actcgctcca gggtgtgaag   14520
acacatgtcg ccctcttcgg catcaaggaa ggtgattggt ttgtaggtgt aggccacgtg   14580
accgggtgtt cctgaagggg ggctataaaa ggggtgggg gcgcgttcgt cctcactctc   14640
ttccgcatcg ctgtctgcga gggccagctg ttggggtgag tactccctct gaaaagcggg   14700
catgacttct gcgctaagat tgtcagtttc caaaaacgag gaggatttga tattcacctg   14760
gcccgcggtg atgcctttga gggtggccga atccatctgg tcagaaaaga caatctttt   14820
gttgtcaagc ttggtggcaa acgacccgta gagggcgttg acagcaact tggcgatgga   14880
gcgcagggtt tggttttgt cgcgatcggc gcgctccttg gccgcgatgt ttagctgcac   14940
gtattcgcgc gcaacgcacc gccattcggg aaagacggtg gcgctcgt cgggcaccag   15000
gtgcacgcgc caaccgcggt tgtgcagggt gacaaggtca acgctggtgg ctacctctcc   15060
gcgtaggcgc tcgttggtcc agcagaggcg ccgccttg cgcagcaga atggcggtag   15120
ggggtctagc tgcgtctcgt ccgggggtc tgcgtccacg gtaaagaccc cgggcagcag   15180
gcgcgcgtcg aagtagtcta tcttgcatcc ttgcaagtct agcgcctgct gccatgcgcg   15240
gcgcagaagc gcgcgctcgt atggttgag tggggaccc catggcatgg ggtgggtgag   15300
cgcggaggcg tacatgccgc aaatgtcgta aacgtagagg gctctctga gtattccaag   15360
atatgtaggg tagcatcttc caccgcggat gctggcgcgc acgtaatcgt atagttcgtg   15420
cgagggagcg aggaggtcgg gaccgaggtt gctacgggcg gctgctctg ctcggaagac   15480
tatctgcctg aagatggcat gtgagttgga tgatatggtt ggacgctgga agacgttgaa   15540
gctggcgtct gtgagaccta ccgcgtcacg cacgaaggag gcgtaggagt cgcgcagctt   15600
```

```
gttgaccagc tcggcggtga cctgcacgtc tagggcgcag tagtccaggg ttttccttgat   15660
gatgtcatac ttatcctgtc cctttttttt ccacagctcg cggttgagga caaactcttc   15720
gcggtctttc cagtactctt ggatcggaaa cccgtcggcc tccgaacggt aagagcctag   15780
catgtagaac tggttgacgg cctggtaggc gcagcatccc tttttctacgg gtagcgcgta   15840
tgcctgcgcg gccttccggc atgaccagca tgaagggcac gagctgcttc ccaaaggccc   15900
ccatccaagt ataggtctct acatcgtagg tgacaaagag acgctcggtg cgaggatgcg   15960
agccgatcgg gaagaactgg atctcccgcc accaattgga ggagtggcta ttgatgtggt   16020
gaaagtagaa gtccctgcga cgggccgaac actcgtgctg gcttttgtaa aaacgtgcgc   16080
agtactggca gcggtgcacg ggctgtacat cctgcacgag gttgacctga cgaccgcgca   16140
caaggaagca gagtgggaat ttgagcccct cgcctgacgg gtttggctgg tggtcttcta   16200
cttcggctgc ttgtccttga ccgtctggct gctcgagggg agttacggtg gatcggacca   16260
ccacgccgcg cgagcccaaa gtccagatgt ccgcgcgcgg cggtcggagc ttgatgacaa   16320
catcgcgcag atgggagctg tccatggtct ggagctcccg cggcgtcagg tcaggcggga   16380
gctcctgcag gtttacctcg catagacggg tcagggcgcg gctagatcc aggtgatacc   16440
taatttccag gggctggttg gtggcggcgt cgatggcttg caagaggccg catcccgcg    16500
gcgcgactac ggtaccgcgc ggcgggcggt gggccgcggg ggtgtccttg gatgatgcat   16560
ctaaaagcgg tgacgcgggc gagccccgg aggtaggggg ggctccggac ccgcggagag    16620
aggggcagg ggcacgtcgg cgccgcgcgg gggcaggagc tggtgctgcg cgcgtaggtt     16680
gctggcgaac gcgacgacgc ggcggttgat ctcctgaatc tggcgcctct gcgtgaagac   16740
gacgggcccg gtgagcttga acctgaaaga gagttcgaca gaatcaattt cggtgtcgtt   16800
gacggcggcc tggcgcaaaa tctcctgcac gtctcctgag ttgtcttgat aggcgatctc   16860
ggccatgaac tgctcgatct cttcctcctg gagatctccg cgtccggctc gctccacggt   16920
ggcggcgagg tcgttggaaa tgcgggccat gagctgcgca aaggcgttga ggcctccctc   16980
gttccagacg cggctgtaga ccacgcccc ttcggcatcg cgggcgcgca tgaccacctg     17040
cgcgagattg agctccacgt gccgggcgaa gacggcgtag tttcgcaggc gctgaaagag   17100
gtagttgagg gtggtggcgg tgtgttctgc cacgaagaag tacataaccc agcgtcgcaa   17160
cgtggattcg ttgataattg ttgtgtaggt actccgccgc cgaggggacct gagcgagtcc   17220
gcatcgaccg gatcggaaaa cctctcgaga aaggcgtcta accagtcaca gtcgcaaggt   17280
aggctgagca ccgtggcggg cggcagcggg cggcggtcgg ggttgtttct ggcggaggtg   17340
ctgctgatga tgtaattaaa gtaggcggtc ttgagacggg ggatggtcga cagaagcacc   17400
atgtccttgg gtccggcctg ctgaatgcgc aggcggtcgg ccatgcccca ggcttcgttt    17460
tgacatcggc gcaggtcttt gtagtagtct tgcatgagcc tttctaccgg cacttcttct   17520
tctccttcct cttgtcctgc atctcttgca tctatcgctg cggcggcggc ggagtttggc   17580
cgtaggtggc gccctcttcc tcccatgcgt gtgacccga agcccctcat cggctgaagc     17640
agggctaggt cggcgacaac gcgctcggct aatatggcct gctgcacctg cgtgagggta   17700
gactggaagt catccatgtc cacaaagcgg tggtatgcgc ccgtgttgat ggtgtaagtg   17760
cagttggcca taacgaacca gttaacggtc tggtgaccccg gctgcgagag ctcggtgtac   17820
ctgagacgcg agtaagccct cgagtcaaat acgtagtcgt tgcaagtccg caccaggtac   17880
tggtatccca ccaaaaagtg cggcggcggc tggcggtaga ggcgcagcg tagggtggcc    17940
ggggctccgg gggcgagatc ttccaacata aggcgatgat atccgtagat gtacctggac   18000
atccaggtga tgccggcggc ggtggtggag gcgcgcggaa agtcgcggac gcggttccag   18060
atgttgcgca gcggcaaaaa gtgctccatg gtcgggacgc tctggccggt caggcgcgcg   18120
caatcgttga cgctctagcg tgcaaaagga gagcctgtaa gcggcactc ttccgtggtc     18180
tggtggataa attcgcaagg gtatcatggc ggacgaccgg ggttcgagcc ccgtatccgg   18240
ccgtccgccg tgatccatgc ggttaccgcc cgcgtgtcga acccaggtgt gcgacgtcag   18300
acaacgggg agtgctcctt ttggcttcct tccaggcgcg gcggctgctg cgctagcttt    18360
tttggccact ggccgcgcgc agcgtaagcg gttaggctgg aaagcgaaag cattaagtgg   18420
ctcgctcctt gtagccggag ggttattttc caagggttga gtcgcgggac ccccggttcg   18480
agtctcggac cggccggact gcggcgaacg ggggtttgcc tccccgtcat gcaagacccc   18540
gcttgcaaat tcctccggaa acaggacga gccccttttt tgcttttccc agatgcatcc    18600
ggtgctggcg cagatgcgcc cccctcctca gcagcggcaa gagcaagagc agcggcagac   18660
atgcagggca ccctcccctc ctcctaccgc gtcaggaggg gcgacatccg cggttgacgg   18720
ggcagcagat ggtgattacg aacccccgcg cgcgccgggcc cggcactacc tggacttgga   18780
ggagggcgag ggcctggcgc ggctaggagc gccctctcct gagcggcacc caagggtgca   18840
gctgaagcgt gatacgcgtg aggcgtacgt gccgcggcaa aacctgttc gcgaccggca    18900
gggagaggag cccgaggaga tgcgggatcg aaagttccac gcagggcgcg agctgcggca   18960
tggcctgaat cgcgagcggt tgctgcgcga ggaggacttt gagcccgacg cgcgaaccgg   19020
gattagtccc gcgcgcgcac acgtggcggc cgccgacctg gtaaccgcat acgagcagac   19080
ggtgaaccag gagattaact ttcaaaaaag cttttaacaac cacgtgcgta cgcttgtggc   19140
gcgcgaggag gtggctatag gactgatgca tctgtgggaa tttgtaagcg cgctgggagca   19200
aaacccaaat agcaagccgc tcatgcgca gctgttcctt atagtgcagc acagcaggga    19260
caacgaggca ttcagggatg cgctgctaaa catagtagag cccgagggcc gctggctgct   19320
cgatttgata aacatcctgc agagcatagt ggtgcaggag cgcagcttga gcctggctga   19380
caaggtgccc gccatcaact attccatgct tagcctgagc aagttttacg cccgcaagat   19440
ataccatacc ccttacgttc ccatagacaa ggaggtaaag atcgaggggt tctacatgcg   19500
catggcgctg aaggtgctta ccttgagcga cgacctgggc gtttatcgca acgagcgcat   19560
ccacaaggcc gtgagcgtga gccggcgcg cgagctcagc gaccgcgagc tgatgcacag   19620
cctgcaaagg gcccctggctg gcacgggcag cggcgataga gaggccgagt cctactttga   19680
cgcgggcgct gacctgcgct gggccccaag gcgacgcgcg ctggaggcag ctggggcgag   19740
acctgggctg gcggtggcac ccgcgcgcgc tggcaacgtc ggcggcgtgg aggaatatga   19800
cgaggacgat gagtacgagc caggacgg cgagtactaa gcgtgatgt ttctgatcag      19860
atgatgcaag acgcaacgga cccggcggtg cgggcggcgc tgcagagcca gccgtccggc   19920
cttaactcca cggacgactg cgccaggtc atggaccgca tcatgtcgct gactgcgcgc   19980
aatcctgacg cgttccggca cgagcgcag gccaacctgg tctccgcaat tctgaagcg    20040
gtggtcccgg cgcgcgcaaa ccccacgcac gagaaggtgc tggcgatcgt aaacgcgctg   20100
gccgaaaaca gggccatccg gcccgacgag gccggcctgg tctacgacgc gctgcttcag   20160
cgcgtggctc gttacaacag cggcaacgtg cagaccaacc tggaccggct ggtggggat    20220
gtgcgcgagg ccgtggcgca gcgtgagcgc gcgcagcagc agggcaacct gggctccatg   20280
gttgcactaa acgccttcct gagtacacag cccgccaacg tgccgcgggg acaggaggac   20340
```

```
tacaccaact ttgtgagcgc actgcggcta atggtgactg agacaccgca aagtgaggtg   20400
taccagtctg ggccagacta ttttttccag accagtagac aaggcctgca gaccgtaaac   20460
ctgagccagg ctttcaaaaa cttgcagggg ctgtgggggg tgcgggctcc cacaggcgac   20520
cgcgcgaccg tgtctagctt gctgacgccc aactcgcgcc tgttgctgct gctaatagcg   20580
cccttcacgg acagtggcag cgtgtcccgg gacacatacc taggtcactt gctgacactg   20640
taccgcgagg ccataggtca ggcgcatgtg gacgagcata cttccagga gattacaagt     20700
gtcagccgcg cgctggggca ggaggacacg ggcagcctgg aggcaaccct aaactacctg   20760
ctgaccaacc ggcggcagaa gatccctcg ttgcacagtt taaacagcga ggaggagcgc    20820
attttgcgct acgtgcagca gagcgtgagc cttaacctga tgcgcgacgg ggtaacgccc   20880
agcgtggcgc tggacatgac cgcgcgcaac atggaaccgg gcatgtatgc ctcaaaccgg   20940
ccgtttatca accgcctaat ggactacttg catcgcgcgg ccgccgtgaa ccccgagtat   21000
ttcaccaatg ccatcttgaa cccgcactgg ctaccgcccc tggtttcta caccggggga    21060
ttcgaggtgc ccgagggtaa cgatggattc ctctgggacg acatagacga cagcgtgttt   21120
tccccgcaac cgcagaccct gctagagttg caacagcgga agcaggcaga ggcgcgctg    21180
cgaaaggaaa gcttccgcag gccaagcagc ttgtccgatc taggcgctgc ggccccgcgg   21240
tcagatgcta gtagcccatt tccaagcttg atagggtctc ttaccagcac tcgcaccacc   21300
cgcccgcgcc tgctgggcga ggaggagtac ctaaacaact cgctgctgca gccgcagcgc   21360
gaaaaaaacc tgcctccggc atttcccaac aacgggatag agagcctagt ggacaagatg   21420
agtagatgga agacgtacgc gcaggagcac agggacgtgc caggcccgcg cccgcccacc   21480
cgtcgtcaaa ggcacgaccg tcagcgggt ctggtgtggg aggacgatga ctcggcagac    21540
gacagcagcg tcctggattt ggagggagt ggcaacccgt ttgcgcacct tcgcccagg     21600
ctggggagaa tgttttaaaa aaaaaaaagc atgatgcaaa ataaaaaact caccaaggcc   21660
atggcaccga gcgttggttt tcttgtattc cccttagtat gcggcgcgcg gcgatgtatg   21720
aggaaggtcc tcctccctcc tacgagagtg tggtgagcgc ggcgcagtg gcggcggcgc    21780
tgggttctcc cttcgatgct ccctggacc cgccgtttgt gcctccgcgg tacctgcggc    21840
ctaccggggg gagaaacagc atccgttact ctgagttgge accccctattc gacaccaccc   21900
gtgtgtacct ggtggacaac aagtcaacg atgtggcatc cctgaactac cagaacgacc    21960
acagcaactt tctgaccacg gtcattcaaa acaatgacta cagcccgggg gaggcaagca   22020
cacagaccat caatcttgac gaccggtcgc actgggcgg cgacctgaaa accatcctgc    22080
ataccaacat gccaaatgtg aacgagttca tgtttaccaa taagttttaag gcgcgggtga   22140
tggtgtcgcg cttgcctact aaggacaatc aggtggagct gaaatacgag tgggtggagt   22200
tcacgctgcc cgagggcaac tactccgaga ccatgaccat agaccttatg aacaacgcga   22260
tcgtggagca ctacttgaaa gtgggcagac agaacgggg tctggaaagc gacatcgggg    22320
taaagtttga cacccgcaac ttcagactgg ggtttgaccc cgtcactggt cttgtcatgc    22380
ctgggggtata tacaaacgaa gccttccatc cagacatcat tttgctgcca ggatgcggag   22440
tggacttcac ccacagccgc ctgagcaact tgttgggcat ccgcaagcgg caaccttcc     22500
aggagggctt taggatcacc tacgatgatc tggaggtgg taacattccc gcactgttgg    22560
atgtggacgc ctaccaggcg agcttgaaag atgcacccga acagggcggg ggtggcgcag   22620
gcggcagcaa cagcagtggc agcggcgcgg aagagaactc caacgcggca gccgcggcaa   22680
tgcagccggt ggaggacatg aacgatcatg ccattcgcgg cgacaccttt gccacacggg   22740
ctgaggagaa gcgcgctgag gccgaagcag cggccgaagc tgccgccccc gctgcgcaac   22800
ccgaggtcga aagcctcag aagaaaccgg tgatcaaacc cctgacagag gacagcaaga   22860
aacgcagtta caacctaata agcaatgaca gcacctttac cagtaccgc agctggtacc    22920
ttgcatacaa ctacgcgac cctcagaccg gaatccgctc atggaccctg cttttgcactc   22980
ctgacgtaac ctgcggctcg gagcaggtct actggtcgtt gccagacatg atgcaagacc   23040
ccgtgacctt ccgctccacg cgccagatca gcaacttcc ggtggtgggc gccgagctgt    23100
tgccgtgca ctccaagagc ttctacaacg accaggccgt ctactcccaa ctcatccgcc    23160
agtttacctc tctgacccac gtgttcaatc gcttcccga gaaccagatt ttggcgcgcg    23220
cgccagcccc caccatcacc accgtcagtg aaaacgttcc tgctctcaca gatcacggga   23280
cgctaccgct gcgcaacagc atcggaggag tccagcgagt gaccattact gacgccgagc   23340
gccgcacctg ccctacgtt tacaaggccc tgggcatagt ctcgccgcgc gtcctatcga    23400
gccgcacttt ttgagcaagc atgtccatcc ttatatcgcc cagcaataac acaggctggg   23460
gcctgcgctt cccaagcaag atgtttggcg gggccaagaa gcgctccgac caacacccag   23520
tgcgcgtgcg cgggcactac cgcgcgccct ggggcgcgca aaacgcggc cgcactgggc    23580
gcaccaccgt cgatgacgcc atcgacgcgg tggtgggaga ggcgcgcaac tacacgccca   23640
cgccgccacc agtgtccaca gtgacgcgg ccattcagac cgtggtgcgc ggagccggge   23700
gctatgctaa aatgaagaga cggcggaggc gcgtagcacg tcgccaccgc cgccgacccg   23760
gcactgccgc ccaacgcgcg gcggcggccc tgcttaaccg cgcacgtcgc accggccgac   23820
gggcggccat gcgggccgct cgaaggctgg ccgcgggtat tgtcactgtg ccccccaggt   23880
ccaggcgacg agccgcgccc gcagcagccg cggccattag tgctatgact caggtcgca    23940
ggggcaacgt gtattgggtg cgcgactcgg ttagcggcct gcgcgtgccc gtgcgcaccc   24000
gccccccgcg caactagatt gcaagaaaaa actacttaga ctcgtactgt tgtatgtatc   24060
cagcggcggc ggcgcgcaac gaagctatgt ccaagcgcaa aatcaaagaa gagatgctcc   24120
aggtcatcgc gccggagatc tatgcccccc cgaagaagga agagcaggat tacaagcccc   24180
gaaagctaaa gcgggtcaaa aagaaaaaga aagatgatga tgatgaactt gacgacgagg   24240
tggaactgct gcacgctacc gcgcccaggg acgggtaca gtggaaaggt cgacgcgtaa    24300
aacgtgtttt gcgacccggc accaccgtag tcttacgcc cggtgagcgc tccaccccgca   24360
cctacaagcg cgtgtatgat gaggtgtacg gcgacgagga cctgcttgag caggccaacg   24420
agcgcctcgg ggagtttgcc tacggaaagc ggcataagga catgctgggc ttgccgctac   24480
acgaggcaa cccaacacct agcctaaagc ccgtaacact gcagcaggtg ctgcccgcgc   24540
ttgcaccgtc cgaagaaaag cgcggcctaa agcgcgagtc tggtgacttg cacccaccgaa  24600
tgcagctgat ggtaccaag cgccagcgac tggaagatgt cttggaaaaa atgaccgtgg    24660
aacctggct ggagcccgag gtccgcgtgc ggccaatcaa gcaggtggcg ccgggactgg    24720
gcgtgcagac cgttgacgac ttcctaccagtag caccagtatt gccaccgcca              24780
cagagggcat ggagacacaa acgtccccgg ttgcctcagc ggtggcggat gccgcggtgc     24840
aggcggtcga tcgcggccgcg tccaagacct tacggaggt gcaaacggac ccgtggatgt     24900
ttcgcgtttc agcccccggc cgccgcgcc gttcgaggaa gtacgcgcc gccagcgcgc     24960
tactgcccga atatgcccta catccttcca ttgcgcctac ccccggctat cgtggctaca    25020
cctaccgccc cagaagacga gcaactaccc gacgccgaac caccactgga accgccgcc     25080
```

```
gccgtcgccg tcgccagccc gtgctggccc cgatttccgt gcgcagggtg gctcgcgaag   25140
gaggcaggac cctggtgctg ccaacagcgc gctaccaccc cagcatcgtt taaaagccgg   25200
tctttgtggt tcttgcagat atggccctca cctgccgcct ccgtttcccg gtgccgggat   25260
tccgaggaag aatgcaccgt aggaggggca tggccggcca cggcctgacg ggcggcatgc   25320
gtcgtgcgca ccaccggcgg cggcgcgcgt cgcaccgtcg catgcgcggc ggtatcctgc   25380
ccctccttat tccactgatc gccgcgcgca ttggcgccgt gcccggaatt gcatccgtgb   25440
ccttgcaggc gcagagacac tgattaaaaa caagttgcat gtggaaaaat caaaataaaa   25500
agtctggact ctcacgctcg cttggtcctg taactatttt gtagaatgga agacatcaac   25560
tttcgtctc tggcccgcg cacggctcg cgcccgttca tgggaaactg gcaagatatc   25620
ggcaccagca atatgagcgg tggcgccttc agctggggct cgctgtggag cggcattaaa   25680
aatttcggtt ccaccgttaa gaactatggc agcaaggcct ggaacagcag cacaggccag   25740
atgctgaggg ataagttgaa agagcaaaat ttccaacaaa aggtggtaga tggcctggcc   25800
tctggcatta gcggggtggt ggacctggcc aaccaggcag tgcaaaataa gattaacagt   25860
aagcttgatc cccgccctcc cgtagaggag cctccaccgg ccgtggagac agtgtctcca   25920
gaggggcgtg gcgaaaagcg tccgcgcccc gacagggaag aaactctggt gacgcaaata   25980
gacgagcctc cctcgtacga ggaggcacta aagcaaggcc tgcccaccac ccgtcccatc   26040
gcgcccatgg ctaccggagt gctgggccag cacacacccg taacgctgga cctgcctccc   26100
cccgccgaca cccagcagaa acctgtgctg ccaggcccga ccgccgttgt tgtaacccgt   26160
cctagccgcg cgtccctgcg ccgcgccgcc agcggtccgc gatcgttgcg gcccgtagcc   26220
agtggcaact ggcaaagcac actgaacagc atcgtgggtc tgggggtgca atccctgaag   26280
cgccgacgat gcttctgata gctaacgtgt cgtatgtgtg tcatgtatgc gtccatgtcg   26340
ccgccaggag agctgctgag ccgccgcgcg cccgcttttcc aagatggcta cccttcgat   26400
gatgccgcag tggtcttaca tgcacatctc gggccaggag gcctcggagt acctgagccc   26460
cgggctggtg cagtttgccc gcgccaccga gacgtactc agcctgaata caagtttag   26520
aaaccccacg gtgcgcccta cgcacgacgt gaccacagac cggtcccagc gtttgacgct   26580
gcggttcatc cctgtggacc gtgaggatac tgcgtactcg tacaaggcgg ggttcaccct   26640
agctgtgggt gataaccgtg tgctggacat ggcttccacg tactttgaca tccgcggcgt   26700
gctggacagg ggccctactt ttaagcccta ctctggcact gcctacaacg ccctggctcc   26760
caagggtgcc ccaaatcctt gcgaatggga tgaagctgct actgctcttg aaataaacct   26820
agaagaagag gacgatgaca acaggaacga agtagacgag caagctgagc ggcaaaaaac   26880
tcacgtattt gggcaggcgc cttattctgg tataaatatt acaaaggagg gtattcaaat   26940
aggtgtcgaa ggtcaaacac ctaaaatatgc cgataaaaca tttcaacctg aacctcaaat   27000
aggagaatct cagtggtacg aaacagaaat taatcatgca gctgggagag tcctaaaaaa   27060
gactaccca atgaaaccat gttacggttc atatgcaaca cccacaaatg aaaatggagg   27120
gcaaggcatt cttgtaaagc aacaaatgg aaagctagaa agtcaagtgg aaatgcaatt   27180
tttctcaact actgaggcag ccgcaggcaa tggtgataac ttgactccta aagtggtatt   27240
gtacagtgaa gatgtagata tagaaacccc agacactcat atttcttaca tgcccactat   27300
taaggaaggt aactcacgag aactaatggg ccaacaatct atgcccaaca ggcctaatta   27360
cattgcttt agggacaatt ttattggtct aatgtattac aacagcacgg gtaatatggg   27420
tgttctggcg ggccaagcat cgcagttgaa tgctgttgta gatttgcaag acagaaacac   27480
agagctttca taccagcttt tgcttgattc cattggtgat agaaccaggt acttttctat   27540
gtggaatcag gctgttgaca gctatgatcc agatgttaga attattgaaa atcatggaac   27600
tgaagatgaa cttccaaatt actgctttcc actgggaggt gtgattaata cagagactct   27660
taccaaggta aaacctaaaa caggtcagga aaatggatgg gaaaaagatg ctacagaatt   27720
ttcagataaa aatgaaataa gagttggaaa taatttttgcc atggaaatca atctaaatgc   27780
caacctgtgg agaaatttcc tgtactccaa catagcgctg tatttgcccg acaagctaaa   27840
gtacagtcct tccaacgtaa aaatttctga taacccaaac acctacgact acatgaacaa   27900
gcgagtggtg gctcccgggc tagtggactg ctacattaac cttggagcac gctggtccct   27960
tgactatatg gacaacgtca acccatttaa ccaccaccgc aatgctggcc tgcgctaccg   28020
ctcaatgttg ctgggcaatg gtcgctatgt gcccttccac atccaggtgc ctcagaagtt   28080
ctttgccatt aaaaaacctcc ttctcctgcc gggctcatac acctacgagt ggaacttcag   28140
gaaggatgtt aacatggttc tgcagagctc cctaggaaat gacctaaggg ttgacggagc   28200
cagcattaag tttgatagca tttgcctttta cgccaccttc ttccccatgg cccacaacac   28260
cgcctccacg cttgaggcca tgcttagaaa cgacaccaac gaccagtcct ttaacgacta   28320
tctctccgcc gccaacatgc tctaccctat acccgccaac gctaccaacg tgcccatatc   28380
catccctcc cgcaactggg cggctttccg cggctgggcc ttcacgcgcc ttaagactaa   28440
ggaaacccca tcactgggct cgggctacga ccccttattac acctactctg gctctatacc   28500
ctacctagat ggaaccttt acctcaacca caccttaag aaggtggcca ttaccttga   28560
ctcttctgtc agctggcctg gcaatgaccg cctgcttacc cccaacgagt tgaaattaa   28620
gcgctcagtt gacggggagg gttacaacgt tgcccagtgt aacatgacca aagactggtt   28680
cctggtacaa atgctagcta actataacat tggctaccag gcttctata tcccagagag   28740
ctacaaggac cgcatgtact ccttcttag aaacttccag cccatgagcc gtcaggtggt   28800
ggatgatact aaatacaagg actaccaaca ggtgggcatc ctaccaac acaacaactc   28860
tggattttgtt ggctaccttg cccccaccat cgcgaagga caggcctacc ctgctaactt   28920
cccctatccg cttataggca agaccgcagt tgacagcatt cccagaaaa gtttctttg   28980
cgatcgcacc ctttggcgca tcccattctc cagtaacttt atgtccatgg gcgcactcac   29040
agacctgggc caaaaccttc tctacgccaa ctccgcccac gcgctagaca tgactttga   29100
ggtggatccc atggacgagc ccacccttct ttatgttttg tttgaagtct ttgacgtggt   29160
ccgtgtgcac cagccgcacc gcggcgtcat cgaaaccgtg tacctgcgca cccttctc    29220
ggccggcaac gccacaacat aaagaagcaa gcaacatcaa caacagctgc cgccatgggc   29280
tccagtgagc aggaactgaa agccattgtc aaagatcttg gttgtgggcc atatttttg    29340
ggcacctatg acaagcgctt ccaggctttt gtttctccac acaagctcgc ctgcgccata   29400
gtcaatacgc cggtcgcga gactggggc gtacactgga tggcctttgc ctggaacccg   29460
cactcaaaaa catgctacct ctttgagccc tttggctttt ctgaccagca actcaaggag   29520
gtttaccagt ttgagtacga gtcactcctg cgccgtagcg ccattgcttc ttcccccgac   29580
cgctgtataa cgctggaaaa gtccaccaa agcgtacagg gcccaactc ggccgcctgt   29640
ggactattct gctgcatgtt tctccacgcc tttgccaact ggcccaaac tcccatggat   29700
cacaacccca ccatgaacct tattaccggg gtacccaact ccatgctcaa cagtcccag   29760
gtacagccca ccctgcgtcg caaccaggaa cagctctaca gcttcctgga gcgccactcg   29820
```

```
ccctacttcc gcagccacag tgcgcagatt aggagcgcca cttcttttg tcacttgaaa   29880
aacatgtaaa aataatgtac tagagacact ttcaataaag gcaaatgctt ttatttgtac   29940
actctcgggt gattatttac ccccaccctt gccgtctgcg ccgtttaaaa atcaaagggg   30000
ttctgccgcg catcgctatg cgccactggc agggacacgt tgcgatactg tgtttagtg    30060
ctccacttaa actcaggcac aaccatccgc ggcagctcgc tgaagttttc actccacagg   30120
ctgcgcacca tcaccaacgc gtttagcagg tcgggcgccg atatcttgaa gtcgcagttg   30180
gggcctccgc cctgcgcgcg cgagttgcga tacacagggt tgcagcactg gaacactatc   30240
agcgccgggt ggtgcacgct ggccagcacg ctcttgtcgg agatcagatc cgcgtccagg   30300
tcctccgcgt tgctcagggc gaacggagtc aactttggta gctgccttcc caaaaaggag   30360
gcgtgcccag gctttgagtt gcactcgcac cgtagtggca tcaaaaggtg accgtgcccg   30420
gtctgggcgt taggatacag cgcctgcata aaagccttga tctgcttaaa agccacctga   30480
gcctttgcgc cttcagagaa gaacatgccg caagacttgc cggaaaactg attggccgga   30540
caggccgcgt cgtgcacgca gcaccttgcg tcggtgttgg agatctgcac cacatttcgg   30600
ccccaccggt tcttcacgat cttggccttg ctagactgct ccttcagccg cgcgtcaccg   30660
ttttcgctcg tcacatccat ttcaatcacg tgctccttat ttatcataat gcttccgtgt   30720
agacacttaa gctcgccttc gatctcagcg cagcggtgca gccacaacgc gcagcccgtg   30780
ggctcgtgat gcttgtaggt caccctctgca aacgactgca ggtacgcctg caggaatcgc   30840
cccatcatcg tcacaaaggt cttgttgctg gtgaaggtca gctgcaaccc gcggtgctcc   30900
tcgttcagcc aggtcttgca tacgccgcc agagcttcca cttggtcagg cagtagtttg    30960
aagttcgcct ttagatcgtt atccacgtgg tacttgtcca tcagcgcgcg cgcagcctcc   31020
atgcccttcc cccacgcaga cacgatcggc acactcagcg ggttcatcac cgtaatttca   31080
ctttcgcttt cgctgggctc ttcctcttcc tcttgcgtcc gcataccacg cgccactgg    31140
tcgtcttcat tcagccgccc cactgtgcgc ttacctcctt tgccatgctt gattagcacc   31200
ggtgggttgc tgaaacccac catttgtagc gccacatctt ctctttcttc ctcgctgtcc   31260
acgattacct ctggtgatgg cgggcgctcg ggcttgggag aagggcgctt cttttcttc    31320
ttgggcgcaa tggccaaatc cgccgccgag gtcgatggcc gcggggctgg tgtgcgcgcg   31380
accagccgcgt cttgtgatga gtcttcctcg tcctcggact cgatacgccg cctcatccgc   31440
ttttttgggg gcgcccgggg aggcggcggc gacgggggacg gggacgacac gtcctccatg   31500
gttggggggac gtcgcgccgc accgcgtccg cgctcggggg tggtttcgcg ctgctcctct   31560
tcccgactgg ccatttcctt ctcctatagg cagaaaaaga tcatgagtc agtcgagaag    31620
aaggacagcc taaccgcccc ctctgagttc gccaccaccg cctccaccga tgccgccaac   31680
gcgcctacca ccttcccgt cgaggcaccc ccgcttgagg aggaggaagt gattatcgag    31740
caggacccag gtttttgtaag cgaagacgac gaggaccgct cagtaccaac agaggataaa   31800
aagcaagacc aggacaacgc agaggcaaac gaggaacaag tcgggcgggg ggacgaaagg   31860
catggcgact acctagatgt gggagacgac gtgctgttga agcatctgca gcgcagtgc   31920
gccattatct gcgacgcgtt gcaagagcgc agcgatgtgc ccctcgccat agcggatgtc   31980
agccttgcct acgaacgcca cctattctca ccgcgcgtac cccccaaacg ccaagaaaac   32040
ggcacatgcg agcccaaccc gcgcctcaac ttctaccccg tatttgccgt gccagaggtg   32100
cttgccacct atcacatctt tttccaaaac tgcaagatac cctatcctg ccgtgccaac    32160
cgcagccgag cggacaagca gctggccttg cggcagggcg ctgtcatacc tgatatcgcc   32220
tcgctcaacg aagtgccaaa aatctttgag ggtcttggac gcgacgagaa gcgcgcggca   32280
aacgctctga acaggaaaaa cagcgaaaat gaaagtcact ctggagtgtt ggtggaactc   32340
gagggtgaca acgcgcgcct agccgtacta aaacgcacga tcgaggtcac ccactttgcc   32400
tacccggcac ttaacctacc ccccaaggtc atgagcacag tcatgagtga gctgatcgtg   32460
cgccgtgcgc agccctgga gagggatgca aatttgcaag aacaaacaga ggagggccta   32520
cccgcagttg gcgacgagca gctagcgcgc tggcttcaaa cgcgcgagcc tgccgacttg   32580
gaggagcgac gcaaactaat gatggccgca gtgctcgtta ccgtggactt tgagtgcatg   32640
cagcggttct ttgctgaccc ggagatgcag cgcaagctag aggaaacatt gcactacacc   32700
tttcgacagg gctacgtacg ccaggcctgc aagatctcca acgtggagct ctgcaacctg   32760
gtctcctacc ttgaatttt gcacgaaaac cgccttgggc aaaacgtgct tcattccacg   32820
ctcaagggcg agcgcgccg cgactacgtc cgcgactgc tttacttatt tctatgctac    32880
acctggcaga cggccatggg cgtttggcag cagtgcttgg aggagtgcaa cctcaaggag   32940
ctgcagaaac tgctaaagca aaacttgaag gacctatgga cggccttcaa cgagcgctcc   33000
gtggccgcgc acctggcgga catcattttc cccgaacgcc tgcttaaaac cctgcaacag   33060
ggtctgccag acttcaccag tcaaagcatg ttgcagaact ttaggaactt tatcctagag   33120
cgctcaggaa tcttgcccgc cacctgctgt gcacttccta gcgactttgt gcccattaag   33180
taccgcgaat gcctccgcc gctttgggc cactgctacc tttctgcagct agccaactac    33240
cttgcctacc actctgacat aatgaaggac gtgagcggtg acgtctact ggagtgtcac    33300
tgtcgctgca acctatgcac cccgcaccgc tcctggttt gcaattcga gctgcttaac    33360
gaaagtcaaa ttatcggtac ctttgagctg cagggtccct cgcctgacga aaagtccgg    33420
gctccggggt tgaaactcac tccgggctg tggacgtcgg cttaccttcg caaatttgta    33480
cctgaggact accacgccca cgagattagg ttctacgaag accatcccg cccgcctaat   33540
gcggagctta ccgcctgcgt cattacccag ggccacattc ttggcaatt gcaagccatc   33600
aacaaagccc gccaagagtt tctgctacga aagggacggg gggtttactt ggaccccag    33660
tccggcgagg agctcaaccc aatcccccg ccgccagc cctatcagca gcagccgcgg      33720
gcccttgctt cccaggatgg cacccaaaaa gaagctgcag ctgccgccgc cacccacgga   33780
cgaggaggaa tactgggaca gtcaggcaga ggaggttttg gacgaggagg aggaggacat   33840
gatggaagac tgggagagcc tagacgagga agcttccga gtcgaagagg tgtcagacga   33900
aacaccgtca ccctcggtcg cattccctc gccggcgcc cagaaatcgc caaccggtc     33960
cagcatggct acaacctccg ctcctcaggc gccgccgcca ctgccccgttc gccgacccaa   34020
ccgtagatgg gacaccactg gaaccagggc cggtaagtcc aagcagccgc gccgttagc    34080
ccaagagcaa caacagcgcc aaggctaccg ctcatgcgc gggcacaaga acgcccatagt   34140
tgcttgcttg caagactgtg ggggcaacat tcccttcgcc cgccgctttc ttctctacca   34200
tcacggcgtg gccttcccc gtaacatcct gcattactac cgtcatcctc acagccataa   34260
ctgcaccgga ggcagccgca gcaacacag cggccacaca gaagcaaagg cgaccggata   34320
gcaagactct gacaaagccc aagaaatcca cagcggcggc agcagcagga ggaggagcgc   34380
tgcgtctggc gcccaacgaa cccgtatcga cccgcgagct tagaaacagg atttttccca   34440
ctctgtatgc tatatttcaa cagagcaggg gccaagaaca agagctgaaa ataaaaaaca   34500
ggtctctgcg atccctcacc cgcagctgcc tgtatcacaa aagcgaagat cagcttcggc   34560
```

```
gcacgctgga agacgcggag gctctcttca gtaaatactg cgcgctgact cttaaggact   34620
agtttcgcgc cctttctcaa atttaagcgc gaaaactacg tcatctccag cggccacacc   34680
cggcgccagc acctgttgtc agcgccatta tgagcaagga aattcccacg ccctacatgt   34740
ggagttacca gccacaaatg ggacttgcgg ctggagctgc ccaagactac tcaacccgaa   34800
taaactacat gagcgcggga ccccacatga tatcccgggt caacgaaata cgcgcccacc   34860
gaaaccgaat tctcctggaa caggcggcta ttaccaccac acctcgtaat aaccttaatc   34920
cccgtagttg gcccgctgcc ctggtgtacc aggaaagtcc cgctcccacc actgtggtac   34980
ttcccagaga cgcccaggcc gaagttcaga tgactaactc aggggcgcag cttgcgggcg   35040
gctttcgtca cagggtgcgg tcgcccgggc agggtataac tcacctgaca atcagagggc   35100
gaggtattca gctcaacgac gagtcggtga gctcctcgct tggtctccgt ccggacgggga  35160
catttcagat cggcggcgcc ggccgctctt cattcacgcc tcgtcaggca atcctaactc   35220
tgcagacctc gtcctctgag ccgcgctctg gaggcattgg aactctgcaa tttattgagg   35280
agtttgtgcc atcggtctac tttaacccct tctcgggacc tcccggccac tatccggatc   35340
aatttattcc taactttgac gcggtaaagg actcggcgga cggctacgac tgaatgttaa   35400
gtggagaggc agagcaactg cgcctgaaac acctggtcca ctgtcgccgc cacaagtgct   35460
ttgcccgcga ctccggtgag ttttgctact ttgaattgcc cgaggatcat atcgagggcc   35520
cggcgcacgg cgtccggctt accgcccagg gagagcttgc ccgtagcctg attcgggagt   35580
ttacccagcg ccccctgcta gttgagcggg acaggggacc ctgtgttctc actgtgattt   35640
gcaactgtcc taaccctgga ttacatcaag atcctctagt taatgtcagg tcgcctaagt   35700
cgattaacta gagtacccgg ggatcttatt ccctttaact aataaaaaaa aataataaag   35760
catcacttac ttaaaatcag ttagcaaatt tctgtccagt ttattcagca gcacctcctt   35820
gccctcctcc cagctctggt attgcagctt cctcctggct gcaaactttc tccacaatct   35880
aaatggaatg tcagtttcct cctgttcctg tccatccgca cccactatct tcatgttgtt   35940
gcagatgaag cgcgcaagac cgtctgaaga taccttcaac cccgtgtatc catatgacac   36000
ggaaaccggt cctccaactg tgccttttct tactcctccc tttgtatccc ccaatggggtt  36060
tcaagagagt cccccctgggg tactctcttt gcgcctatcc gaacctctag ttacctccaa   36120
tggcatgctt gcgctcaaaa tgggcaacgg cctctctctg gacgaggccg gcaaccttac   36180
ctcccaaaat gtaaccactg tgagcccacc tctcaaaaaa accaagtcaa acataaaacct  36240
ggaaatatct gcacccctca cagttacctc agaagcccta actgtggctg ccgccgcacc   36300
tctaatggtc gcgggcaaca cactcaccat gcaatcacga gccccgctaa ccgtgcacga   36360
ctccaaactt agcattgcca cccaaggacc cctcacagtg tcagaaggaa agctagccct   36420
gcaaacatca ggcccccctca ccaccaccga tagcagtacc cttactatca ctgcctcacc   36480
ccctctaact actgccactg gtagcttggg cattgacttg aaagagccca tttatacaca   36540
aaatggaaaa ctaggactaa agtacggggc tcctttgcat gtaacagacg acctaaacac   36600
tttgaccgta gcaactggtc caggtgtgac tattaataat acttccttgc aaactaaagt   36660
tactggagcc ttgggttttg attcacaagg caatatgcaa cttaatgtag caggaggact   36720
aaggattgat tctcaaaaca gacgcctttat acttgatgtt agttatccgt ttgatgctca   36780
aaaccaacta aatctaagac taggacaggg ccctcttttt ataaactcag cccacaactt   36840
ggatattaac tacaacaaag gcctttactt gtttacagct tcaaacaatt ccaaaaagct   36900
tgaggttaac ctaagcactg ccaagggggtt gatgtttgac gctacagcca tagccattaa   36960
tgcaggagat gggcttgaat ttggttcacc taatgcacca aacacaaatc ccctcaaaac   37020
aaaaattggc catggcctag aatttgattc aaacaaggct atggttccta aactaggaac   37080
tggccttagt tttgacagca caggtgccat tacagtagga aacaaaaata atgataagct   37140
aactttgtgg accacaccag ctccatctcc taactgtaga ctaaatgcag agaaagatgc   37200
taaactcact ttggtcttaa caaaatgtgg cagtcaaata cttgctacag tttcagtttt   37260
ggctgttaaa ggcagtttgg ctccaatatc tggaacagtt caaagtgctc atcttattat   37320
aagatttgac gaaaatggag tgctactaaa caattccttc ctggacccag aatattggaa   37380
ctttagaaat ggagatctta ctgaaggcac agcctataca aacgctgttg gatttatgcc   37440
taacctatca gcttatccaa aatctcacgg taaaactgcc aaaagtaaca ttgtcagtca   37500
agtttactta aacggagaca aaactaaacc tgtaacacta accattacac taaacggtac   37560
acaggaaaca ggagacacaa ctccaagtgc atactctagg tcattttcat gggactggtc   37620
tggccacaac tacattaatg aaatatttgc cacatcctct tacactttt catacattgc   37680
ccaagaataa agaatcgttt gtgttatgtt tcaacgtgtt tatttttcaa ttgcagaaaa   37740
tttcaagtca ttttttcattc agtagtatag cccaccacc acatagctta tacagatcac   37800
cgtaccttaa tcaaactcac agaaccctag tattcaacct gccacctcc tcccaacaca   37860
cagagtacac agtccttttct ccccggctgg ccttaaaaag catcatatca tgggtaacag   37920
acatattctt aggtgttata ttccacacgg tttcctgtcg agccaaacgc tcatcagtga   37980
tattaataaa ctccccgggc agctcactta agttcatgtc gctgtccagc tgctgagcca   38040
caggctgctg tccaacttgc ggttgcttaa cgggcggcga aggagaagtc cacgcctaca   38100
tgggggtaga gtcataatcg tgcatcagga taggcgggtg gtgctgcagc agcgcgcgaa   38160
taaactgctg ccgccgccgc tccgtcctgc aggaatacaa catggcagtg gtctcctcag   38220
cgatgattcg caccgcccgc agcataaggc gccttgtcct ccgggcacag cagcgcaccc   38280
tgatctcact taaatcagca cagtaactgc agcacagcac cacaatattg ttcaaaatcc   38340
cacagtgcaa ggcgctgtat ccaaagctca tggcggggac cacagaaccc acgtggccat   38400
cataccacaa gcgcaggtag attaagtggc gaccctcat aaaacacgctg gacataaaca   38460
ttacctcttt tggcatgttg taattcacca cctcccggta ccatataaac ctctgattaa   38520
acatggcgcc atccaccacc atcctaaacc agctggccaa aacctgcccg ccggctatac   38580
actgcaggga accgggactg gaacaatgac agtggagagc ccaggctcg taaccatgga   38640
tcatcatgct cgtcatgata tcaatgttgg cacaacacag cgcacacgtg atacacttcc   38700
tcaggattac aagctcctcc cgcgttagaa ccatatccca gggaacaacc cattcctgaa   38760
tcagcgtaaa tcccacactg cagggaagac ctcgcacgta actcacgttg tgcattgtca   38820
aagtgttaca ttcgggcagc agcggatgat cctccagtat ggtagcgcgg gtttctgtct   38880
caaaaggagg tagacgatcc ctactgtacg gagtgcgccg agacaaccga gatcgtgttg   38940
gtcgtatgtg catgccaaat ggaacgccgg acgtagtcat atttcctgaa gcaaaaccag   39000
gtgcgggcgt gacaaacaga tctgcgtctc cggtctcgcc gcttagatcg ctctgtgtag   39060
tagttgtagt atatccactc tctcaaagca tccaggcgcc cctggcttc gggttctatg   39120
taaactcctt catgcgccgc tgccctgata acatccacca ccgcagaata agccacaccc   39180
agccaaccta cacattcgtt ctgcgagtca cacacggag gagcgggaag agctggaaga   39240
accatgtttt ttttttttatt ccaaaagatt atccaaaacc tcaaaatgaa gatctattaa   39300
```

-continued

```
gtgaacgcgc tcccctccgg tggcgtggtc aaactctaca gccaaagaac agataatggc  39360
atttgtaaga tgttgcacaa tggcttccaa aaggcaaacg gccctcacgt ccaagtggac  39420
gtaaaggcta aacccttcag ggtgaatctc ctctataaac attccagcac cttcaaccat  39480
gcccaaataa ttctcatctc gccaccttct caatatatct ctaagcaaat cccgaatatt  39540
aagtccggcc attgtaaaaa tctgctccag agcgccctcc accttcagcc tcaagcagcg  39600
aatcatgatt gcaaaaattc aggttcctca cagacctgta taagattcaa aagcggaaca  39660
ttaacaaaaa taccgcgatc ccgtaggtcc cttcgcaggg ccagctgaac ataatcgtgc  39720
aggtctgcac ggaccagcgc ggccacttcc ccgccaggaa ccatgacaaa agaacccaca  39780
ctgattatga cacgcatact cggagctatg ctaaccagcg tagccccgat gtaagcttgt  39840
tgcatgggcg gcgatataaa atgcaaggtg ctgctcaaaa aatcaggcaa agcctcgcgc  39900
aaaaaagaaa gcacatcgta gtcatgctca tgcagataaa ggcaggtaag ctccggaacc  39960
accacagaaa aagacaccat ttttctctca aacatgtctg cgggtttctg cataaacaca  40020
aaataaaata acaaaaaaac atttaaacat tagaagcctg tcttacaaca ggaaaaacaa  40080
cccttataag cataagacgg actacggcca tgccggcgtg accgtaaaaa aactggtcac  40140
cgtgattaaa aagcaccacc gacagctcct cggtcatgtc cggagtcata atgtaagact  40200
cggtaaacac atcaggttga ttcacatcgg tcagtgctaa aaagcgaccg aaatagcccg  40260
ggggaataca tacccgcagg cgtagagaca acattacagc cccatagga ggtataacaa  40320
aattaatagg agagaaaaac acataaacac ctgaaaaacc ctcctgccta ggcaaaatag  40380
caccctcccg ctccagaaca acatacagcg cttccacagc ggcagccata acagtcagcc  40440
ttaccagtaa aaaagaaaac ctattaaaaa aacaccactc gacacggcac cagctcaatc  40500
agtcacagtg taaaaaaggg ccaagtgcag agcgagtata tataggacta aaaaatgacg  40560
taacggttaa agtccacaaa aaacacccag aaaaccgcac gcgaacctac gcccagaaac  40620
gaaagccaaa aaacccacaa cttcctcaaa tcgtcacttc cgttttccca cgttacgtca  40680
cttcccattt taagaaaact acaattccca acacatacaa gttactccgc cctaaaacct  40740
acgtcacccg ccccgttccc acgccccgcg ccacgtcaca aactccaccc cctcattatc  40800
atattggctt caatccaaaa taaggta                                      40827
```

SARS-COV-2 VACCINES COMPRISING HUMAN ADENOVIRUS VECTORS ENCODING SPIKE AND NUCLEOCAPSID-ETSD IMMUNOGENS

This application is a CON of Ser. No. 17/198,164 (filed Mar. 10, 2021), which claims benefit of 63/121,102 (filed Dec. 3, 2020) and claims benefit of 63/117,847 (filed Nov. 24, 2020) and claims benefit of 63/115,127 (filed Nov. 18, 2020) and is a CIP of Ser. No. 17/082,994 (filed Oct. 28, 2020), which claims benefit of 62/991,504 (filed Mar. 18, 2020) and claims benefit of 62/988,328 (filed Mar. 11, 2020). This application claims benefit of 63/082,145 (filed Sep. 23, 2020) and claims benefit of 63/080,887 (filed Sep. 21, 2020) and claims benefit of 63/069,598 (filed Aug. 24, 2020) and claims benefit of 63/067,033 (filed Aug. 18, 2020) and claims benefit of 63/053,691 (filed Jul. 19, 2020) and claims benefit of 63/036,445 (filed Jun. 9, 2020) and is a CIP of Ser. No. 16/880,804 (filed May 21, 2020), which claims benefit of 63/022,146 (filed May 8, 2020) and claims benefit of 63/016,048 (filed Apr. 27, 2020) and claims benefit of 63/016,241 (filed Apr. 27, 2020) and claims benefit of 63/009,960 (filed Apr. 14, 2020) and claims benefit of 63/010,010 (filed Apr. 14, 2020) and claims benefit of 62/991,504 (filed Mar. 18, 2020) and claims benefit of 62/988,328 (filed Mar. 11, 2020). This application is a CIP of Ser. No. 16/883,263 (filed May 26, 2020, now U.S. Pat. No. 11,684,668), which claims benefit of 63/022,146 (filed May 8, 2020) and claims benefit of 63/016,048 (filed Apr. 27, 2020) and claims benefit of 63/016,241 (filed Apr. 27, 2020) and claims benefit of 63/009,960 (filed Apr. 14, 2020) and claims benefit of 63/010,010 (filed Apr. 14, 2020) and claims benefit of 62/991,504 (filed Mar. 18, 2020) and claims benefit of 62/988,328 (filed Mar. 11, 2020). This application claims benefit of 63/117,922 (filed Nov. 24, 2020) and claims benefit of 63/117,460 (filed Nov. 24, 2020) and claims benefit of 63/064,157 (filed Aug. 11, 2020) and claims benefit of 63/059,975 (filed Aug. 1, 2020) and claims benefit of 63/135,380 (filed Jan. 8, 2021) and claims benefit of 63/118,697 (filed Nov. 26, 2020). Each of the above applications are incorporated by reference in its entirety, including the drawings and the sequence listings.

INCORPORATION OF SEQUENCE LISTING

This application contains references to nucleic acid and polypeptide sequences which have been submitted concurrently herewith as the sequence listing XML file "102538.0080US3-CON", created on 11 Oct. 2023. The file is 116 kilobytes (kb) in size. The aforementioned sequence listing is hereby incorporated by reference in its entirety pursuant to 37 C.F.R. § 1.52(e).

FIELD

The present disclosure relates to composition and methods for administering a vaccine to a patient and monitoring induced immunity in the patient in a stabilized patient sample.

BACKGROUND

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

After several noteworthy coronavirus outbreaks in the recent years, including SARS and MERS, Corona Virus Disease 2019 (COVID-19) is yet another example of a serious infectious disease precipitated by a member of the corona virus family. While diagnostic tests have become available in a relatively short time, testing is not efficient, and numerous attempts to treat the disease have so far not had significant success. Most typically, patients with severe symptoms are treated to maintain respiration/blood oxygenation, and supportive treatment is provided to reduce or prevent multi-organ damage or even failure. Despite such interventions, the mortality rate is significant, particularly in elderly, immune compromised individuals, and individuals with heart disease, lung disease, or diabetes.

Thus, even though various methods of addressing symptoms in patients with COVID-19 are known in the art, all or almost all of them suffer from various disadvantages. Consequently, there is a need to provide improved vaccine compositions and methods that render a therapeutic effect, reduce or prevent viral entry into a cell, reduce direct and indirect toxicity of the virus to the patient, and produce an immune response that is effective to clear the virus from the patient.

SUMMARY

The present disclosure is directed to various immune therapeutic compositions and methods suitable for treating and/or preventing a coronavirus disease. In one aspect, disclosed herein is a replication defective adenovirus, wherein the adenovirus comprises an E1 gene region deletion; an E2b gene region deletion; an E3 gene region deletion; a nucleic acid encoding a coronavirus 2 (CoV2) nucleocapsid protein CoV2 nucleocapsid protein fused to an endosomal targeting sequence (N-ETSD), and a nucleic acid encoding a CoV2 spike protein sequence optimized for cell surface expression (S-Fusion). In a second aspect of this disclosure, provided herein is a recombinant yeast comprising a nucleic acid encoding a coronavirus 2 (CoV2) nucleocapsid protein CoV2 nucleocapsid protein fused to an endosomal targeting sequence (N-ETSD), and a nucleic acid encoding a CoV2 spike protein sequence optimized for cell surface expression (S-Fusion). comprising a nucleic acid encoding a coronavirus 2 (CoV2) nucleocapsid protein CoV2 nucleocapsid protein fused to an endosomal targeting sequence (ETSD), and a nucleic acid encoding a CoV2 spike protein sequence optimized for cell surface expression (S-Fusion). Preferably, the recombinant yeast is *Saccharomyces cerevisiae*.

In one embodiment of each of the above two aspects, the CoV2 nucleocapsid protein has at least 85% identity to SEQ ID NO:1. It is further contemplated that the fusion protein contains a linker between the ETSD domain and the nucleocapsid protein. For example this linker may be a 16 amino acid linker having the sequence $(GGGS)_4$. In one embodiment, the fusion protein has at least 85% identity of SEQ ID NO:2. The CoV2 spike protein is contemplated to have at least 85% identity to SEQ ID NO:6. The nucleic acid encoding the CoV2 spike protein has at least 99% identity to SEQ ID NO:5 or SEQ ID NO:7.

In another embodiment of this disclosure, the adenoviruses and yeasts disclosed herein may further comprise a nucleic acid encoding a trafficking sequence, a co-stimulatory molecule, and/or an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine may be selected from the group consisting of IL-2, IL-12, IL-15, nogapendekin alfa-imbakicept, IL-21, IPS1, and LMP1.

In yet another embodiment, disclosed herein is a vaccine composition comprising the adenovirus or yeast as disclosed above, and wherein the composition is formulated for injection. The vaccine composition may be used for inducing immunity against CoV2 in a patient in need thereof, by administering to the patient the vaccine composition In another aspect, the method includes administering to the subject an immunotherapy composition comprising a recombinant entity, wherein the recombinant entity comprises a nucleic acid that encodes a nucleocapsid protein of coronavirus 2 (CoV2) and/or a spike protein of CoV2. In one embodiment, the nucleocapsid protein is ETSD.

Preferably, the nucleic acid that encodes a nucleocapsid protein of coronavirus 2 further encodes a trafficking sequence for the nucleocapsid protein. It is further contemplated that the recombinant entity may also comprise a sequence that encodes at least one of a co-stimulatory molecule and an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine is selected from the group consisting of IL-2, IL-12, IL-15, IL-15 super agonist (N803), IL-21, IPS1, and LMP1. In some preferred embodiments, the immune stimulatory cytokine is IL-15 super agonist N803.

The immunotherapy compositions disclosed herein to be administered subcutaneously or intravenously.

The recombinant entity contemplated herein may be a recombinant virus, such as a recombinant adenovirus. The recombinant entity may also be a recombinant yeast, such as *Saccharomyces cerevisiae.*

In some preferred embodiments, the coronavirus disease is COVID-19.

In yet another aspect of the present disclosure, disclosed herein is a vaccine formulation comprising a recombinant entity, wherein the recombinant entity comprises a nucleic acid that encodes a nucleocapsid protein of coronavirus 2 (CoV2); and/or wherein the recombinant entity encodes a spike protein of CoV2. As discussed throughout, the recombinant entity is preferably a recombinant adenovirus or *Saccharomyces cerevisiae.* The vaccine formulation may administered to a patient having a coronavirus disease for treatment and/or prevention of the coronavirus disease.

The present disclosure further provides methods and compositions for administering, monitoring, and assaying a vaccine. The contemplated methods include inducing immunity against a virus in a patient, administering a vaccine composition to the patient by administering a vaccine composition to the patient by delivery to the nasal mucosa, oral mucosa, and/or alimentary mucosa of the patient. Preferably, the vaccine targets severe acute respiratory syndrome (SARS)-like coronavirus (SARS-CoV2). The oral vaccine compositions described herein can serve as a booster vaccination to any initial prime vaccination against SARS-CoV2 S or N protein.

Notably, the disclosed methods also include obtaining a sample of saliva from the patient at a period of time after administering the vaccine. Typically, the sample of saliva is preserved in a stabilizing solution comprising glutaraldehyde, sodium benzoate, citric acid, propyl gallate, EDTA, zinc, actin, chitosan, parabens, sodium azide, or any combination thereof. More typically, the stabilizing solution comprises glutaraldehyde at 0.10 to 2.0% weight per volume (w/v), sodium benzoate at 0.10 to 1.0% w/v, and/or citric acid at 0.025 to 0.20% w/v. Additional embodiments include analyzing the sample of saliva for at least one selected from antibodies targeting the virus or a protein specific to the virus, wherein in the absence of antibodies in the sample saliva, the method further comprises administering a booster of the vaccine to the patient.

The oral vaccine compositions described herein can be used as a universal booster vaccine to any anti-SARS-CoV2 vaccine directed against the SARS-CoV2 spike (S) and/or nucleocapsid (N) proteins. This booster can work even in patients who were immunized with an anti-S or anti-N vaccine other than those described herein. In particular embodiments, the initial prime vaccine can be a lipid nanoparticle vaccine containing mRNA encoding the S protein, such as those vaccines currently being tested by Moderna and by Pfizer. In certain embodiments, the boost described herein is administered at least 7 days after the initial prime vaccination, for example at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 28 days, at least 35 days, or at least 42 days. The boost as described herein can effectively improve both antibody production against SARS-CoV2 and cell-mediate immunity against SARS-CoV2. The efficacy of the booster vaccine can be measured by any standard quantification of immune response (e.g., a QuantiFERON assay).

Additionally, the stabilizing solution further comprises aragonite particle beads having an average particle size of between 100 nm to 1 mm. The aragonite particle beads are capable of binding to immunoglobulin (Ig) proteins, anti-SARS-CoV2 antibodies, or a SAR-CoV2 viral protein. In exemplary embodiments, the aragonite particle beads are coupled to a recombinant ACE2 protein or a recombinant ACE2 alpha helix protein.

The contemplated subject matter also includes an aragonite composition formulated for binding an immunoglobulin (Ig) protein, an anti-SARS-CoV2 antibody protein, or a SARS-CoV2 viral protein. The aragonite composition includes a plurality of aragonite particle beads having an average particle size of between 100 nm to 1 mm, wherein the plurality of aragonite particle beads are functionalized with a moiety capable of binding to an immunoglobulin (Ig) protein, the anti-SARS-CoV2 antibody protein and/or the SARS-CoV2 viral protein.

In specific embodiments, the plurality of aragonite particle beads are functionalized with a moiety capable of binding to the anti-SARS-CoV2 comprises a recombinant ACE2 protein. For example, the moiety capable of binding to the anti-SARS-CoV2 may be selected from a recombinant ACE2 protein having at least 85% sequence identity to SEQ ID NO:1, a recombinant alpha-helix ACE2 protein of SEQ ID NO: 2, or the recombinant alpha-helix ACE2 protein having at least one mutation selected from T27F, T27W, T27Y, D30E, H34E, H34F, H34K, H34M, H34W, H34Y, D38E, D38M, D38W, Q24L, D30L, H34A, and/D355L.

Various objects, features, aspects, and advantages will become more apparent from the following detailed description of preferred embodiments, along with the accompanying drawing in which like numerals represent like components.

BRIEF DESCRIPTION OF THE DRAWING

FIG. 1 exemplarily depicts vaccine constructs for Phase 1*b* clinical trials.

FIG. 2 exemplarily depicts in vitro Expression, Construct Expression via Western Blot, and detection of spike and nucleocapsid expression in by Western Blot.

FIG. 3 exemplarily depicts COVID-19 vaccine constructs.

FIG. 4 exemplarily depicts antibody response to N with a Th1 phenotype. Humoral Immune Responses $T_H1$ vs $T_H2$ associated isotype analysis is shown.

FIG. 5 exemplarily depicts cell mediated immunity (CMI) response to N focus phenotype—IFN-γ and IL-2 ELISpot.

Figure 6:
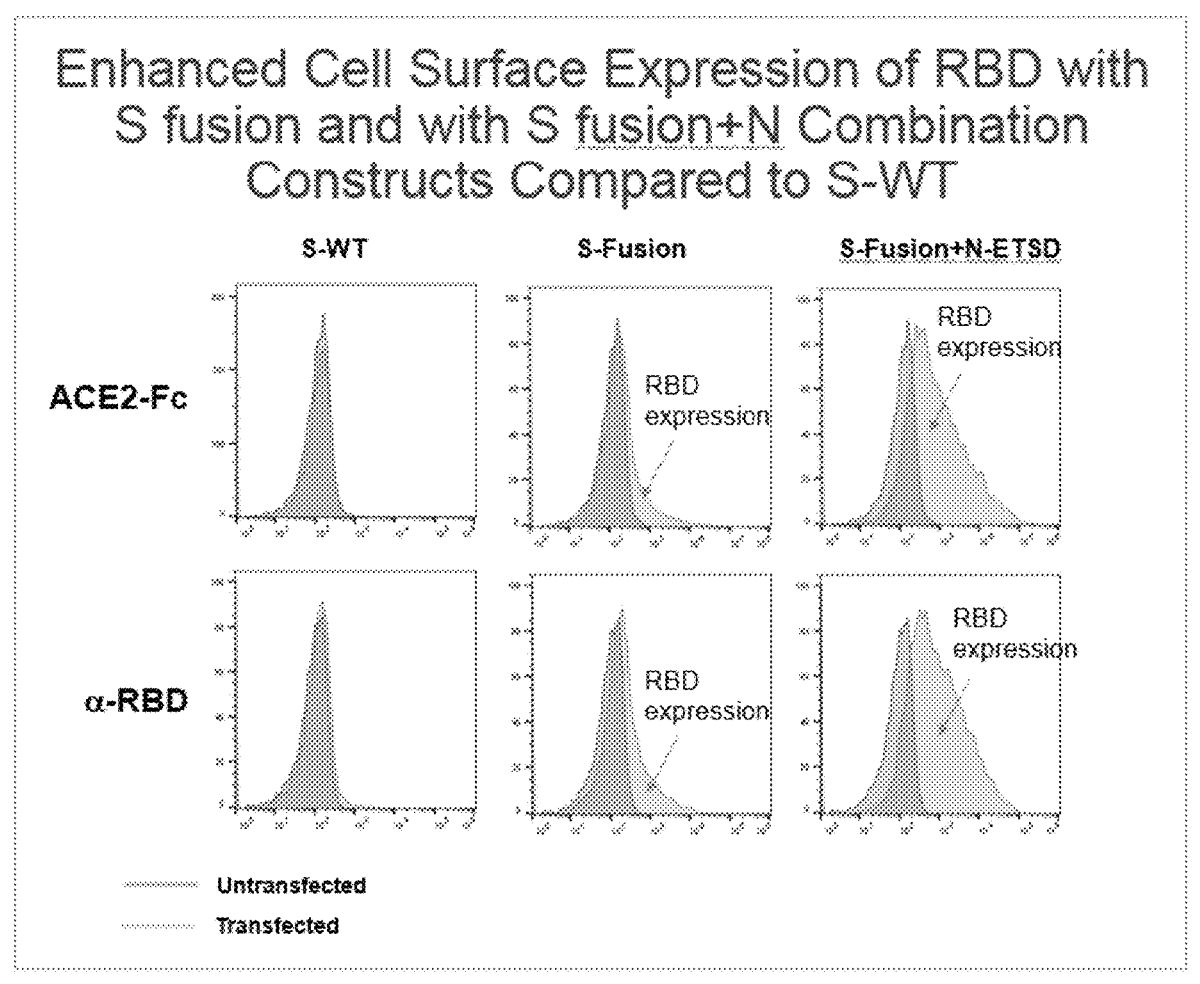

FIG. 6 exemplarily depicts enhanced cell surface expression of RBD with S Fusion and with S Fusion+N combination constructs compared to S-WT.

FIG. 7 exemplarily depicts that recovered COVID-19 patient plasma recognizes antigens expressed by NANT's RBD-ETSD and NANT fusion S/N-ETSD constructs.

FIG. 8 exemplarily depicts the SARS-CoV-2 virus, spike, the hAd5 [E1-, E2b-, E3-] vector and vaccine candidate constructs. (a) Trimeric spike (S) protein (orange triangle) is displayed on the viral surface; the nucleocapsid (N) protein (blue circle) is associated with the viral RNA. (b) The Receptor Binding Domain (RBD) is within the S1 region, followed by other functional regions, the transmembrane domain (TM) and the C-terminus (CT), which is within the virus. (c) The second-generation human adenovirus serotype 5 (hAd5) vector used has the E1, E2b, and E3 regions deleted. Constructs are shown for (d) S wild type (S-WT), (e) S-RBD with the Enhanced T-cell Stimulation Domain (S RBD-ETSD), (f) S-Fusion, (g) N-ETSD, and (h) bivalent hAd5 S-Fusion+N-ETSD; LP—Leader peptide FIG. 9 exemplarily depicts transfection of HEK293T cells with hAd5 S-Fusion+ETSD results in enhanced surface expression of the spike receptor binding domain (RBD). Flow cytometric analysis of an anti-RBD antibody with construct-transfected cells reveals no detectable surface expression of RBD in either S-WT or (b) S-WT+N-ETSD transfected cells. Surface RBD expression was high for S RBD-ETSD and S RBD-ETSD+N-ETSD (c, d). Expression was low in (e) S-Fusion transfected cells. Cell surface expression of the RBD was high in (f) S-Fusion+N-ETSD transfected cells, particularly at day 1 and 2. (g) No expression was detected the N-ETSD negative control. Y-axis scale is normalized to mode (NM).

FIG. 10 exemplarily depicts immunoblot analysis of S expression. Cell surface RBD expression with (a) hAd5 S-WT, S-Fusion, and (c) S-Fusion+N-ETSD in HEK 293T cells shows high correlation with (d) expression of S in immunoblots of HEK 293T cell lysates probed using anti-full length (S2) antibody. Y-axis scale is normalized to mode (NM).

FIG. 11 exemplarily depicts binding of recombinant ACE2-Fc HEK293T cell-surface expressed RBD after transfection confirms native protein folding. Flow cytometric analysis of binding between recombinant ACE2-Fc, with which the spike RBD interacts in vivo to initiate infection, and cell-surface antigens expressed after transfection of HEK293T cells with (a) hAd5 S-WT, (b) hAd5 S-Fusion, (c) hAd5 S-Fusion+N-ETSD, (d) hAd5 S RBD-ETSD, or (e) hAd5 S RBD-ETSD+N-ETSD constructs reveals the highest binding is seen for both ACE-Fc and an anti-RBD specific antibody (f-j) after transfection with the bivalent S-Fusion+N-ETSD. Both S RBD-ETSD-containing constructs also showed binding. Y-axis scale is normalized to mode (NM).

FIG. 12 exemplarily depicts N expressed from hAd5 N-ETSD is localized to the endosomal/lysosomal compartment. In HeLa cells infected with N-ETSD, (a) N (red) co-localizes with the endosomal marker CD71 (b) as indicated by the arrow in (c). In transfected HeLa cells, (d) N-ETSD also co-localizes with the lysosomal marker Lamp1, whereas (e) N wild type (N-WT) does not, showing instead diffuse cytoplasmic distribution.

FIG. 13 exemplarily depicts ICS detection of cytokine-expressing splenocytes from hAd5 S-Fusion+N-ETSD inoculated Day 28 CD-1 mice in response to peptide pools. (a) The highest CD8/3' splenocyte IFN-γresponse was in hAd5 S-Fusion+N-ETSD-inoculated mouse splenocytes exposed to S peptide pool 1 (S-pep pool 1); splenocytes from these mice also expressed IFN-γ in response to the N peptide pool (N-pep pool). (b) CD4+splenocytes from hAd5 S-Fusion+N-ETSD-inoculated mice only expressed IFN-γ in response to the N peptide pool. (c) IFN-γ TNF-α responses of CD8J3* splenocytes from hAd5 S-Fusion+N-ETSD-inoculated mice were very similar to those in (a); as were (d) CD4+splenocytes to the N peptide pool to those in (b). N=5 mice per group. All data sets graphed as the mean with SEM and all statistics performed using the Mann-Whitney test where *<0.05, <0.01, *<0.001, and ****<0.0001.

FIG. 14 exemplarily depicts anti-spike and anti-nucleocapsid antibody responses in sera from hAd5 S-Fusion+N-ETSD vaccinated mice. Based on absorbance, there was significant production of both (a) anti-S antibodies and (c) anti-nucleocapsid antibodies. (b, d) The ng equivalents are shown. Sera diluted 1:30 for anti-spike and 1:90 for anti-nucleocapsid antibodies. Data graphed as the mean and SEM. Statistical analysis was performed using an unpaired two-tailed Student's t-test where *<0.05, <0.01, *<0.001, and ****<0.0001.

FIG. 15 exemplarily depicts cPass and Vero E6 cell SARS-CoV-2 confirm neutralization by antibodies. (a) In the cPass assay, inhibition of S RBD interaction with ACE2 was significant at both 1:20 and 1:60 dilutions of serum from hAd5 S-Fusion+N-ETSD vaccinated mice. (b) The results in the Vero E6 cell SARS-CoV-2 viral infection for mice that showed S-specific antibodies by ELISA also showed high neutralization for mice and very high neutralization for pooled sera (G4 pool, blue line) even compared to COVID-19 convalescent serum. G4 pool—mice with S-specific antibodies; M1, M2, M3, M4—mouse ID; +C—convalescent serum; and media—media only negative control.

FIG. 16 exemplarily depicts isotypes for anti-spike and anti-nucleocapsid antibodies. (a, c) IgG2a and IgG2b isotype anti-spike and anti-nucleocapsid antibodies were significantly increased for hAd5 S-Fusion+N-ETSD mice compared to hAd5 Null mice. (b, d) The ng equivalents for antibody isotypes are shown. Data graphed as the mean and SEM. Statistical analysis was performed using an unpaired two-tailed Student's t-test where *<0.05, <0.01, *<0.001, and ****<0.0001.

FIG. 17 exemplarily depicts ELISpot detection of secreted cytokines. (a) IFN-111 secretion by hAd5 S-Fusion+N-ETSD splenocytes was significantly higher than hAd5 Null in response to both S peptide pool 1 and the N peptide pool; but (b) IL-4 was only secreted with hAd5 S-Fusion+N-ETSD in response to the N peptide pool (one high outlier in hAd5 null removed). N=5 mice per group. All data sets graphed as the mean with SEM and all statistics performed using the Mann-Whitney test where *<0.05, <0.01, *<0.001, and ****<0.0001.

FIG. 18 exemplarily depicts ratios for T-cell and humoral responses reveal Th1 predominance. (a) The ratio of total Th1 (IFN-7) to Th2 (IL-4) spot-forming units is shown for responses to the combined S pools and to the N pool. (b) The Th1/Th2 ratio for antibodies against S and N is shown. For both (a) and (b) the dashed line indicates a ratio of 1 or a balance of Th1 and Th2 (no predominance).

FIG. 19 shows ELISA results detecting IgG seroreactivity against SARS-CoV2 spike in sera samples drawn from immunized macaques.

FIG. 20 breaks out the ELISA results in FIG. 1 for the Group 1 macaques.

FIG. 21 breaks out the ELISA results in FIG. 1 for the Group 1 macaques.

Figure 28:
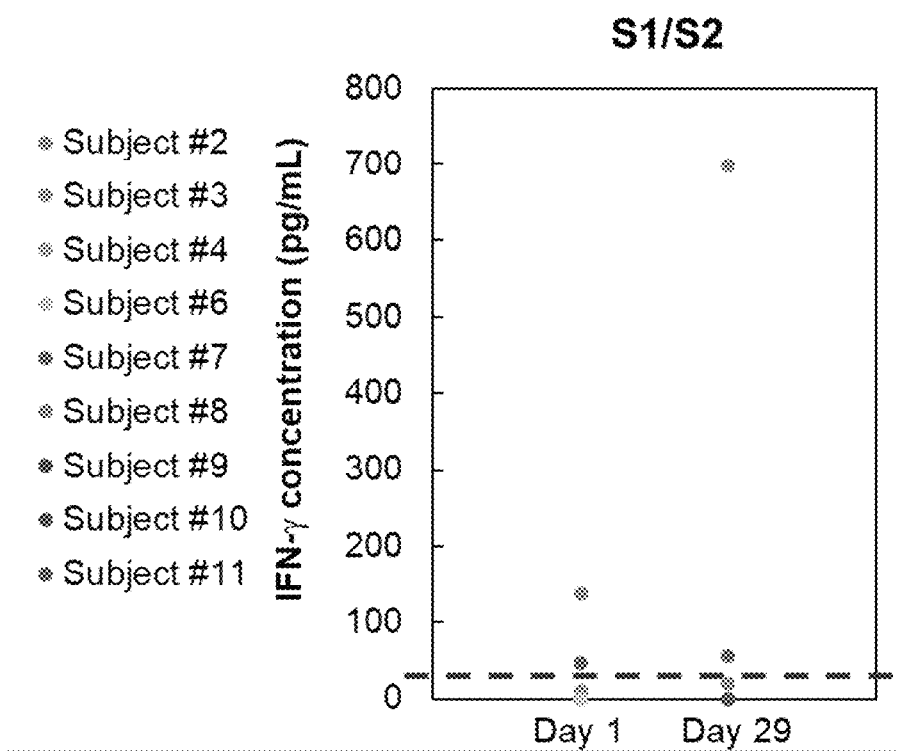

FIG. 28 shows the results of a QuantiFERON assay on blood samples drawn from nine immunized patients on days 1 and 29 of the vaccination regime. The dashed line near the bottom of the panel indicates the threshold of detection. The dashed-line boxes indicate the results from subject #8.

DETAILED DESCRIPTION

Disclosed herein are recombinant viruses and yeasts. The viruses and yeasts disclosed herein may be useful for a variety of purposes, such as treating and/or preventing a coronavirus disease. In one aspect, disclosed herein is a replication defective adenovirus, wherein the adenovirus comprises an E1 gene region deletion; an E2b gene region deletion; an E3 gene region deletion, a nucleic acid encoding a coronavirus 2 (CoV2) nucleocapsid protein CoV2 nucleocapsid protein fused to an endosomal targeting sequence (N-ETSD), and a nucleic acid encoding a CoV2 spike protein sequence optimized for cell surface expression (S-Fusion).

In one embodiment, the N-ETSD may comprises a sequence with at least 80% identity to SEQ ID NO:2. In other embodiments, the identity value is at least 85%. In still other embodiments, the identity value is at least 90%. In some embodiments, the identity value is at least 95%. In some embodiments, the identity value is at least 99%. In some embodiments, the identity value is 100%. It is further contemplated that the fusion protein contains a linker between the N-ETSD domain and the nucleocapsid protein. For example this linker may be a 16 amino acid linker having the sequence $(GGGS)_4$. In certain embodiments, methods are disclosed herein for enhancing the immunogenicity of an intracellular antigen, the methods comprising tagging the antigen with ETSD and expressing the tagged antigen in an antigen-presenting cell (e.g., a dendritic cell).

In some embodiments, the fusion protein comprising N-ETSD and CoV2 nucleocapsid protein may be encoded by a nucleic acid sequence having at least 80% identity to SEQ ID NO:3. In some embodiments, the identity value is at least 85%. In some embodiments, the identity value is at least 90%. In some embodiments, the identity value is at least 95%. In some embodiments, the identity value is at least 99%. In some embodiments, the identity value is 100%.

The CoV2 spike protein is contemplated to have at least 85% identity to SEQ ID NO:6. The nucleic acid encoding the CoV2 spike protein has at least 99% identity to SEQ ID NO:5 or SEQ ID NO:7.

In a second aspect of this disclosure, provided herein is a recombinant yeast comprising a nucleic acid encoding a protein selected from the group consisting of coronavirus 2 (CoV2) nucleocapsid protein, CoV2 spike protein, and a combination thereof. Preferably, the recombinant yeast is *Saccharomyces cerevisiae.*

In some embodiments of this second aspect, the CoV2 nucleocapsid protein comprises a sequence with at least 80% identity to SEQ ID NO:2 or SEQ ID NO:3. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiment of this second aspect, the CoV2 spike protein comprises a sequence with at least 80% identity to SEQ ID NO:5. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiments, the nucleic acid encoding the CoV2 spike protein comprises a sequence with at least 80% identity to SEQ ID NO:5 or SEQ ID NO:7. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

The adenoviruses and yeasts disclosed herein may further comprise a nucleic acid encoding a trafficking sequence, a co-stimulatory molecule, and/or an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine may be selected from the group consisting of IL-2, IL-12, IL-15, nogapendekin alfa-imbakicept, IL-21, IPS1, and LMP1.

Additionally or alternatively, the vaccines disclosed herein may also encode SARS-CoV-2 M protein, with or without an ETSD tag.

In yet another embodiment, disclosed herein is a vaccine composition comprising the adenovirus or yeast as disclosed above, and wherein the composition is formulated for injection. The vaccine composition may be used for inducing immunity against CoV2 in a patient in need thereof, by administering to the patient the vaccine composition Also disclosed herein are methods for preventing and/or treating coronavirus diseases, and especially COVID-19. Preferably, the method includes using a viral or yeast vector that encodes the nucleocapsid protein and/or spike protein of the coronavirus in an immunogenic composition that is administered to a subject individual. The virus and/or yeast vaccine, thus administered, would infect the individual with CoV2 nucleocapsid or spike protein. With that in place, the individual would have an immune response against it, and be vaccinated. Notably, as the nucleocapsid protein and the spike protein are relatively conserved polypeptides, immune responses can be elicited for a variety of members of the coronavirus family.

Where the recombinant vector is an adenovirus, the adenoviral vector may be modified to encode the nucleocapsid protein, and/or the spike protein. Similarly, in case of yeast, the yeast vector may also be modified to encode the nucleocapsid protein, and/or the spike protein. Positive responses were obtained on cell mediated immunity upon administration of immunogenic compositions comprising the viral and/or yeast vectors in patients in need thereof. Thus, in one embodiment, the present disclosure envision creating the coronaviral spikes to be expressed on the yeast surface. So, in this embodiment, the yeast is acting as an avatar coronavirus to stimulate the B cells. The stimulation of the B cells then results in humoral immunity.

In another embodiment, disclosed herein is a next generation bivalent human adenovirus serotype 5 (hAd5) vaccine capable of inducing immunity in patients with pre-existing adenovirus immunity, comprising both an S sequence optimized for cell surface expression (S-Fusion) and a conserved nucleocapsid (N) antigen designed to be transported to the endosomal subcellular compartment, with the potential to generate durable immune protection. As further described in this disclosure, this bivalent vaccine has been found to be is optimized for immunogenicity as evidenced by the following findings:

- The optimized S-Fusion displayed improved S receptor binding domain (RBD) cell surface expression compared to S-WT where little surface expression was detected;
- The expressed RBD from S-Fusion retained conformational integrity and recognition by ACE2-Fc;
- The viral N protein modified with an enhanced T-cell stimulation domain (ETSD) localized to endosomal/lysosomal subcellular compartments for MHC I/II presentation; and
- These optimizations to S and N (S-Fusion and N-ETSD) generated enhanced de novo antigen-specific B cell and CD4+ and CD8+ T-cell responses in antigen-naive pre-clinical models.

Both the T-cell and antibody immune responses to S and N demonstrated a T-helper 1 (Th1) bias. The antibody responses were neutralizing as demonstrated by two independent SARS-CoV-2 neutralization assays. Thus, in one embodiment, this next generation bivalent hAd5 S-Fusion+ N-ETSD vaccine provides robust, durable cell-mediated and humoral immunity against SARS-CoV-2 infection. This vaccine construct may be administered orally, intranasaly or sublingually. Thus, in one embodiment, the instant disclosure provides vaccine construct in oral, intranasal, and sublingual formulations to induce mucosal immunity in addition to cell-mediated and humoral immunity. In one embodiment, the COVID-19 vaccine disclosed herein generates long-term T and B cell memory.

Coronaviruses and Vaccines Therefor

Coronaviruses are found in avian and mammalian species. They resemble each other in morphology and chemical structure: for example, the coronaviruses of humans and cattle are antigenically related. There is no evidence, however, that human coronaviruses can be transmitted by animals. In animals, various coronaviruses invade many different tissues and cause a variety of diseases in humans. One such disease was Severe acute respiratory syndrome (SARS) coronavirus disease that spread to several countries in Asia, Europe and North America in late 2002/early 2003. Another such disease is the novel Coronavirus Disease of 2019 (COVID 19) that has spread to several countries in the world. In December of 2019, reports emerged from Wuhan, China concerning a new infectious respiratory disease with high morbidity and mortality 1-3 that displayed human-to-human transmission.4 The causative agent was rapidly identified as a novel coronavirus and was designated SARS-coronavirus 2 (SARS-CoV-2). The disease it causes is referred to as COVID-19 and has rapidly become a worldwide pandemic that has disrupted socioeconomic life and resulted in more than 32 million infections and more than 1,100,000 deaths worldwide as of late October 2020.

COVID 19 usually begins with a fever greater than 38° C. Initial symptoms can also include cough, sore throat, malaise and mild respiratory symptoms. Within two days to a week, patients may have trouble breathing. Patients in more advanced stages of COVID 19 develop either pneumonia or respiratory distress syndrome. Public health interventions, such as surveillance, travel restrictions and quarantines, are being used to contain the spread of COVID 19. It is unknown, however, whether these draconian containment measures can be sustained with each appearance of the COVID 19 in humans. Furthermore, the potential of this new and sometimes lethal CoV as a bio-terrorism threat is obvious.

Coronavirus virions are spherical to pleomorphic enveloped particles. The envelope is studded with projecting glycoproteins, and surrounds a core consisting of matrix protein enclosed within which is a single strand of positive-sense RNA (Mr $6\times10^6$) associated with nucleocapsid protein. In that regard, it should be noted that the terms "nucleocapsid protein," "nucleoprotein," and "nucleocapsid" are used interchangeably throughout this disclosure. The coronavirus nucleocapsid (N) is a structural protein found in all coronaviruses, including COVID 19. The nucleocapsid protein forms complexes with genomic RNA, interacts with the viral membrane protein during virion assembly and plays a critical role in enhancing the efficiency of virus transcription and assembly.

Another protein found throughout all coronavirus virions is the viral spike(S) protein. Coronaviruses are large positive-stranded RNA viruses typically with a broad host range. Like other enveloped viruses, CoV enter target cells by fusion between the viral and cellular membranes, and that process is mediated by the viral spike (S) protein.

Figure 8:
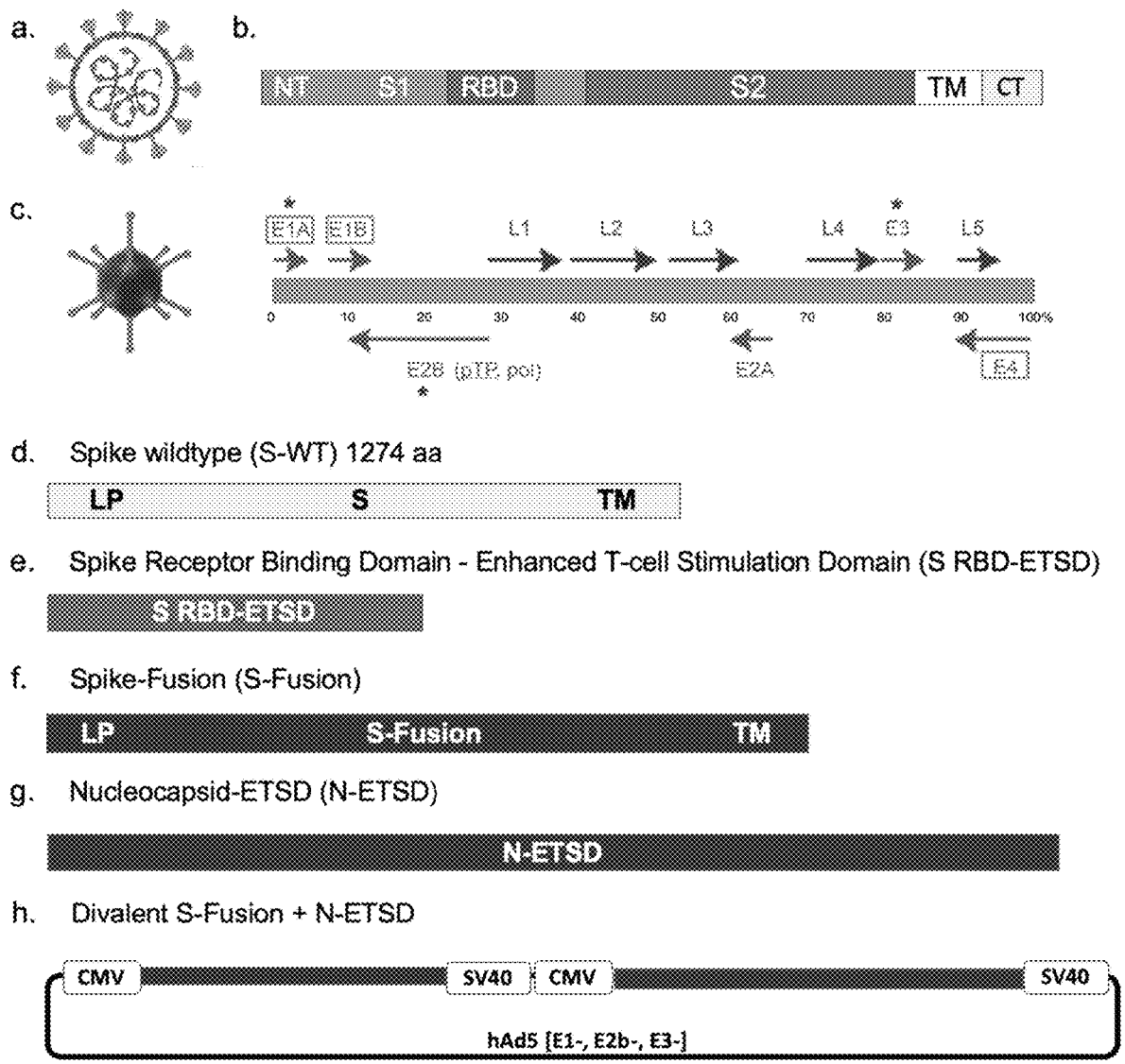

SARS-CoV-2 is an enveloped positive sense, single-strand RNA β coronavirus primarily composed of four structural proteins—spike (S), nucleocapsid (N), membrane (M), and envelope—as well as the viral membrane and genomic RNA. Of these, S is the largest and N the most prevalent. The S glycoprotein is displayed as a trimer on the viral surface (FIG. 8a), whereas N is located within the viral particle. A schematic of the S primary structure is shown in FIG. 8b. The sequence of SARS-CoV-2 was published8 and compared to that of previous coronaviruses. This was soon followed by reports on the crystal structure of the S protein. The virus uses S protein to enter host cells by interaction of the S receptor binding domain (S RBD) with angiotensin-converting enzyme 2 (ACE2), an enzyme expressed broadly on a variety of cell types in the nose, mouth, gut and lungs as well as other organs, and importantly on the alveolar epithelial cells of the lung where infection is predominantly manifested. As represented in FIG. 8b, the S RBD is found within the S1 region of spike.

The methods and compositions disclosed herein target the nucleoprotein and the spike protein that is conserved in all types of coronaviruses. In one embodiment, the present disclosure provides a vaccine formulation comprising a recombinant entity, wherein the recombinant entity comprises a nucleic acid that encodes a nucleocapsid protein of coronavirus 2 (CoV2); and/or wherein the recombinant entity encodes a spike protein of CoV2. The vaccine formulation may be useful for treating a disease, such as a coronavirus mediated disease or infection. Thus, in another embodiment, disclosed is a method for treating a coronavirus disease, in a patient in need thereof, comprising: administering to the subject an immunotherapy composition comprising a recombinant entity, wherein the recombinant entity comprises a nucleic acid that encodes a nucleocapsid protein of coronavirus 2 (CoV2). The coronavirus contemplated herein may be coronavirus disease 2019 (COVID-19) and/or severe acute respiratory syndrome coronavirus 2 (SARS-CoV2)

The instant disclosure also provides a method for treating coronavirus disease 2019 (COVID-19) and/or severe acute respiratory syndrome coronavirus 2 (SARS-CoV2), in a patient in need thereof, comprising: administering to the subject a first immunotherapy composition comprising a recombinant virus, wherein the recombinant virus comprises a nucleic acid that encodes a nucleocapsid protein of coronavirus 2 (CoV2), administering to the subject a second immunotherapy composition comprising a recombinant yeast, wherein the recombinant yeast comprises a nucleic acid that encodes a spike protein of CoV2. The first and second immunotherapy compositions may be administered concurrently or sequentially to the patient.

Viewed form a different perspective, contemplated herein is a viral vector (e.g., recombinant adenovirus genome, optionally with a deleted or non-functional E2b gene) that comprises a nucleic acid that encodes (a) at least a nucleocapsid protein; and (b) at least one spike protein. The viral vector may further comprise co-stimulatory molecule. Most typically, the nucleic acid will further include a trafficking signal to direct a peptide product encoded by the nucleic acid to the cytoplasm, the endosomal compartment, or the lysosomal compartment, and the peptide product will further comprise a sequence portion that enhances intracellular turnover of the peptide product.

The majority of current SARS-CoV-2 vaccines under development target S because of the potential to neutralize the ability of the virus to bind host cells by production of antibodies against the RBD. Support for RBD as a key antigen was recently confirmed, and it was reported that in 44 hospitalized COVID-19 patients, RBD-specific IgG responses and neutralizing antibody titers are detectable in all patients by 6 days post-PCR confirmation of infection, and that the two are correlated. See Suthar, M. S. et al. Rapid generation of neutralizing antibody responses in COVID-19 patients. Cell Reports Medicine, 2020, which is incorporated by reference herein. They confirmed this finding in an additional 231 PCR-confirmed COVID-19 patient samples. In addition to humoral responses, S epitopes are also frequent targets of COVID-19 recovered patient T cells, providing further justification for inclusion of S in prophylactic immunization strategies.

Despite the urgent need for rapid development of SARS-CoV-2 vaccines, reliance on any one antigen cargo or immunological pathway as occurring in the monovalent vaccines under development is not without risk. Evaluation of nearly 4000 SARS-CoV-2 genomic sequences has identified numerous mutations in S with the D614G variant emerging recently as a potentially more infectious strain six months after identification of the original virus.

In designing the vaccine disclosed herein, to overcome the risk of the emergence of new strains of the virus with mutations in S and to provide additional antigens against which responses can be elicited, an optimized N sequence was added. The N protein is a highly conserved and antigenic SARS-CoV-2-associated protein that has been studied previously as an antigen in coronavirus vaccine design for SARS-CoV. N associates with viral RNA within the virus and has a role in viral RNA replication, virus particle assembly, and release. SARS-CoV-2 N is a highly antigenic protein and recent studies have shown that nearly all patients infected with SARS-CoV-2 have antibody responses to N. Furthermore, another study reported that most, if not all, COVID-19 survivors tested were shown to have N-specific CD4+ T-cell responses.

Currently, there is keen focus on generation of humoral responses to vaccines with, arguably, less attention being paid to T-cell responses. The natural history of SARS-CoV-2 infection would suggest, however, that a robust T-cell response to vaccination is at least as important as the production of antibodies and should be a critical consideration for COVID-19 vaccine efficacy.

First, the humoral and T-cell responses are highly correlated, with titers of neutralizing antibodies being proportional to T-cell levels, suggesting the T response is necessary for an effective humoral response. It is well established that the activation of CD4+T helper cells enhances B-cell production of antibodies. Second, virus-specific CD4+ and CD8+ T cells are not only widely detected in COVID-19 patients, based on findings from patients recovered from the closely-related SARS-CoV, but such T cells persist for at least 6-17 years, suggesting that T cells may be an important part of long-term immunity. These T-cell responses were predominantly to N, and it has been reported that in all 36 convalescent COVID-19 patients in their study, the presence of CD4+ and CD8+ T cells recognizing multiple regions of the N protein could be demonstrated. Examination of blood from 23 individuals who had recovered from SARS-CoV and found that the memory T cells acquired 17 years ago also recognized multiple proteins of SARS-CoV-2. These findings emphasize the importance of designing a vaccine with the highly conserved nucleocapsid present in both SARS-CoV and SARS-CoV-2. Third, recovered patients exposed to SARS-CoV-2 have been found without seroconversion, but with evidence of T-cell responses. The T-cell based responses become even more critical given the finding in at least one study that neutralizing antibody titers decline in some COVID-19 patients after about 3 months.

In one embodiment, the vaccines disclosed herein results in the generation of T-cell in addition to humoral responses.

A bivalent vaccine comprising many antigens—S RBD as displayed by inclusion of full-length S including SD1, S1 and S2 epitopes, along with N—would be more effective in eliciting both T-cell and antibody-based responses than a construct with either antigen alone by presenting both unique and conserved SARS-CoV-2 antigenic sites to the immune system. The importance of both S and N was highlighted by identifying that both S and N antigens as a priori potential B and T-cell epitopes for the SARS-CoV virus that shows close similarity to SARS-CoV-2 that are predicted to induce both T and B cell responses.

An additional consideration for design of an effective vaccine is the likelihood of antigen presentation on the surface of the vectored-protein-expressing cell and in a conformation that recapitulates natural virus infection. First, because wild type N does not have a signaling domain that directs it to endosomal processing and ultimately MEW class II complex presentation to CD4+ T cells, the wild type N sequence is not optimal for induction of a vigorous CD4+ T-cell responses, a necessity for both cell-mediated and B cell memory. To overcome this limitation, we have designed an Enhanced T-cell Stimulation Domain (ETSD) to N to allow the necessary processing and presentation. Second, to display the highly antigenic RBD region of S on the cell surface, we have optimized the wild type S protein "S Fusion sequence", to increase the likelihood of native folding, increased stability, and proper cell surface expression of RBD. Thus, in one embodiment, the vaccine construct design comprises an S-Fusion+N-ETSD sequence.

The vaccine platform utilized here is a next-generation recombinant human adenovirus serotype 5 (hAd5) vector with deletions in the E1, E2b, and E3 gene regions (hAd5 [E1-, E2b-, E3-]). This hAd5 [E1-, E2b-, E3-] vector (FIG. 8c) is primarily distinguished from other first-generation [E1-, E3-] recombinant Ad5 platforms by having additional deletions in the early gene 2b (E2b) region that remove the expression of the viral DNA polymerase (pol) and in pre terminal protein (pTP) genes, and its propagation in the E.C7 human cell line. Removal of these E2b regions confers advantageous immune properties by minimizing immune responses to Ad5 viral proteins such as viral fibers, 37 thereby eliciting potent immune responses to specific antigens in patients with pre-existing adenovirus (Ad) immunity. As a further benefit of these deletions, the vector has an expanded gene-carrying/cloning capacity compared to the first generation Ad5 [E1-, E3-] vectors. This next generation hAd5 [E1-, E2b-, E3-] vaccine platform, in contrast to Ad5 [E1-, E3-]-based platforms, does not promote activities that suppress innate immune signaling, thereby allowing for improved vaccine efficacy and a superior safety profile independent of previous Ad immunity. Since these deletions allow the hAd5 platform to be efficacious even in the presence of existing Ad immunity, this platform enables relatively long-term antigen expression without significant induction of anti-vector immunity. It is therefore also possible to use the same vector/construct for homologous prime-boost therapeutic regimens unlike first-generation Ad platforms which face the limitations of pre-existing and vaccine-induced Ad immunity. Importantly, this next generation Ad vector has demonstrated safety in over 125 patients with solid tumors. In these Phase I/II studies, CD4+ and CD8+antigen-specific T cells were successfully generated to multiple somatic antigens (CEA, MUC1, brachyury) even in the presence of pre-existing Ad immunity.

The instant disclosure provides findings of confirmed enhanced cell-surface expression and physiologically-relevant folding of the expressed S RBD from S-Fusion by ACE2-Fc binding. The N-ETSD protein was successfully localized to the endosomal/lysosomal subcellular compartment for MHC presentation and consequently generated both CD4+ and CD8+ T-cell responses. Immunization of CD-1 mice with the hAd5 S Fusion+N-ETSD vaccine elicited both humoral and cell-mediated immune responses to vaccine antigens. CD8+ and CD4+ T-cell responses were noted for both S and N. Statistically significant IgG responses were seen for antibody generation against S and N. Potent neutralization of SARS-CoV-2 by sera from hAd5 S Fusion+N-ETSD-immunized mice was confirmed by two independent SARS-CoV-2 neutralization assays: the cPass assay measuring competitive inhibition of RBD binding to ACE2, 44 and in the live SARS-CoV-2 virus assay with infected Vero E6 cells. Analysis of T-cell responses as well as humoral responses to S and N were skewed toward a Th1-specific response.

Taken together, these findings illustrate that hAd5 S-Fusion+N-ETSD vaccine would be particularly effective against the SARS-CoV-2.

Recombinant Viruses

With respect to recombinant viruses it is contemplated that all known manners of making recombinant viruses are deemed suitable for use herein, however, especially preferred viruses are those already established in therapy, including adenoviruses, adeno-associated viruses, alphaviruses, herpes viruses, lentiviruses, etc. Among other appropriate choices, adenoviruses are particularly preferred.

Moreover, it is further generally preferred that the virus is a replication deficient and non-immunogenic virus. For example, suitable viruses include genetically modified alphaviruses, adenoviruses, adeno-associated viruses, herpes viruses, lentiviruses, etc. However, adenoviruses are particularly preferred. For example, genetically modified replication defective adenoviruses are preferred that are suitable not only for multiple vaccinations but also vaccinations in individuals with preexisting immunity to the adenovirus (see e.g., WO 2009/006479 and WO 2014/031178, which are incorporated by reference in its entirety). In some embodiments, the replication defective adenovirus vector comprises a replication defective adenovirus 5 vector. In some embodiments, the replication defective adenovirus vector comprises a deletion in the E2b region. In some embodiments, the replication defective adenovirus vector further comprises a deletion in the E1 region. In that regard, it should be noted that deletion of the E2b gene and other late proteins in the genetically modified replication defective adenovirus to reduce immunogenicity. Moreover, due to these specific deletions, such genetically modified viruses were replication deficient and allowed for relatively large recombinant cargo.

For example, WO 2014/031178 describes the use of such genetically modified viruses to express CEA (colorectal embryonic antigen) to provide an immune reaction against colon cancer. Moreover, relatively high titers of recombinant viruses can be achieved using genetically modified human 293 cells as has been reported (e.g., J Virol. 1998 February; 72(2): 926-933).

E1-deleted adenovirus vectors Ad5 [E1-] are constructed such that a trans gene replaces only the E1 region of genes. Typically, about 90% of the wild-type Ad5 genome is retained in the vector. Ad5 [E1-] vectors have a decreased ability to replicate and cannot produce infectious virus after infection of cells not expressing the Ad5 E1 genes. The recombinant Ad5 [E1-] vectors are propagated in human cells allowing for Ad5 [E1-] vector replication and packaging. Ad5 [E1-] vectors have a number of positive attributes;

one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germ-line transmission is extremely low if at all. Conventional Ad5 [E1-] vectors have a carrying capacity that approaches 7 kb.

One obstacle to the use of first generation (E1-deleted) Ad5-based vectors is the high frequency of pre-existing anti-adeno virus type 5 neutralizing antibodies. Attempts to overcome this immunity is described in WO 2014/031178, which is incorporated by reference herein. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. E2b deleted adenovirus vectors provide an improved Ad-based vector that is safer, more effective, and more versatile than First Generation adenovirus vectors.

In a further embodiment, the adenovirus vectors contemplated for use in the present disclosure include adenovirus vectors that have a deletion in the E2b region of the Ad genome and, optionally, deletions in the E1, E3 and, also optionally, partial or complete removal of the E4 regions. In a further embodiment, the adenovirus vectors for use herein have the E1 and/or the preterminal protein functions of the E2b region deleted. In some cases, such vectors have no other deletions. In another embodiment, the adenovirus vectors for use herein have the E1, DNA polymerase and/or the preterminal protein functions deleted.

The term "E2b deleted", as used herein, refers to a specific DNA sequence that is mutated in such a way so as to prevent expression and/or function of at least one E2b gene product. Thus, in certain embodiments, "E2b deleted" is used in relation to a specific DNA sequence that is deleted (removed) from the Ad genome. E2b deleted or "containing a deletion within the E2b region" refers to a deletion of at least one base pair within the E2b region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E2b region of the Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both of the DNA polymerase and the preterminal protein of the E2b region. In a further embodiment, "E2b deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

As noted before, the desired nucleic acid sequences (for expression from virus infected cells) are under the control of appropriate regulatory elements well known in the art. In view of the above, it should be appreciated that compositions and methods presented are not only suitable for directing virally expressed antigens specifically to one or another (or both) MHC systems, but will also provide increased stimulatory effect on the CD8+ and/or CD4+ cells via inclusion of various co-stimulatory molecules (e.g., ICAM-1 (CD54), ICOS-L, LFA-3 (CD58), and at least one of B7.1 (CD80) and B7.2 (CD86)), and via secretion or membrane bound presentation of checkpoint inhibitors.

With respect to viral expression and vaccination systems it is contemplated that all therapeutic recombinant viral expression systems are deemed suitable for use herein so long as such viruses are capable to lead to expression of the recombinant payload in an infected cell.

Regardless of the type of recombinant virus it is contemplated that the virus may be used to infect patient (or non-patient) cells ex vivo or in vivo. For example, the virus may be injected subcutaneously or intravenously, or may be administered intranasaly or via inhalation to so infect the patient's cells, and especially antigen presenting cells. Alternatively, immune competent cells (e.g., NK cells, T cells, macrophages, dendritic cells, etc.) of the patient (or from an allogeneic source) may be infected in vitro and then transfused to the patient. Alternatively, immune therapy need not rely on a virus but may be effected with nucleic acid transfection or vaccination using RNA or DNA, or other recombinant vector that leads to the expression of the neoepitopes (e.g., as single peptides, tandem mini-gene, etc.) in desired cells, and especially immune competent cells.

As noted above, the desired nucleic acid sequences (for expression from virus infected cells) are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc.

The replication defective adenovirus comprising an E1 gene region deletion, an E2b gene region deletion, and a nucleic acid encoding a coronavirus 2 (CoV2) nucleocapsid protein and/or a CoV2 spike protein, as disclosed herein may be administered to a patient in need for inducing immunity against CoV2. Routes and frequency of administration of the therapeutic compositions described herein, as well as dosage, may vary from individual to individual, and the severity of the disease, and may be readily established using standard techniques. In some embodiments, the administration comprises delivering $4.8$-$5.2 \times 10^{11}$ replication defective adenovirus particles, or $4.9$-$5.1 \times 10^{11}$ replication defective adenovirus particles, or $4.95$-$5.05 \times 10^{11}$ replication defective adenovirus particles, or $4.99$-$5.01 \times 10^{11}$ replication defective adenovirus particles.

The administration of the virus particles can be through a variety of suitable paths for delivery. One preferred route contemplated herein is by injection, such as intracutaneous injection, intramuscular injection, intravenous injection or subcutaneous injection. In some embodiments, a subcutaneous delivery may be preferred.

Recombinant Yeasts

With respect to yeast expression and vaccination systems, it is contemplated that all known yeast strains are deemed suitable for use herein. However, it is preferred that the yeast is a recombinant *Saccharomyces* strain that is genetically modified with a nucleic acid construct encoding a protein selected from the group consisting of coronavirus 2 (CoV2) nucleocapsid protein, CoV2 spike protein, and a combination thereof, to thereby initiate an immune response against the CoV2 viral disease. In one aspect of any of the embodiments of the disclosure described above or elsewhere herein, the yeast vehicle is a whole yeast. The whole yeast, in one aspect is killed. In one aspect, the whole yeast is heat-inactivated. In one preferred embodiment, the yeast is a whole, heat-inactivated yeast from *Saccharomyces cerevisiae*.

The use of a yeast based therapeutic compositions are disclosed in the art. For example, WO 2012/109404 discloses yeast compositions for treatment of chronic hepatitis b infections.

It is noted that any yeast strain can be used to produce a yeast vehicle of the present disclosure. Yeasts are unicellular microorganisms that belong to one of three classes: *Ascomycetes, Basidiomycetes* and *Fungi Imperfecti*. One consideration for the selection of a type of yeast for use as an immune modulator is the pathogenicity of the yeast. In preferred embodiments, the yeast is a non-pathogenic strain such as *Saccharomyces cerevisiae* as non-pathogenic yeast strains minimize any adverse effects to the individual to whom the yeast vehicle is administered. However, pathogenic yeast may also be used if the pathogenicity of the yeast can be negated using pharmaceutical intervention.

For example, suitable genera of yeast strains include *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in a preferred aspect, *Saccharomyces* is used. Species of yeast strains that may be used include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe,* and *Yarrowia* hpolytica.

It should further be appreciated that a number of these species include a variety of subspecies, types, subtypes, etc. that are intended to be included within the aforementioned species. In one aspect, yeast species used in the instant disclosure include *S. cerevisiae, C. albicans, H. polymorpha, P. pastoris* and *S. pombe. S. cerevisiae* is useful due to it being relatively easy to manipulate and being "Generally Recognized As Safe" or "GRAS" for use as food additives (GRAS, FDA proposed Rule 62FR18938, Apr. 17, 1997). Therefore, particularly contemplated herein is a yeast strain that is capable of replicating plasmids to a particularly high copy number, such as a *S. cerevisiae* cir⁰ strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used, including those that exhibit reduced post-translational modifications of expressed target antigens or other proteins, such as mutations in the enzymes that extend N-linked glycosylation.

Expression of contemplated peptides/proteins in yeast can be accomplished using techniques known to those skilled in the art. Most typically, a nucleic acid molecule encoding at least one protein is inserted into an expression vector such manner that the nucleic acid molecule is operatively linked to a transcription control sequence to be capable of effecting either constitutive or regulated expression of the nucleic acid molecule when transformed into a host yeast cell. As will be readily appreciated, nucleic acid molecules encoding one or more proteins can be on one or more expression vectors operatively linked to one or more expression control sequences. Particularly important expression control sequences are those which control transcription initiation, such as promoter and upstream activation sequences.

Any suitable yeast promoter can be used in the methods and compositions of the present disclosure and a variety of such promoters are known to those skilled in the art and have generally be discussed above. Promoters for expression in *Saccharomyces cerevisiae* include promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SEC7) and acid phosphatase (PH05), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the alpha-factor, GAPDH, and CYC1 genes. Transcription control sequences to express genes in methyltrophic yeast include the transcription control regions of the genes encoding alcohol oxidase and formate dehydrogenase.

Likewise, transfection of a nucleic acid molecule into a yeast cell according to the present disclosure can be accomplished by any method by which a nucleic acid molecule administered into the cell and includes diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins. Further exemplary yeast expression systems, methods, and conditions suitable for use herein are described in US20100196411A1, US2017/0246276, or US 2017/0224794, and US 2012/0107347.

So produced recombinant viruses and yeasts may then be individually or in combination used as a therapeutic vaccine in a pharmaceutical composition, typically formulated as a sterile injectable composition with a virus of between $10^4$-$10^{13}$ virus or yeast particles per dosage unit, or more preferably between $10^9$-$10^{12}$ virus or yeast particles per dosage unit. Alternatively, virus or yeast may be employed to infect patient cells ex vivo and the so infected cells are then transfused to the patient. However, alternative formulations are also deemed suitable for use herein, and all known routes and modes of administration are contemplated herein.

Second Generation hAd5 [E1-, E2b-, E3-] Based Vaccines Disclosed Herein Overcome Pre-Existing Anti-Ad5 Immunity To avoid the Ad immunization barrier and circumvent the adverse conditions for first generation Ad5 [E1-E3-] vectors, an advanced 2nd generation human adenoviral (hAd5) vector was constructed having two (2) additional deletions in the E2b region, removing the DNA polymerase and the preterminal protein genes [E1-, E2b-, E3-]. (Former names of our adenovirus vector were Ad5, ETBX in literature)

E2b-deleted hAd5 vectors have up to a 12-14 kb gene-carrying capacity as compared to the 7-kb capacity of first generation Ad5 [E1-] vectors, providing space for multiple genes if needed. hAd5 [E1-, E2b-, E3-] based recombinant vectors are produced using the human E.C7 cell line. Deletion of the E2b region also confers advantageous immune properties on these novel Ad vectors, eliciting potent immune responses to specific, non-viral antigens while minimizing the immune responses to Ad viral proteins.

hAd5 [E1-, E2b-, E3-] vectors induce a potent cell mediated immune (CMI) response, as well as Abs against the vectored antigens even in the presence of Ad immunity. hAd5 [E1-, E2b-, E3-] vectors also have reduced adverse reactions as compared to Ad5 [E1-] vectors, in particular the appearance of hepatotoxicity and tissue damage. In one embodiment, the reduced inflammatory response against hAd5 [E1-, E2b-, E3-] vector viral proteins and the resulting evasion of pre-existing Ad immunity increases the capability for the hAd5 [E1-, E2b-, E3-] vectors to infect dendritic cells (DC), resulting in greater immunization of the vaccine. In addition, increased infection of other cell types provides high levels of antigen presentation needed for a potent CD8+ and CD4+ T cell responses, leading to memory T cell development. In one embodiment, hAd5 [E1-, E2b-, E3-] vectors are superior to Ad5 [E1-] vectors in immunogenicity and safety and will be the best platform to develop a COVID-19 vaccine in a rapid and efficient manner. In one embodiment, a prophylactic vaccine is tested against COVID-19 by taking advantage of this new hAd5 vector system that overcomes barriers found with other Ad5 systems and permits the immunization of people who have previously been exposed to Ad5.

Track Record of Rapid Vaccine Development Utilizing Second Generation Human (hAd5) Adenovirus Platform During Pandemic Treats: H1N1 Experience in 2009

To address emerging pathogen threats, especially in times of pandemic, it is critical that modernized vaccine technologies be deployed. These technologies will utilize the power of genomic sequencing, rapid transfection in well-established vaccine vectors to rapidly identify constructs with high immunogenicity.

Vaccines against emerging pathogens such as the 2009 H1N1 pandemic virus can benefit from current technologies such as rapid genomic sequencing to construct the most biologically relevant vaccine. A novel platform (hAd5 [E1-, E2b-, E3-]) has been utilized to induce immune responses to various antigenic targets. This vector platform expressed hemagglutinin (HA) and neuraminidase (NA) genes from 2009 H1N1 pandemic viruses. Inserts were consensuses sequences designed from viral isolate sequences and the vaccine was rapidly constructed and produced. Vaccination induced H1N1 immune responses in mice, which afforded protection from lethal virus challenge. In ferrets, vaccination protected from disease development and significantly reduced viral titers in nasal washes. H1N1 cell mediated immunity as well as antibody induction correlated with the prevention of disease symptoms and reduction of virus replication. The hAd5 [E1-, E2b-, E3-] has thus demonstrated the capability for the rapid development of effective vaccines against infectious diseases.

hAd5 Vaccine Constructs and Results

Figure 1:
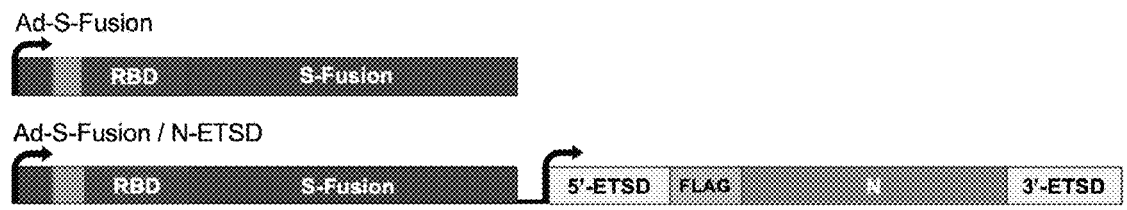
Figure 2:
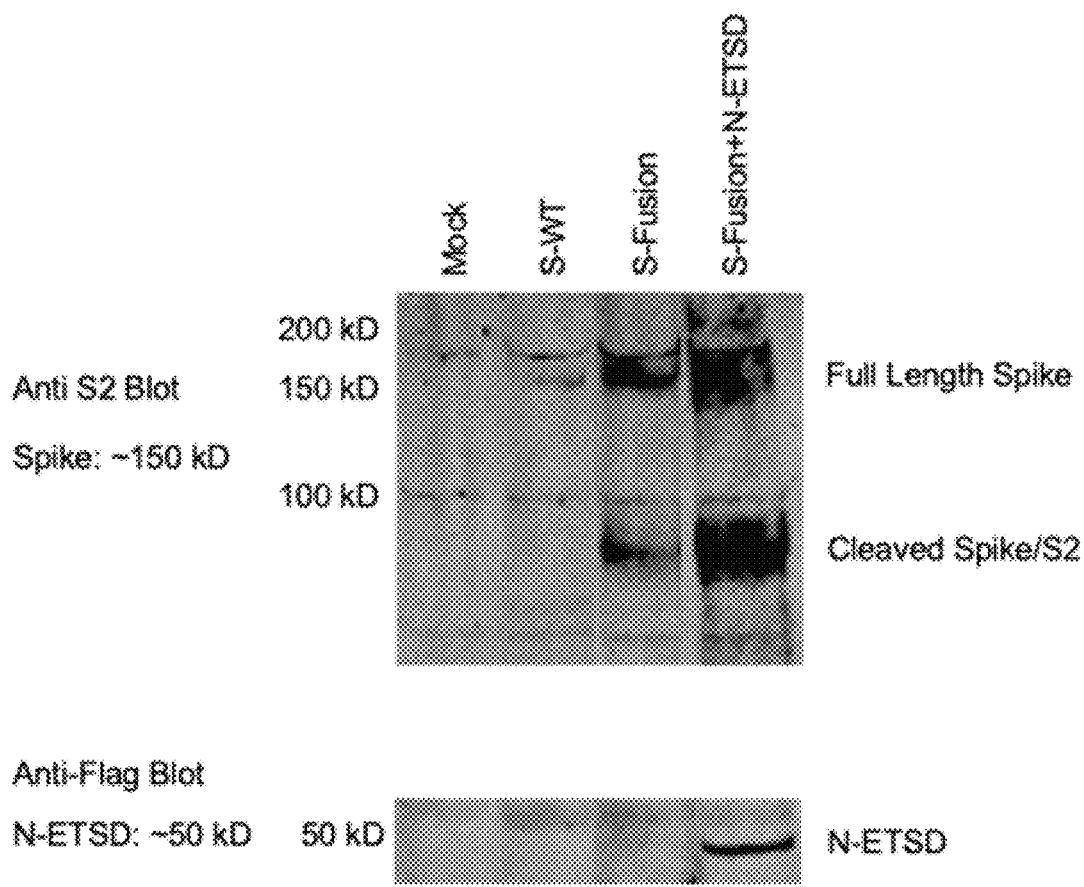

Disclosed herein are constructs that have been constructed and tested, a hAd5-COVID-19 vaccine construct E1-, E2b-, E3-hAd5 vector with SARS-CoV-2 (S/N) protein insert (FIG. 1). This construct has been tested in preclinical experiments, including in vitro expression (FIG. 2) and small animal immunogenicity.

Figure 3:
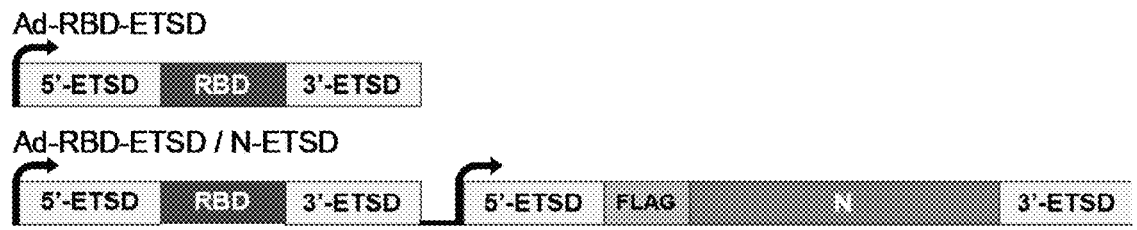
Figure 4:
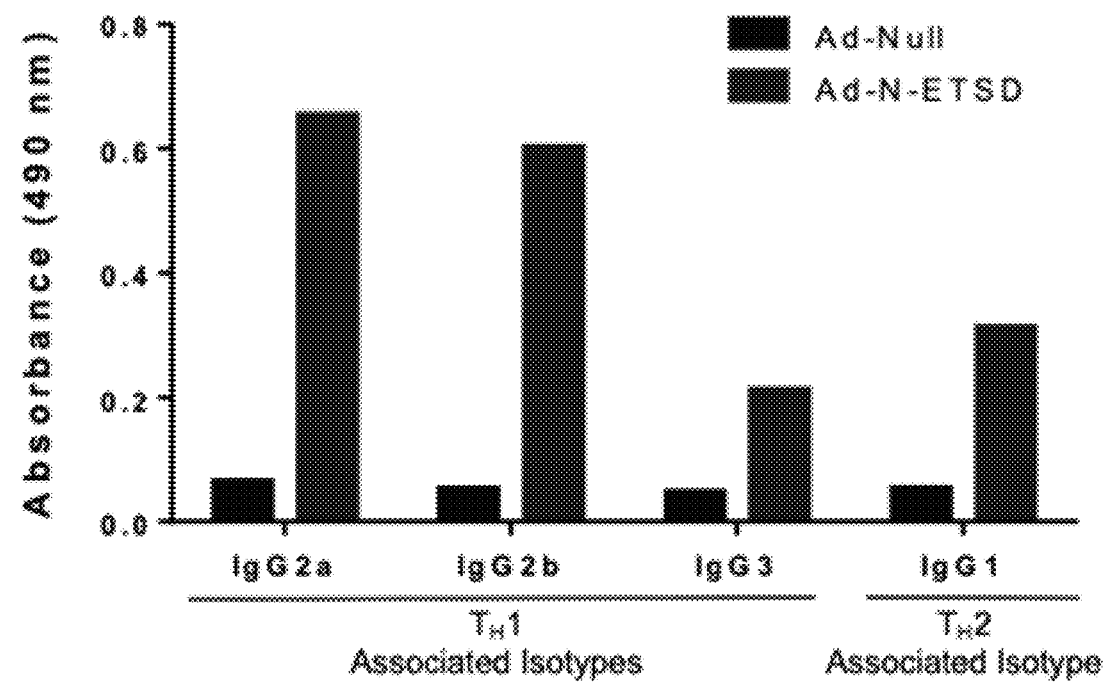
Figure 5:
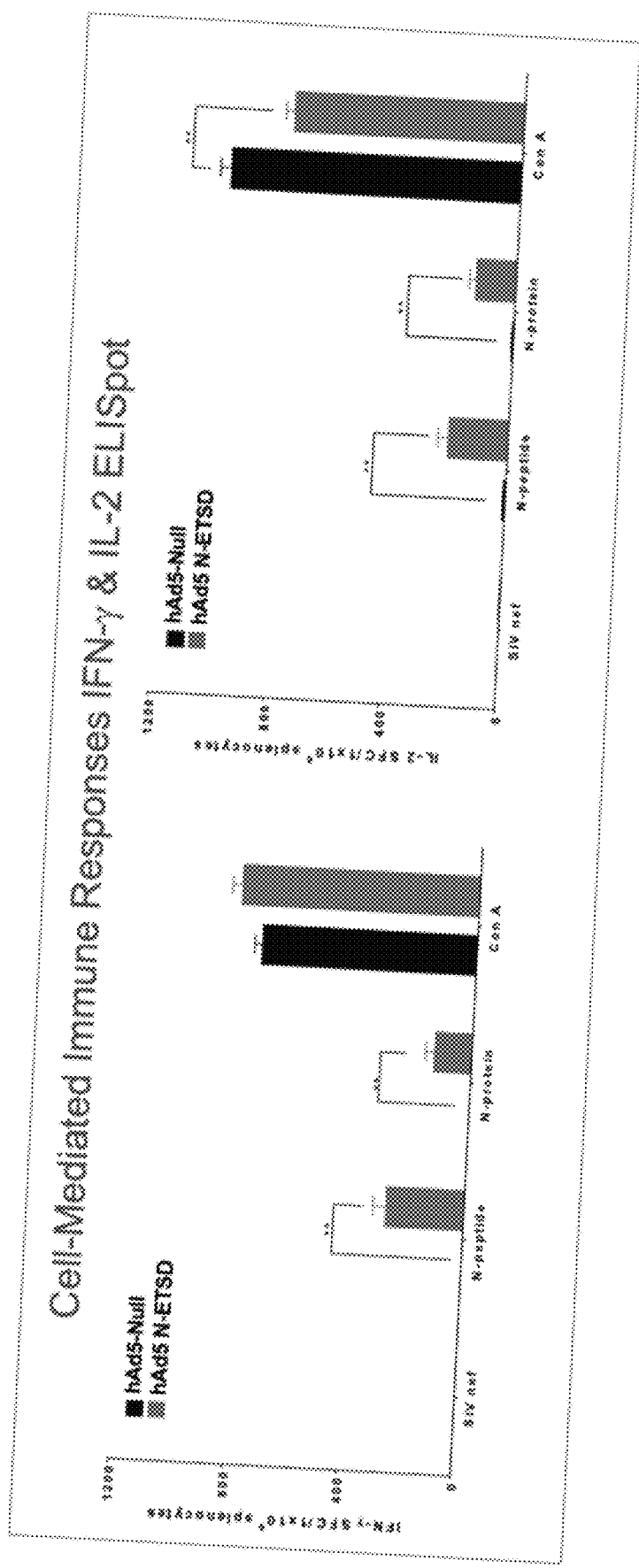
Figure 7:
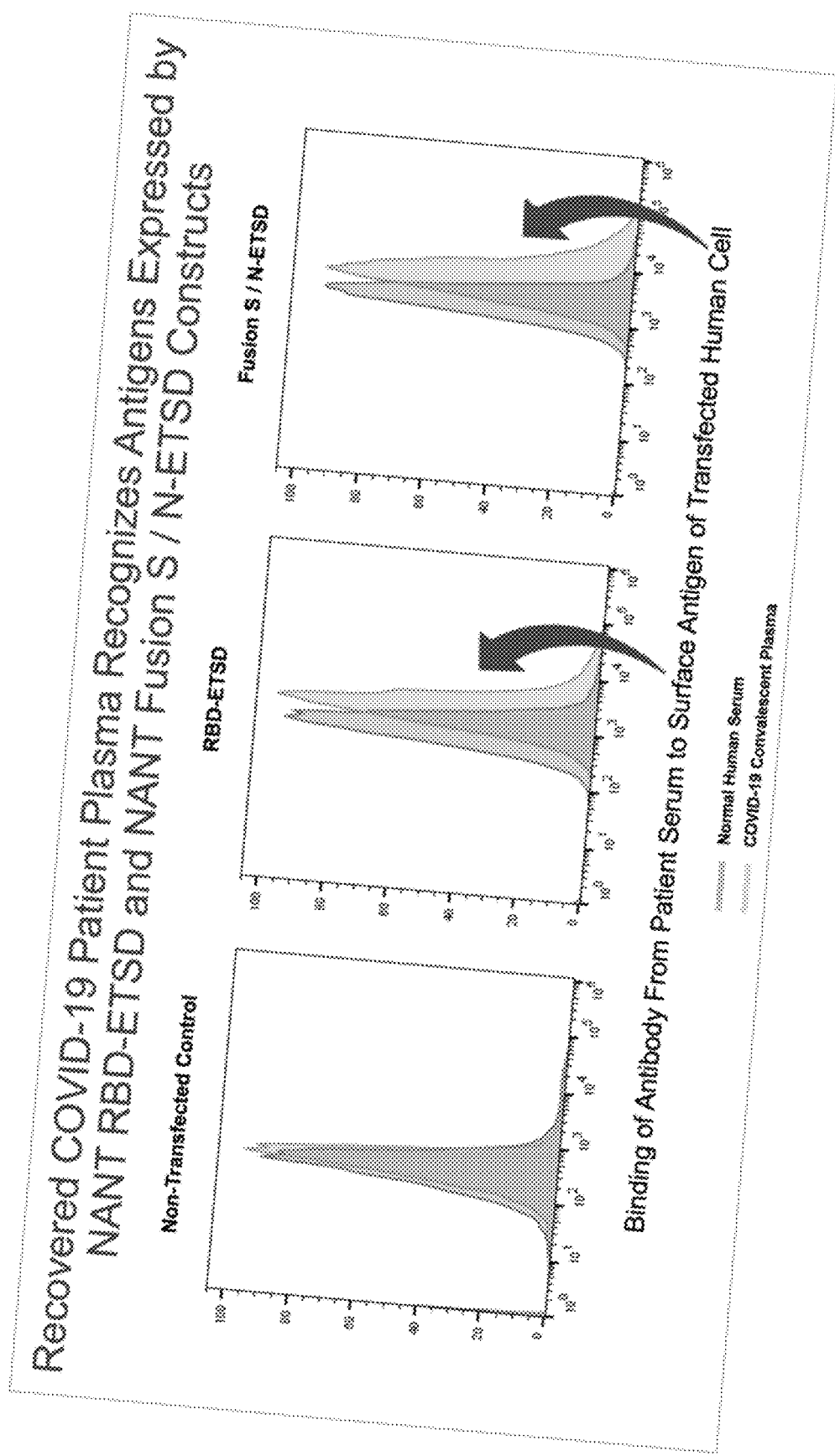

In addition, ImmunityBio has developed multiple COVID-19 constructs including RBD-alone, S1-alone, S1-fusion proteins, and combinations of RBD, S1 and S1 fusions with N. Preliminary in-vitro studies demonstrate that these constructs (FIG. 3) recognize convalescent serum antibodies and could serve as alternative vaccines following analysis of the two (2) constructs above (FIG. 1) which is intended to initiate in our first in human Phase 1b study.

Rationale for Inclusion of Nucleocapsid (N) in hAd5 Constructs for COVID-19

The nucleocapsid (N) protein of SARS-CoV-2 is highly conserved and highly expressed. Previous research with the related coronavirus that causes SARS demonstrated that N protein is immunogenic (Gupta, 2006), when integrated with intracellular trafficking constructs. To date, vaccine strategies in development all involve developing immunogenicity against spike (S) protein. However, very recent evidence in patients who recovered from COVID-19 demonstrates Th1 immunity generated against the nucleocapsid (N) (Grifoni, 2020). A second report by Grifoni et al. further confirmed that in the predictive bioinformatics model, T and B cell epitopes were highest for both spike glycoprotein and nucleoprotein (Grifoni, 2020). The present disclosure confirms the potential that combining S with N, that long-term cell-mediated immunity with a Th1 phenotype can be induced. The potential exists for this combination vaccine to serve as a long-term "universal" COVID-19 vaccine in light of mutations undergoing in S and the finding that the structural N protein is highly conserved in the coronavirus family. The clinical trial is designed to compare S alone versus S+N, to demonstrate safety and to better inform the immunogenicity of S and S+N. A single construct having S & N would be selected to induce potent humoral and cell mediated immunity.

Immunogenicity Studies (Small Animal Model):

Homologous prime-boost immunogenicity in BALB-c mice. Mice have been treated with 1, 2 or 3 doses of the hAd5 COVID-19 vaccine and serum and splenocyte samples are being tested for SARS-CoV-2 antigen-specific immune responses. Serum is tested for anti-spike and anti-nucleocapsid antibody responses by ELISA. Splenocytes is tested for spike- and nucleocapsid-specific cell mediated immune responses by ELISPOT and intracellular cytokine simulation assays.

The results show promising immunogenic activity. In one embodiment, hAd5 [E1-,E2b-, E3-] N-ETSD, a vaccine containing SARS-CoV-2 nucleocapsid plus an enhanced T cell stimulation domain (ETSD), alters T cell responses to nucleocapsid. Mice were immunized subcutaneously (SC) with a dose of 1010 VP twice at 7-day intervals. Blood was collected at several time points and spleen was collected upon sacrifice in order to perform immunogenicity experiments. Splenocytes were isolated and tested for cell mediated immune (CMI) responses. The results showed that SARS-CoV-2 nucleocapsid antigen specific CMI responses were detected by ELISpot and flow cytometry analyses in the spleens of all the mice immunized with hAd5 [E1-, E2b-, E3-] N-ETSD vaccine but not vector control (hAd5 [E1-, E2b-, E3-] null) immunized mice.

In addition, antibody responses were detected in all the mice immunized with hAd5 [E1-, E2b-, E3-]-N-ETSD vaccine but not vector control (Ad5 [E1-, E2b-, E3-]-null) immunized mice (FIG. 4 & FIG. 5). Additional studies to confirm and extend these results are ongoing.

Enhanced RBD Cell Surface Expression:

Further evidence of the potential enhancing immunogenicity value of N when combined with S was the surprising finding of enhanced surface expression of the RBD protein in 293 cells transfected with the N-ETSD+S construct as seen in FIG. 6. Expression and presentation of RBD appears to be highly important as evidenced by the recent report by Robbiani et al who showed that rare but recurring RBD-specific antibodies with potent antiviral activity were found in all individuals tested who had recovered from COVID-19 infections (Robbiani 2020).

This finding of enhanced expression of RBD when N is combined with S-Fusion was corroborated in studies using plasma from a patient recovered from COVID-19 infection (FIG. 7). The alternative construct of RBD-ETSD could serve as alternative vaccines following analysis of the two (2) constructs above (FIG. 1) which is intended to initiate in human Phase 1*b* studies.

In summary, on the basis of enhanced expression and exposure of the RBD protein with S Fusion and S Fusion+N construct, both were tested in the hAd5 vector. Furthermore, on the basis of recent clinical data from patients recovered from COVID-19, as well as the corroborating preclinical data that the N construct induces long lasting $CD4^+$ and Th1 cell-mediated immunity, this combination of S Fusion+N construct could provide long-lasting immunity beyond short term neutralizing antibodies.

Immunogenicity Testing of Candidate COVID-19 Vaccine Constructs

Two (2) Adenovirus-based COVID-19 vaccine constructs will be tested in preclinical experiments, including in vitro expression; small animal immunogenicity, and non-human primate immunogenicity and efficacy.

Constructs description: ImmunityBio has generated two (2) second generation hAd5-based COVID-19 vaccine constructs for preclinical testing and clinical evaluation. First is a hAd5 vector with SARS-CoV-2 with spike protein insert (see FIG. 1). Second is E1-, E2b-, E3-hAd5 vector with SARS-CoV-2 wild type spike protein (S) insert and Nucleocapsid protein (N) insert containing an Endosomal-targeting domain sequence (ETSD) in the same vector backbone.

Immunogenicity Studies: Homologous prime-boost immunogenicity in mice was examined by treating Mice with 1, 2 or 3 doses of the ImmunityBio adenovirus vaccine candidates listed in FIG. 1 and serum and splenocyte samples will be tested for SARS-CoV-2 antigen-specific immune responses. Serum is being tested for anti-spike and anti-nucleocapsid antibody responses by ELISA. Splenocytes will be tested for spike- and nucleocapsid-specific cell mediated immune responses by ELISPOT and intracellular cytokine simulation assays. Data from these studies are disclosed throughout this disclosure.

SARS-CoV-2 Virus Neutralization Studies: Serum from the mice immunized during the course of the immunogenicity studies described above is used will be sent to a third-party subcontractor for SARS-CoV-2 neutralization studies to be performed in their ABSL-3 facility. Serum will be tested for COVID 19 virus neutralizing activity by mixing various dilutions of serum with COVID 19 virus, incubating the mixture, and then exposing the mixture to Vero cells to detect cytopathic effect (CPE). The last dilution that prevents CPE will be considered the endpoint neutralizing titer.

Immunogenicity and Efficacy Evaluation in Non-Human Primates (third-party subcontractor): Rhesus macaques will be treated with three doses of the ImmunityBio adenovirus vaccine candidates listed in FIG. 1. SARS-CoV-2 antigen-specific immune responses will be monitored in serum and PBMCs by ELISA, ELISPOT and ICS throughout the course of the therapy. Four weeks after the final vaccination, animals will be challenged with SARS-CoV-2 and monitored for disease hallmarks and virus shedding.

Phase Ib Clinical trial: ImmunityBio has submitted an IND for Phase Ib clinical trial testing of hAd5 [E1-, E 2b-, E3-] CoV-2 vaccine.

Study Design: This is a Phase 1*b* open-label study in adult healthy subjects. This clinical trial is designed to assess the safety, reactogenicity, and immunogenicity of the hAd5-COVID-19-S and hAd5-COVID-19-S/N vaccines. The hAd5-COVID-19-S and hAd5-COVID-19-S/N vaccines are hAd5 [E1-, E2b-, E3-] vector-based targeting vaccines encoding the SARS-CoV-2 Spike (S) protein alone or together with the SARS-CoV-2 nucleocapsid (N) protein. The hAd5 [E1-, E2b-, E3-] vector is the platform technology for targeted vaccines that has demonstrated safety in over 125 patients with cancer to date at doses as high as 5×1011 virus particles per dose. Co-administration of three different hAd5 [E1-, E2b-, E3-] vector-based vaccines on the same day at 5×1011 virus particles per dose each (1.5×1012 total virus particles) has also been demonstrated to be safe.

COVID-19 infection causes significant morbidity and mortality in a worldwide population. The hAd5-COVID-19-S and hAd5-COVID-19-S/N vaccines are designed to induce both a humoral and cellular response even in individuals with pre-existing adenoviral immunity. Thus, the potential exists for the hAd5-COVID-19-S and hAd5-COVID-19-S/N to induce anti-COVID-19 immunity and prevent or lessen the health impact of COVID-19 infection in healthy subjects.

Phase 1*b* Safety Analysis: In the initial safety analysis of phase 1*b*, a total of 40 healthy subjects will be divided into 4 dosing cohorts (cohorts 1A, 1B, 2A, 2B; n=10 for each cohort):

- Cohort 1A—hAd5-COVID-19-S at 5×1010 viral particles (VP) per dose (n=10),
- Cohort 1B—hAd5-COVID-19-S at 1×1011 VP per dose (n=10),
- Cohort 2A—hAd5-COVID-19-S/N at 5×1010 VP per dose (n=10),
- Cohort 2B—hAd5-COVID-19-S/N at 1×1011 VP per dose (n=10).

Each subject will receive a subcutaneous (SC) injection of hAd5-COVID-19-S or hAd5-COVID-19-S/N on Day 1 and Day 22 (ie, 2 doses). This dosing schedule is consistent with hAd5 [E1-, E2b-, E3-] vector-based vaccines currently in clinical trials. Cohorts 1-2 will enroll in parallel and may be opened at the same time or in a staggered manner depending upon investigational product supply. Subjects in cohorts 1A and 2A will complete the low-dose vaccination regimen first. After all subjects in cohorts 1A and 2A have completed at least a single dose and follow-up assessments during the toxicity assessment period through study day 8, enrollment will proceed if ImmunityBio Safety Review Committee (SRC) and at least one qualified infectious disease physician, independent of the Sponsor and trial, confirms absence of safety concerns. Subjects will then be enrolled in higher-dose cohorts 1B and 2B, and vaccinated. For all subjects, follow-up study visits will occur at days 8, 22, 29, 52, and at months 3, 6, and 12 following the final vaccination. Additional follow up for safety information will occur via telephone contact as noted in the Schedule of Events. The primary objectives of the initial safety phase 1b are to evaluate preliminary safety and reactogenicity of the hAd5-COVID-19-S and hAd5-COVID-19-S/N vaccines. The secondary objectives are to evaluate the extended safety and immunogenicity of the hAd5-COVID-19-S and hAd5-COVID-19-S/N vaccines.

Expanded Phase 1b: Safety and Immunogenicity for Construct Selection

Phase 1b expansion will proceed if the SRC determines it is safe to do so based on a review of safety data from the phase 1b safety assessment. In phase 1b expansion, a total of 60 healthy subjects will be divided into 4 dosing cohorts (cohorts 1A, 1B, 2A, 2B; n=15 for each cohort):

Cohort 1A—hAd5-COVID-19-S at 5×1010 VP per dose (n=15)

Cohort 1B—hAd5-COVID-19-S at 1×1011 VP per dose (n=15)

Cohort 2A—hAd5-COVID-19-S/N at 5×1010 VP per dose (n=15)

Cohort 2B—hAd5-COVID-19-S/N at 1×1011 VP per dose (n=15)

Each subject will receive a SC injection of hAd5-COVID-19-S or hAd5-COVID-19-S/N on Day 1 and Day 22 (i.e., 2 doses). For all subjects, follow-up study visits will occur at days 8, 22, 29, 52, and at months 3, 6, and 12 following the final vaccination. Additional follow up for safety information will occur via telephone contact as noted in the Schedule of Events. The primary objective of the expanded phase 1b is to select the most immunogenic construct between hAd5-COVID-19-S and hAd5-COVID-19-S/N and dose level as determined by changes in humoral and cellular immunogenicity indexes. The secondary objectives are to assess safety and reactogenicity of hAd5-COVID-19-S and hAd5-COVID-19-S/N.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the recombinant virus is administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient.

In one aspect of any of the embodiments described above or elsewhere herein, the composition is formulated in a pharmaceutically acceptable excipient suitable for administration to a subject.

It is still further contemplated that the recombinant viruses and yeasts contemplated herein may further comprises a sequence that encodes at least one of a co-stimulatory molecule, an immune stimulatory cytokine, and a protein that interferes with or down-regulates checkpoint inhibition. For example, suitable co-stimulatory molecules include CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and/or LFA3, while suitable immune stimulatory cytokine include IL-2, IL-12, IL-15, IL-15 super agonist (N803), IL-21, IPS1, and/or LMP1, and/or suitable proteins that interfere include antibodies against or antagonists of CTLA-4, PD-1, TIM1 receptor, 2B4, and/or CD160.

It should be appreciated that all of the above noted co-stimulatory genes are well known in the art, and sequence information of these genes, isoforms, and variants can be retrieved from various public resources, including sequence data bases accessible at the NCBI, EMBL, GenBank, RefSeq, etc. Moreover, while the above exemplary stimulating molecules are preferably expressed in full length form as expressed in human, modified and non-human forms are also deemed suitable so long as such forms assist in stimulating or activating T-cells. Therefore, muteins, truncated forms and chimeric forms are expressly contemplated herein.

The immunotherapeutic compositions disclosed herein may be either "prophylactic" or "therapeutic". When provided prophylactically, the compositions of the present disclosure are provided in advance of the development of, or the detection of the development of, a coronavirus disease, with the goal of preventing, inhibiting or delaying the development of the coronavirus disease; and/or generally preventing or inhibiting progression of the coronavirus disease in an individual. Therefore, prophylactic compositions can be administered to individuals that appear to be coronavirus disease free (healthy, or normal, individuals), or to individuals who has not yet been detected of coronavirus. Individuals who are at high risk for developing a coronavirus disease, may be treated prophylactically with a composition of the instant disclosure.

When provided therapeutically, the immunotherapy compositions are provided to an individual who is diagnosed with a coronavirus disease, with the goal of ameliorating or curing the coronavirus disease; increasing survival of the individual; preventing, inhibiting, reversing or delaying development of coronavirus disease in the individual.

The contemplated subject matter further includes methods for administering a vaccine to a patient by more than one route of administration to induce both local and systemic immune responses to the vaccine. The contemplated subject matter also includes compositions and methods for assaying the presence or absence of the relevant antibodies (e.g., anti-SARS-CoV2 antibodies) in a patient sample (e.g., saliva, nasal mucosa, alimentary mucosa, or serum). The antibody status in the patient's sample may be used to assess the need for an additional vaccine dose (e.g., a booster dose/shot).

In addition to the coveted molecular epitopes presented in a vaccine, the route of administration of the vaccine as well as the regimen for administering additional (i.e., booster)

doses of the vaccine, can also affect whether or not the patient's immune response is robust enough to establish protection.

For an emerging virus such as the severe acute respiratory syndrome (SARS)-like coronavirus (SARS-CoV2), the duration of immunity (both humoral and cell-mediated) in a patient recovered from a SARS-CoV2 infection is not yet completely known, and furthermore, a vaccine protocol has not yet been tested across a varied population. Considering the current SARS-CoV2 pandemic and the high rate of transmission for the SARS-CoV2 virus, there is a need for a robust vaccination protocol and effective testing for the virus or immunity to the virus (e.g., presence of anti-SARS-CoV2 antibodies).

Vaccine Administration. The presently disclosed contemplated methods for inducing immunity in a patient include administering a vaccine by at least oral administration, and preferably by oral administration and by injection to the blood supply. Many vaccines are given via the intramuscular (IM) route to optimize immunogenicity with the direct delivery of the vaccine to the blood supply in the muscle to induce systemic immunity. The IM administration is typically preferred over subcutaneous (SC) injection which is more likely to have adverse reactions at the injection site than IM injections.

In addition to IM injection, induction of mucosal immunity has been reported to be essential to stop person-to-person transmission of pathogenic microorganisms and to limit their multiplication within the mucosal tissue. Furthermore, for protective immunity against mucosal pathogens, (e.g., SARS coronaviruses) immune activation in mucosal tissues instead of the more common approach of tolerance to maintain mucosal homeostasis allows for enhanced mucosal immune responses and better local protection. For example, nasal vaccination (delivery of a vaccine by nasal administration) induces both mucosal immunity as well as systemic immunity. See, e.g., Fujkuyama et al., 2012, Expert Rev Vaccines, 11:367-379 and Birkhoff et al., 2009, Indian J. Pharm. Sci., 71:729-731.

In order to induce both mucosal and systemic immunity in a patient, embodiments of the present disclosure include providing a vaccine to the patient by at least administration to the nasal mucosa, oral mucosa, and/or alimentary mucosa of the patient. In some embodiments, the routes of administration include administering the vaccine to the nasal mucosa, oral mucosa, and/or alimentary mucosa of the patient together with injection into the blood supply (e.g., intramuscular (IM), intravenous (IV), or subcutaneous (SC)). As used herein, oral administration of a vaccine composition includes nasal injection, nasal inhalation, ingestion by mouth, and administration (e.g., inhalation, ingestion, injection) to the alimentary mucosa. Preferably, the routes of administering the vaccine include oral administration selected from delivery to the alimentary mucosa, nasal injection, nasal inhalation, ingestion by mouth, or inhalation by mouth together with administration by intramuscular (IM) injection.

Notably, the vaccine administered for inducing immunity in the mucosal tissue of a patient is a vaccine against SARS-CoV2. In exemplary embodiments, the vaccine a replication defective adenovirus construct, comprising an E1 gene region deletion and an E2b gene region deletion. In certain embodiments the adenovirus comprises a sequence (e.g. SEQ ID NO:11) encoding a SARS-CoV2 spike protein antigen with at least 80% (e.g., at least 85%, at least 90%, at least 95%, at least 96%, at least 97%, at least 98%, at least 99%) primary sequence identity to SEQ ID NO:10. In certain embodiments the adenovirus comprises a sequence (e.g. SEQ ID NO:13) encoding a SARS-CoV2 spike protein antigen with at least 80% (e.g., at least 85%, at least 90%, at least 95%, at least 96%, at least 97%, at least 98%, at least 99%) primary sequence identity to SEQ ID NO:12. In certain embodiments, the adenovirus includes a sequence encoding a soluble ACE2 protein coupled to an immunoglobulin Fc portion, forming an ACE2-Fc hybrid construct that may also include a J-chain portion, as disclosed in U.S. Ser. No. 16/880,804 and U.S. 63/016,048, the entire contents of both of which are herein incorporated by reference. In other exemplary embodiments, the SARS-CoV2 vaccine (e.g., an adenovirus construct) includes a mutant variant of a recombinant soluble ACE2 protein (e.g., SEQ ID NO: 9), wherein the mutant variant has at least one mutated amino acid residue (e.g., by substitution) that imparts an increased binding affinity of the ACE2 protein for the RBD protein domain of the SARS-CoV2 spike protein as disclosed in U.S. 63/022,146, the entire content of which is herein incorporated by reference. In another exemplary embodiment, the SARS-CoV2 vaccine (e.g., an adenovirus construct) includes a CoV2 nucleocapsid protein or a CoV2 spike protein fused to an endosomal targeting sequence (N-ETSD), as disclosed in U.S. Ser. No. 16/883,263 and U.S. 63/009,960, the entire contents of both of which are herein incorporated by reference. Additionally or alternatively, the SARS-CoV2 vaccine includes modified yeast cells (e.g., *Saccharomyces cerevisiae*) genetically engineered to express coronaviral spike proteins on the yeast cell surface thereby creating yeast presenting cells to stimulate B cells (e.g., humoral immunity) as disclosed in U.S. 63/010,010.

In some embodiments, more than one vaccine composition as disclosed herein may be administered to a patient to induce immunity to SARS-CoV2. For example, a patient may be administered genetically modified yeast cells expressing corona viral spike proteins as a single type of vaccine, or the genetically modified yeast cells may be administered together or concurrently with one or more SARS-CoV2 adenovirus constructs as disclosed herein.

Monitoring presence of antibodies. The contemplated subject matter also includes monitoring or assessing a patient's immune response either to a vaccine administered as disclosed herein (e.g., by oral administration and injection into the blood supply), or to infection by the virus. In particular, disclosed herein are compositions and methods for assessing the continued presence of antibodies in a patient's respiratory and digestive mucosa following infection with SARS-CoV2 or following inoculation against SARS-CoV2 with administration of a SAR coronavirus vaccine.

For assaying a sample from a patient having received a vaccine against a pathogenic infection (e.g., targeting SARS-CoV2) and/or having been infected with a virus (e.g., SARS-CoV2), the presence of antibodies against the pathogen may be carried out using any one of many diagnostic tests. In some embodiments, the diagnostic test is a cell viability assay that allows for the detection of antibodies in the presence of antigen. Diagnostic tests using a cell viability assay for anti-SARS-CoV2 antibody detection are disclosed in U.S. 62/053,691, the entire contents of which are herein incorporated by reference. The cellular diagnostic assay relies on the expression of the target receptor for a given pathogen (e.g., ACE2 for SARS-CoV2 infection) on the surface of an immune effector cell line (e.g., killer T cells, natural killer cells, NK92® cells and derivatives thereof, etc.) and the expression of the pathogen ligand (e.g., Spike proteins for SARS-CoV2 infection) on the surface of a surrogate cell line (e.g., HEK293 cells or SUP-B15 cells).

Additional diagnostic tests using recombinant protein variants of the ACE2 protein (the human receptor targeted by SARS-CoV2 spike protein) are disclosed in U.S. Ser. No. 16/880,804, the entire contents of which are herein incorporated by reference.

Antibody testing in saliva samples. In order to more easily monitor a patient for the presence of anti-pathogen antibodies, assaying a saliva sample from the patient allows for expedited sample collection, increased patient participation, and may allow for the patient to obtain the sample themselves and either mail or transport the sample to the lab for testing. However, in order to assay saliva for the presence of neutralizing antibodies against SARS-CoV2, it may be necessary to stabilize proteins in the saliva against degradation during transport and storage after sample collection prior to testing.

Upon collection of the saliva sample, the saliva is placed into a preservative solution to stabilize the components (e.g., anti-SARS CoV2 antibody or viral spike protein) therein. Preservatives for biological samples are disclosed, for example, in Cunningham & al. (2018) report ("Effective Long-term Preservation of Biological Evidence," U.S. Department of Justice grant #2010-DN-BX-K193) and U.S. Pat. No. 6,133,036 to Putcha et al. For example, a stabilizing preservative solution for a patient's saliva sample may include any one of glutaraldehyde, sodium benzoate, citric acid, propyl gallate, EDTA, zinc, actin, chitosan, parabens, sodium azide, and any combination thereof.

In specific embodiments, saliva samples may be mixed with stabilizing preservative solutions of glutaraldehyde to achieve a final glutaraldehyde concentration between 0.1% (w/v) and 2.0% (w/v), for example about 0.2% (w/v), about 0.3% (w/v), about 0.4% (w/v), about 0.5% (w/v), about 0.6% (w/v), about 0.7% (w/v), about 0.8% (w/v), about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), or about 1.9% (w/v).

In additionally or alternatively embodiments, saliva samples may be mixed with a stabilizing preservative solution of about 0.10% to about 1.00% sodium benzoate (weight/volume of sample) and/or about 0.025% to about 0.20% citric acid (weight/volume of sample). For example, the saliva sample may be mixed with 0.10%, 0.20%, 0.30%, 0.40%, 0.50%, 0.60%, 0.70%, 0.80%, 0.90%, or 1.00% w/v sodium benzoate. In additional embodiments, the saliva sample is mixed a stabilizing preservative solution of at least 0.5 mg/mL (for example, at least 0.6 mg/mL, at least 0.7 mg/mL, at least 0.8 mg/mL, at least 0.9 mg/mL, at least 1 mg/mL, at least 1.5 mg/mL, at least 2 mg/mL, at least 2.5 mg/mL, at least 3 mg/mL, at least 3.5 mg/mL, at least 4 mg/mL, at least 4.5 mg/mL, or even 5 mg/mL) of benzoic acid and/or at least 0.2 mg/mL (for example, at least 0.2 mg/mL, at least 0.25 mg/mL, at least 0.3 mg/mL, at least 0.35 mg/mL, at least 0.40 mg/mL, at least 0.50 mg/mL, at least 0.75 mg/mL, at least 1.0 mg/mL, at least 1.25 mg/mL, at least 1.5 mg/mL, at least 1.75 mg/mL, or even 2.0 mg/mL) of citric acid. As used herein, "benzoic acid" is interchangeable with benzoate salt (e.g., sodium benzoate) and "citric acid" is interchangeable with citrate salt (e.g., sodium citrate).

The saliva samples with preservatives as described above are stable for storage at temperatures between 15° C. and 40° C. for at least one hour (e.g., at least 5 hours, at least 10 hours, at least 12 hours, at least 24 hours, at least 48 hours, or even 36 hours). Therefore, disclosed herein is a method of preserving a saliva sample for neutralizing antibody testing, the method including mixing the saliva sample with the stabilizing solution made of one or more of glutaraldehyde, sodium benzoate, citric acid, propyl gallate, EDTA, zinc, actin, chitosan, parabens, and/or sodium azide and storing between 15° C. and 25° C. for at least one hour, and up to 2, 3, 4, 5, 6, 7, 8, 9, 10, 11, 12, 13, 14, 15, 16, 17, 18, 19, 20, 21, 22, 23, 24, 36, or 48 hours. In some embodiments, the saliva sample is mixed with a glutaraldehyde concentration between 0.1% (w/v) and 2.0% (w/v), and the glutaraldehyde-saliva is stored between 15° C. and 25° C. In certain embodiments, the glutaraldehyde-saliva may further comprise citric acid and/or benzoic acid at a concentration of as disclosed herein.

Aragonite. In some embodiments, any antibody proteins or any specific antibody protein may be captured from the saliva sample with oolitic aragonite particles. For example, the saliva preserving solution of glutaraldehyde, sodium benzoate and citric acid, propyl gallate, EDTA, zinc, actin, chitosan, parabens, sodium azide, and any combination thereof as disclosed herein, may also include oolitic aragonite (calcium carbonate, $CaCO_3$) particles. Use of aragonite particles for binding to proteins is disclosed, for example, in U.S. Ser. No. 16/858,548 and PCT/US20/29949, the entire contents of both of which are herein incorporated by reference. Accordingly, aragonite particles may be added to that have been modified to capture (e.g., bind to) any antibodies present in the saliva sample or specifically capture an antibody against a specific antigen. For example, aragonite may be functionalized with moieties capable of binding to an immunoglobulin (Ig) protein. Preferably, the Ig protein is an immunoglobulin A (IgA), immunoglobulin G (IgG), or immunoglobulin E (IgE) protein. More preferably, the aragonite is functionalized to bind to an IgA protein. Most preferably, the aragonite particles are functionalized with moieties capable of binding to specific antibodies. For example, the aragonite particles may be coupled with a moiety specific to anti-SARS-CoV2 antibodies. Preferably, the aragonite particle is coupled with a recombinant ACE2 protein as disclosed, for example, in U.S. Ser. No. 16/880,804, supra. In typical embodiments, the aragonite particle is coupled with a recombinant human ACE2 protein having at least 85%, at least 90%, or at least 95% sequence identity to SEQ ID NO: 8.

In additional or alternative embodiments, the aragonite particle is functionalized (e.g., coupled to) a recombinant soluble ACE2 protein (e.g., SEQ ID NO: 9). For more efficient capture or binding of an anti-SARS-CoV2 antibody or the spike protein of SARS CoV-2, the recombinant soluble ACE2 may be mutated to form ACE2 variants having higher binding affinities for SARS-CoV2 spike protein (e.g., the RBD domain of the spike protein). These ACE2 variant mutants of the recombinant soluble ACE2 protein include T27F, T27W, T27Y, D30E, H34E, H34F, H34K, H34M, H34W, H34Y, D38E, D38M, D38W, Q24L, D30L, H34A, and/or D355L.

As used herein, the term "functionalized" refers to coupling or binding of a moiety to the aragonite particle thereby imparting any function of the coupled moiety to the aragonite particle. For example, the aragonite particle may be functionalized with a protein moiety. Methods for preparing and using aragonite particle beads are disclosed in U.S. Ser. No. 16/858,548 and PCT/US20/29949. In some embodiments, the aragonite composition includes a plurality of aragonite particle beads. Preferably, the plurality of aragonite particle beads have an average particle size of between 100 nm to 1 mm, In some embodiments a protein moiety is coupled directly to the natural, untreated surface of aragonite particles. Aragonite particles approximately 2-3% amino acid content including aspartic acid and glutamic acid rendering the aragonite surface hydrophilic. Accordingly, in some embodiments, protein moieties may be directly coupled to the surface of the aragonite particles.

In alternative embodiments, the aragonite particle surface may be treated to modify the binding surface. For example, treatment with stearic acid (i.e., octadecanoic acid) provides for a hydrophobic surface, as disclosed in U.S. Ser. No. 16/858,548 and PCT/US20/29949. For protein loading, treatment of the aragonite with phosphoric acid forms lamellar structures. Additional conjugation techniques for coupling reactive groups to the amino acid surface of aragonite are known in the art as disclosed, for example, in Bioconjugate Techniques, Third Edition, Greg T. Hermanson, Academic Press, 2013.

Monitoring of Vaccine Protocol. Patients who do not show sufficient titers of (e.g., presence of) neutralizing antibody in their saliva may be sent oral dosages of the respective vaccine (e.g., a SARS-CoV2 vaccine as disclosed herein). The patients inhale or ingest these vaccine dosages, and then two weeks later send another saliva sample—prepared and stored in the same manner as above—to the test facility to confirm that the oral vaccine dose has restored their anti-SARS-CoV2 antibody (e.g., IgA) titers.

Accordingly, in additional embodiments, a kit for collecting a saliva sample from a patient includes a collection container with the saliva preservative solution as disclosed herein. For example, the kit includes a collection container with a solution of any of one or combination of glutaraldehyde, sodium benzoate and/or citric acid, propyl gallate, EDTA, zinc, actin, chitosan, parabens, and sodium azide. The kit may also include adhesive packaging and/or mailing supplies in order to secure the collection container with the saliva sample for transport or mailing. In some embodiments, the kit may also include at least one dose of the vaccine for oral administration.

Recited ranges of values herein are merely intended as a shorthand referring individually to each separate value falling within the range. Unless otherwise indicated herein, each individual value is incorporated into the specification as if it were individually recited herein.

EXAMPLES

The advantageous features of the compositions and methods described herein are further illustrated (but not limited) by the following examples.

Example 1. Two groups of Rhesus macaques (5 per group) were immunized subcutaneously on day 0 with an adenoviral anti-SARS-CoV2 vaccine as described above. Blood was drawn from each macaque before immunization. On day 14, one group of macaques (Group 1) received another subcutaneous booster injection of the same vaccine, while another group (Group 2) received an oral vaccine as described herein (E1-/E2b-Ad5 with SEQ ID NO:11 or SEQ ID NO:13). On day 28, both groups received an oral vaccine booster dose. Two macaques (Control) were vaccinated at the indicated time points with shams. Blood was drawn on days 14, 21, 28, 35, & 42.

Figure 19:
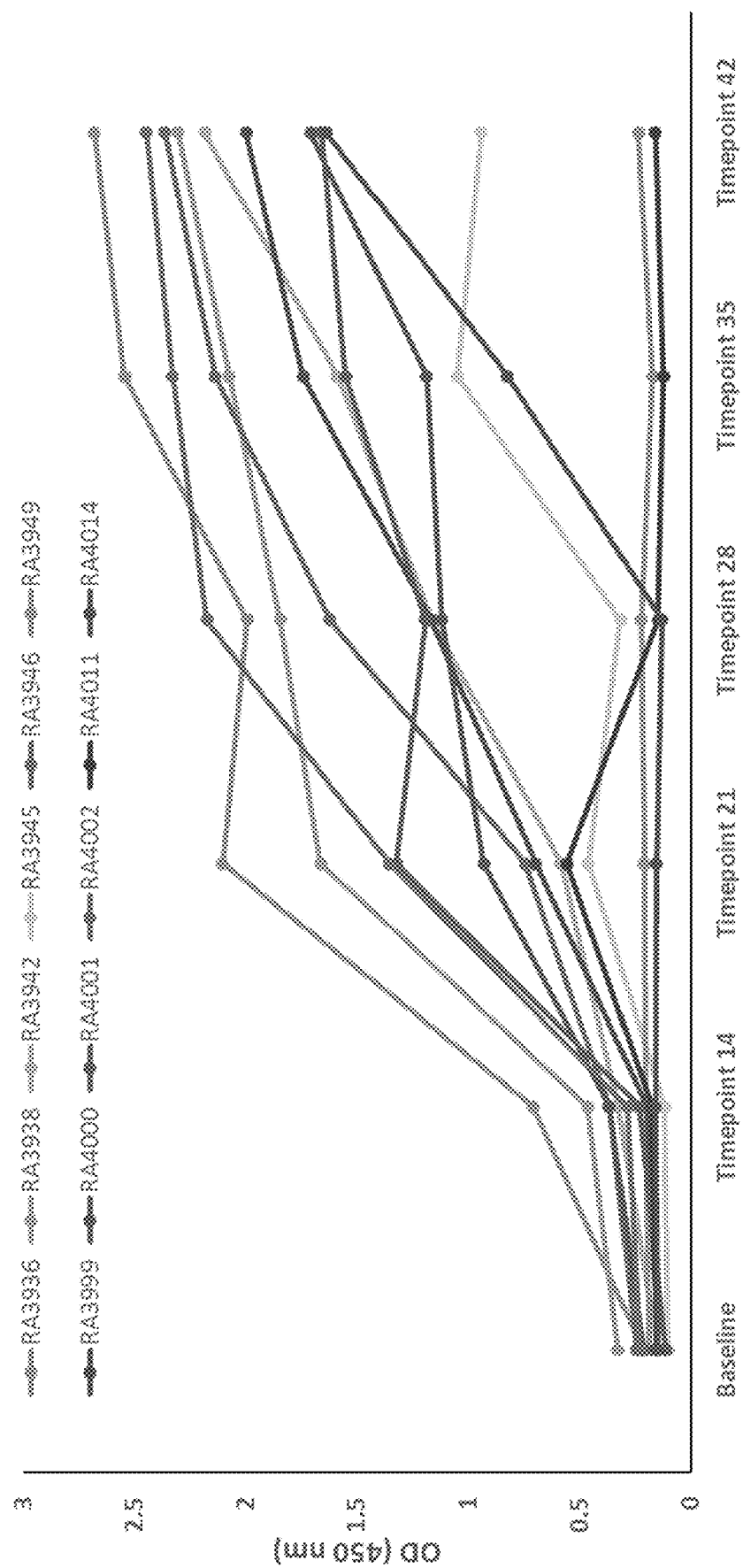
Figure 20:
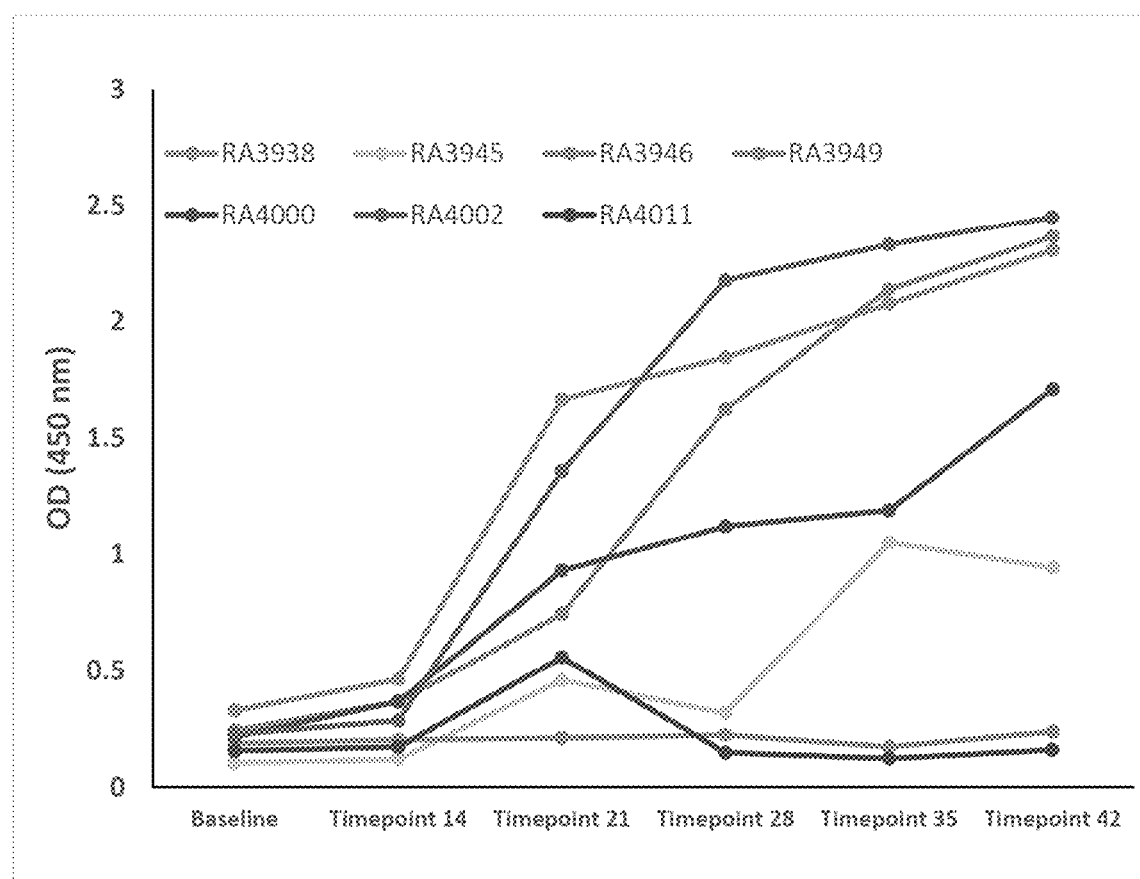
Figure 21:
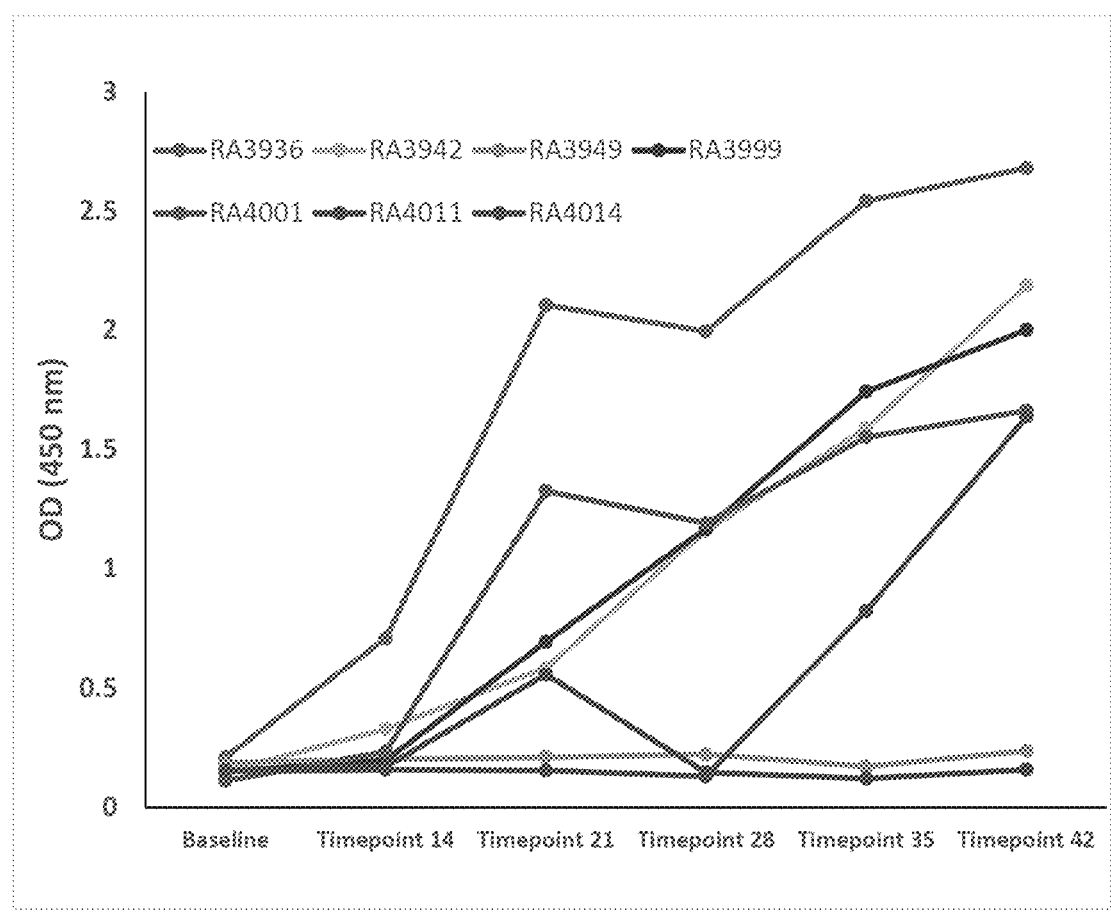

Serum samples drawn at the indicated time points from these macaques was then assessed by ELISA for anti-spike protein IgG and IgM seroreactivity. Briefly, 96 well EIA/RIA plates (ThermoFisher, Cat #07-200-642) were coated with 50 µL/well of 1 µg/mL solution of purified recombinant SARS-CoV-2-derived Spike protein (S-Fusion. ImmunityBio, Inc.) suspended in coating buffer (0.05 M Carbonate-Bicarbonate, pH 9.6) and incubated overnight at 4° C. Individual 96 well plates were prepared for each immunoglobulins type (IgG or IgM) by washing three times each per well with 150 µL of TPBS solution (PBS+0.05% Tween 20). 100 µL/well of blocking solution (2% non-fat milk in TPBS) was then added and incubated for 1 hour at room temperature (RT). Plasma and serum samples were heat-inactivated at 56° C. for 1 hour before use. Serial dilutions of plasma, serum or antibody samples were prepared in 1% non-fat milk in TPBS. Plates were washed as described above and 50 µL/well of each serial dilution were added to the plate and incubated at RT for 1 hour. Plates were washed three times with 200 µL of TPBS. Dilutions (1:6000) of each goat anti-Human IgG (H+L) Cross-Adsorbed, HRP, Polyclonal; or Goat anti-Human IgM (Heavy chain) Cross-Adsorbed Secondary Antibody, HRP (ThermoFisher, Cat #62-842-0 or A18841 respectively) were 1 prepared in 1% non-fat milk/TPBS and 50 µL/well of these secondary antibodies were added in separate reactions/plates per immunoglobulin type (IgG or IgM) and incubated for 1 hour at RT. Plates were washed three times with 200 RL of TPBS. One component (3,3',5,5'-tetramethylbenzidine (TMB) substrate, 50 VWR, Cat #100359-156) was added to each well and incubated at RT for 10 minutes and then the reaction was stopped by addition of 50 µL/well of 1N Sulfuric acid (H2SO4). The optical density at 450 nm was measured with a Synergy 2 plate reader (BioTek Instruments, Inc). Data were analyzed using Prism 8 (GraphPad Software, LLC), and shown in FIG. 19.

Figure 22:
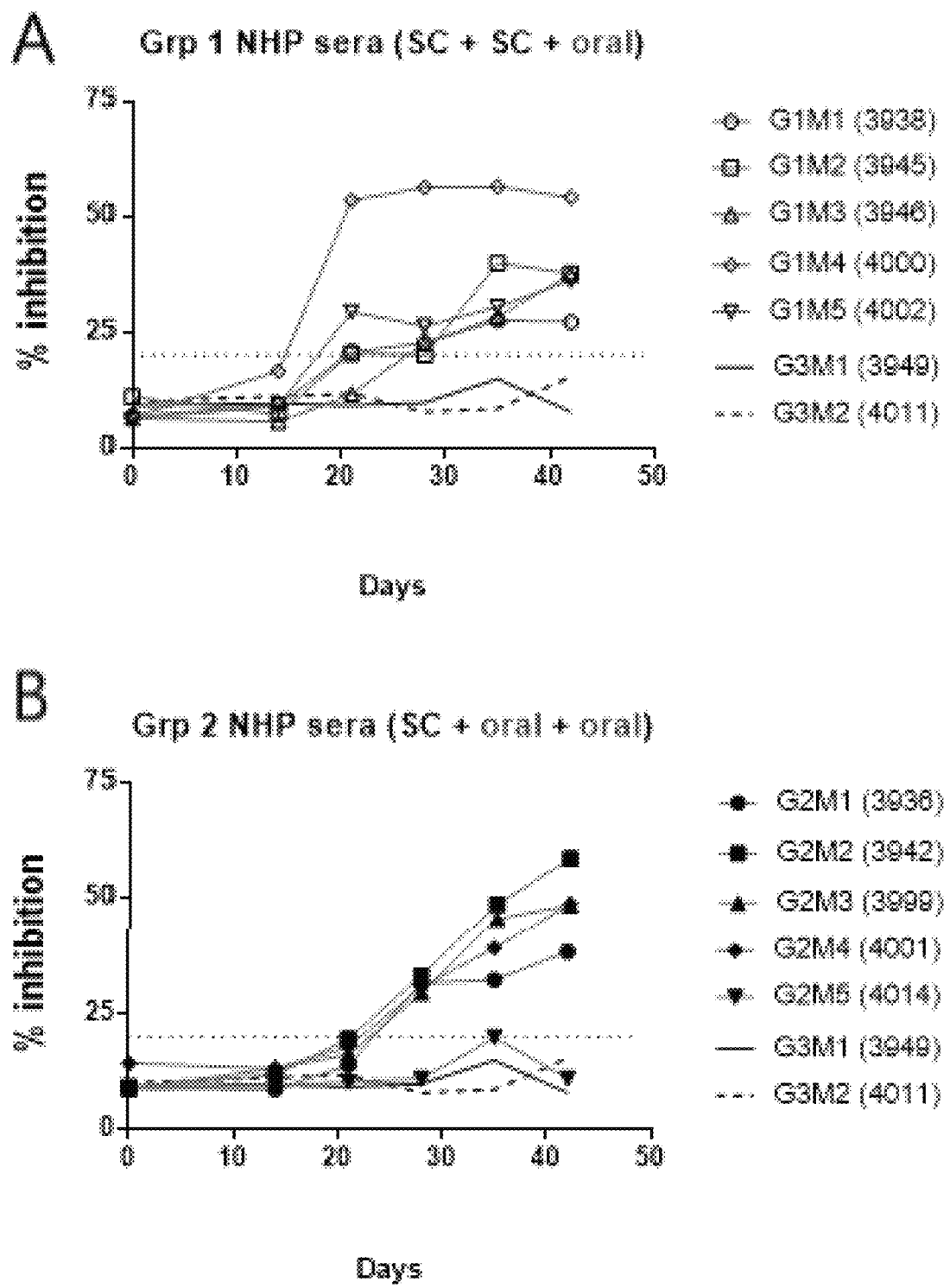
FIG. 22 illustrates one embodiment of the disclosure herein. (A) shows the ability of sera from vaccinated Group 1 macaques to inhibit SARS-CoV2 infectivity in vitro. (B) shows the ability of sera from vaccinated Group 2 macaques to inhibit SARS-CoV2 infectivity in vitro. The dotted line indicates 20% inhibition.
Figure 23:
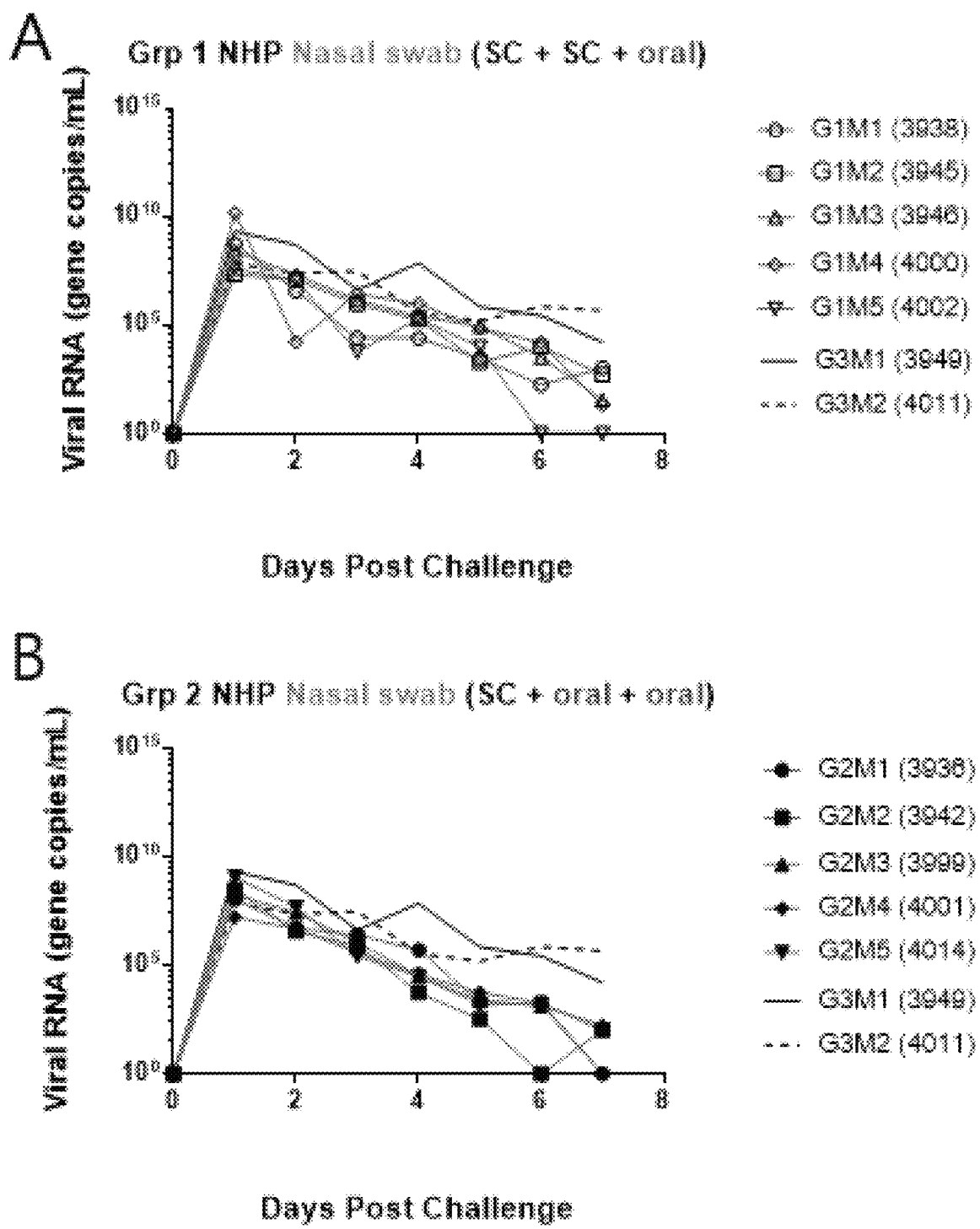
FIG. 23 illustrates one embodiment of the disclosure herein. (A) shows viral load (qPCR) in nasal swabs from Group 1 macaques. (B) shows viral load in nasal swabs from Group 2 macaques.
Figure 24:
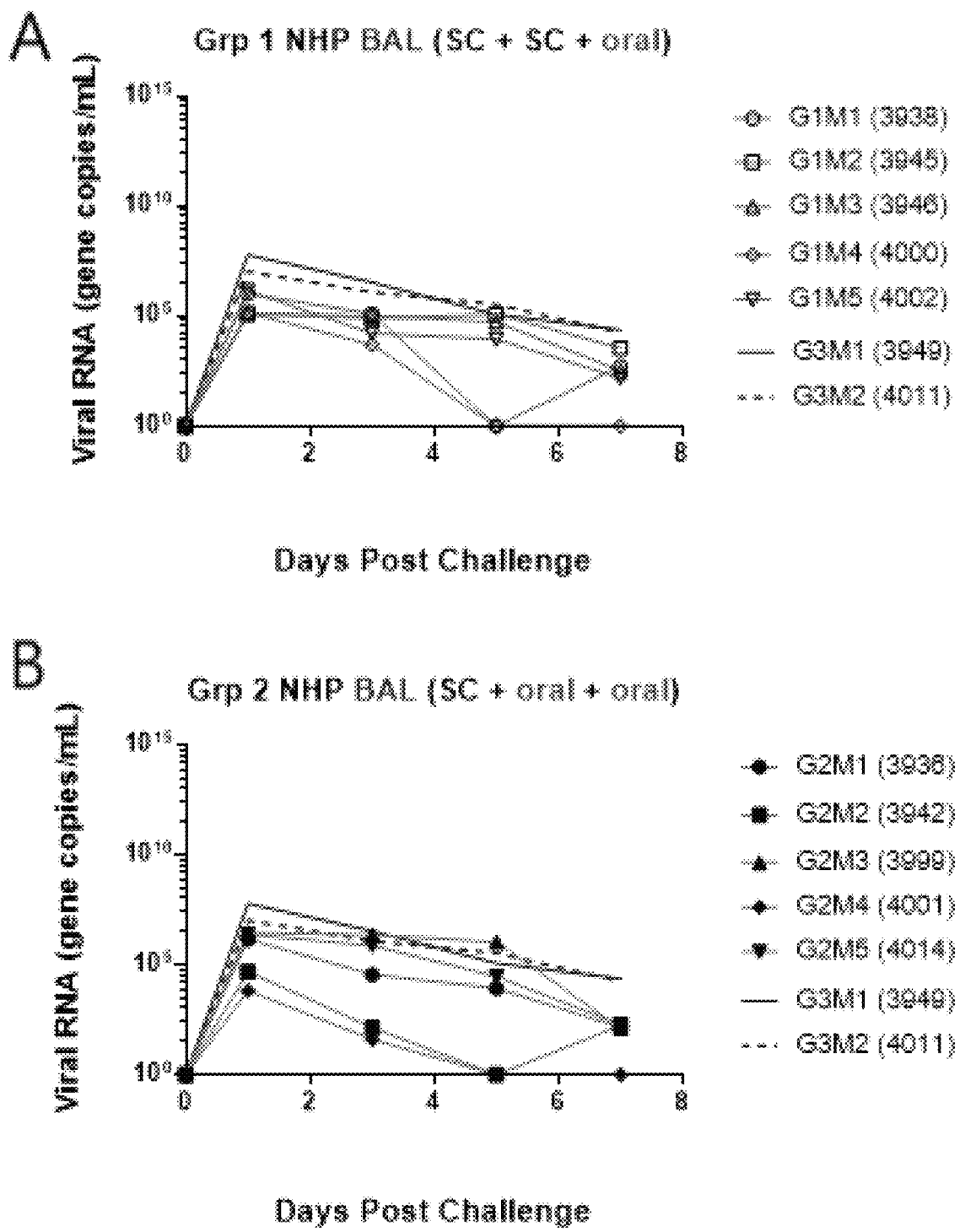
FIG. 24 illustrates one embodiment of the disclosure herein. (A) shows viral load (qPCR) in BAL from Group 1 macaques. (B) shows viral load in BAL from Group 2 macaques.

Example 2. On day 56, the macaques were challenged with respiratory exposure to the SARS-CoV2 virus. Nasal swabs were collected daily from these macaques on days 56-63. Bronchoalveolar lavage (BAL) fluid was collected on days 57, 59, 61, & 63. The ability of serum to inhibit SARS-CoV2 infectivity from the samples collected is shown in FIG. 22. As can be seen, the sera from both the Group 1 and Group 2 macaques inhibited infectivity, with later collected sera inhibited more powerfully than early collected sera. Sera from control macaques had no inhibitory effect at any time point tested. Viral load over time in the nasopharynx is shown in FIG. 23. Viral load over time in the lungs is shown in FIG. 24.

Figure 25:
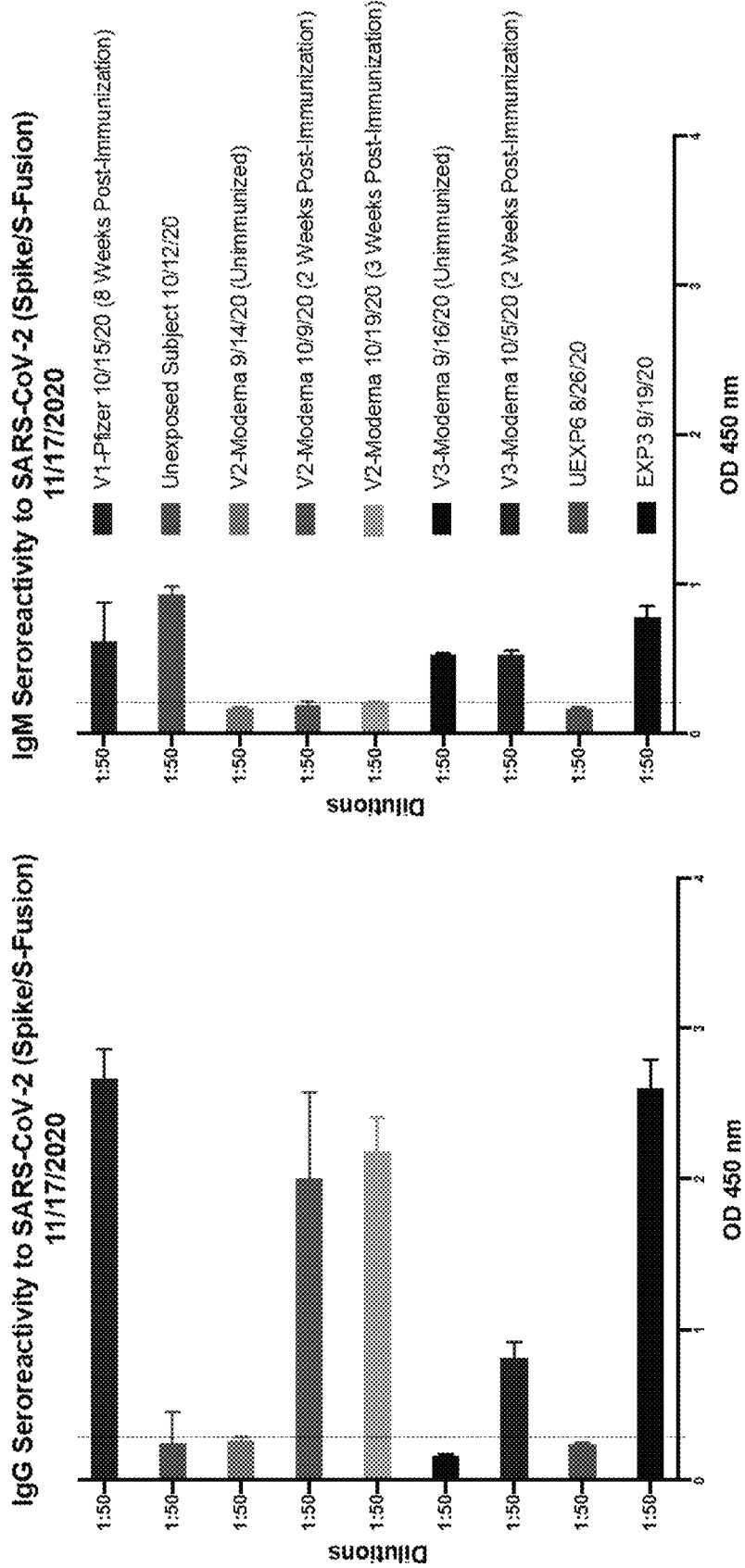
FIG. 25 shows ELISA results detecting IgG & IgM seroreactivity against SARS-CoV2 spike in sera samples drawn from human patients immunized with various experimental anti-SARS-CoV2 vaccines.

Example 3. Serum samples from various human volunteers who have received various experimental anti-SARS-CoV2 vaccines were collected and assayed by ELISA as described above for IgG and IgM seroreactivity against SARS-CoV2 S protein. The results are shown in FIG. 25.

Example 4. Human volunteers were divided into three cohorts. Cohort 1 (10 individuals) was immunized by subcutaneous injection with $5 \times 10^{10}$ viral particles of a vaccine as described herein (E1-/E2b-Ad5 containing SEQ ID NO:11 or SEQ ID NO:13). Cohort 2 (10 individuals) was immunized by subcutaneous injection with $10^{11}$ viral particles of a vaccine as described herein. Cohort 3 (15 individuals) was immunized by subcutaneous injection with $10^{11}$ viral particles of a vaccine as described herein (or $5 \times 10^{10}$ viral particles if safety concerns indicated a lower dose). Blood was drawn from each volunteer on the same day as the initial prime vaccination was administered. Blood was drawn again on days 8, 15, & 22. A booster injection of the same vaccine was administered on day 22.

ELISpot tests were run on the blood collected on days 1 & 15 to assess cell-mediated immunity against SARS-CoV2. 400,000 viable PBMCs from each blood draw per well (Cellometer K2 w/AO/PI viability stain) were stimulated with empty medium, SARS-CoV2 S, SARS-CoV2 N, SARS-CoV2 M, CD3/CD28/CD2, and CEFT. After 48 hrs of stimulation, supernatants were frozen (−80° C.) for later testing.

Figure 26:
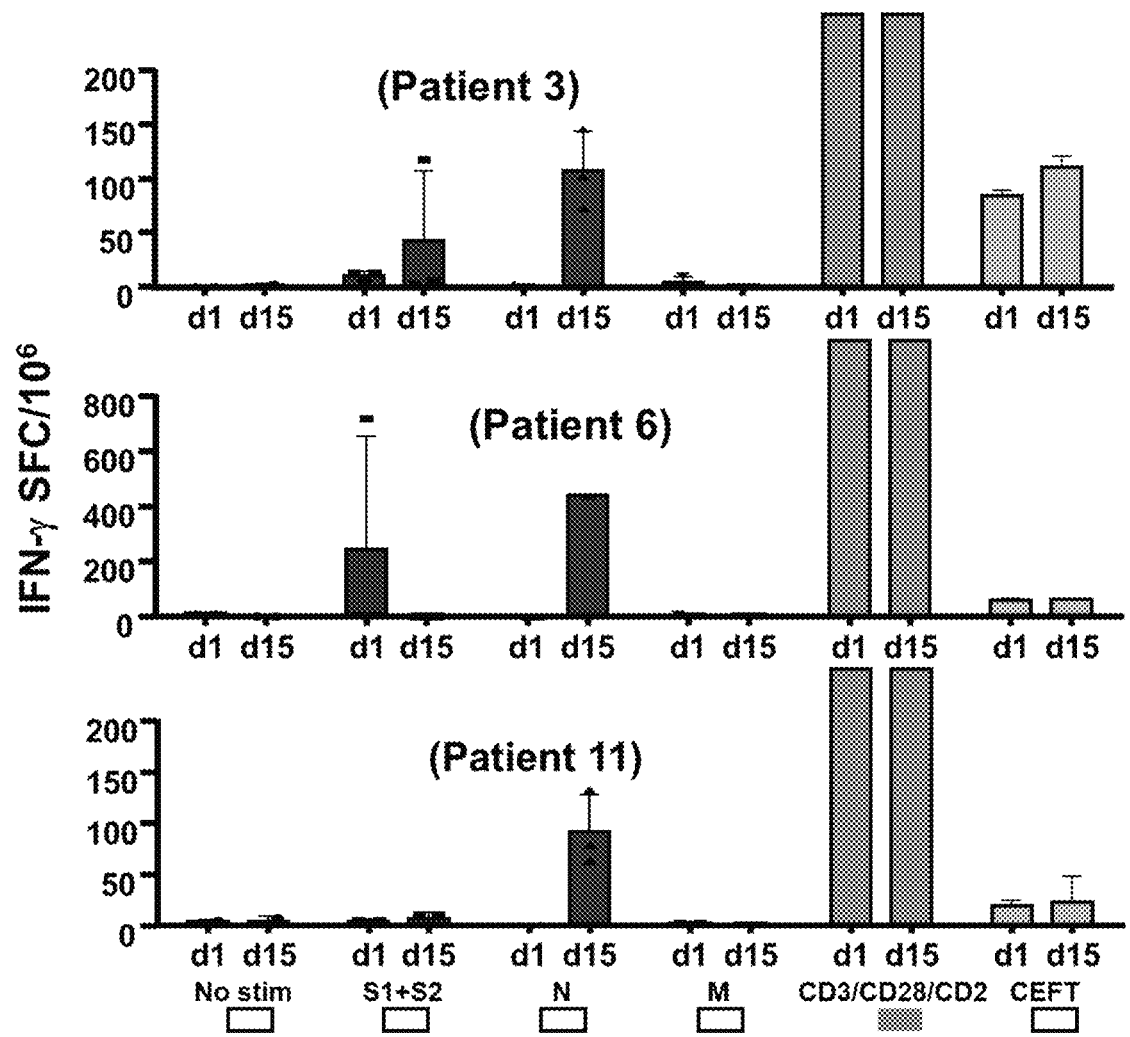
FIG. 26 shows Th1 ELISpot results from human patients 3, 6, & 11.
Figure 27:
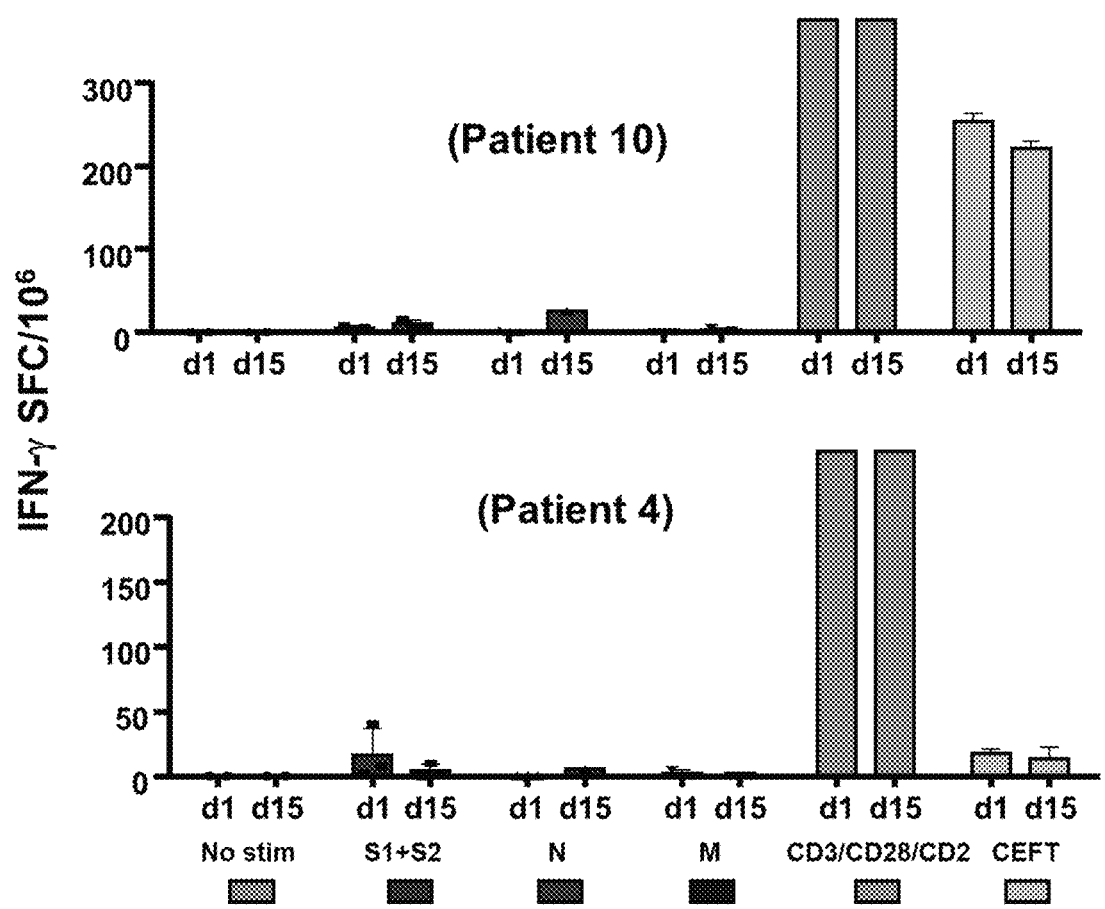
FIG. 27 shows Th1 ELISpot results from human patients 4 & 10.

FIG. 26 shows the results of this test from Th1 N-responsive patients 3, 6, & 11. FIG. 27 shows results from patient 4 (N-unresponsive) and patient 10 (weakly Th1 N-responsive). None of these patients showed a Th2 response to N.

Example 5. Human volunteers received $5\times10^{10}$ viral particles of vaccine by subcutaneous injection on day 1 of the study, and again on day 22. Blood was drawn from each subject on days 1 and 29. These blood samples were assayed for immune reactivity to the SARS-CoV2 S protein by the methods described in co-pending U.S. 63/124,979 (filed 14 Dec. 2020). FIG. 28 shows the results of these assays. As can be seen, subject #8 shown a level of immune response to the S protein above the level of detection already on the first day of the experiment, indicating that this particular individual had already been previously infected with SARS-CoV2. The course of immunization produced a notable increase in immune response relative to baseline. This result constitutes in vivo evidence that the vaccines described herein can serve as vaccine boosts even to individuals whose immunity derives from some other source than prior immunization with the vaccines described herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The present disclosure, therefore, is not to be restricted except in the scope of the appended claims. Moreover, in interpreting both the specification and the claims, all terms should be interpreted in the broadest manner consistent with the context.

Example 6: The hAd5 [E1-, E2b-, E3-] platform and constructs For studies here, the next generation hAd5 [E1-, E2b-, E3-] vector was used (FIG. 1c) to create viral vaccine candidate constructs. As shown in FIG. 8d-h, a variety of constructs were created:

FIG. 8(d): S WT: S protein comprising 1273 amino acids and all S domains: extracellular (1-1213), transmembrane (1214-1234), and cytoplasmic (1235-1273) (Unitprot PODTC2);

FIG. 8(e): S RBD-ETSD: S Receptor Binding Domain with an Enhanced T-cell Stimulation Domain (ETSD);

FIG. 8(f): S Fusion: S optimized to enhance surface expression and display of RBD;

FIG. 8(g): N-ETSD: The nucleocapsid (N) sequence with the ETSD; and

FIG. 8(h): Bivalent S-Fusion+N-ETSD; S-WT+N-ETSD and S RBD-ETSD+N-ETSD constructs were also produced, but are not shown.

Figure 9:
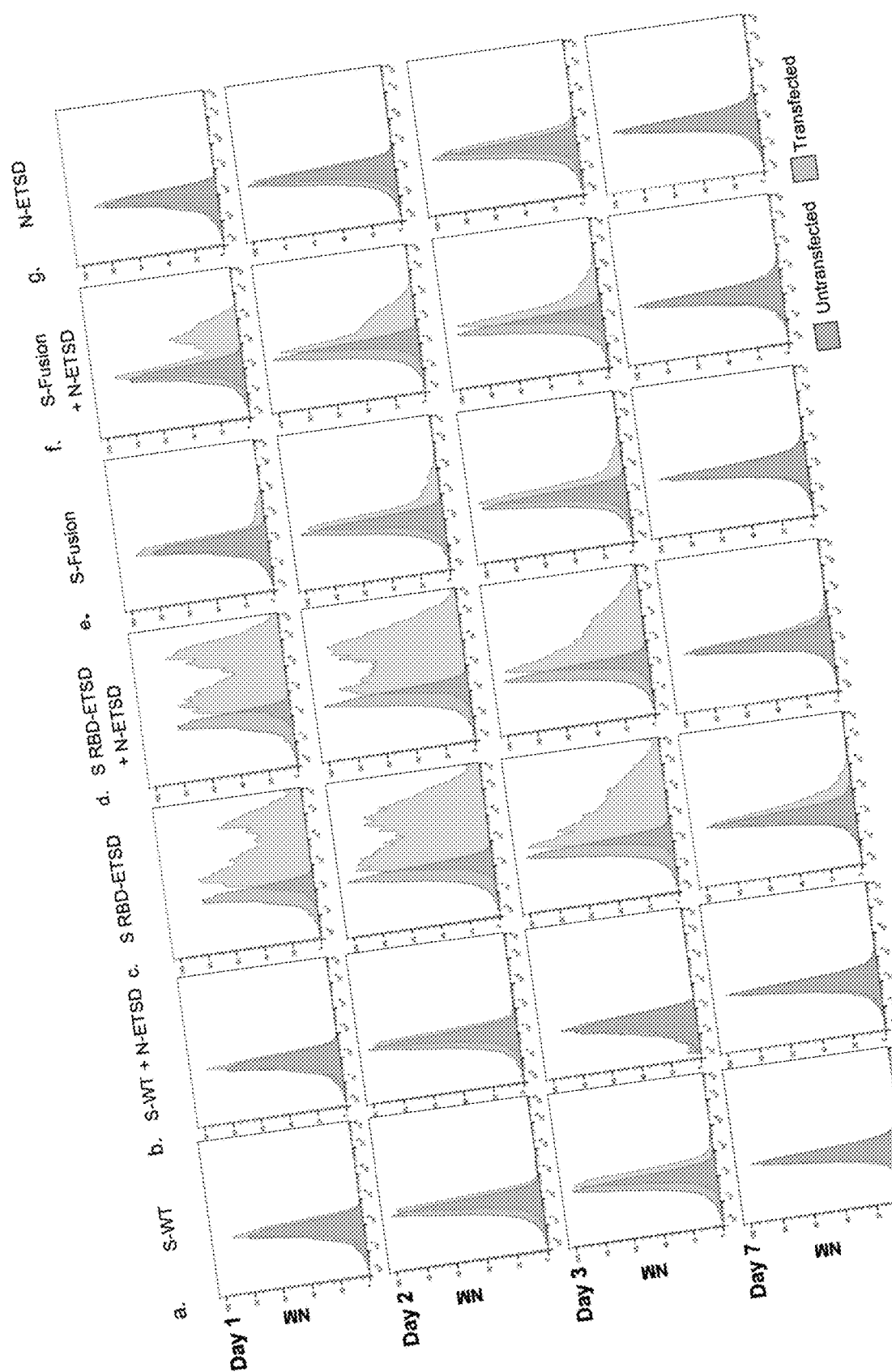

Example 7: Enhanced HEK 293T Cell-Surface Expression of RBD Following Transfection with Ad5 S-Fusion+N-ETSD As shown in FIG. 9, anti-RBD-specific antibodies did not detect RBD on the surface of HEK 293T cells transfected with hAd5 S-WT (FIG. 9a) or hAd5 S-WT+N-ETSD (FIG. 9b) constructs, while hAd5 S-Fusion alone was slightly higher (FIG. 9e). As expected, both constructs with RBD, hAd5 RBD-ETSD and RBD-ETSD+N-ETSD, showed high binding of anti-RBD antibody (FIGS. 9c and d). Notably, high cell-surface expression of RBD was detected after transfection with bivalent hAd5 S-Fusion+N-ETSD (FIG. 9f). These findings support our proposition that an hAd5 S-Fusion+N-ETSD construct, containing a high number and variety of antigens provided by both full-length, optimized S with proper folding and N leads to enhanced expression and cell surface display of RBD in a vaccine construct.

Figure 10:
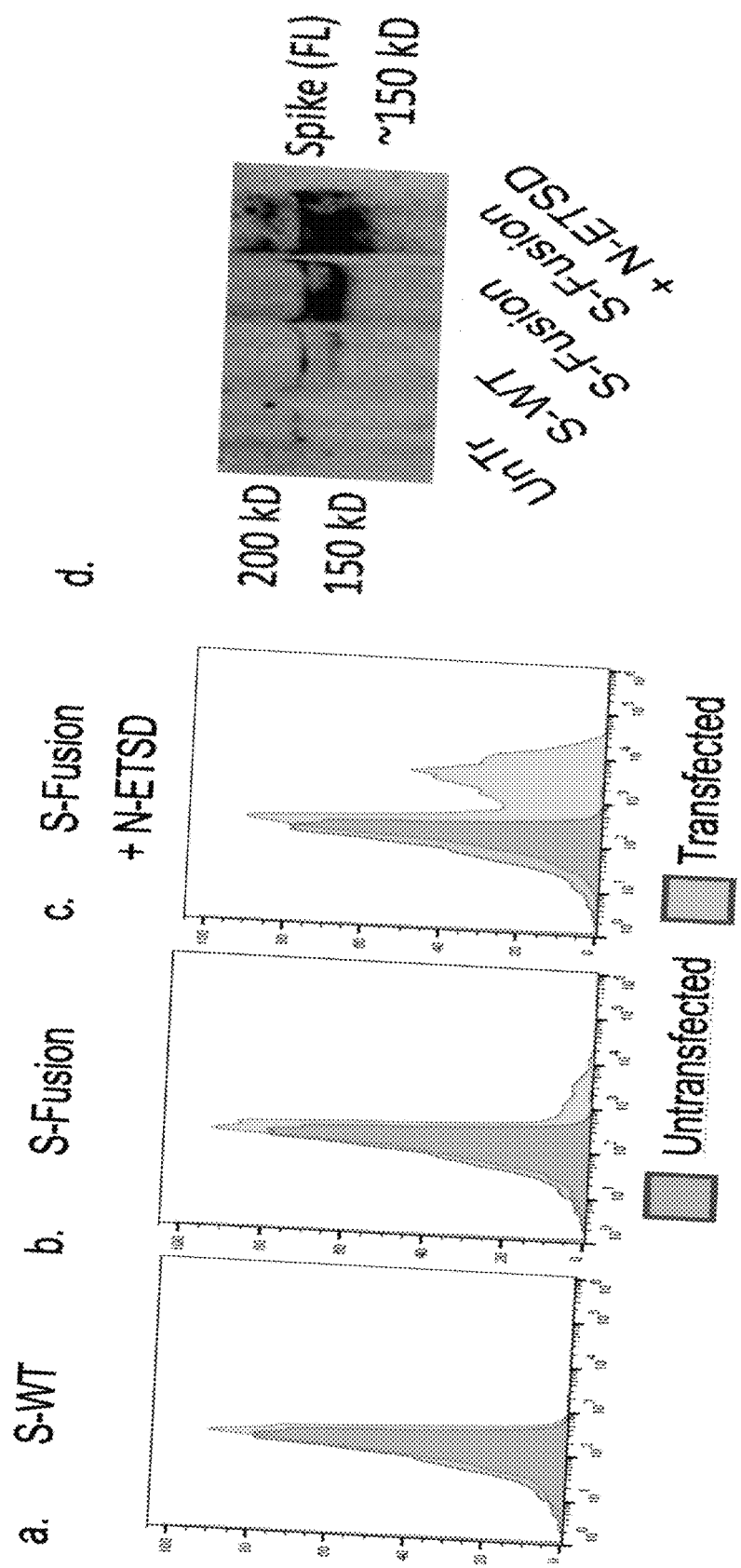

Example 8: Immunoblot Correlation of Enhanced S Expression with hAd5 S-Fusion+N-ETSD Immunoblot analysis of S expression correlated with enhanced S expression (FIG. 10), showing again that the bivalent hAd5 S-Fusion+N-ETSD construct enhances expression of S compared to S-Fusion alone.

Figure 11:
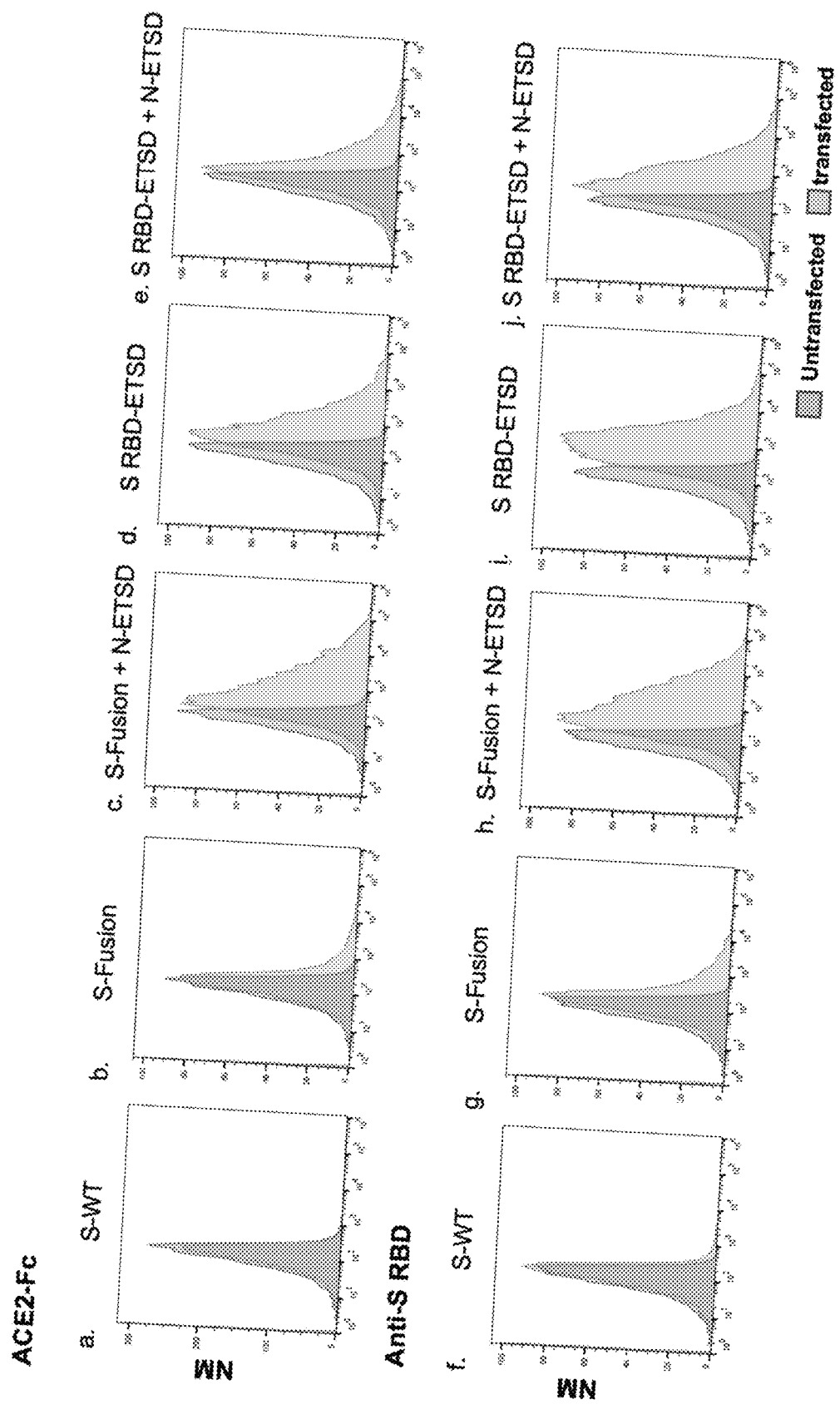

Example 9: Confirmation of Native Folding of Enhanced Surface RBD Following hAd5 S-Fusion+N-ETSD Transfection Determination of the binding of recombinant ACE2-Fc was performed to confirm the native, physiologically-relevant folding of the S RBD after expression from the hAd5 S-Fusion+N-ETSD vaccine candidate. S RBD binds ACE2 during the course of SARS-CoV-2 infection and an effective neutralizing antibody prevents this interaction and thus infection. Such a neutralizing antibody is more likely to be effective if raised in response to S presented in the correct conformation. In addition to enhancement of cell surface expression, the optimized S allows for proper protein folding. It was found that compared to either hAd5 S-WT or hAd5 S-Fusion (FIGS. 11a and b, respectively), ACE2-Fc binding to S RBD expressed from the hAd5 S-Fusion+N-ETSD was clearly enhanced (FIG. 11c). Anti-RBD antibody binding studies (FIG. 1 if j) performed with the same experiment, confirmed the enhanced surface expression findings noted by ACE2-Fc binding. These findings of conformationally correct and enhanced S RBD expression, important for production of neutralizing antibodies, directed us to elect the hAd5 S-Fusion+N-ETSD vaccine candidate for clinical trials.

Figure 12:
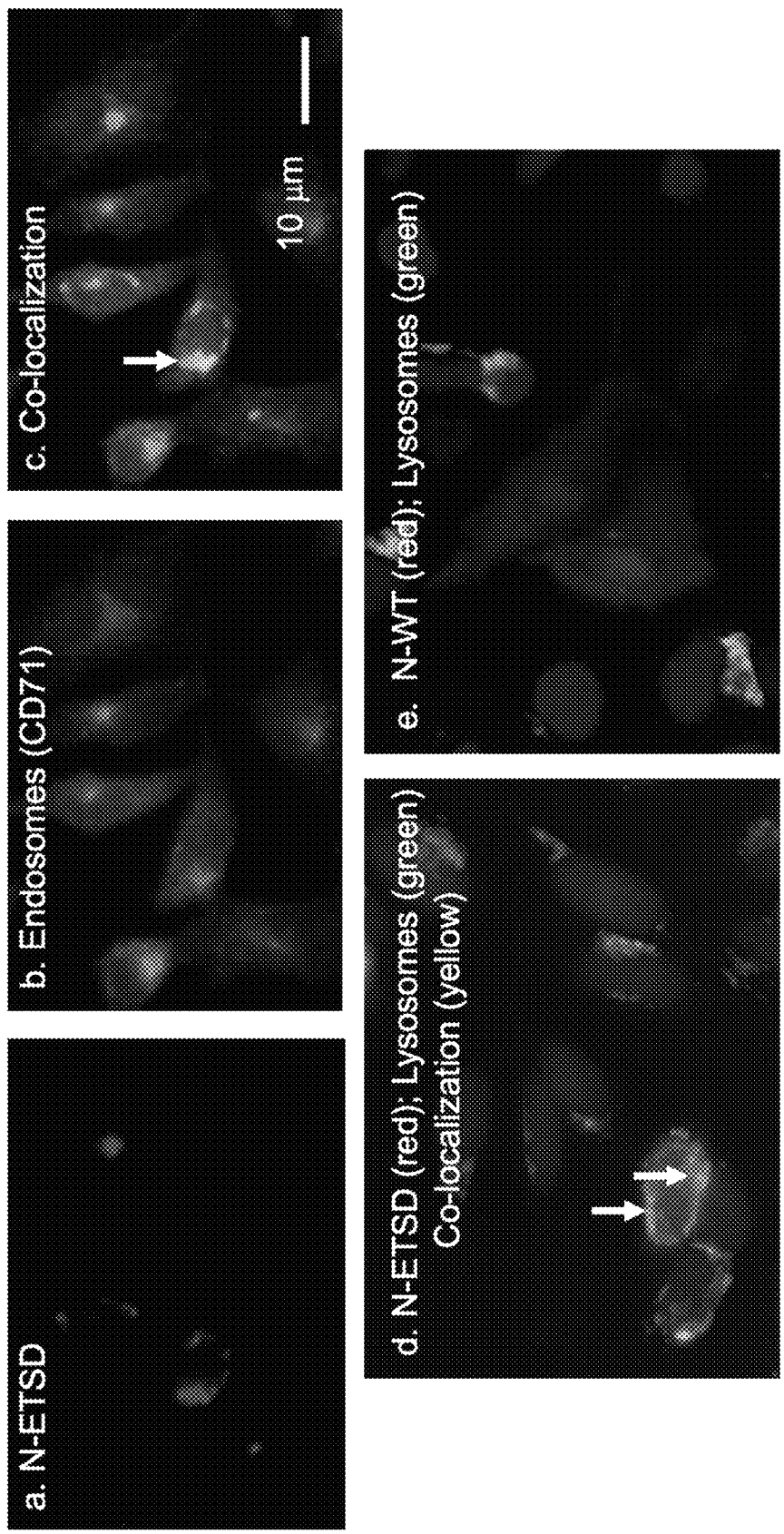
Figure 13:
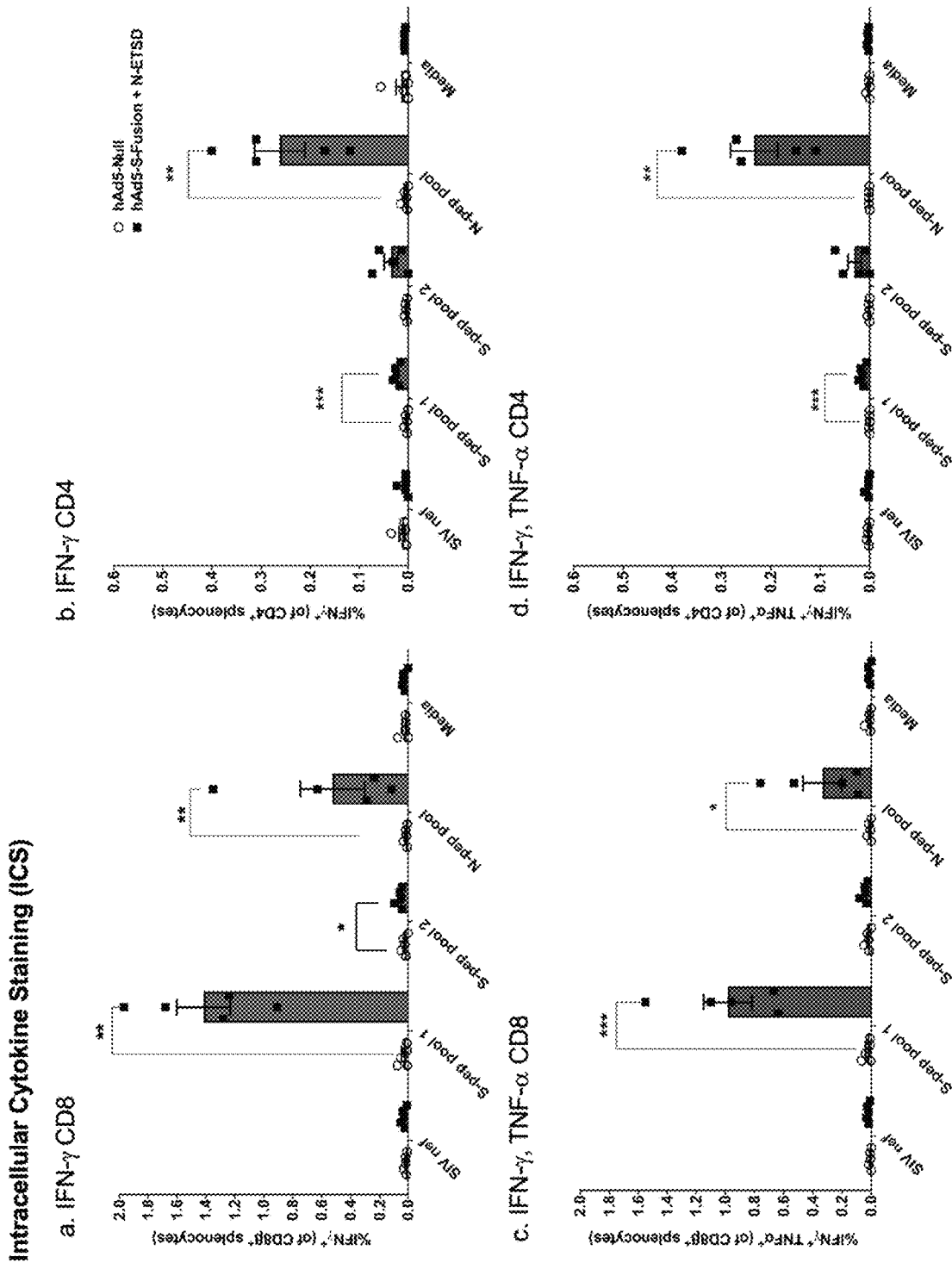
Figure 14:
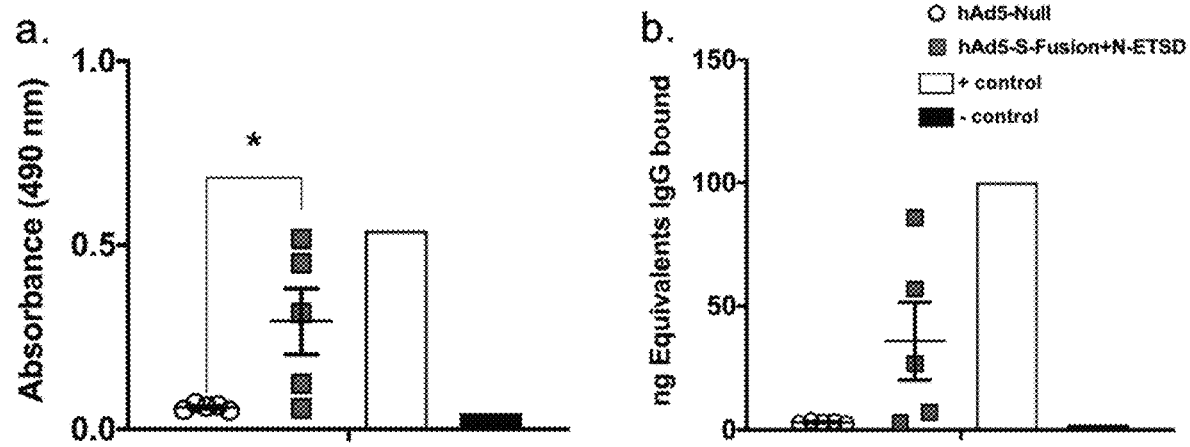
Figure 14:
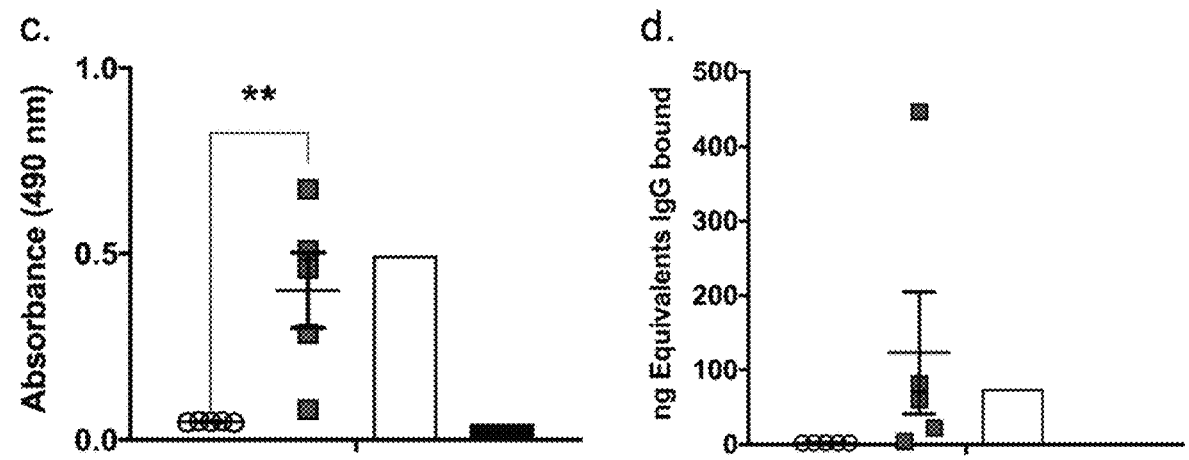
Figure 15:
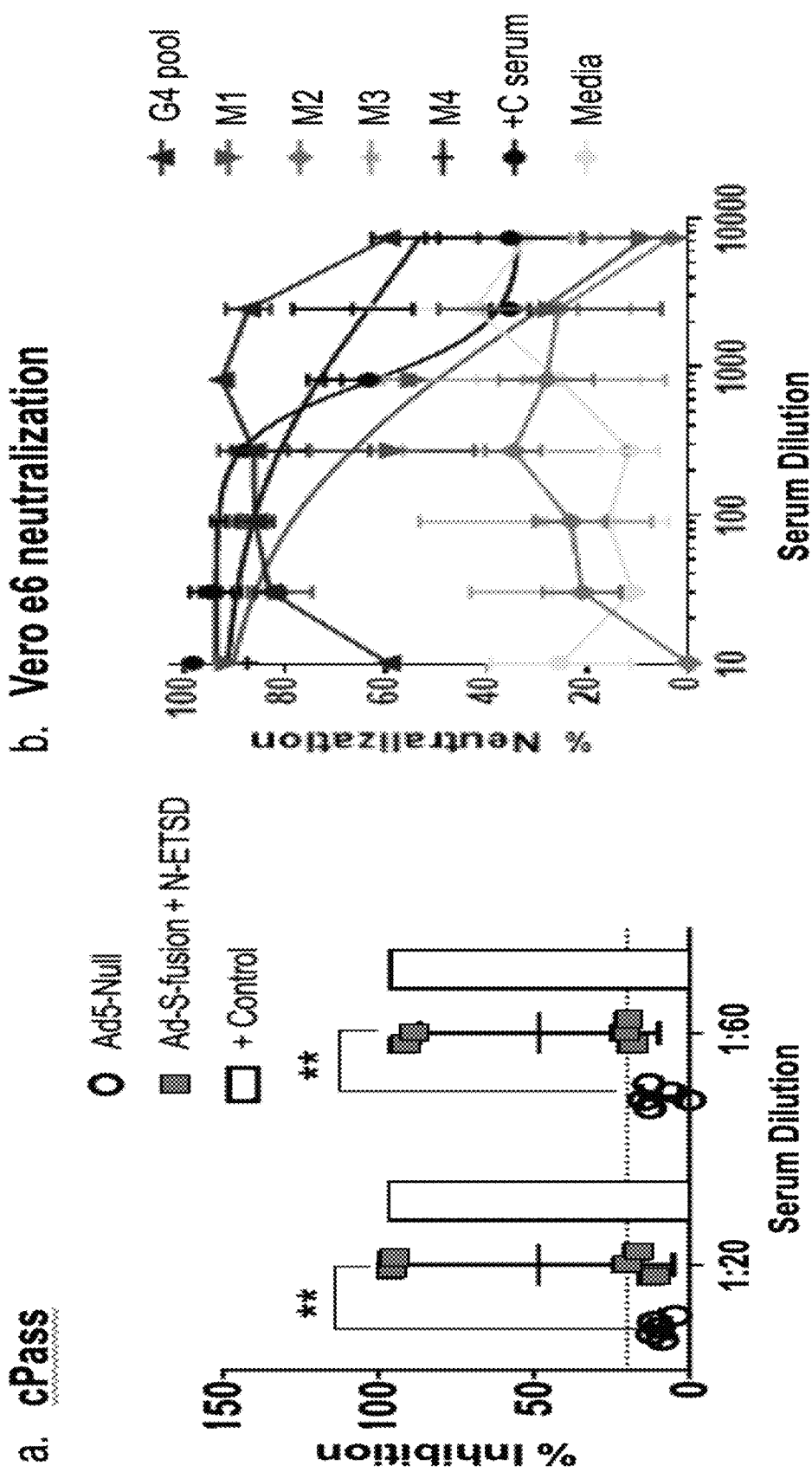
Figure 16:
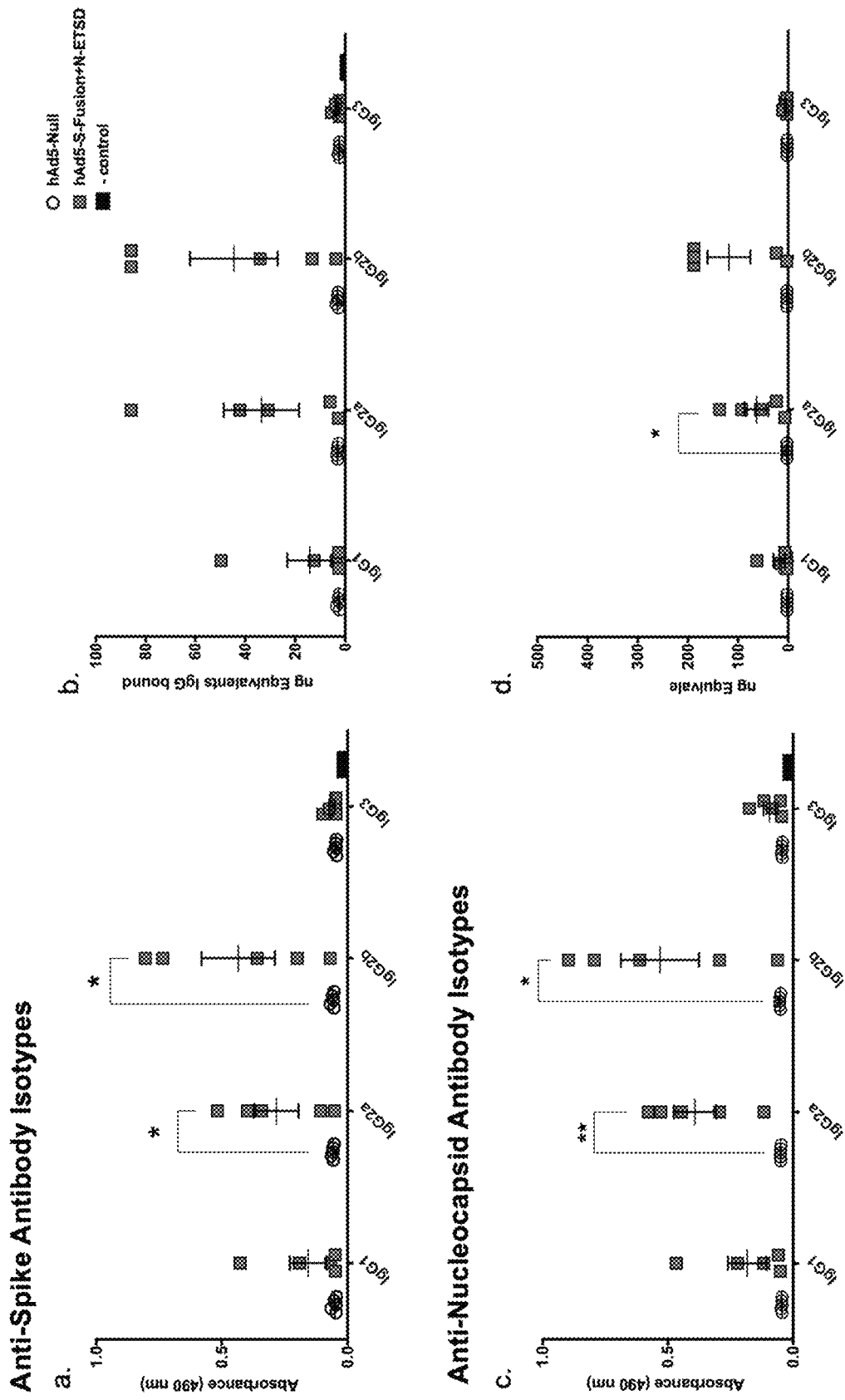
Figure 17:
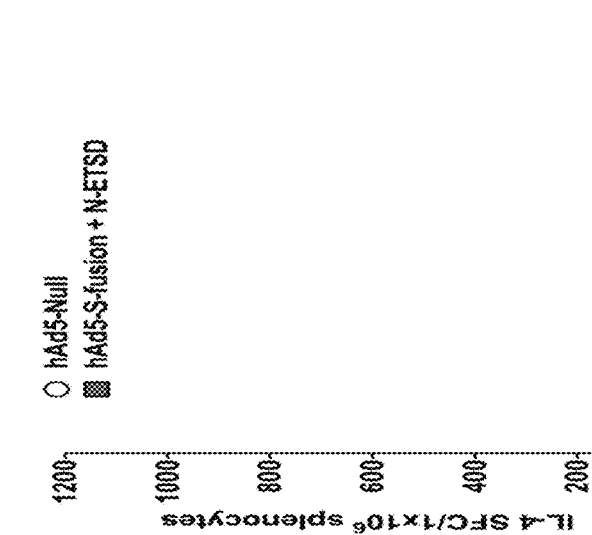
Figure 17:
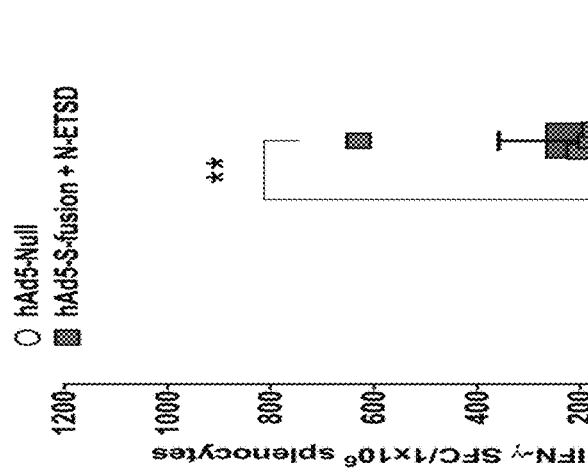

Example 10: hAd5 N-ETSD Successfully Directs N to an Endosomal/Lysosomal Compartment The ETSD design successfully translocated N to the endosomal subcellular compartment. After infection of HeLa cells with N-ETSD, N co-localized with the endosomal marker 45 transferrin receptor (CD71), as shown in FIG. 12c, and also co-localized with the lysosomal marker Lamp1 (FIG. 12d), demonstrating that N-ETSD is translocated throughout the endosomal pathway to lysosomes, enabling processing for MHC II presentation. N-wild type (N-WT), compared to N-ETSD, shows diffuse cytoplasmic distribution and does not co-localize with the lysosomal marker (FIG. 12e). These findings confirm the role of the ETSD in directing N to an endosomal/lysosomal compartment that will result in increased MHC II presentation and CD4+activation by N.

Figure 18:
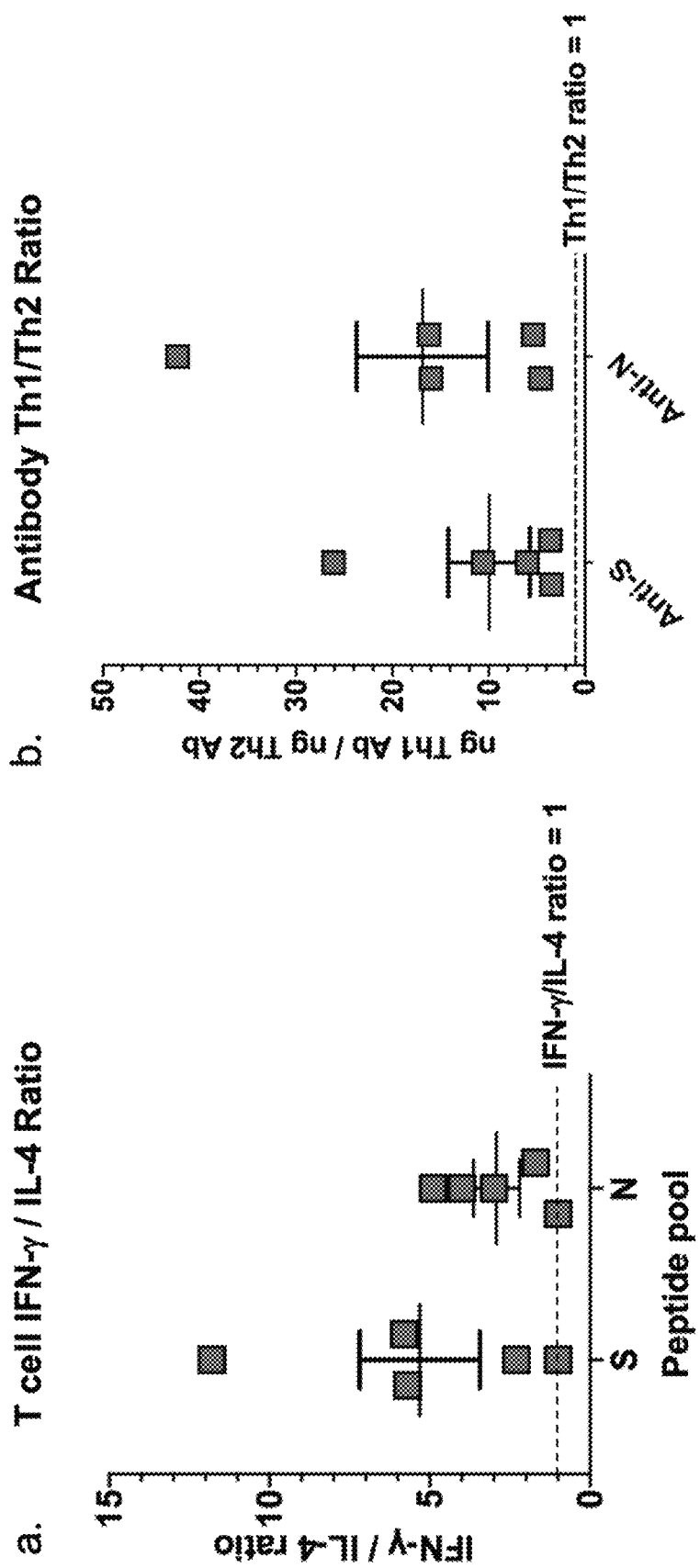

Example 11: In Vivo hAd5 S-Fusion+N-ETSD Vaccine Immunogenicity Studies

Based on the evidence that S-Fusion+N-ETSD resulted in enhanced expression of physiologically-relevant RBD and that N-ETSD successfully translocated to the endosomal/lysosomal compartment, the bivalent hAd5 S-Fusion+N-ETSD vaccine was chosen for inoculation of 7-week old female CD-1 mice. The unique properties of this construct would result in the generation of both CD8+ and CD4+ T-cell responses and neutralizing antibodies. As described in Methods, mice received an initial injection on Day 0 and a second injection on Day 21. Sera were collected on Day 0 and at the end of the study on Day 28 for antibody and neutralization analyses. Splenocytes were also collected on Day 28 for intracellular cytokine staining (ICS) and ELISpot analyses. All age- and gender-matched animals assigned to the study appeared normal with no site reactions and no loss of body weight throughout the dosing were seen, consistent with previous observations with the hAd5 [E1-, E2b-, E3-] platform Example 12: hAd5 S-Fusion+N-ETSD Generates Both CD8□ and CD4+ T-Cell Responses CD8+activation by both S and N: CD80+splenocytes from hAd5 S-Fusion+N-ETSD vaccinated mice exposed to S peptide pool 1 (containing RBD and S1) show IFN-γ expression that is significantly higher compared to hAd5 null mice (FIG. 13*a*); splenocytes from these mice also expressed intracellular IFN-γ in response to the N peptide pool. Evaluation of simultaneous IFN-γ/TNF-α expression from CD8 f3+splenocytes (FIG. 13*c*) mirrored those for IFN-γ expression alone. These results indicate that both S and N activate CD8+ T cells.

CD4+activation by N: Although CD8+ cytotoxic T cells mediate killing of virus infected cells, CD4+ T cells are required for sustained cytotoxic T lymphocyte (CTL) activity. Thus, CD4+ T cells in the vaccinated animals was evaluated. In contrast to CD8 β+splenocytes, only the N peptide pool stimulated CD4+splenocytes from hAd5 S-Fusion+N-ETSD-inoculated mice to express IFN-γ (FIG. 13*b*) or IFN-γ/TNF-α (FIG. 13*d*) at levels that were substantially higher than hAd5 Null control. The contribution by N of CD4+ T-cell responses is vital to an effective immune response to the candidate vaccine.

Example 13: hAd5 S-Fusion+N-ETSD Generates Antibody Responses to Both S and N Antigens The primary objective of coronavirus vaccines currently in development are neutralizing antibodies against spike, thus we examined antibody production in mice vaccinated with our bivalent vaccine. There was significant production of both anti-S (FIG. 14*a*) and anti-N (FIG. 14*c*) antibodies in the sera from CD-1 mice vaccinated with hAd5 S-Fusion+N-ETSD at Day 28 in the study. Compared to anti-S antibodies, anti-N antibodies were higher in sera, given the dilution factor for sera was 1:90 for anti-N antibody analysis and 1:30 for anti-S antibody analysis.

A standard curve of IgG was generated, then absorbance values were converted into mass equivalents for both anti-S and anti-N antibodies (FIGS. 14*b* and *d*). These values were used to calculate that hAd5 S-Fusion+NETSD vaccination generated a geometric mean value of 5.8 μg S-specific IgG and 42 μg N-specific IgG per mL of serum, therefore the relative μg amount of anti-N antibodies is higher than that for anti-S antibodies and reflects the strong contribution of N to anti-SARS-CoV-2 antibody production.

Example 14: hAd5 S-Fusion+N-ETSD Vaccine Generates Potent Neutralizing Antibodies as Assessed by Both cPass and Live Virus Neutralization Assays Neutralizing antibody activity was evaluated using a cell free assay (cPass) as well as live virus infection in vitro. As seen in FIG. 15*a*, the cPass assay showed inhibition of S RBD:ACE2 binding for all mice and ~100% inhibition for two mice at both dilutions of 1:20 and 1:60. The Vero E6 neutralization assay results are shown for the four mice that showed S-specific antibodies by ELISA. The high persistent neutralization seen even at the high dilution factors suggests the intriguing possibility that the bivalent, multi-antigen, multi-epitope generation by hAd5 S-Fusion+N-ETSD vaccine, could result in synergies of neutralizing immune responses (FIG. 15*b*); at epitopes in addition to those associated with RBD-ACE2 binding. As can be seen in FIG. 15*b*, the value for 50% neutralization (IC50) is present at 1:10,000 serum dilution for the G4 pool of sera from mice that showed S-specific antibodies, ten times higher than the convalescent serum with a dilution of 1:1,000. The potent neutralization, confirmed by two assays, supports the predicted efficacy of the hAd5 S-Fusion+ETSD vaccine candidate and its advancement to clinical trials Example 15: hAd5 S-Fusion+N-ETSD Generates Th1 Dominant Responses Both in Humoral and T-Cell Immunity Antibody Th1 dominance in response to N and S: IgG2a, IgG2b, and IgG3 represent Th1 dominance; while IgG1 represents Th2 dominance. For both anti-S (FIG. 16*a*) and anti-N (FIG. 16*c*) antibodies in sera from hAd5 S-Fusion+N-ETSD vaccinated mice, IgG2a and IgG2b isotypes were predominant and significantly higher compared to the hAd5 Null control. These data show the Th1 dominance of antibody production in response to the hAd5 S-Fusion+N-ETSD vaccine T-cell Th1 dominance in response to N and S: IFN-γ production correlates with CTL activity 47 (Th1 dominance), whereas, IL-4 causes delayed viral clearance 48 (Th2 dominance). A ratio of IFN-γ to IL-4 of 1 is balanced and a ratio greater than 1 is demonstrative of Th1 dominance. Thus, we examined IFN-γ and IL-4 production in animals immunized with the bivalent S plus N vaccine. As determined by ELISpot, IFN-γ secretion was significantly higher for hAd5 S-Fusion+N-ETSD than for hAd5 Null splenocytes in response to both S peptide pool 1 and the N peptide pool (FIG. 17*a*), but IL-4 was only secreted at significantly higher levels for hAd5 S-Fusion+N-ETSD in response to the N peptide pool (FIG. 17*b*).

The Th1-type predominance is also seen when the ratio of IFN-□ to IL-4 based on spot forming units in response to the combined S peptide pools and the N peptide pool, is considered (FIG. 18*a*).

Th1 predominance was seen again in humoral responses, where the ratio based on ng equivalence of Th1 related antibodies (IgG2a, IgG2b, and IgG3) to Th2 related antibodies (IgG1) for both anti-S and anti-N antibodies is greater than 1 in all mice (FIG. 18b).

This Th1 dominant profile of the hAd5 S-Fusion+N-ETSD vaccine candidate provides further justification for hAd5 S-Fusion+N-ETSD to be our lead candidate for clinical testing The hAd5 S-Fusion+N-ETSD vaccine was designed to overcome the risks of an S-only vaccine and elicit both T-cell immunity and neutralizing antibodies, leveraging the vital role T cells play in generating long-lasting antibody responses and in directly killing infected cells. Both CD4+ and CD8+ T cells are multifunctional, and induction of such multifunctional T cells by vaccines correlated with better protection against infection. We posit that enhanced CD4+ T-cell responses and Th1 predominance resulting from expression of an S antigen optimized for surface display and an N antigen optimized for endosomal/lysosomal subcellular compartment localization and thus MHC I and II presentation, led to increased dendritic cell presentation, cross-presentation, B cell activation, and ultimately high neutralization capability. Furthermore, the potent neutralization capability at high dilution seen for the pooled sera from hAd5 S-Fusion+N-ETSD vaccinated mice, combined with Th1 dominance of antibodies generated in response to both S and N antigens, supports the objective of this vaccine design.

Contemporaneous MHC I and MHC II presentation of an antigen by the antigen presenting cell activates CD4+ and CD8+ T cells simultaneously and is optimal for the generation of memory B and T cells. A key finding of our construct is that N-ETSD, which we show is directed to the endosomal/lysosomal compartment, elicits a CD4+response, a necessity for induction of memory T cells and helper cells for B cell antibody production. Others have also reported on the importance of lysosomal localization for eliciting the strongest T-cell IFN-γ and CTL responses, compared to natural N.50, 51

The T-cell responses to the S and N antigens expressed by hAd5 S-Fusion+N-ETSD were polycytokine, including IFN-g and TNF-α, consistent with successful antimicrobial immunity in bacterial and viral infections. Post-vaccination polycytokine T-cell responses have been shown to correlate with vaccine efficacy, including those with a viral vector. Highly relevant here, polycytokine T-cell responses to SARS-CoV-2 N protein are consistent with recovered COVID-19 patients, suggesting that the bivalent hAd5 S-Fusion+N-ETSD vaccine will provide vaccine subjects with greater protection against SARS-CoV-2.

In contrast to N, the S protein, here expressed as S-Fusion with confirmed enhanced RBD cell-surface expression and conformational integrity as evidenced by high ACE2-Fc binding, generated predominantly CD8+ T cells. Our results confirmed our vaccine design goal, showing that S-Fusion induced elevated levels of antigen-specific T-cell responses against S compared to S-WT. To ensure MHC presentation to both MHC I (for CD8+ T-cell activation) and MHC II (for CD4+ T-cell activation), it is necessary to vaccinate with both S and N antigens optimized to produce this coordinated response.

The neutralization data with live SARS-CoV-2 virus demonstrated the potency of the antibody response generated following vaccination with hAd5 S-Fusion+N-ETSD, with evidence of high neutralization even at a high dilution factor. In addition, a striking synergistic effect of pooled sera was evident, with potent neutralization even greater than control convalescent serum at >1:1,000 dilution.

The hAd5 S-Fusion+N-ETSD construct described above is delivered by a next generation hAd5 [E1-, E2b-, E3-] platform wherein the E2b deletion (pol) alone enables prolonged transgene production and allows homologous vaccination (prime and the boost formulation is the same) in the presence of pre-existing adenoviral immunity.38 In addition to the generation of cellular and humoral immunity by the subcutaneous injection of hAd5 S-Fusion+N-ETSD, we are also exploring the potential of inducing IgA mucosal immunity by utilizing the same vaccine in an oral or sublingual formulation in clinical trials.

Example 16: Methods

The hAd5 [E1-, E2b-, E3-] platform and constructs

For studies herein, the 2nd generation hAd5 [E1-, E2b-, E3-] vector was used (FIG. 1c) to create viral vaccine candidate constructs. hAd5 [E1-, E2b-, E3-] backbones containing SARS-CoV-2 antigen expressing inserts and virus particles were produced as previously described.37 In brief, high titer adenoviral stocks were generated by serial propagation in the E1- and E2b-expressing E.C7 packaging cell line, followed by CsCl2 purification, and dialysis into storage buffer (2.5% glycerol, 20 mM Tris pH 8, 25 mM NaCl) by ViraQuest Inc. (North Liberty, IA). Viral particle counts were determined by sodium dodecyl sulfate disruption and spectrophotometry at 260 and 280 nm and viral titers were determined using the Adeno-X™ Rapid Titer Kit (Takara Bio). The constructs created included:

S-WT: S protein comprising 1273 amino acids and all S domains: extracellular (1-1213), transmembrane (1214-1234), and cytoplasmic (1235-1273) (Unitprot PODTC2);
S RBD-ETSD: S Receptor Binding Domain (S RBD) with an ETSD;
N-ETSD: Nucleocapsid (N) with ETSD;
S-WT+N-ETSD: S-WT with an Enhanced T-cell Stimulation Domain (ETSD);
S-RBD-ETSD+N-ETSD;
S Fusion: S optimized to enhance surface expression and display of RBD; and Bivalent S-Fusion+N-ETSD;

Transfection of HEK 293T Cells with hAd5 Constructs

To determine surface expression of the RBD epitope by vaccine candidate constructs, we transfected HEK 293T cells with hAd5 construct DNA and quantified surface RBD by flow cytometric detection using anti-RBD antibodies. There were seven constructs tested: S-WT, S-WT+N-ETSD, S RBD-ETSD, S RBD-ETSD+N-ETSD, S-Fusion, S-Fusion+N-ETSD, and N-ETSD. HEK 293T cells (2.5×10 5 cells/well in 24 well plates) were grown in DMEM (Gibco Cat #11995-065) with 10% FBS and 1X PSA (100 units/mL penicillin, 100 µg/mL streptomycin, 0.25 ug/mL Amphotericin B) at 37° C. Cells were transfected with 0.5 µg of hAd5 plasmid DNA using a JetPrime transfection reagent (Polyplus Catalog #89129-924) according to the manufacturer's instructions. Cells were harvested 1, 2, 3, and 7 days post transfection by gently pipetting cells into medium and labeled with an anti-RBD monoclonal antibody (clone D003 Sino Biological Catalog #40150-D003) and F(ab')2-Goat anti-Human IgG-Fc secondary antibody conjugated with R-phycoerythrin (ThermoFisher Catalog #H10104). Labeled cells were acquired using a Thermo-Fisher Attune NxT flow cytometer and analyzed using Flowjo Software.

Immunocytochemical labeling of hAd5 infected HeLa cells

To determine subcellular localization of N after infection or transfection of HeLa cells with hAd5 N-wild type (WT) or hAd5 N-ETSD (each with a flag tag to allow labeling), 48 hours after infection or transfection cells were fixed with 4% paraformaldehyde (PFA) and permeabilized with 0.4% Triton X100, in PBS) for 15 min. at room temperature. To label N, cells were then incubated with an anti-flag monoclonal (Anti-Flag M2 produced in mouse, Sigma cat #F1804) antibody at 1:1000 in phosphate buffered saline with 3% BSA overnight at 4° C., followed by washes in PBS and a 1 hour incubation with a goat anti-Mouse IgG (H+L) Highly Cross-Adsorbed Secondary Antibody, Alexa Fluor Plus 555 (Life Technologies, Cat #A32727) at 1:500. For co-localization studies, cells were also incubated overnight at 4° C. with a sheep anti-Lamp1 Alexa Fluor 488-conjugated (lysosomal marker) antibody (R&D systems, Cat #IC7985G) at 1:10 or a rabbit anti-CD71 (transferrin receptor, endosomal marker) antibody (ThermoFisher Cat #PA5-83022) at 1:200. After removal of the primary antibody, two washes in PBS and three 3 washes in PBS with 3% BSA, cells were incubated with fluor-conjugated secondary antibodies when applicable at 1:500 (Goat anti-Rabbit IgG (H+L) Highly Cross-Adsorbed Secondary Antibody, Alexa Fluor 488, Life technologies, A-11034) for 1 hour at room temperature. After brief washing, cells were mounted with Vectashield Antifade mounting medium with DAPI (Fisher Scientific, Cat #NC9524612) and immediately imaged using a Keyence all-in-one Fluorescence microscope camera and Keyence software.

Immunoblot Analysis of S Antigen Expression

HEK 293T cells transfected with hAd5 S-WT, S-Fusion, or S-Fusion+N-ETSD constructs were cultured and transfected as described in the main manuscript and harvested 3 days after transfection in 150 mL RIPA lysis buffer with 1× final Protease Inhibitor cocktail (Roche). After protein assay, equivalent amounts of total protein were loaded into and run on a 4 to 12% gradient polyacrylamide gel (type) and transferred to nitrocellulose membranes using semi-dry transfer apparatus. Anti-Spike S2 (SinoBiological Cat #40590-T62) was used as the primary antibody and IRDye® 800CW Goat anti-Rabbit IgG (H+L) (Li-Cor, 925-32211) as the secondary antibody using the Ibind Flex platform. Antibody-specific signals were detected with an infrared Licor Odyssey instrument.

ACE2-IgG1Fc binding to hAd5 transfected HEK 293T cells

HEK 293T cells were cultured at 37° C. under conditions described above for transfection with hAd5 S-WT, S-Fusion, S-Fusion+N-ETSD, S RBD-ETSD, or S RBD-ETSD+N-ETSD and were incubated for 2 days and harvested for ACE2-Fc binding analysis. Recombinant ACE2-IgG1Fc protein was produced using Maxcyte transfection in CHO-S cells that were cultured for 14 days. ACE2-IgG1Fc was then purified using a MabSelect SuRe affinity column on AKTA Explorer.

Purified ACE2-IgG1Fc was dialyzed into 10 mM HEPES, pH7.4, 150 mM NaCl and concentrated to 2.6 mg/mL. For binding studies, the ACE2-IgG1Fc was used at a concentration of 1 □g/mL for binding. Cells were incubated with ACE2-Fc for 20 minutes and, after a washing step, were then labeled with a PE conjugated F(ab')2-goat anti-human IgG Fc secondary antibody at a 1:100 dilution, incubated for 20 minutes, washed and acquired on flow cytometer. Histograms are based on normalized mode (NM) of cell count— count of cells positive for signal in PE channel.

Vaccination of CD-1 Mice with the hAd5 S-Fusion+N-ETSD Vaccine Candidate

CD-1 female mice (Charles River Laboratories) 7 weeks of age were used for immunological studies performed at the vivarium facilities of Omeros Inc. (Seattle, WA). After an initial blood draw, mice were injected with either hAd5 Null (a negative control) or vaccine candidate hAd5 S-Fusion+N-ETSD on Day 0 at a dose of 1×1010 viral particles (VP). There were 5 mice per group. Mice received a second vaccine dose on Day 21 and on Day 28, blood was collected via the submandibular vein from isoflurane-anesthetized mice for isolation of sera and then mice were euthanized for collection of spleen and other tissues.

Splenocyte Collection and Intracellular Cytokine Staining (ICS)

Spleens were removed from each mouse and placed in 5 mL of sterile medium of RPMI (Gibco Cat #22400105), HEPES (Hyclone Cat #SH30237.01), 1X Pen/Strep (Gibco Cat #15140122), and 10% FBS (Gibco Cat #16140-089). Splenocytes were isolated within 2 hours of collection. ICS for flow cytometric detection of CD80+ and CD4+ T-cell-associated IFN-γ and IFN-γ/TNFα+production in response to stimulation by S and N peptide pools.

Stimulation assays were performed using 106 live splenocytes per well in 96-well U-bottom plates. Splenocytes in RPMI media supplemented with 10% FBS were stimulated by the addition of peptide pools at 2 µg/mL/peptide for 6 h at 37° C. in 5% CO2, with protein transport inhibitor, GolgiStop (BD) added two hours after initiation of incubation. Stimulated splenocytes were then stained for lymphocyte surface markers CD8Dand CD4, fixed with CytoFix (BD), permeabilized, and stained for intracellular accumulation of IFN-γ and TNF-α. Fluorescent-conjugated antibodies against mouse CD8Dantibody (clone H35-17.2, ThermoFisher), CD4 (clone RM4-5, BD), IFN-γ (clone XMG1.2, BD), and TNF-α (clone MP6-XT22, BD) and staining was performed in the presence of unlabeled anti-CD16/CD32 antibody (clone 2.4G2). Flow cytometry was performed using a Beckman-Coulter Cytoflex S flow cytometer and analyzed using Flowjo Software.

ELISpot Assay

ELISpot assays were used to detect cytokines secreted by splenocytes from inoculated mice. Fresh splenocytes were used on the same day, as were cryopreserved splenocytes containing lymphocytes. The cells (2-4×105 cells per well of a 96-well plate) were added to the ELISpot plate containing an immobilized primary antibodies to either IFN-γ or IL-4 (BD), and were exposed to various stimuli (e.g. control peptides, target peptide pools/proteins) comprising 2 µg/mL peptide pools or 10 µg/mL protein for 36-40 hours. After aspiration and washing to remove cells and media, extracellular cytokine was detected by a secondary antibody to cytokine conjugated to biotin (BD). A streptavidin/horseradish peroxidase conjugate was used detect the biotin-conjugated secondary antibody. The number of spots per well, or per 2-4×105 cells, was counted using an ELISpot plate reader.

ELISA for Detection of Antibodies

For antibody detection in sera from inoculated mice, ELISAs specific for spike and nucleocapsid antibodies, as well as for IgG subtype (IgG1, IgG2a, IgG2b, and IgG3) antibodies were used. A microtiter plate was coated overnight with 100 ng of either purified recombinant SARS-CoV-2 S-FTD (full-length S with fibritin trimerization domain, constructed and purified in-house by ImmunityBio), SARS-CoV-2 S RBD (Sino Biological, Beijing, China; Cat #401591-VO8B1-100) or purified recombinant SARS-CoV-2 nucleocapsid (N) protein (Sino Biological, Beijing, China; Cat #40588-VO8B) in 100 µL of coating buffer (0.05 M Carbonate Buffer, pH 9.6). The wells were washed three times with 250 µL PBS containing 1% Tween 20 (PBST) to remove unbound protein and the plate was blocked for 60 minutes at room temperature with 250 µL PBST. After blocking, the wells were washed with PBST, 100 μL of diluted serum samples were added to wells, and samples incubated for 60 minutes at room temperature. After incubation, the wells were washed with PBST and 100 μL of a 1/5000 dilution of anti-mouse IgG HRP (GE Health Care; Cat #NA9310V), or anti-mouse IgG1 HRP (Sigma; Cat #SAB3701171), or anti-mouse IgG2a HRP (Sigma; Cat #SAB3701178), or anti-mouse IgG2b HRP (Sigma; catalog #SAB3701185), or anti-mouse IgG3 HRP conjugated antibody (Sigma; Cat #SAB3701192) was added to wells. For positive controls, a 100 μL of a 1/5000 dilution of rabbit anti-N IgG Ab or 100 μL of a 1/25 dilution of mouse anti-S serum (from mice immunized with purified S antigen in adjuvant) were added to appropriate wells. After incubation at room temperature for 1 hour, the wells were washed with PBS-T and incubated with 200 μL o-phenylenediamine-dihydrochloride (OPD substrate (Thermo Scientific Cat #A34006) until appropriate color development. The color reaction was stopped with addition of 50 μL 10% phosphoric acid solution (Fisher Cat #A260-500) in water and the absorbance at 490 nm was determined using a microplate reader (SoftMax® Pro, Molecular Devices).

Calculation of Relative μg Amounts of Antibodies

A standard curve of IgG was generated and absorbance values were converted into mass equivalents for both anti-S and anti-N antibodies. Using these values, we were able to calculate that hAd5 S-Fusion+N-ETSD vaccination generated a geometric mean value of 5.8 μg S-specific IgG and 42 μg N-specific IgG per milliliter of serum.

cPassTM Neutralizing Antibody Detection

The GenScript cPassTM (https://www.genscript.com/cpass-sars-cov-2-neutralization-antibody-detection-Kit.html) for detection of neutralizing antibodies was used according to the manufacturer's instructions.44 The kit detects circulating neutralizing antibodies against SARS-CoV-2 that block the interaction between the S RBD with the ACE2 cell surface receptor. It is suitable for all antibody isotypes and appropriate for use with in animal models without modification.

Vero E6 Cell Neutralization Assay

All aspects of the assay utilizing virus were performed in a BSL3 containment facility according to the ISMMS Conventional Biocontainment Facility SOPs for SARS-CoV-2 cell culture studies. Vero e6 kidney epithelial cells from Cercopithecus aethiops (ATCC CRL-1586) were plated at 20,000 cells/well in a 96-well format and 24 hours later, cells were incubated with antibodies or heat inactivated sera previously serially diluted in 3-fold steps in DMEM containing 2% FBS, 1% NEAAs, and 1% Pen-Strep; the diluted samples were mixed 1:1 with SARS-CoV-2 in DMEM containing 2% FBS, 1% NEAAs, and 1% Pen-Strep at 10,000 TCID 50/mL for 1 hr. at 37° C., 5% CO2. This incubation did not include cells to allow for neutralizing activity to occur prior to infection. The samples for testing included sera from the four mice that showed >20% inhibition of ACE2 binding in cPass, pooled sera from those four mice, sera from a COVID-19 convalescent patient, and media only. For detection of neutralization, 120 μL of the virus/sample mixture was transferred to the Vero E6 cells and incubated for 48 hours before fixation with 4% PFA. Each well received 60 μL of virus or an infectious dose of 600 TCID50. Control wells including 6 wells on each plate for no virus and virus-only controls were used. The percent neutralization was calculated as 100-((sample of interest-[average of "no virus"])/[average of "virus only"])*100) with a stain for CoV-2 Np imaged on a Celigo Imaging Cytometer (Nexcelom Bioscience).

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosures herein, and does not pose a limitation on the scope of the invention otherwise claimed. No language in the specification should be construed as indicating any non-claimed element essential to the practice of the claimed invention.

Many more modifications besides those already described are possible without departing from the concepts disclosed herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A boost vaccine composition for use in inducing immunity against a severe acute respiratory syndrome (SARS) coronavirus 2 (SARS-CoV2) in mucosal tissue of a patient, wherein the patient has been primed with a SARS-CoV2 vaccine, and wherein the boost vaccine composition comprises a replication defective human adenovirus serotype 5 (hAd5), and wherein the hAd5 comprises an E1 gene region deletion, an E2b gene region deletion, a nucleic acid portion that encodes a SARS-CoV2 S protein, and a nucleic acid portion that encodes a chimeric protein comprising a SARS-CoV2 nucleocapsid (N) protein and an endosomal targeting sequence.

2. The vaccine composition of claim 1, further comprising administering by injection to the patient a second boost vaccine comprising an anti-SARS-CoV2 vaccine, wherein the anti-SARS-CoV2 vaccine injection comprises a nucleotide encoding SARS-CoV2 spike(S) and/or nucleocapsid (N) protein, and wherein injection includes intramuscular (IM) injection, (IV) intravenous injection, and/or subcutaneous injection.

3. The vaccine composition of claim 1, wherein the boost immunization is administered at least 7 days after the initial prime vaccination, for example at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 28 days, at least 35 days, or at least 42 days after the prime vaccination.

4. The vaccine composition of claim 1, wherein the prime vaccination further comprises an RNA encoding a SARS-CoV2 N protein.

5. The vaccine composition of claim 1, wherein the adenoviral vaccine composition comprises SEQ ID NO:3.

6. The vaccine composition of claim 1, wherein the adenoviral vaccine composition comprises SEQ ID NO:7.

7. The vaccine composition of claim 1, wherein the boost vaccine composition is formulated for administration to nasal mucosa.

8. The vaccine composition of claim 1, wherein the boost vaccine composition is formulated for oral administration to the patient.

9. The vaccine composition of claim 1, wherein the boost vaccine composition is formulated for subcutaneous administration to the patient.

10. The vaccine composition of claim 1, wherein the boost vaccine composition is formulated for sublingual administration to the patient.

11. The vaccine composition of claim 1, wherein the boost vaccine composition is formulated for intramuscular administration to the patient.

* * * * *